(12) United States Patent
Levy et al.

(10) Patent No.: US 10,610,603 B2
(45) Date of Patent: *Apr. 7, 2020

(54) THYMIDINE KINASE GENE

(71) Applicant: GenVivo, Inc., San Marino, CA (US)

(72) Inventors: John P. Levy, Lake Elsinore, CA (US); Rebecca A. Reed, Sherman Oaks, CA (US); Joseph McNulty, Pasadena, CA (US); Robert G. Johnson, Jr., Lafayette, CA (US)

(73) Assignee: GenVivo, Inc., San Marino, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 15/892,295

(22) Filed: Feb. 8, 2018

(65) Prior Publication Data

US 2018/0236101 A1    Aug. 23, 2018

Related U.S. Application Data

(63) Continuation of application No. 14/214,522, filed on Mar. 14, 2014, now Pat. No. 9,925,276.

(60) Provisional application No. 61/784,901, filed on Mar. 14, 2013.

(51) Int. Cl.
| | | |
|---|---|---|
| *A61K 48/00* | (2006.01) | |
| *C12N 9/12* | (2006.01) | |
| *A61K 31/713* | (2006.01) | |
| *A61K 31/522* | (2006.01) | |
| *C07K 14/005* | (2006.01) | |

(52) U.S. Cl.
CPC .......... *A61K 48/00* (2013.01); *A61K 31/522* (2013.01); *A61K 31/713* (2013.01); *A61K 48/005* (2013.01); *C07K 14/005* (2013.01); *C12N 9/1211* (2013.01); *C12Y 207/01021* (2013.01); *C12N 2710/16622* (2013.01); *C12N 2740/13034* (2013.01)

(58) Field of Classification Search
CPC .... A61K 48/00; A61K 31/522; A61K 31/713; A61K 48/005; C07K 14/005; C12Y 207/01021

See application file for complete search history.

(56) References Cited

U.S. PATENT DOCUMENTS

| | | | |
|---|---|---|---|
| 4,399,216 A | 8/1983 | Axel et al. | |
| 4,704,362 A | 11/1987 | Itakura et al. | |
| 4,766,075 A | 8/1988 | Goeddel et al. | |
| 4,777,127 A | 10/1988 | Suni et al. | |
| 4,784,950 A | 11/1988 | Hagen et al. | |
| 4,801,542 A | 1/1989 | Murray et al. | |
| 4,851,341 A | 7/1989 | Hopp et al. | |
| 4,897,355 A | 1/1990 | Eppstein et al. | |
| 4,935,349 A | 6/1990 | McKnight et al. | |
| 5,171,678 A | 12/1992 | Behr et al. | |
| 5,219,740 A | 6/1993 | Miller et al. | |
| 5,279,833 A | 1/1994 | Rose | |
| 5,283,185 A | 2/1994 | Epand et al. | |
| 5,705,385 A | 1/1998 | Bally et al. | |
| 5,952,225 A | 9/1999 | Pensiero et al. | |
| 5,962,429 A | 10/1999 | Welsh et al. | |
| 5,976,567 A | 11/1999 | Wheeler et al. | |
| 5,980,935 A | 11/1999 | Kirpotin et al. | |
| 5,981,501 A | 11/1999 | Wheeler et al. | |
| 6,096,335 A | 8/2000 | Thierry | |
| 6,110,745 A | 8/2000 | Zhang et al. | |
| 6,120,798 A | 9/2000 | Allen et al. | |
| 6,825,033 B2 | 11/2004 | Gordon et al. | |
| 7,820,157 B2 | 10/2010 | Hall et al. | |
| 9,925,276 B2 * | 3/2018 | Levy | A61K 31/522 |
| 2001/0046491 A1 | 11/2001 | Valerie | |
| 2003/0004405 A1 | 1/2003 | Townsend et al. | |
| 2003/0008398 A1 | 1/2003 | Mueller et al. | |
| 2004/0229361 A1 | 11/2004 | Mason | |
| 2005/0130132 A1 | 6/2005 | Day et al. | |
| 2006/0216299 A1 | 9/2006 | Hitoshi et al. | |
| 2009/0123428 A1 | 5/2009 | Hall et al. | |
| 2009/0176260 A1 | 7/2009 | Wu et al. | |
| 2009/0285783 A1 | 11/2009 | Freytag et al. | |
| 2010/0135902 A1 | 6/2010 | Roberts et al. | |
| 2010/0322861 A1 | 12/2010 | Gambhir et al. | |
| 2011/0178282 A1 | 7/2011 | Freytag et al. | |
| 2011/0189159 A1 | 8/2011 | Chatterjee et al. | |
| 2013/0263296 A1 | 10/2013 | Pomper et al. | |
| 2014/0271640 A1 | 9/2014 | Bowdish et al. | |
| 2014/0294772 A1 | 10/2014 | Levy et al. | |
| 2015/0307576 A1 | 10/2015 | Bowdish et al. | |

FOREIGN PATENT DOCUMENTS

| | | |
|---|---|---|
| CN | 1884496 A | 12/2006 |
| CN | 101070548 A | 11/2007 |
| EP | 0345242 A2 | 12/1989 |
| EP | 1914304 A1 | 4/2008 |
| GB | 2200651 A | 8/1988 |
| JP | 2006524057 A | 10/2006 |
| KR | 20110005336 A | 1/2011 |
| WO | WO-9007936 A1 | 7/1990 |
| WO | WO-9102805 A2 | 3/1991 |
| WO | WO-9303769 A1 | 3/1993 |
| WO | WO-9305162 A1 | 3/1993 |
| WO | WO-9310218 A1 | 5/1993 |
| WO | WO-9311230 A1 | 6/1993 |

(Continued)

OTHER PUBLICATIONS

Australia Patent Application No. 2014236208 Examination Report No. 1 dated Jun. 26, 2017.

(Continued)

*Primary Examiner* — Karen Cochrane Carlson
(74) *Attorney, Agent, or Firm* — Wilson Sonsini Goodrich & Rosati

(57) ABSTRACT

Nucleic acid sequences encoding improved Herpes Simplex Virus Thymidine Kinases are provided, including their use in diagnostic and therapeutic applications. The thymidine kinases may be mutated using conservative mutations, non-conservative mutations, or both. Also provided are gene therapeutic systems, including viral and retroviral particles.

27 Claims, 36 Drawing Sheets
(19 of 36 Drawing Sheet(s) Filed in Color)
Specification includes a Sequence Listing.

(56) References Cited

FOREIGN PATENT DOCUMENTS

| | | |
|---|---|---|
| WO | WO-9319191 A1 | 9/1993 |
| WO | WO-9325234 A1 | 12/1993 |
| WO | WO-9325698 A1 | 12/1993 |
| WO | WO-9403622 A1 | 2/1994 |
| WO | WO-9412649 A2 | 6/1994 |
| WO | WO-9428938 A1 | 12/1994 |
| WO | WO-9500655 A1 | 1/1995 |
| WO | WO-9511984 A2 | 5/1995 |
| WO | WO-9858630 A1 | 12/1998 |
| WO | WO-0106574 A1 | 1/2001 |
| WO | WO-2004093810 A2 | 11/2004 |
| WO | WO-2007109335 A2 | 9/2007 |
| WO | WO-2008054826 A2 | 5/2008 |
| WO | WO-2008054826 A3 | 12/2008 |
| WO | WO-2010071587 A1 | 6/2010 |
| WO | WO-2012058522 A2 | 5/2012 |
| WO | WO-2014153205 A1 | 9/2014 |
| WO | WO-2014153258 A2 | 9/2014 |

OTHER PUBLICATIONS

Balzarini et al., Engineering of a single conserved amino acid residue of herpes simplex virus Type 1 thymidine kinase allows a predominant shift from pyrimidine to purine nucleoside phosphorylation. Journal of Biological Chemistry, p. 1-15, 2006.

Bar-Shir et al., Transforming thymidine into a magnetic resonance imaging probe for gene expression. J. Am. Chem. Soc. Jan. 2013; 135:1617-24.

Behr et al. Gene transfer with synthetic cationic amphiphiles: prospects for gene therapy. Bioconjugate Chem. 5:382-389 (1994).

Bender et al., J. Virol. Vo. 61, pp. 1639-1649 (1987).

Black et al., Creation of drug-specific herpes simplex virus type 1 thymidine kinase mutants for gene therapy. Proc. Nat. Acad. Sci. USA, 93:3525-3529, 1996.

Black et al., Herpes simplex virus-1 thymidine kinase mutants created by semi-random sequence mutagenesis improve prodrug-mediated tumor cell killing. Cancer Research, 61:3022-3026, 2001.

Bottger, et al., The central half of Pit2 is not required for its function as a retroviral receptor. J Virol. Sep. 2004;78(17):9564-9567.

Bouvet et al., In vivo color-coded imaging of the interaction of colon cancer cells and splenocytes in the formation of liver metastases. Cancer Res. Dec. 1, 2006;66(23):11293-11297.

Chalmers et al., Elimination of the truncated message from the herpes simplex virus thymidine kinase suicide gene. Mol. Ther. 4:146-148 (2001).

Chaudry et al, Gibbon Ape Leukemia Virus Receptor Functions of Type III Phosphate Transporters from CHOK1 Cells are Disrupted by Two Distinct Mechanisms, J of Virology, 73(4):2916-2920 (1999).

Chen et al., FL-CTL assay: fluorolysometric determination of cell-mediated cytotoxicity using green fluorescent protein and red fluorescent protein expressing target cells. J Immunol Methods. May 2005;300(1-2):100-114.

Chen et al., Micro-positron emission tomography imaging of cardiac gene expression in rats using bicistronic adenoviral vector-mediated gene delivery. Circulation. Mar. 23, 2004;109(11):1415-1420.

Chin et al., Semiautomated radiosynthesis and biological evaluation of [18F]FEAU: a novel PET imaging agent for HSV1-tk/sr39tk reporter gene expression. Mol Imaging Biol. Mar.-Apr. 2008;10(2):82-91.

Chu et al. SV40 DNA transfection of cells in suspension: analysis of efficiency of transcription and translation of T-antigen. Gene 13:197-202 (1981).

Curiel, D. et al., High-efficiency gene transfer mediated by adenovirus coupled to DNA-polylysine complexes. Hum. Gene Ther. (1992) 3:147-154.

Czako, et al., The herpes simplex virus thymidine kinase gene as a conditional negative-selection marker gene in *Arabidopsis thaliana*. Plant Physiol. Mar. 1994;104(3):1067-1071.

Dahle, et al., Gap junctional intercellular communication is not a major mediator in the bystander effect in photodynamic treatment of MDCK II cells. Radiat Res. Sep. 2000;154(3):331-341.

Degreve, et al., Differential intracellular compartmentalization of herpetic thymidine kinases (TKs) in TK gene-transfected tumor cells: molecular characterization of the nuclear localization signal of herpes simplex virus type 1 TK. Journal of Virology, 72(12):9535-9543, 1998.

Degreve et al., Selective abolishment of pyrimidine nucleoside kinase activity of herpes simplex virus type 1 thymidine kinase by mutation of alanine-167 to tyrosine. Molecular Pharmacology, 58(6):1326-1332, 2000.

Deroose et al., Multimodality imaging of tumor xenografts and metastases in mice with combined small-animal PET, small-animal CT, and bioluminescence imaging. J Nucl Med. Feb. 2007;48(2):295-303.

European Patent Application No. 14769346.9 extended European Search Report dated Dec. 19, 2016.

European Patent Application No. 14769552.2 Extended European Search Report dated Sep. 23, 2016.

Farrell et al., Fusion defective gibbon ape leukemia virus vectors can be rescued by homologous but not heterologous soluble envelope proteins. J. Virol. May 2002; 76:4267-4274.

Farrell et al., New structural arrangement of the extracellular regions of the phosphate transporter SLC20A1, the receptor for gibbon ape leukemia virus. J. Biol. Chem. Oct. 2009; 284:29979-29987.

Fasbender et al. Complexes of adenovirus with polycationic polymers and cationic lipids increase the efficiency of gene transfer in vitro and in vivo. J. Biol. Chem. 272:6479-6489.

Feldman, et al., Identification of an extracellular domain within the human PiT2 receptor that is required for amphotropic murine leukemia virus binding. J Virol. Jan. 2004;78(2):595-602.

Fuchita et al., Bacterial cytosine deaminase mutants created by molecular engineering show improved 5-fluorocytosine-mediated cell killing in vitro and in vivo. Cancer Res. Jun. 2009; 69:4791-4799.

Gambhir et al. A mutant herpes simplex virus Type 1 thymidine kinase reporter gene shows improved sensitivity for imaging reporter gene expression with positron emission tomography. PNAS 97(6):2785-2790, 2000.

Ghosh, P. Reproducible quantification in PET-CT: Clinical relevance and technological approaches. White Paper; Siemens (Feb. 2012).

Grabarczyk et al., Expression of PiT-1 and PiT-2 retroviral receptors and transduction efficiency of tumor cells. Acta Biochim. Pol. 2002; 49:333-339.

Graham, F. et al. A new technique for the assay of infectivity of human adenovirus 5 DNA. Virology 52(2):456-467 (1973).

Green et al., A tracer kinetic model for 18F-FHBG for quantitating herpes simplex virus type 1 thymidine kinase reporter gene expression in living animals using PET. J Nucl Med. Sep. 2004;45(9):1560-1570.

Green et al., Indirect monitoring of endogenous gene expression by positron emission tomography (PET) imaging of reporter gene expression in transgenic mice. Mol Imaging Biol. Jan. 2002;4(1):71-81.

Guan Jing, et al., Characteristics of ovarian cancer cells transduced by the bicistronic retroviral vector containing GM-CSF and HSV-TK genes, Chinese Medical Journal, 2001; 114(2): 147-151.

Hawley-Nelson, P. et al. LipofectAMINE reagent: a new, higher efficiency polycationic liposome transfection reagent. Focus 15(3):73-79 (1993).

Hinnen, et al., Transformation of yeast. Proc Natl Acad Sci U S A. Apr. 1978;75(4):1929-1933.

Hodgson and Solaiman, Virosomes: cationic liposomes enhance retroviral transduction. Nature Biotechnology 14:339-342 (1996).

Hoffman et al., Subcellular imaging in the live mouse. Nat Protoc. 2006;1(2):775-782.

(56) References Cited

OTHER PUBLICATIONS

Hoffman RM. In vivo imaging with fluorescent proteins: the new cell biology. Acta Histochem. 2004;106(2):77-87.
Hopp, et al., A short polypeptide marker sequence useful for recombinant protein identification and purification. Nature Biotechnology 1988; 6:1204-1210.
Jellinek, D. et al. Potent 2'-amino-2'-deoxypyrimidine RNA inhibitors of basic fibroblast growth factor. (1995) Biochemistry 34:11363-11372.
Johnson et al., Titration of variant HSV1-tk gene expression to determine the sensitivity of 18F-FHBG PET imaging in a prostate tumor. J Nucl Med. May 2009;50(5):757-764.
Kim et al., Quantitative micro positron emission tomography (PET) imaging for the in vivo determination of pancreatic islet graft survival. Nat Med. Dec. 2006;12(12):1423-1428.
Kokoris and Black, Characterization of herpes simplex virus Type 1 thymidine kinase mutants engineered for improved ganciclovir or acyclovir activity Protein Science, 11:2267-2272, 2002.
Kokoris et al., In Vitro evaluaton of mutant HSV-1 thymidine kinases for suicide gene therapy. Anticancer Research, 20:959-964, 2000.
Lee et al., Stem cell-mediated accelerated bone healing observed with in vivo molecular and small animal imaging technologies in a model of skeletal injury. J Orthop Res. Mar. 2009;27(3):295-302.
Leventis, R., et al., Interactions of mammalian cells with lipid dispersions containing novel metabolizable cationic amphiphiles. Biochem. Biophys. Acta 1023:124-132 (1990).
Likar et al., PET imaging of HSV1-tk mutants with acquired specificity toward pyrimidine- and acycloguanosine-based radiotracers. Eur J Nucl Med Mol Imaging, 36:1273-1282, 2009.
Lin Y., et al., Modified RNA sequence pools for in vitro selection. (1994) Nucl. Acids Res. 22(24):5229-5234.
Luker, et al., Noninvasive imaging of protein-protein interactions in living animals. Proc Natl Acad Sci U S A. May 14, 2002;99(10):6961-6966.
MacDonald et al, Effect of Changes in Expression of the Amphotropic Retroviral Receptor PiT-2 on Transduction Efficiency and Viral Titer: Implications for Gene Therapy, Human Gene Therapy, 11:587-595 (2000).
McElroy et al., Fluorescent LYVE-1 antibody to image dynamically lymphatic trafficking of cancer cells in vivo. J Surg Res. Jan. 2009;151(1):68-73.
Mescic et al. C-5 hydroxyethyl and hydroxypropyl acyclonucleosides as substrates for thymidine kinase of Herpes simplex virus type 1 (HSV-1 TK): Syntheses and biological evaluation. Molecules 2013; 18:5104-24.
Miller, A.D. Retrovirus packaging cells. Human Gene Therapy 1990; 1(1): 5-14.
Miller et al., Improved retroviral vectors for gene transfer and expression. Biotechniques Oct. 1989; 7(9):980-982; 984-986; 989-990.
Miller et al, Murine retroviruses use at least six different receptors for entry into Mus dunni cells. J. Virol. Jun. 1997; 9:4531-4535.
Miyagawa et al, PET of cardiac transgene expression: comparison of 2 approaches based on herpesviral thymidine kinase reporter gene. J Nucl Med. Nov. 2004;45(11):1917-1923.
Muller et al., Synthesis and pre-clinical evaluation of a new C-6 alkylated pyrimidine derivative as a PET imaging agent for HSV1-tk gene expression. Am. J. Nucl. Med. Mol. Imaging 2013; 3:71-84.
Najjar, et al., Molecular-genetic PET imaging using an HSV1-tk mutant reporter gene with enhanced specificity to acycloguanosine nucleoside analogs. J Nucl Med. Mar. 2009;50(3):409-416.
Naviaus et al., The pCL vector system: rapid production of helper-free, high-titer, recombinant retroviruses. J. Virol. Aug. 1996; 70:5701-5705.
Orlic et al, The level of mRNA encoding the amphotropic retrovirus receptor in mouse and human hematopoietic stem cells is low and correlates with the efficiency of retrovirus transduction, Proc. Natl. Acad. Sci. USA, 93:11097-11102 (1996).

Pañeda et al., Adeno-associated virus liver transduction efficiency measured by in vivo [18F]FHBG positron emission tomography imaging in rodents and nonhuman primates. Hum Gene Ther. Aug. 2011;22(8):999-1009.
Pagratis, N., et al., Potent 2'-amino-, and 2'-fluoro-2'-deoxyribonucleotide RNA inhibitors of keratinocyte growth factor. (1997) Nature Biotechnol. 15:68-73.
Paszkowski, et al., Direct gene transfer to plants. 1984. Biotechnology. 1992;24:387-392.
PCT/US14/29600 International Search Report and Written Opinion dated Aug. 18, 2014.
PCT/US14/29814 International Search Report and Written Opinion dated Oct. 24, 2014.
PCT/US2014/029814 International Preliminary Report on Patentability dated Sep. 24, 2015.
Peñuelas et al., Positron emission tomography imaging of adenoviral-mediated transgene expression. Liver Cancer Patients Gastro (2005)128:1787.
Ponomarev, et al., A novel triple-modality reporter gene for whole-body fluorescent, bioluminescent, and nuclear noninvasive imaging. Eur J Nucl Med Mol Imaging. May 2004;31(5):740-751.
Ponomarev et al., Cytoplasmically retargeted HSV1-tk/GFP reported gene mutants for optimization of non-invasive molecular genetic imaging Neoplasia, 5(3):245-254, 2003.
Puyal, C., et al., A new cationic liposome encapsulating genetic material. A potential delivery system for polynucleotides. Eur. J. Biochem. 228(3):697-703 (1995).
Roberts, J. Insertional mutagenesis from a viral vector. The Scientist, May 2005, pp. 1-4.
Roelants et al., Comparison between adenoviral and retroviral vectors for the transduction of the thymidine kinase PET reporter gene in rat mesenchymal stem cells. J Nucl Med. Nov. 2008;49(11):1836-1844.
Sangro et al., A phase I clinical trial of thymidine kinase-based gene therapy in advanced hepatocellular carcinoma. Can. Gene Ther. (2010) 17: 837-843.
Schagen et al., Insertion vectors for gene therapy. Gene Therapy, 7(4):271-272, 2002.
Sen et al., Noninvasive imaging of ex vivo intracoronarily delivered nonviral therapeutic transgene expression in heart. Mol Ther. Jul. 2005;12(1):49-57.
Serganova et al., Human reporter genes: potential use in clinical studies. Nuclear Medicine and Biology, 34:791-807, 2007.
Shankar et al., Consensus recommendations for the use of 18F-FDG as an indicator of therapeutic response in National Cancer Institute trials. J. Nucl. Med. Jun. 2006; 47:1059-66.
Shu et al., Visualization of a primary anti-tumor immune response by positron emission tomography. Proc Natl Acad Sci U S A. Nov. 29, 2005;102(48):17412-17417.
Skotzko et al., Retroviral vector-mediated gene transfer of antisense cyclin G1 (CYCG1) inhibits proliferation of human osteogenic sarcoma cells. Cancer Research, 55:5493-5498, 1995.
Sliva et al., Murine leukemia virus (MLV) replication monitored with fluorescent proteins. Virol J. Dec. 20, 2004;1:14.
Sauce et al., Preferential retroviral-mediated transduction of EBV- and CMV-specific T cells after polyclonal T-cell activation, Gene Therapy, 2004; 11(12): 1019-1022.
Stamatatos, L., et al., Interactions of cationic lipid vesicles with negatively charged phospholipid vesicles and biological membranes. Biochemistry 27:3917-3925 (1988).
Stefani et al., Systemic efficacy of combined suicide/cytokine gene therapy in a murine model of hepatocellular carcinoma. Journal of Hepatology, May 2005;42(5):728-735.
Stolworthy et al., Yeast cytosine deaminase mutants with increased thermostability impart sensitivity to 5-fluorocytosine. J. Mol. Biol. Mar. 2008; 377:854-869.
Study record detail for clinical trial NCT00185848 (3 pgs) ($1^{st}$ recv'd Sep. 12, 2005).
Study record detail for clinical trial NCT00871702 (6 pgs.) ($1^{st}$ recv'd Mar. 27, 2009).
Study record detail for clinical trial NCT01082926 (5 pgs) ($1^{st}$ recv'd Mar. 5, 2010).

(56) References Cited

OTHER PUBLICATIONS

Stuelton et al., Lentiviral reporter constructs for fluorescence tracking of the temporospatial pattern of Smad3 signaling. Biotechniques. Sep. 2007;43(3):289-90, 292, 294.
Su et al., Quantitation of cell number by a positron emission tomography reporter gene strategy. Mol Imaging Biol. May-Jun. 2004;6(3):139-148.
Sundaresan et al., MicroPET imaging of Cre-loxP-mediated conditional activation of a herpes simplex virus type 1 thymidine kinase reporter gene. Gene Ther. Apr. 2004;11(7):609-618.
Tsuji et al., Dual-color imaging of nuclear-cytoplasmic dynamics, viability, and proliferation of cancer cells in the portal vein area. Cancer Res. Jan. 1, 2006;66(1):303-306.
U.S. Appl. No. 14/214,448 Office Action dated Aug. 17, 2016.
U.S. Appl. No. 14/214,448 Office Action dated Feb. 1, 2018.
U.S. Appl. No. 14/214,448 Office Action dated Jul. 26, 2017.
U.S. Appl. No. 14/214,448 Office Action dated Mar. 23, 2016.
U.S. Appl. No. 14/214,448 Restriction Requirement dated Dec. 24, 2015.
U.S. Appl. No. 14/214,522 Office Action dated Dec. 1, 2016.
U.S. Appl. No. 14/214,522 Office Action dated Jul. 6, 2017.
U.S. Appl. No. 14/214,522 Office Action dated May 25, 2016.
U.S. Appl. No. 14/214,522 Office Action dated Oct. 25, 2017.
U.S. Appl. No. 14/214,522 Restriction Requirement dated Feb. 26, 2016.
U.S. Appl. No. 14/214,522 Notice of Allowance and Fees Due dated Dec. 26, 2017.
U.S. Appl. No. 14/214,522 Notice of Allowance and Fees Due dated Feb. 1, 2017.
Veerisetty and Gentry, HSV1-Specific thymidylate kinase activity in infected cells. Intervirology, 24:42-49, 1985.
Willmann et al., Imaging gene expression in human mesenchymal stem cells: from small to large animals. Radiology. Jul. 2009;252(1):117-127.
Willmon et al., The role of herpes simplex virus-1 thymidine kinase alanine 168 in substrate specificity. The Open Biochemistry Journal, 2:60-66, 2008.
Wu et al., Molecular imaging of the kinetics of vascular endothelial growth factor gene expression in ischemic myocardium. Circulation. Aug. 10, 2004;110(6):685-691.
Xiong et al., Imaging chemically modified adenovirus for targeting tumors expressing integrin alphavbeta3 in living mice with mutant herpes simplex virus type 1 thymidine kinase PET reporter gene. J Nucl Med. Jan. 2006;47(1):130-139.
Xu et al., Primate gammaretroviruses require an ancillary factor not required for murine gammaretroviruses to infect BHK cells. J. Virol. Apr. 2011; 85:3498-3506.
Yaghoubi et al., Human pharmacokinetic and dosimetry studies of [(18)F]FHBG: a reporter probe for imaging herpes simplex virus type-1 thymidine kinase reporter gene expression. J Nucl Med. Aug. 2001;42(8):1225-1234.
Yaghoubi et al, Imaging progress of herpes simplex virus type 1 thymidine kinase suicide gene therapy in living subjects with positron emission tomography. Cancer Gene Ther. Mar. 2005;12(3):329-339.
Yaghoubi et al., Noninvasive detection of therapeutic cytolytic T cells with 18F-FHBG PET in a patient with glioma. Nat Clin Pract Oncol. Jan. 2009;6(1):53-58.
Yaghoubi et al., PET imaging of herpes simplex virus type 1 thymidine kinase (HSV1-tk) or mutant HSV1-sr39tk reporter gene expression in mice and humans using [18F]FHBG. Nat Protoc. 2006;1(6):3069-3075.
Yaghoubi et al., Preclinical safety evaluation of 18F-FHBG: a PET reporter probe for imaging herpes simplex virus type 1 thymidine kinase (HSV1-tk) or mutant HSV1-sr39tk's expression. J Nucl Med. Apr. 2006;47(4):706-715.
Yamamoto et al., Cellular dynamics visualized in live cells in vitro and in vivo by differential dual-color nuclear-cytoplasmic fluorescent-protein expression. Cancer Res. Jun. 15, 2004;64(12):4251-4256.
Yamamoto et al., Real-time imaging of individual fluorescent-protein color-coded metastatic colonies in vivo. Clin Exp Metastasis. 2003;20(7):633-638.
Yamauchi et al., Color-coded real-time subcellular fluorescence imaging of the interaction between cancer and host cells in live mice. Anticancer Res. Jan. 2012;32(1):39-43.
Yang et al., Real-time whole-body imaging of an orthotopic metastatic prostate cancer model expressing red fluorescent protein. Prostate. Mar. 1, 2005;62(4):374-379.
Yu, et al., Lentivirus-based DsRed-2-transfected pancreatic cancer cells for deep in vivo imaging of metastatic disease. Methods Mol Biol. 2012;872:69-83.
Zeijl et al., A human amphotrophic retrovirus receptor is a second member of the gibbon ape leukemia virus receptor family. Proc. Nat'l Acad. Sci. Feb. 1994; 91:1168-1172.
Zhou et al., Lentivirus-based DsRed-2-transfected pancreatic cancer cells for deep in vivo imaging of metastatic disease. J Surg Res. Nov. 2009;157(1):63-70.

* cited by examiner

Schematic for Phase 1B

FIG.4

SCHEDULE OF EVENTS: PHASE IA Cohorts 1 to 3 (q3 week cycle)

| STUDY | Pre-Study[2] | Day Of Dosing Day 1 | Image Day 4 Only 1st cycle | Day Of Dosing Day 5 Only 1st Cycle | Image Day 8 Only 1st cycle | Weekly | Prior To Each Cycle (q3 wks) | Every 6 Weeks | Off-Study | Post Study Follow-Up[15] |
|---|---|---|---|---|---|---|---|---|---|---|
| Signed Informed Consent | X | | | | | | | | | |
| Medical History | X | | | | | | | | | |
| EKG | X | | | | | | | | | |
| PE, Weight | X | | | | | X | X | | X | |
| Toxicity Evaluation[3] | X | | | | | X | X | | X | X[6] |
| Vital Signs (HR, temp) | X | X[5] | | X | | | | | X | |
| CBC, Diff, Platelets[7] | X | | | | | X[8] | X[7] | | X | |
| PT/PTT | X | | | | | X | X[7] | | X | |
| Serum Chemistry[9] | X | | | | | X | X[7] | | X | |
| Urinalysis | X | | | | | | X | | X | |
| Premedication | | | | | | | | | | |

FIG.4 Continued
SCHEDULE OF EVENTS: PHASE IA Cohorts 1 to 3 (q3 week cycle)

| | | | | | | | | | | |
|---|---|---|---|---|---|---|---|---|---|---|
| Reximmune-C2 Infusion | | $X^{10}$ | | $X^{10}$ | | | | $X$ | | |
| Plasma PK sampling | | $X^{11}$ | | $X^{11}$ | | | | | | |
| Urine PK sampling | | | | | | | | | | |
| Research plasma samples | | $X^{13}$ | | $X^{13}$ | | | | | | |
| Tumor Measurement[14] | $X$ | | | | $X$ | | | $X$ | | $X$ |
| [$^{18}$F]FHBG PET Scan | | | | | | $X$ | | | | |
| Ganciclovir Day 8-12 | | | | | | | | | | |

FIG. 5

SCHEDULE OF EVENTS: PHASE IA Cohort 4 and Above (q3 week cycle)

| STUDY | Pre-Study[1] | Weekly | Prior To Each Cycle | Dosing Day 1 | Dosing Day 3 | Dosing Day 5 | Image Day 8 | Every 6 Weeks | Off-Study | Post Study Follow-Up[15] |
|---|---|---|---|---|---|---|---|---|---|---|
| Signed Informed Consent | X | | | | | | | | | |
| Medical History | X | | | | | | | | | |
| EKG | X | | | | | | | | | |
| PE[2], Weight | X | | X | | | | | | X | |
| Toxicity Evaluation[3] | X | X | X | | | | | | | |
| Vital Signs (HR, temp) | X | X | | X[5] | X[5] | X[5] | | | X | |
| CBC, Diff, Platelets[7] | X | X[8] | X[7] | | | | | X[6] | X | |
| PT/PTT | X | X | X[7] | | | | | | X | |
| Serum Chemistry[9] | X | X | X[7] | | | | | | X | |
| Urinalysis | X | | X | | | | | | X | |
| Premedication | | | | | | | | | | |
| Reximmune-C2 or Reximmune-C3 | | | | X[10] | X[10] | X[10] | | | | |
| Plasma PK sampling | | | | X[11] | | X[11] | | | | |
| Urine PK Sampling | | | | X[12] | | X[12] | | | | |
| Research plasma samples | | | | X[13] | | X[13] | | | | |
| Tumor Measurement[14] | X | | | | | | | X | | X |
| [18F]PET scan | | | | | | | X | | | |
| Ganciclovir Day 8-12 | | | | | | | | | | |

FIG. 6
SCHEDULE OF EVENTS: PHASE IB (q3 week cycle)

| STUDY | Pre-Study[1] | Weekly | Prior To Each Cycle | Dosing Day 1 | Dosing Day 3 | Dosing Day 5 | Image Day 8 | Every 6 Weeks | Off-Study | Post Study Follow-Up[15] |
|---|---|---|---|---|---|---|---|---|---|---|
| Signed Informed Consent | X | | | | | | | | | |
| Medical History | X | | | | | | | | | |
| EKG | X | | | | | | | | | |
| PE[2], Weight | X | X | X | | | | | | | |
| Toxicity Evaluation[3] | X | X | X | | | | | | | |
| Vital Signs (HR, temp) | X | X | X[7] | X[5] | X[5] | X[5] | | | X | |
| CBC, Diff, Platelets[7] | X | X[8] | X[7] | | | | | | X | |
| PT/PTT | X | X | X[7] | | | | | | X | |
| Serum Chemistry[9] | X | X | X | | | | | | X | |
| Urinalysis | X | | X | | | | | | X | |
| Premedication | | | | | | | | | | |
| Reximmune-C2/Reximmune-C3 | | | | X[10] | X[10] | X[10] | | | | |
| Plasma PK sampling | | | | X[11] | | X[11] | | | | |
| Research plasma samples | | | | X[13] | | X[13] | | | | |
| Tumor Measurement[14] | X | | | | | | | X | | X |
| [18F]PET scan | | | | | | | X | | | |
| Ganciclovir Day 8-12 | | | | | | | | | | |

FIG. 7

SCHEDULE OF EVENTS: SCHEDULE (A)

| STUDY | Pre-Study[1] | Weekly | Prior To Each Cycle | Day Of Dosing Day 1 | Day 2 | Every 6 Weeks | Off-Study | Post Study Follow-Up[15] |
|---|---|---|---|---|---|---|---|---|
| Signed Informed Consent | X | | | | | | | |
| Medical History | X | | | | | | | |
| EKG | X | | | | | | | |
| PE[2], Weight | X | | X | | | | X | |
| Toxicity Evaluation[3] | X | | X | | | | X | X[6] |
| Neurological assessment[4] | X | | X | | | | X | |
| Vital Signs (HR, temp) | X | | | X[5] | | | X | |
| CBC, Diff, Platelets[7] | X | X[8] | X[7] | | | | X | |
| PT/PTT | X | | X[7] | | | | X | |
| Serum Chemistry[9] | X | | X[7] | | | | X | |
| Urinalysis | X | | X | | | | X | |
| Premedication | | | | X[10] | | | | |
| EpoD infusion | | | | X[10] | | | | |
| Plasma PK sampling | | | | X[11] | X[11] | | | |
| Urine PK sampling | | | | X[12] | X[12] | | | |
| Research plasma samples | | | | X[13] | | | | |
| Tumor Measurement[14] | X | | | | | X | | X |

FIG. 8
SCHEDULE OF EVENTS: SCHEDULE (B)

| Study | Pre-Study[1] | Weekly | Prior To Each Cycle | Dosing Day 1 | Dosing Day 2 | Dosing Day 3 | Day 4 | Every 6 Weeks | Off-Study | Post Study Follow-Up[15] |
|---|---|---|---|---|---|---|---|---|---|---|
| Signed Informed Consent | X | | | | | | | | | |
| Medical History | X | | | | | | | | | |
| EKG | X | | | | | | | | | |
| PE[2], Weight | X | | X | | | | | | | |
| Toxicity Evaluation[3] | X | | X | | | | | X[6] | X | |
| Neurological assessment[4] | X | | X | | | | | | | |
| Vital Signs (HR, temp) | X | | | X[5] | X[5] | X[5] | | | X | |
| CBC, Diff, Platelets[7] | X | X[8] | X[7] | | | | | | X | |
| PT/PTT | X | | X[7] | | | | | | X | |
| Serum Chemistry[9] | X | | X[7] | | | | | | X | |
| Urinalysis | X | | X | | | | | | X | |
| Premedication | | | | X[10] | X[10] | X[10] | | | | |
| EpoD infusion | | | | X[10] | X[10] | X[10] | | | | |
| Plasma PK sampling | | | | X[11] | X[11] | X[11] | X[11] | | | |
| Research plasma samples | | | | X[13] | X[13] | X[13] | X[13] | | | |
| Tumor Measurement[14] | X | | | | | | | X | | X |

RexRed-TK A168F

RexRed-TK A167F (GCV Specific)

Rex-Hygro-R-TK A168F

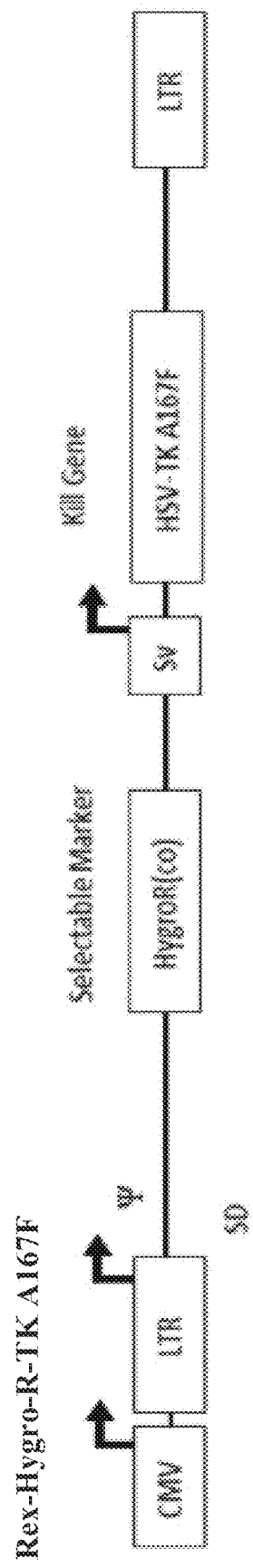
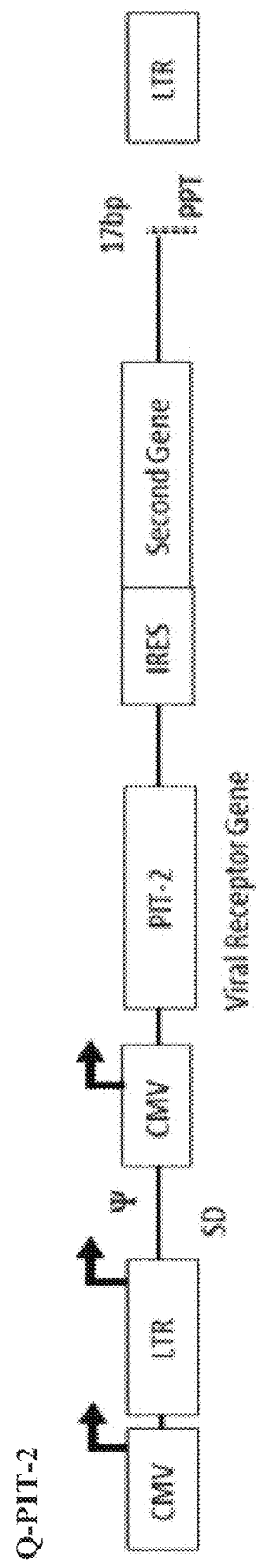
FIG. 16A
FIG. 16B

RexRed-TK(-)

Rex-Hygro-R-TK(-)

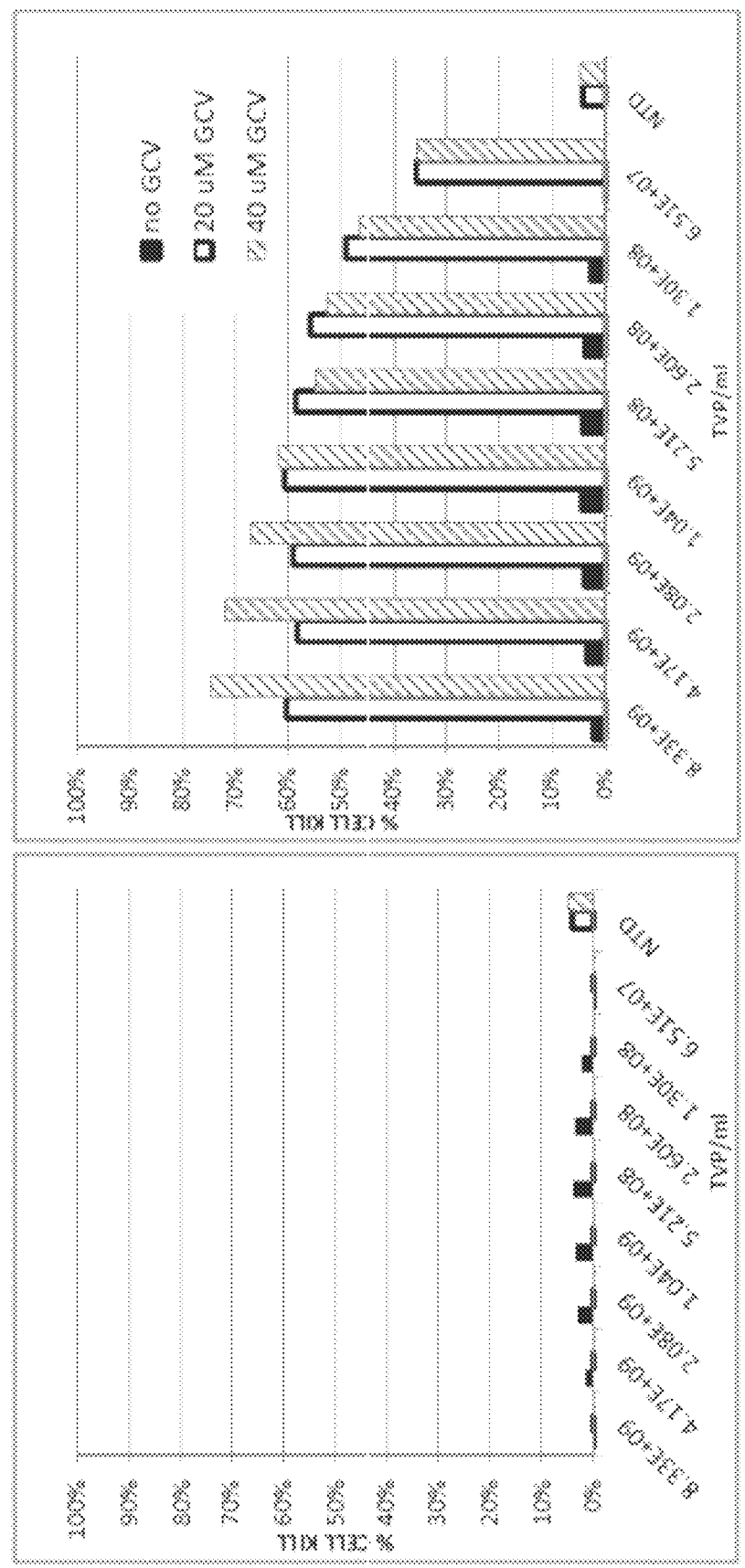

FIG. 34
ImmunoHistoChemistry of HSVTK sub cell Localization in 293T cells
Transient Transfection, 24 hour Primary AB (Santa Cruz)
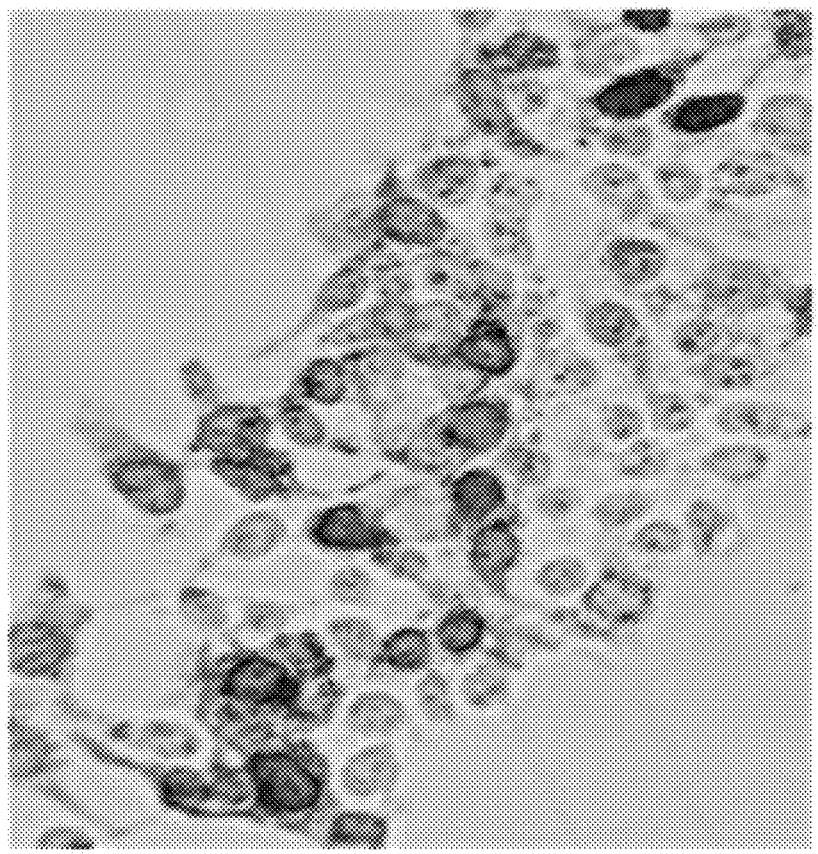
RexC2 HSVTK
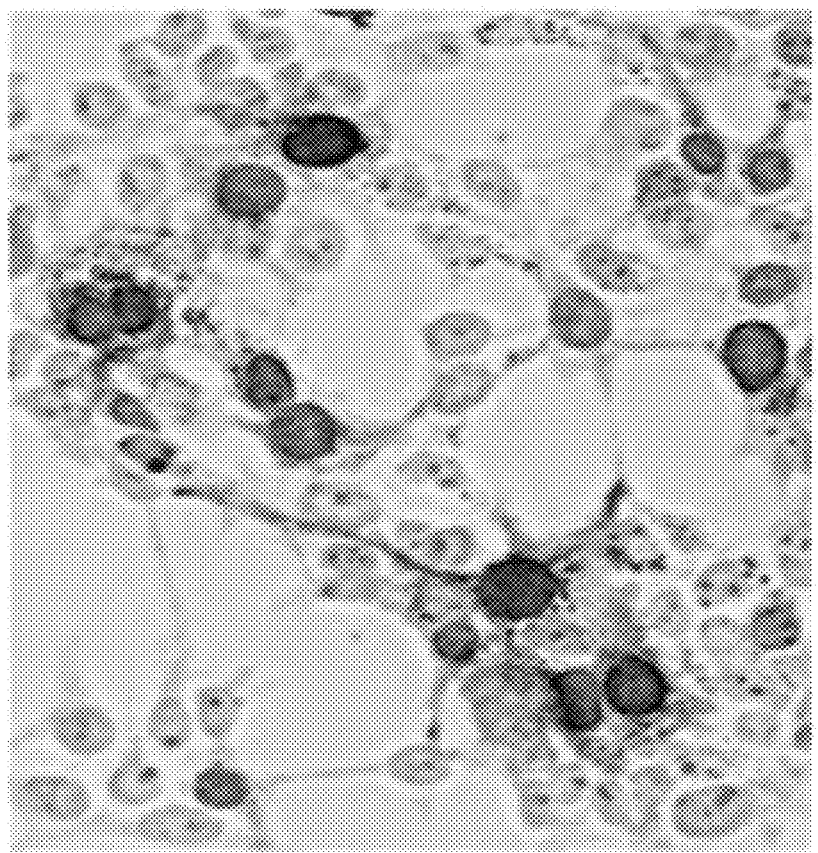
RexC1 HSVTK

SEQUENCE LISTING

<160> NUMBER OF SEQ ID NOS: 36

<210> SEQ ID NO 1
<211> LENGTH: 1131
<212> TYPE: DNA
<213> ORGANISM: Herpes simplex virus 1

<400> SEQUENCE: 1

```
atggcttcgt accccggcca tcaacacgcg tctgcgttcg accaggctgc gcgttctcgc    60
ggccatagca accgacgtac ggcgttgcgc cctcgccggc agcaagaagc cacggaagtc   120
cgcccggagc agaaaatgcc cacgctactg cgggtttata tagacggtcc ccacgggatg   180
gggaaaacca ccaccacgca actgctggtg gccctgggtt cgcgcgacga tatcgtctac   240
gtacccgagc cgatgactta ctggcgggtg ctggggggctt ccgagacaat cgcgaacatc   300
tacaccacac aacaccgcct cgaccagggt gagatatcgg ccggggacgc ggcggtggta   360
atgacaagcg cccagataac aatgggcatg ccttatgccg tgaccgacgc cgttctggct   420
cctcatatcg gggggaggc tgggagctca catgccccgc cccggccct caccctcatc   480
ttcgaccgcc atcccatcgc cgccctcctg tgctacccgg ccgcgcggta ccttatgggc   540
agcatgaccc ccaggccgt gctggcgttc gtggccctca tcccgccgac cttgccggc   600
accaacatcg tgcttgggggc ccttccggag gacagacaca tcgaccgcct ggccaaacgc   660
cagcgccccg gcgagcggct ggacctggct atgctggctg cgattcgccg cgtttacggg   720
ctacttgcca atacggtgcg gtatctgcag tgcggcgggt cgtggcggga ggactgggga   780
cagcttttcgg ggacggccgt gccgccccag ggtgccgagc ccagagcaa cgcgggccca   840
cgaccccata tcggggacac gttatttacc ctgtttcggg ccccgagtt gctggcccc   900
aacggcgacc tgtataacgt gtttgcctgg gccttggacg tcttggccaa cgcctccgt   960
```

```
tccatgcacg tctttatcct ggattacgac caatcgcccg ccggctgccg ggacgccctg    1020
ctgcaactta cctccgggat ggtccagacc cacgtcacca ccccggctc cataccgacg     1080 atatgcgacc tggcgcgcac gtttgcccgg gagatggggg aggctaactg a             1131
```

<210> SEQ ID NO 2
<211> LENGTH: 376
<212> TYPE: PRT
<213> ORGANISM: Herpes simplex virus 1

<400> SEQUENCE: 2

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350
```

Thr Thr Pro Gly Ser Ile Pro Thr Ile Cys Asp Leu Ala Arg Thr Phe
        355                 360                 365

Ala Arg Glu Met Gly Glu Ala Asn
        370                 375

<210> SEQ ID NO 3
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggcctcgt accccggcca tcaacacgcg tctgcgttcg accaggctgc gcgttctcgc      60
ggccatagca acggatccac ggcgttgcgc cctcgccggc agcaagaagc cacggaagtc     120
cgcccggagc agaaaatgcc cacgctactg cgggtttata tagacggtcc ccacgggatg     180
gggaaaacca ccaccacgca actgctggtg ccctgggtt cgcgcgacga tatcgtctac      240
gtacccgagc cgatgactta ctggcgggtg ctggggctt ccgagacaat cgcgaacatc      300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg ggggggaggc tgggagctca catgccccgc cccgggccct caccatcttc     480
ctcgaccgcc atcccatcgc cttcatgctg tgctacccgg ccgcgcggta ccttatgggc     540
agcatgaccc ccaggccgt gctggcgttc gtggccctca tcccgccgac cttgcccggc      600
accaacatcg tgcttggggc ccttccggag acagacaca tcgaccgcct ggccaaacgc      660
cagcgccccg gcgagcggct ggacctggct atgctggctg cgattcgccg cgtttacggg     720
ctacttgcca atacggtgcg gtatctgcag tgcggcgggt cgtggcggga ggactgggga     780
cagctttcgg ggacggccgt gccgccccag ggtgccgagc ccagagcaa cgcgggccca      840
cgaccccata tcggggacac gttatttacc ctgtttcggg ccccgagtt gctggccccc      900
aacggcgacc tgtataacgt gttttgcctgg gccttggacg tcttggccaa cgcctccgt     960
tccatgcacg tctttatcct ggattacgac caatcgcccg ccggctgccg ggacgccctg    1020
ctgcaactta cctccgggat ggtccagacc cacgtcacca ccccggctc ataccgacg      1080
atatgcgacc tggcgcgcac gtttgcccgg gagatgggggg aggctaactg a           1131

<210> SEQ ID NO 4
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Ser Tyr Pro Gly His Gln His Ala Ser Ala Phe Asp Gln Ala
1               5                   10                  15

Ala Arg Ser Arg Gly His Ser Asn Gly Ser Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

```
Thr Thr Gln Leu Leu Val Ala Leu Gly Ser Arg Asp Asp Ile Val Tyr
 65                  70                  75                  80

Val Pro Glu Pro Met Thr Tyr Trp Arg Val Leu Gly Ala Ser Glu Thr
                 85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
130                 135                 140

Gly Glu Ala Gly Ser Ser His Ala Pro Pro Ala Leu Thr Ile Phe
145                 150                 155                 160

Leu Asp Arg His Pro Ile Ala Phe Met Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
370                 375
```

<210> SEQ ID NO 5
<211> LENGTH: 1131
<212> TYPE: DNA
<213> ORGANISM: Herpes simplex virus 1
<220> FEATURE:
<221> NAME/KEY: CDS
<222> LOCATION: (1)..(1128)

<400> SEQUENCE: 5

```
atg gcc tcg tac ccc ggc cat caa cac gcg tct gcg ttc gac cag gct    48
Met Ala Ser Tyr Pro Gly His Gln His Ala Ser Ala Phe Asp Gln Ala
  1               5                  10                  15 gcg cgt tct cgc ggc cat agc aac cga cgt acg gcg ttg cgc cct cgc    96
Ala Arg Ser Arg Gly His Ser Asn Arg Arg Thr Ala Leu Arg Pro Arg
             20                  25                  30
```

| | |
|---|---:|
| cgg cag caa gaa gcc acg gaa gtc cgc ccg gag cag aaa atg ccc acg<br>Arg Gln Gln Glu Ala Thr Glu Val Arg Pro Glu Gln Lys Met Pro Thr<br>       35                      40                     45 | 144 |
| cta ctg cgg gtt tat ata gac ggt ccc cac ggg atg ggg aaa acc acc<br>Leu Leu Arg Val Tyr Ile Asp Gly Pro His Gly Met Gly Lys Thr Thr<br> 50                       55                     60 | 192 |
| acc acg caa ctg ctg gtg gcc ctg ggt tcg cgc gac gat atc gtc tac<br>Thr Thr Gln Leu Leu Val Ala Leu Gly Ser Arg Asp Asp Ile Val Tyr<br>65                     70                     75                     80 | 240 |
| gta ccc gag ccg atg act tac tgg cgg gtg ctg ggg gct tcc gag aca<br>Val Pro Glu Pro Met Thr Tyr Trp Arg Val Leu Gly Ala Ser Glu Thr<br>                       85                     90                     95 | 288 |
| atc gcg aac atc tac acc aca caa cac cgc ctc gac cag ggt gag ata<br>Ile Ala Asn Ile Tyr Thr Thr Gln His Arg Leu Asp Gln Gly Glu Ile<br>                100                       105                   110 | 336 |
| tcg gcc ggg gac gcg gcg gtg gta atg aca agc gcc cag ata aca atg<br>Ser Ala Gly Asp Ala Ala Val Val Met Thr Ser Ala Gln Ile Thr Met<br>             115                     120                   125 | 384 |
| ggc atg cct tat gcc gtg acc gac gcc gtt ctg gct cct cat atc ggg<br>Gly Met Pro Tyr Ala Val Thr Asp Ala Val Leu Ala Pro His Ile Gly<br>130                    135                     140 | 432 |
| ggg gag gct ggg agc tca cat gcc ccc ccg gcc ctc acc ctc atc<br>Gly Glu Ala Gly Ser Ser His Ala Pro Pro Ala Leu Thr Leu Ile<br>145                    150                     155                   160 | 480 |
| ttc gac cgc cat ccc atc gcc gcc ctc ctg tgc tac ccg gcc gcg cgg<br>Phe Asp Arg His Pro Ile Ala Ala Leu Leu Cys Tyr Pro Ala Ala Arg<br>                   165                     170                   175 | 528 |
| tac ctt atg ggc agc atg acc ccc cag gcc gtg ctg gcg ttc gtg gcc<br>Tyr Leu Met Gly Ser Met Thr Pro Gln Ala Val Leu Ala Phe Val Ala<br>                    180                     185                     190 | 576 |
| ctc atc ccg ccg acc ttg ccc ggc acc aac atc gtg ctt ggg gcc ctt<br>Leu Ile Pro Pro Thr Leu Pro Gly Thr Asn Ile Val Leu Gly Ala Leu<br>              195                     200                   205 | 624 |
| ccg gag gac aga cac atc gac cgc ctg gcc aaa cgc cag cgc ccc ggc<br>Pro Glu Asp Arg His Ile Asp Arg Leu Ala Lys Arg Gln Arg Pro Gly<br>210                    215                     220 | 672 |
| gag cgg ctg gac ctg gct atg ctg gct gcg att cgc cgc gtt tac ggg<br>Glu Arg Leu Asp Leu Ala Met Leu Ala Ala Ile Arg Arg Val Tyr Gly<br>225                    230                     235                   240 | 720 |
| cta ctt gcc aat acg gtg cgg tat ctg cag tgc ggc ggg tcg tgg cgg<br>Leu Leu Ala Asn Thr Val Arg Tyr Leu Gln Cys Gly Gly Ser Trp Arg<br>                    245                     250                   255 | 768 |
| gag gac tgg gga cag ctt tcg ggg acg gcc gtg ccg ccc cag ggt gcc<br>Glu Asp Trp Gly Gln Leu Ser Gly Thr Ala Val Pro Pro Gln Gly Ala<br>                    260                     265                   270 | 816 |
| gag ccc cag agc aac gcg ggc cca cga ccc cat atc ggg gac acg tta<br>Glu Pro Gln Ser Asn Ala Gly Pro Arg Pro His Ile Gly Asp Thr Leu<br>              275                     280                   285 | 864 |
| ttt acc ctg ttt cgg gcc ccc gag ttg ctg gcc ccc aac ggc gac ctg<br>Phe Thr Leu Phe Arg Ala Pro Glu Leu Leu Ala Pro Asn Gly Asp Leu<br>290                    295                     300 | 912 |
| tat aac gtg ttt gcc tgg gcc ttg gac gtc ttg gcc aaa cgc ctc cgt<br>Tyr Asn Val Phe Ala Trp Ala Leu Asp Val Leu Ala Lys Arg Leu Arg<br>305                    310                     315                   320 | 960 |
| tcc atg cac gtc ttt atc ctg gat tac gac caa tcg ccc gcc ggc tgc<br>Ser Met His Val Phe Ile Leu Asp Tyr Asp Gln Ser Pro Ala Gly Cys<br>                           325                     330                   335 | 1008 |
| cgg gac gcc ctg ctg caa ctt acc tcc ggg atg gtc cag acc cac gtc<br>Arg Asp Ala Leu Leu Gln Leu Thr Ser Gly Met Val Gln Thr His Val<br>                    340                     345                   350 | 1056 |

```
acc acc ccc ggc tcc ata ccg acg ata tgc gac ctg gcg cgc acg ttt    1104
Thr Thr Pro Gly Ser Ile Pro Thr Ile Cys Asp Leu Ala Arg Thr Phe
            355                 360                 365 gcc cgg gag atg ggg gag gct aac tga                                1131
Ala Arg Glu Met Gly Glu Ala Asn
    370                 375
```

```
<210> SEQ ID NO 6
<211> LENGTH: 89
<212> TYPE: DNA
<213> ORGANISM: Herpes simplex virus 1

<400> SEQUENCE: 6
gagctcacat gccccgcccc cggccctcac catcttcctc gaccgccatc ccatcgcctt    60
catgctgtgc tacccggccg cgcggtacc                                     89

<210> SEQ ID NO 7
<211> LENGTH: 89
<212> TYPE: DNA
<213> ORGANISM: Herpes simplex virus 1

<400> SEQUENCE: 7
ctcgagtgta cggggcgggg gccgggagtg gtagaaggag ctggcggtag ggtagcggaa    60
gtacgacacg atgggccggc gcgccatgg                                     89

<210> SEQ ID NO 8
<211> LENGTH: 83
<212> TYPE: DNA
<213> ORGANISM: Herpes simplex virus 1

<400> SEQUENCE: 8
cacatgcccc gccccggcc ctcaccatct tcctcgaccg ccatcccatc gccttcatgc     60
tgtgctaccc ggccgcgcgg tac                                           83

<210> SEQ ID NO 9
<211> LENGTH: 79
<212> TYPE: DNA
<213> ORGANISM: Herpes simplex virus 1

<400> SEQUENCE: 9
tcgagtgtac ggggcggggg ccgggagtgg tagaaggagc tggcggtagg gtagcggaag    60
tacgacacga tgggccggc                                                79

<210> SEQ ID NO 10
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cacatgcccc gccccggcc ctcaccatct tcctcgaccg ccatcccatc gccttcatgc     60
tgtgctaccc ggccgcgcgg tac                                           83

<210> SEQ ID NO 11
<211> LENGTH: 83
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 11
cgcgcggccg ggtagcacag catgaaggcg atgggatggc ggtcgaggaa gatggtgagg    60
gccgggggcg gggcatgtga gct                                            83

<210> SEQ ID NO 12
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gtcagcggcc gcaccggtac gcgtccacca tggccagcta ccccggccac cagcacgcca    60
gcgccttcga ccaggccgcc cgcagccgcg ccacagcaa cggcagcacc gcactgcggc   120
cacggcgcca gcaggaggcc accgaggtgc gccccgagca agatgcccc accctgctgc   180 gcgtgtacat cgacggacca cacggcatgg gcaagaccac caccacccag ctgctggtgg   240
ccctgggcag ccgcgacgac atcgtgtacg tgcccgagcc catgacctac tggcgcgtgc   300
tgggcgccag cgagaccatc gccaacatct acaccaccca gcaccgcctg gaccaaggcg   360
agatcagcgc cggcgacgcc gccgtggtga tgaccagcgc ccagattaca atgggcatgc   420
cctacgccgt gaccgacgcc gtgctggcac cacacatcgg cggcgaggcc ggcagcagcc   480
acgcaccacc accagcactg accctgatct tcgaccggca cccaatcgca cacctgctgt   540 gctaccggc agcacgctac ctgatgggct ccatgacacc acaagccgtg ctggccttcg   600
tggccctgat cccaccaaca ctgcccggca ccaacatcgt gctgggcgcc ctgcccgagg   660
accgccacat cgaccgcctg gccaagcgcc agcgccccgg cgagcgcctg gacctggcca   720
tgctggccgc catccgccgc gtgtacggcc tgctggccaa caccgtgcgc tacctgcagt   780
gcggcggcag ctggcgcgag gactgggcc agctgagcgg caccgccgtg ccaccacagg   840
gcgccgagcc acagagcaac gccggaccac gaccacacat cggcgacacc ctgttcaccc   900
tgttccgggc accagagctg ctggcaccaa acgcgacct gtacaacgtg ttcgcctggg   960
ccctggacgt gctggccaag cgcctgcgct ccatgcacgt gttcatcctg gactacgacc  1020
agtcaccggc cggctgccgc gacgccctgc tgcagctgac cagcggcatg gtgcagaccc  1080
acgtgacaac acccggcagc atcccaacaa tctgcgacct ggcccgcacc ttcgcccgcg  1140
agatgggcga ggccaactaa tagggatccc tcgagaagct tgtca              1185

<210> SEQ ID NO 13
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gtcagcggcc gcaccggtac gcgtccacca tggccagcta ccccggccac cagcacgcca    60
gcgccttcga ccaggccgcc cgcagccgcg ccacagcaa cggcagcacc gcactgcggc   120
cacggcgcca gcaggaggcc accgaggtgc gccccgagca agatgcccc accctgctgc   180 gcgtgtacat cgacggacca cacggcatgg gcaagaccac caccacccag ctgctggtgg   240
ccctgggcag ccgcgacgac atcgtgtacg tgcccgagcc catgacctac tggcgcgtgc   300
tgggcgccag cgagaccatc gccaacatct acaccaccca gcaccgcctg gaccaaggcg   360

```
agatcagcgc cggcgacgcc gccgtggtga tgaccagcgc ccagattaca atgggcatgc    420
cctacgccgt gaccgacgcc gtgctggcac cacacatcgg cggcgaggcc ggcagcagcc    480
acgcaccacc accagcactg accctgatct tcgaccggca cccaatcttc gcactgctgt    540 gctaccggc agcacgctac ctgatgggct ccatgacacc acaagccgtg ctggccttcg    600
tggccctgat cccaccaaca ctgcccggca ccaacatcgt gctgggcgcc ctgcccgagg    660
accgccacat cgaccgcctg gccaagcgcc agcgccccgg cgagcgcctg gacctggcca    720
tgctggccgc catccgccgc gtgtacggcc tgctggccaa caccgtgcgc tacctgcagt    780
gcggcggcag ctggcgcgag gactgggcc agctgagcgg caccgccgtg ccaccacagg     840
gcgccgagcc acagagcaac gccggaccac gaccacacat cggcgacacc ctgttcaccc    900
tgttccgggc accagagctg ctggcaccaa acggcgacct gtacaacgtg ttcgcctggg    960
ccctggacgt gctggccaag cgcctgcgct ccatgcacgt gttcatcctg gactacgacc    1020
agtcaccggc cggctgccgc gacgccctgc tgcagctgac cagcggcatg gtgcagaccc    1080
acgtgacaac acccggcagc atcccaacaa tctgcgacct ggcccgcacc ttcgcccgcg    1140
agatgggcga ggccaactaa tagggatccc tcgagaagct tgtca                    1185
```

<210> SEQ ID NO 14
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
gtcagcggcc gcaccggtac gcgtccacca tggccagcta ccccggccac cagcacgcca    60
gcgccttcga ccaggccgcc cgcagccgcg gccacagcaa cggcagcacc gcactgcggc    120
cacggcgcca gcaggaggcc accgaggtgc gccccgagca gaagatgccc accctgctgc    180
gcgtgtacat cgacggacca cacggcatgg gcaagaccac caccacccag ctgctggtgg    240
ccctgggcag ccgcgacgac atcgtgtacg tgcccgagcc catgacctac tggcgcgtgc    300
tgggcgccag cgagaccatc gccaacatct acaccaccca gcaccgcctg gaccaaggcg    360
agatcagcgc cggcgacgcc gccgtggtga tgaccagcgc ccagattaca atgggcatgc    420
cctacgccgt gaccgacgcc gtgctggcac cacacatcgg cggcgaggcc ggcagcagcc    480
acgcaccacc accagcactg accctgatct tcgaccggca cccaatcttc cacctgctgt    540 gctaccggc agcacgctac ctgatgggct ccatgacacc acaagccgtg ctggccttcg    600
tggccctgat cccaccaaca ctgcccggca ccaacatcgt gctgggcgcc ctgcccgagg    660
accgccacat cgaccgcctg gccaagcgcc agcgccccgg cgagcgcctg gacctggcca    720
tgctggccgc catccgccgc gtgtacggcc tgctggccaa caccgtgcgc tacctgcagt    780
gcggcggcag ctggcgcgag gactgggcc agctgagcgg caccgccgtg ccaccacagg     840
gcgccgagcc acagagcaac gccggaccac gaccacacat cggcgacacc ctgttcaccc    900
tgttccgggc accagagctg ctggcaccaa acggcgacct gtacaacgtg ttcgcctggg    960
ccctggacgt gctggccaag cgcctgcgct ccatgcacgt gttcatcctg gactacgacc    1020
agtcaccggc cggctgccgc gacgccctgc tgcagctgac cagcggcatg gtgcagaccc    1080
acgtgacaac acccggcagc atcccaacaa tctgcgacct ggcccgcacc ttcgcccgcg    1140
agatgggcga ggccaactaa tagggatccc tcgagaagct tgtca                    1185
```

<210> SEQ ID NO 15
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

| | | | | | |
|---|---|---|---|---|---|
| gtcagcggcc | gcaccggtac | gcgtccacca | tggccagcta | ccccggccac | cagcacgcca | 60 |
| gcgccttcga | ccaggccgcc | cgcagccgcg | gccacagcaa | cggcagcacc | gcactgcggc | 120 |
| cacggcgcca | gcaggaggcc | accgaggtgc | gccccgagca | gaagatgccc | accctgctgc | 180 |
| gcgtgtacat | cgacggacca | cacggcatgg | gcaagaccac | caccacccag | ctgctggtgg | 240 |
| ccctgggcag | ccgcgacgac | atcgtgtacg | tgcccgagcc | catgacctac | tggcgcgtgc | 300 |
| tgggcgccag | cgagaccatc | gccaacatct | acaccaccca | gcaccgcctg | gaccaaggcg | 360 |
| agatcagcgc | cggcgacgcc | gccgtggtga | tgaccagcgc | ccagattaca | atgggcatgc | 420 |
| cctacgccgt | gaccgacgcc | gtgctggcac | cacacatcgg | cggcgaggcc | ggcagcagcc | 480 |
| acgcaccacc | accagcactg | accatcttcc | tggaccggca | cccaatcgca | cacctgctgt | 540 |
| gctacccggc | agcacgctac | ctgatgggct | ccatgacacc | acaagccgtg | ctggccttcg | 600 |
| tggccctgat | cccaccaaca | ctgcccggca | ccaacatcgt | gctgggcgcc | ctgcccgagg | 660 |
| accgccacat | cgaccgcctg | gccaagcgcc | agcgccccgg | cgagcgcctg | gacctggcca | 720 |
| tgctggccgc | catccgccgc | gtgtacggcc | tgctggccaa | caccgtgcgc | tacctgcagt | 780 |
| gcggcggcag | ctggcgcgag | gactgggccc | agctgagcgg | caccgccgtg | ccaccacagg | 840 |
| gcgccgagcc | acagagcaac | gccggaccac | gaccacacat | cggcgacacc | ctgttcaccc | 900 |
| tgttccgggc | caccagagctg | ctggcaccaa | acggcgacct | gtacaacgtg | ttcgcctggg | 960 |
| ccctggacgt | gctggccaag | cgcctgcgct | ccatgcacgt | gttcatcctg | gactacgacc | 1020 |
| agtcaccggc | cggctgccgc | gacgcccgtc | tgcagctgac | cagcggcatg | gtgcagaccc | 1080 |
| acgtgacaac | acccggcagc | atcccaacaa | tctgcgacct | ggcccgcacc | ttcgcccgcg | 1140 |
| agatgggcga | ggccaactaa | tagggatccc | tcgagaagct | tgtca | | 1185 |

<210> SEQ ID NO 16
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

| | | | | | |
|---|---|---|---|---|---|
| gtcagcggcc | gcaccggtac | gcgtccacca | tggccagcta | ccccggccac | cagcacgcca | 60 |
| gcgccttcga | ccaggccgcc | cgcagccgcg | gccacagcaa | cggcagcacc | gcactgcggc | 120 |
| caggatctca | gcaggaggcc | accgaggtgc | gccccgagca | gaagatgccc | accctgctgc | 180 |
| gcgtgtacat | cgacggacca | cacggcatgg | gcaagaccac | caccacccag | ctgctggtgg | 240 |
| ccctgggcag | ccgcgacgac | atcgtgtacg | tgcccgagcc | catgacctac | tggcgcgtgc | 300 |
| tgggcgccag | cgagaccatc | gccaacatct | acaccaccca | gcaccgcctg | gaccaaggcg | 360 |
| agatcagcgc | cggcgacgcc | gccgtggtga | tgaccagcgc | ccagattaca | atgggcatgc | 420 |
| cctacgccgt | gaccgacgcc | gtgctggcac | cacacatcgg | cggcgaggcc | ggcagcagcc | 480 |
| acgcaccacc | accagcactg | accctgatct | tcgaccggca | cccaatcgca | cacctgctgt | 540 |

```
gctacccggc agcacgctac ctgatgggct ccatgacacc acaagccgtg ctggccttcg      600
tggccctgat cccaccaaca ctgcccggca ccaacatcgt gctgggcgcc ctgcccgagg      660
accgccacat cgaccgcctg gccaagcgcc agcgccccgg cgagcgcctg gacctggcca      720
tgctggccgc catccgccgc gtgtacggcc tgctggccaa caccgtgcgc tacctgcagt      780
gcggcggcag ctggcgcgag gactggggcc agctgagcgg caccgccgtg ccaccacagg      840
gcgccgagcc acagagcaac gccggaccac gaccacacat cggcgacacc ctgttcaccc      900
tgttccgggc accagagctg ctggcaccaa acggcgacct gtacaacgtg ttcgcctggg      960
ccctggacgt gctggccaag cgcctgcgct ccatgcacgt gttcatcctg gactacgacc     1020
agtcaccggc cggctgccgc gacgccctgc tgcagctgac cagcggcatg gtgcagaccc     1080
acgtgacaac acccggcagc atcccaacaa tctgcgacct ggcccgcacc ttcgcccgcg     1140
agatgggcga ggccaactaa tagggatccc tcgagaagct tgtca                    1185
```

<210> SEQ ID NO 17
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gtcagcggcc gcaccggtac gcgtccacca tggccagcta ccccggccac cagcacgcca       60
gcgccttcga ccaggccgcc cgcagccgcg ccacagcaa cggcagcacc gcactgcggc      120
caggatctca gcaggaggcc accgaggtgc gccccgagca gaagatgccc accctgctgc      180
gcgtgtacat cgacggacca cacggcatgg gcaagaccac caccacccag ctgctggtgg      240
ccctgggcag ccgcgacgac atcgtgtacg tgcccgagcc catgacctac tggcgcgtgc      300
tgggcgccag cgagaccatc gccaacatct acaccaccca gcaccgcctg gaccaaggcg      360
agatcagcgc cggcgacgcc gccgtggtga tgaccagcgc ccagattaca atgggcatgc      420
cctacgccgt gaccgacgcc gtgctggcac acacatcgg cggcgaggcc ggcagcagcc      480
acgcaccacc accagcactg accctgatct tcgaccggca cccaatcttc gcactgctgt      540
gctacccggc agcacgctac ctgatgggct ccatgacacc acaagccgtg ctggccttcg      600
tggccctgat cccaccaaca ctgcccggca ccaacatcgt gctgggcgcc ctgcccgagg      660
accgccacat cgaccgcctg gccaagcgcc agcgccccgg cgagcgcctg gacctggcca      720
tgctggccgc catccgccgc gtgtacggcc tgctggccaa caccgtgcgc tacctgcagt      780
gcggcggcag ctggcgcgag gactggggcc agctgagcgg caccgccgtg ccaccacagg      840
gcgccgagcc acagagcaac gccggaccac gaccacacat cggcgacacc ctgttcaccc      900
tgttccgggc accagagctg ctggcaccaa acggcgacct gtacaacgtg ttcgcctggg      960
ccctggacgt gctggccaag cgcctgcgct ccatgcacgt gttcatcctg gactacgacc     1020
agtcaccggc cggctgccgc gacgccctgc tgcagctgac cagcggcatg gtgcagaccc     1080
acgtgacaac acccggcagc atcccaacaa tctgcgacct ggcccgcacc ttcgcccgcg     1140
agatgggcga ggccaactaa tagggatccc tcgagaagct tgtca                    1185
```

<210> SEQ ID NO 18
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

| | | | | | |
|---|---|---|---|---|---|
| gtcagcggcc | gcaccggtac | gcgtccacca | tggccctgca | gaaaaagctg | gaagagctgg | 60 |
| aactggatgg | cagctacccc | ggccaccagc | acgccagcgc | cttcgaccag | gccgcccgca | 120 |
| gccgcggcca | cagcaacggc | agcaccgcac | tgcggccagg | atctcagcag | gaggccaccg | 180 |
| aggtgcgccc | cgagcagaag | atgcccaccc | tgctgcgcgt | gtacatcgac | ggaccacacg | 240 |
| gcatgggcaa | gaccaccacc | acccagctgc | tggtggccct | gggcagccgc | gacgacatcg | 300 |
| tgtacgtgcc | cgagcccatg | acctactggc | gcgtgctggg | cgccagcgag | accatcgcca | 360 |
| acatctacac | cacccagcac | cgcctggacc | aaggcgagat | cagcgccggc | gacgccgccg | 420 |
| tggtgatgac | cagcgcccag | attacaatgg | gcatgcccta | cgccgtgacc | gacgccgtgc | 480 |
| tggcaccaca | catcggcggc | gaggccggca | gcagccacgc | accaccacca | gcactgaccc | 540 |
| tgatcttcga | ccggcaccca | atcgcacacc | tgctgtgcta | cccggcagca | cgctacctga | 600 |
| tgggctccat | gacaccacaa | gccgtgctgg | ccttcgtggc | cctgatccca | ccaacactgc | 660 |
| ccggcaccaa | catcgtgctg | ggcgccctgc | ccgaggaccg | ccacatcgac | cgcctggcca | 720 |
| agcgccagcg | ccccggcgag | cgcctggacc | tggccatgct | ggccgccatc | cgccgcgtgt | 780 |
| acggcctgct | ggccaacacc | gtgcgctacc | tgcagtgcgg | cggcagctgg | cgcgaggact | 840 |
| ggggccagct | gagcggcacc | gccgtgccac | acagggcgc | cgagccacag | agcaacgccg | 900 |
| gaccacgacc | acacatcggc | gacaccctgt | tcaccctgtt | ccgggcacca | gagctgctgg | 960 |
| caccaaacgg | cgacctgtac | aacgtgttcg | cctgggccct | ggacgtgctg | gccaagcgcc | 1020 |
| tgcgctccat | gcacgtgttc | atcctggact | acgaccagtc | accggccggc | tgccgcgacg | 1080 |
| ccctgctgca | gctgaccagc | ggcatggtgc | agacccacgt | gacaacaccc | ggcagcatcc | 1140 |
| caacaatctg | cgacctggcc | cgcaccttcg | cccgcgagat | gggcgaggcc | aactaatagg | 1200 |
| gatccctcga | agagcttgtc | a | | | | 1221 |

<210> SEQ ID NO 19
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | | | | | |
|---|---|---|---|---|---|
| gtcagcggcc | gcaccggtac | gcgtccacca | tggccctgca | gaaaaagctg | gaagagctgg | 60 |
| aactggatgg | cagctacccc | ggccaccagc | acgccagcgc | cttcgaccag | gccgcccgca | 120 |
| gccgcggcca | cagcaacggc | agcaccgcac | tgcggccagg | atctcagcag | gaggccaccg | 180 |
| aggtgcgccc | cgagcagaag | atgcccaccc | tgctgcgcgt | gtacatcgac | ggaccacacg | 240 |
| gcatgggcaa | gaccaccacc | acccagctgc | tggtggccct | gggcagccgc | gacgacatcg | 300 |
| tgtacgtgcc | cgagcccatg | acctactggc | gcgtgctggg | cgccagcgag | accatcgcca | 360 |
| acatctacac | cacccagcac | cgcctggacc | aaggcgagat | cagcgccggc | gacgccgccg | 420 |
| tggtgatgac | cagcgcccag | attacaatgg | gcatgcccta | cgccgtgacc | gacgccgtgc | 480 |
| tggcaccaca | catcggcggc | gaggccggca | gcagccacgc | accaccacca | gcactgaccc | 540 |

```
tgatcttcga ccggcaccca atcttcgcac tgctgtgcta cccggcagca cgctacctga    600
tgggctccat gacaccacaa gccgtgctgg ccttcgtggc cctgatccca ccaacactgc    660
ccggcaccaa catcgtgctg ggcgccctgc ccgaggaccg ccacatcgac cgcctggcca    720
agcgccagcg ccccggcgag cgcctggacc tggccatgct ggccgccatc cgccgcgtgt    780
acggcctgct ggccaacacc gtgcgctacc tgcagtgcgg cggcagctgg cgcgaggact    840
ggggccagct gagcggcacc gccgtgccac cacagggcgc cgagccacag agcaacgccg    900
gaccacgacc acacatcggc gacaccctgt tcaccctgtt ccgggcacca gagctgctgg    960
caccaaacgg cgacctgtac aacgtgttcg cctgggccct ggacgtgctg gccaagcgcc   1020
tgcgctccat gcacgtgttc atcctggact acgaccagtc accggccggc tgccgcgacg   1080
ccctgctgca gctgaccagc ggcatggtgc agacccacgt gacaacaccc ggcagcatcc   1140
caacaatctg cgacctggcc cgcaccttcg cccgcgagat gggcgaggcc aactaatagg   1200
gatccctcga gaagcttgtc a                                             1221

<210> SEQ ID NO 20
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gtcagcggcc gcaccggtac gcgtccacca tggctctgca gaaaaagctg gaagagctgg     60
aactggatgg ctcttatcct ggacatcagc atgcttctgc ttttgatcag gctgccagat    120
ctagaggaca ttctaatggc agcacagcac tgcggccagg atctcagcag gaagctacag    180
aagtgagacc tgaacagaaa atgcctacac tgctgagagt gtatattgat ggaccacatg    240
gaatgggaaa acaaccaca acccagctgc tggtggctct cggatctaga gatgatattg    300
tgtatgtgcc tgaacctatg acatattgga gagtgctggg agcttctgaa acaattgcta    360
atatctatac aacacagcat agactggatc aaggagaaat ttctgccgga gatgctgccg    420
tggtgatgac atctgctcag attacaatgg gaatgcctta tgctgtgaca gatgctgtgc    480
tggcaccaca tattggaggc gaagctggaa gctctcatgc accaccacca gcactgacac    540
tgatttttga tcggcatcca attgcacatc tgctgtgtta ccggcagca agatatctga    600
tgggaagcat gacaccacaa gccgtgctgg cttttgtggc tctgattcca ccaacactgc    660
ctggaacaaa catcgtgctg ggagctctgc ctgaagatag acatatcgat cggctggcca    720
aacggcagag acctggagaa cggctggatc tggccatgct ggctgccatt cggagagtgt    780
atggcctgct ggctaacaca gtgagatatc tgcagtgtgg aggctcttgg agagaggatt    840
ggggacagct gtctggcaca gctgtgccac acagggagc cgaaccacag agcaatgctg    900
gaccacgacc acatatcgga gacacactgt ttcacactgtt tcgggcacca gaactgctgg    960
caccaaatgg agacctgtac aacgtgtttg cctgggctct ggatgtgctg gctaaacggc   1020
tgagatctat gcatgtgttt atcctggact atgatcagtc accggccgga tgtcgcgatg   1080
ccctgctgca gctgacatct gggatggtgc agacacatgt gacaacacct ggatctatcc   1140
caacaatctg tgatctggct agaacattcg ctagggagat gggagaggcc aactaatgag   1200
gatccctcga gaagcttgtc a                                             1221
```

<210> SEQ ID NO 21
<211> LENGTH: 1221
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

| | | | | | | |
|---|---|---|---|---|---|---|
| gtcagcggcc | gcaccggtac | gcgtccacca | tggctctgca | gaaaaagctg | gaagagctgg | 60 |
| aactggatgg | ctcttatcct | ggacatcagc | atgcttctgc | ttttgatcag | gctgccagat | 120 |
| ctagaggaca | ttctaatggc | agcacagcac | tgcggccagg | atctcagcag | gaagctacag | 180 |
| aagtgagacc | tgaacagaaa | atgcctacac | tgctgagagt | gtatattgat | ggaccacatg | 240 |
| gaatgggaaa | acaaccaca | acccagctgc | tggtggctct | cggatctaga | gatgatattg | 300 |
| tgtatgtgcc | tgaacctatg | acatattgga | gagtgctggg | agcttctgaa | acaattgcta | 360 |
| atatctatac | aacacagcat | agactggatc | aaggagaaat | ttctgccgga | gatgctgccg | 420 |
| tggtgatgac | atctgctcag | attacaatgg | gaatgcctta | tgctgtgaca | gatgctgtgc | 480 |
| tggcaccaca | tattggaggc | gaagctggaa | gctctcatgc | accaccacca | gcactgacac | 540 |
| tgattttga | tcggcatcca | atttcgcac | tgctgtgtta | tccggcagca | agatatctga | 600 |
| tgggaagcat | gacaccacaa | gccgtgctgg | cttttgtggc | tctgattcca | ccaacactgc | 660 |
| ctggaacaaa | catcgtgctg | ggagctctgc | ctgaagatag | acatatcgat | cggctggcca | 720 |
| aacggcagag | acctggagaa | cggctggatc | tggccatgct | ggctgccatt | cggagagtgt | 780 |
| atggcctgct | ggctaacaca | gtgagatatc | tgcagtgtgg | aggctcttgg | agagaggatt | 840 |
| ggggacagct | gtctggcaca | gctgtgccac | cacagggagc | cgaaccacag | agcaatgctg | 900 |
| gaccacgacc | acatatcgga | gacacactgt | ttacactgtt | tcgggcacca | gaactgctgg | 960 |
| caccaaatgg | agacctgtac | aacgtgtttg | cctgggctct | ggatgtgctg | gctaaacggc | 1020 |
| tgagatctat | gcatgtgttt | atcctggact | atgatcagtc | accggccgga | tgtcgcgatg | 1080 |
| ccctgctgca | gctgacatct | gggatggtgc | agacacatgt | gacaacacct | ggatctatcc | 1140 |
| caacaatctg | tgatctggct | agaacattcg | ctagggagat | gggagaggcc | aactaatgag | 1200 |
| gatccctcga | gaagcttgtc | a | | | | 1221 |

<210> SEQ ID NO 22
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

| | | | | | | |
|---|---|---|---|---|---|---|
| gtcagcggcc | gcaccggtac | gcgtccacca | tggccagcta | ccccggccac | cagcacgcca | 60 |
| gcgccttcga | ccaggccgcc | cgcagccgcg | gccacagcaa | cggcagcacc | gcactgcggc | 120 |
| caggatctca | gcaggaggcc | accgaggtgc | gccccgagca | gaagatgccc | accctgctgc | 180 |
| gcgtgtacat | cgacggacca | cacggcatgg | gcaagaccac | caccacccag | ctgctggtgg | 240 |
| ccctgggcag | ccgcgacgac | atcgtgtacg | tgcccgagcc | catgacctac | tggcgcgtgc | 300 |
| tgggcgccag | cgagaccatc | gccaacatct | acaccaccca | gcaccgcctg | gaccaaggcg | 360 |
| agatcagcgc | cggcgacgcc | gccgtggtga | tgaccagcgc | ccagattaca | atgggcatgc | 420 |
| cctacgccgt | gaccgacgcc | gtgctggcac | acacatcgg | cggcgaggcc | ggcagcagcc | 480 |

```
acgcaccacc accagcactg accctgatct tcgaccggca cccaatcgca cacctgctgt    540
gctacccggc agcacgctac ctgatgggct ccatgacacc acaagccgtg ctggccttcg    600
tggccctgat cccaccaaca ctgcccggca caacatcgt gctgggcgcc ctgcccgagg     660
accgccacat cgaccgcctg gccaagcgcc agcgccccgg cgagcgcctg gacctggcca    720
tgctggccgc catccgccgc gtgtacggcc tgctggccaa caccgtgcgc tacctgcagt    780
gcggcggcag ctggcgcgag gactgggggcc agctgagcgg caccgccgtg ccaccacagg   840
gcgccgagcc acagagcaac gccggaccac gaccacacat cggcgacacc ctgttcaccc    900
tgttccgggc accagagctg ctggcaccaa acggcgacct gtacaacgtg ttcgcctggg    960
ccctggacgt gctggccaag cgcctgcgct ccatgcacgt gttcatcctg gactacgacc   1020
agtcaccggc cggctgccgc gacgccctgc tgcagctgac cagcggcatg gtgcagaccc   1080
acgtgacaac acccggcagc atcccaacaa tctgcgacct ggcccgcacc ttcgcccgcg   1140
agatgggcga ggccaactaa tagggatccc tcgagaagct tgtca                   1185
```

<210> SEQ ID NO 23  
<211> LENGTH: 36  
<212> TYPE: DNA  
<213> ORGANISM: Unknown  
<220> FEATURE:  
<223> OTHER INFORMATION: Description of Unknown: Nuclear export signal oligonucleotide

<400> SEQUENCE: 23

```
ctgcagaaaa agctggaaga gctggaactg gatggc                              36
```

<210> SEQ ID NO 24  
<211> LENGTH: 12  
<212> TYPE: PRT  
<213> ORGANISM: Unknown  
<220> FEATURE:  
<223> OTHER INFORMATION: Description of Unknown: Nuclear export signal peptide

<400> SEQUENCE: 24

```
Leu Gln Lys Lys Leu Glu Glu Leu Glu Leu Asp Gly
1               5                   10
```

<210> SEQ ID NO 25  
<211> LENGTH: 19  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 25

```
cggcggtggt aatgacaag                                                 19
```

<210> SEQ ID NO 26  
<211> LENGTH: 17  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 26

```
gcgtcggtca cggcata                                                   17
```

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM

<400> SEQUENCE: 27

```
ccagataaca atgggc                                                   16
```

<210> SEQ ID NO 28
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
atggccagct accccggcca ccagcacgcc agcgccttcg accaggccgc ccgcagccgc     60
ggccacagca acggcagcac cgccctgcgc ccccgccgcc agcaggaggc caccgaggtg    120
cgccccgagc agaagatgcc caccctgctg cgcgtgtaca tcgacggccc ccacggcatg    180
ggcaagacca ccaccaccca gctgctggtg gccctgggca ccgcgacga catcgtgtac    240 gtgcccgagc ccatgaccta ctggcgcgtg ctgggcgcca gcgagaccat cgccaacatc    300
tacaccaccc agcaccgcct ggaccaaggc gagatcagcg ccggcgacgc cgccgtggtg    360
atgaccagcg cccagatcac catgggcatg ccctacgccg tgaccgacgc cgtgctggcc    420
ccccacatcg gcggcgaggc cggcagcagc cacgcccccc ccccgccct gaccatcttc    480 ctggaccgcc accccatcgc cttcatgctg tgctacccc cgcccgcta cctgatgggc    540 agcatgacac acaagccgt gctggccttc gtgcccctga tccccccac cctgcccggc    600 accaacatcg tgctgggcgc cctgcccgag gaccgccaca tcgaccgcct ggccaagcgc    660
cagcgccccg cgagcgcct ggacctggcc atgctggccg ccatccgccg cgtgtacggc    720
ctgctggcca acaccgtgcg ctacctgcag tgcggcggca gctggcgcga ggactggggc    780
cagctgagcg gcaccgccgt gccccccag ggcgccgagc cccagagcaa cgccggcccc    840
cgcccccaca tcggcgacac cctgttcacc ctgttccgcg ccccgagct gctggccccc    900 aacggcgacc tgtacaacgt gttcgcctgg gccctggacg tgctggccaa gcgcctgcgc    960
agcatgcacg tgttcatcct ggactacgac cagagcccg ccggctgccg cgacgccctg   1020
ctgcagctga ccagcggcat ggtgcagacc cacgtgacca ccccggcag catccccacc   1080 atctgcgacc tggcccgcac cttcgcccgc gagatgggcg aggccaacta a          1131
```

<210> SEQ ID NO 29
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gtcagcggcc gcaccggtac gcgtccacca tggccagcta ccccggccac cagcacgcca     60
gcgccttcga ccaggccgcc cgcagccgcg gccacagcaa cggcagcacc gcactgcggc    120
cacggcgcca gcaggaggcc accgaggtgc gccccgagca gaagatgccc accctgctgc    180
```

```
gcgtgtacat cgacggacca cacggcatgg gcaagaccac caccacccag ctgctggtgg      240
ccctgggcag ccgcgacgac atcgtgtacg tgcccgagcc catgacctac tggcgcgtgc      300
tgggcgccag cgagaccatc gccaacatct acaccaccca gcaccgcctg gaccaaggcg      360
agatcagcgc cggcgacgcc gccgtggtga tgaccagcgc ccagattaca atgggcatgc      420
cctacgccgt gaccgacgcc gtgctggcac acacatcgg cggcgaggcc ggcagcagcc       480
acgcaccacc accagcactg accctgatct tcgaccggca cccaatcgca cacctgctgt      540
gctacccggc agcacgctac ctgatgggct ccatgacacc acaagccgtg ctggccttcg      600
tggccctgat cccaccaaca ctgcccggca ccaacatcgt gctgggcgcc ctgcccgagg      660
accgccacat cgaccgcctg gccaagcgcc agcgccccgg cgagcgcctg gacctggcca      720
tgctggccgc catccgccgc gtgtacggcc tgctggccaa caccgtgcgc tacctgcagt      780
gcggcggcag ctggcgcgag gactgggcc agctgagcgg caccgccgtg ccaccacagg       840
gcgccgagcc acagagcaac gccggaccac gaccacacat cggcgacacc ctgttcaccc      900
tgttccgggc accagagctg ctggcaccaa acggcgacct gtacaacgtg ttcgcctggg      960
ccctggacgt gctggccaag cgcctgcgct ccatgcacgt gttcatcctg gactacgacc     1020
agtcaccggc cggctgccgc gacgccctgc tgcagctgac cagcggcatg gtgcagaccc     1080
acgtgacaac acccggcagc atcccaacaa tctgcgacct ggcccgcacc ttcgcccgcg     1140
agatgggcga ggccaactaa tagggatccc tcgagaagct tgtca                    1185
```

<210> SEQ ID NO 30
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
gtcagcggcc gcaccggtac gcgtccacca tggccagcta ccccggccac cagcacgcca       60
gcgccttcga ccaggccgcc cgcagccgcg gccacagcaa cggcagcacc gcactgcggc      120
cacggcgcca gcaggaggcc accgaggtgc gccccgagca gaagatgccc accctgctgc      180
gcgtgtacat cgacggacca cacggcatgg gcaagaccac caccacccag ctgctggtgg      240
ccctgggcag ccgcgacgac atcgtgtacg tgcccgagcc catgacctac tggcgcgtgc      300
tgggcgccag cgagaccatc gccaacatct acaccaccca gcaccgcctg gaccaaggcg      360
agatcagcgc cggcgacgcc gccgtggtga tgaccagcgc ccagattaca atgggcatgc      420
cctacgccgt gaccgacgcc gtgctggcac acacatcgg cggcgaggcc ggcagcagcc       480
acgcaccacc accagcactg accctgatct tcgaccggca cccaatcgca cacctgctgt      540
gctacccggc agcacgctac ctgatgggct ccatgacacc acaagccgtg ctggccttcg      600
tggccctgat cccaccaaca ctgcccggca ccaacatcgt gctgggcgcc ctgcccgagg      660
accgccacat cgaccgcctg gccaagcgcc agcgccccgg cgagcgcctg gacctggcca      720
tgctggccgc catccgccgc gtgtacggcc tgctggccaa caccgtgcgc tacctgcagt      780
gcggcggcag ctggcgcgag gactgggcc agctgagcgg caccgccgtg ccaccacagg       840
gcgccgagcc acagagcaac gccggaccac gaccacacat cggcgacacc ctgttcaccc      900
tgttccgggc accagagctg ctggcaccaa acggcgacct gtacaacgtg ttcgcctggg      960
ccctggacgt gctggccaag cgcctgcgct ccatgcacgt gttcatcctg gactacgacc     1020
```
agtcaccggc cggctgccgc gacgccctgc tgcagctgac cagcggcatg gtgcagaccc    1080
acgtgacaac acccggcagc atcccaacaa tctgcgacct ggcccgcacc ttcgcccgcg    1140
agatgggcga ggccaactaa tagggatccc tcgagaagct tgtca                   1185

<210> SEQ ID NO 31
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gtcagcggcc gcaccggtac gcgtccacca tggccctgca gaaaaagctg aagagctgg      60 aactggatgg ctcttatcct ggacatcagc atgcttctgc ttttgatcag gctgccagat    120
ctagaggaca ttctaatggc agcacagcac tgcggccagg atctcagcag gaagctacag    180
aagtgagacc tgaacagaaa atgcctacac tgctgagagt gtatattgat ggaccacatg    240
gaatgggaaa acaaccaca acccagctgc tggtggctct cggatctaga gatgatattg     300
tgtatgtgcc tgaacctatg acatattgga gagtgctggg agcttctgaa acaattgcta    360
atatctatac aacacagcat agactggatc aaggagaaat ttctgccgga gatgctgccg    420
tggtgatgac atctgctcag attacaatgg aatgcctta tgctgtgaca gatgctgtgc      480
tggcaccaca tattggaggc gaagctggaa gctctcatgc accaccacca gcactgacac    540 tgattttga tcggcatcca attgcacatc tgctgtgtta tccggcagca agatatctga     600
tgggaagcat gacaccacaa gccgtgctgg cttttgtggc tctgattcca ccaacactgc    660
ctggaacaaa catcgtgctg ggagctctgc ctgaagatag acatatcgat cggctggcca    720
aacggcagag acctggagaa cggctggatc tggccatgct ggctgccatt cggagagtgt    780
atggcctgct ggctaacaca gtgagatatc tgcagtgtgg aggctcttgg agagaggatt    840
ggggacagct gtctggcaca gctgtgccac cacagggagc cgaaccacag agcaatgctg    900
gaccacgacc acatatcgga gacacactgt ttacactgtt tcgggcacca gaactgctgg    960
caccaaatgg agacctgtac aacgtgtttg cctgggctct ggatgtgctg gctaaacggc    1020
tgagatctat gcatgtgttt atcctggact atgatcagtc accggccgga tgtcgcgatg    1080
ccctgctgca gctgacatct gggatggtgc agacacatgt gacaacacct ggatctatcc    1140
caacaatctg tgatctggct agaacattcg ctagggagat gggagaggcc aactaatagg    1200
gatccctcga agcttgtc a                                                1221

<210> SEQ ID NO 32
<211> LENGTH: 652
<212> TYPE: PRT
<213> ORGANISM: Homo sapiens

<400> SEQUENCE: 32

Met Ala Met Asp Glu Tyr Leu Trp Met Val Ile Leu Gly Phe Ile Ile
1               5                   10                  15

Ala Phe Ile Leu Ala Phe Ser Val Gly Ala Asn Asp Val Ala Asn Ser
            20                  25                  30

Phe Gly Thr Ala Val Gly Ser Gly Val Val Thr Leu Arg Gln Ala Cys
        35                  40                  45

Ile Leu Ala Ser Ile Phe Glu Thr Thr Gly Ser Val Leu Leu Gly Ala
    50                  55                  60

```
Lys Val Gly Glu Thr Ile Arg Lys Gly Ile Ile Asp Val Asn Leu Tyr
 65                  70                  75                  80

Asn Glu Thr Val Glu Thr Leu Met Ala Gly Glu Val Ser Ala Met Val
                 85                  90                  95

Gly Ser Ala Val Trp Gln Leu Ile Ala Ser Phe Leu Arg Leu Pro Ile
                100                 105                 110

Ser Gly Thr His Cys Ile Val Gly Ser Thr Ile Gly Phe Ser Leu Val
                115                 120                 125

Ala Ile Gly Thr Lys Gly Val Gln Trp Met Glu Leu Val Lys Ile Val
            130                 135                 140

Ala Ser Trp Phe Ile Ser Pro Leu Leu Ser Gly Phe Met Ser Gly Leu
145                 150                 155                 160

Leu Phe Val Leu Ile Arg Ile Phe Ile Leu Lys Lys Glu Asp Pro Val
                165                 170                 175

Pro Asn Gly Leu Arg Ala Leu Pro Val Phe Tyr Ala Ala Thr Ile Ala
                180                 185                 190

Ile Asn Val Phe Ser Ile Met Tyr Thr Gly Ala Pro Val Leu Gly Leu
            195                 200                 205

Val Leu Pro Met Trp Ala Ile Ala Leu Ile Ser Phe Gly Val Ala Leu
            210                 215                 220

Leu Phe Ala Phe Phe Val Trp Leu Phe Val Cys Pro Trp Met Arg Arg
225                 230                 235                 240

Lys Ile Thr Gly Lys Leu Gln Lys Glu Gly Ala Leu Ser Arg Val Ser
                245                 250                 255

Asp Glu Ser Leu Ser Lys Val Gln Glu Ala Glu Ser Pro Val Phe Lys
                260                 265                 270

Glu Leu Pro Gly Ala Lys Ala Asn Asp Asp Ser Thr Ile Pro Leu Thr
                275                 280                 285

Gly Ala Ala Gly Glu Thr Leu Gly Thr Ser Glu Gly Thr Ser Ala Gly
            290                 295                 300

Ser His Pro Arg Ala Ala Tyr Gly Arg Ala Leu Ser Met Thr His Gly
305                 310                 315                 320

Ser Val Lys Ser Pro Ile Ser Asn Gly Thr Phe Gly Phe Asp Gly His
                325                 330                 335

Thr Arg Ser Asp Gly His Val Tyr His Thr Val His Lys Asp Ser Gly
                340                 345                 350

Leu Tyr Lys Asp Leu Leu His Lys Ile His Ile Asp Arg Gly Pro Glu
            355                 360                 365

Glu Lys Pro Ala Gln Glu Ser Asn Tyr Arg Leu Leu Arg Arg Asn Asn
            370                 375                 380

Ser Tyr Thr Cys Tyr Thr Ala Ala Ile Cys Gly Leu Pro Val His Ala
385                 390                 395                 400

Thr Phe Arg Ala Ala Asp Ser Ser Ala Pro Glu Asp Ser Glu Lys Leu
                405                 410                 415

Val Gly Asp Thr Val Ser Tyr Ser Lys Lys Arg Leu Arg Tyr Asp Ser
                420                 425                 430

Tyr Ser Ser Tyr Cys Asn Ala Val Ala Glu Ala Glu Ile Glu Ala Glu
            435                 440                 445

Glu Gly Gly Val Glu Met Lys Leu Ala Ser Glu Leu Ala Asp Pro Asp
            450                 455                 460

Gln Pro Arg Glu Asp Pro Ala Glu Glu Lys Glu Glu Lys Asp Ala
465                 470                 475                 480
```

```
Pro Glu Val His Leu Leu Phe His Phe Leu Gln Val Leu Thr Ala Cys
            485                 490                 495

Phe Gly Ser Phe Ala His Gly Gly Asn Asp Val Ser Asn Ala Ile Gly
        500                 505                 510

Pro Leu Val Ala Leu Trp Leu Ile Tyr Lys Gln Gly Val Thr Gln
        515                 520                 525

Glu Ala Ala Thr Pro Val Trp Leu Leu Phe Tyr Gly Val Gly Ile
    530                 535                 540

Cys Thr Gly Leu Trp Val Trp Gly Arg Arg Val Ile Gln Thr Met Gly
545                 550                 555                 560

Lys Asp Leu Thr Pro Ile Thr Pro Ser Ser Gly Phe Thr Ile Glu Leu
                565                 570                 575

Ala Ser Ala Phe Thr Val Val Ile Ala Ser Asn Ile Gly Leu Pro Val
                580                 585                 590

Ser Thr Thr His Cys Lys Val Gly Ser Val Val Ala Val Gly Trp Ile
                595                 600                 605

Arg Ser Arg Lys Ala Val Asp Trp Arg Leu Phe Arg Asn Ile Phe Val
            610                 615                 620

Ala Trp Phe Val Thr Val Pro Val Ala Gly Leu Phe Ser Ala Ala Val
625                 630                 635                 640

Met Ala Leu Leu Met Tyr Gly Ile Leu Pro Tyr Val
                645                 650

<210> SEQ ID NO 33
<211> LENGTH: 9
<212> TYPE: PRT
<213> ORGANISM: Herpes simplex virus 1

<400> SEQUENCE: 33

Arg Arg Thr Ala Leu Arg Pro Arg Arg
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ser Thr Ala Leu Arg Pro Arg Arg
1               5

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Ala Leu Gln Lys Lys Leu Glu Glu Leu Glu Leu Asp Gly
1               5                   10

<210> SEQ ID NO 36
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 36

Gly Ser Thr Ala Leu Arg Pro Gly Ser
1               5
```

THYMIDINE KINASE GENE

CROSS-REFERENCE

This application is a continuation of U.S. application Ser. No. 14/214,522, filed on Mar. 14, 2014, which claims the benefit of U.S. Provisional Application No. 61/784,901, filed Mar. 14, 2013, both of which are incorporated herein by reference in their entireties.

This application is related to the following co-pending patent application: U.S. application Ser. No. 14/214,448, filed on Mar. 14, 2014, which application is incorporated herein by reference in its entirety.

This instant application contains a Sequence Listing which has been submitted electronically in ASCII format and is hereby incorporated by reference in its entirety. The ASCII copy, created Feb. 8, 2018, is named "30863722301.txt" and is 53,248 bytes in size.

BACKGROUND OF THE INVENTION

Proliferative diseases, such as cancer, pose a serious challenge to society. Cancerous growths, including malignant cancerous growths, possess unique characteristics such as uncontrollable cell proliferation resulting in, for example, unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation. Cancer encompasses a large category of medical conditions, affecting millions of individuals worldwide. Cancer cells can arise in almost any organ and/or tissue of the body. Worldwide, more than 10 million people are diagnosed with cancer every year and it is estimated that this number will grow to 15 million new cases every year by 2020. Cancer causes six million deaths every year or 12% of the deaths worldwide.

SUMMARY OF THE INVENTION

Provided herein are polynucleotide sequences encoding mutated forms of thymidine kinase from a human herpes simplex virus (HSV-TK), wherein the encoded HSV-TK is mutated at amino acid residue 25, 26, 32, 33, 167, 168 or a combination thereof, wherein the polynucleotide sequence is mutated compared to a polynucleotide sequence of SEQ ID NO: 1 or 3.

A polynucleotide sequence encoding a mutated form of thymidine kinase from a human herpes simplex virus (HSV-TK), wherein the encoded HSV-TK is mutated at amino acid residue 25, 26, 32, 33, 167, 168 or a combination thereof, wherein the polynucleotide sequence is mutated compared to a polynucleotide sequence of SEQ ID NO: 3. In one embodiment, the encoded HSV-TK is mutated at amino acid residues 167, 168, or a combination thereof to a polar, non-polar, basic or acidic amino acid. In another embodiment, the encoded HSV-TK is mutated at amino acid residue 167 to a polar, non-polar, basic or acidic amino acid. In yet another embodiment, the encoded HSV-TK is mutated at amino acid residue 168 to a polar, non-polar, basic or acidic amino acid. In still another embodiment, the encoded HSV-TK is mutated at both amino acid residues 167 and 168 to a polar, non-polar, basic or acidic amino acid.

In one embodiment, amino acid residue 167 of the encoded HSV-TK is mutated to serine or phenylalanine. In another embodiment, amino acid residue 168 of the encoded HSV-TK is mutated to an amino acid selected from the group consisting of: histidine, lysine, cysteine, serine, and phenylalanine. In still another embodiment, the encoded HSV-TK is mutated at amino acids 25 and 26. In yet another embodiment, amino acid residues 25 and 26 are mutated to an amino acid chosen from the group consisting of: glycine, serine, and glutamic acid. In another embodiment, the encoded HSV-TK is mutated at amino acid residues 32 and 33. In one embodiment, the amino acid residues 32 and 33 are mutated to an amino acid chosen from the group consisting of: glycine, serine, and glutamic acid. In one embodiment, the encoded HSV-TK is mutated at amino acid residues 25, 26, 32 and 33. In another embodiment, amino acid residues 25, 26, 32 and 33 are mutated to an amino acid chosen from the group consisting of: glycine, serine, and glutamic acid. In still another embodiment, the encoded HSV-TK comprises at least one mutation chosen from the group consisting of amino acid residues 25, 26, 32 and 33, and at least one mutation chosen from the group consisting of amino acid residues 167 and 168.

In still other embodiments, the encoded HSV-TK sequence further comprises a nuclear export signal (NES). In another embodiment, the nuclear export signal sequence is inserted at or near the 5' terminus of the HSV-TK sequence. In another embodiment, the nuclear export signal sequence is LQKKLEELELDG (SEQ ID NO: 24). In one embodiment, the encoded mutant HSV-TK does not localize exclusively to the nuclear region.

In one embodiment, the encoded modified HSV-TK exhibits a reduced amount of thymidine kinase activity as compared to wild-type HSV-TK. In another embodiment, the activity of the encoded modified HSV-TK is reduced by about 1.5 fold, about 2-fold, about 5-fold, about 10-fold, about 20-fold, about 30-fold, or about 50-fold. In still another embodiment, the activity of the encoded modified HSV-TK is reduced by about 1.5%, about 2%, about 5%, about 10%, about 20%, about 30%, about 40%, about 50%, about 60%, about 70%, about 80%, about 90%, about 95%, or about 100%.

In one embodiment, the encoded HSV-TK comprises mutations at amino acid residues 25, 26, 32, 33 and 168. In another embodiment, the encoded HSV-TK comprises mutations R25G, R26S, R32G, R33S and A168H.

In one embodiment, modified polynucleotide sequence comprises a nucleic acid sequence set forth as any one of SEQ ID NOS: 12-22. In still another embodiment, the modified polynucleotide sequence comprises a nucleic acid sequence set forth as any one of SEQ ID NOS: 16-22. In one embodiment, the sequence comprises TK168dmNES (SEQ ID NO: 18). In still another embodiment, the polynucleotide encodes a modified HSV-TK polypeptide.

In still other embodiments, the polynucleotide further comprises a polynucleotide sequence coding for a second polypeptide, wherein said second polypeptide is a therapeutic polypeptide. In still other embodiments, the second therapeutic polypeptide is a second suicide gene or a growth factor. In some embodiments, the growth factor is chosen from the group consisting of epidermal growth factor (EGF), vascular endothelial growth factor (VEGF), erythropoietin, G-CSF, GM-CSF, TGF-α, TGF-β and fibroblast growth factor. In some embodiments, the second suicide gene is chosen from the group consisting of: a cytosine deaminase, a VSV-tk, IL-2, nitroreductase (NR), carboxylesterase, beta-glucuronidase, cytochrome p450, beta-galactosidase, diphtheria toxin A-chain (DT-A), carboxypeptide G2 (CPG2), purine nucleoside phosphorylase (PNP), and deoxycytidine kinase (dCK).

In some embodiments, the polynucleotides further comprises a polynucleotide encoding for a PiT-2 polypeptide. In still other embodiments, the polynucleotides disclosed herein further comprises a polynucleotide encoding for a targeting polypeptide. In one embodiment, the targeting polypeptide binds to an extracellular protein. In another embodiment, the extracellular protein is collagen.

Also provided herein are methods of killing neoplastic cells in a subject in need thereof, the method comprising administering a therapeutically effective amount of a retroviral particle, the retroviral vector encoding an HSV-TK modified peptide as described herein.

In some embodiments, the retroviral particle is administered intravenously, intramuscularly, subcutaneoustly, intra-arterially, intra-hepatic arterially, intra-thecally, intra-peritoneally and/or intra-tumorally. In other embodiments, the retroviral particle is administered intra-tumorally or intravenously. In yet other embodiments, the retroviral vector particle is administered intra-arterially. In other embodiments, at least $1 \times 10^{12}$ TVP of retroviral vector is administered cumulatively to the subject in need thereof. In still other embodiments, at least $1 \times 10^9$ TVP of retroviral vector is administered at one time to the subject in need thereof.

In still other embodiments, the prodrug is administered between about 1-2 days after administration of the retroviral vector particle. In some embodiments, the prodrug is chosen from the group consisting of ganciclovir, valganciclovir, aciclovir, valaciclovir, penciclovir. In some embodiments, the prodrug is ganciclovir.

Also provided herein are methods for treating cancer in a patient in need thereof, the method comprising delivering a therapeutically effective amount of a retroviral vector particle, the retroviral vector encoding an HSV-TK modified peptide as described herein, followed by administration of a nucleoside prodrug to the patient in need thereof.

Also provided herein are methods of increasing HSV-TK ganciclovir, valganciclovir, aciclovir, valaciclovir, penciclovir-mediated killing of neoplastic cells in a subject, the method comprising delivering a therapeutically effective amount of a retroviral vector particle comprising an HSV-TK to the subject in conjunction with a gap junction intracellular communication (GJIC)-increasing treatment. In some embodiments, the GJIC-increasing treatment comprises delivering a polynucleotide sequence encoding at least one gap junction subunit. In other embodiments, the gap junction subunit is connexin 43, connexin 30, or connexin 26. In yet other embodiments, the gap junction subunit is a gap junction subunit modified to prevent posttranslational modifications. In still other embodiments, the GJIC-increasing treatment comprises delivering a polynucleotide sequence encoding E-cadherin. In still other embodiments, the GJIC-increasing treatment comprises delivering to the subject a compound from the group consisting of: gemcitabine; cAMP; a retinoic acid; a carotenoid; a glucocorticoid, a flavanoid, apigenin, or lovastatin. In yet other embodiments, the GJIC-increasing treatment comprises proteasome inhibition. In one embodiment, the proteasome inhibition comprises administration of N-Acetyl-Leu-Leu-Nle-CHO (ALLN) and/or chloroquine. In other embodiments, the GJIC-increasing treatment comprises radiation or electrical treatment.

Also provided herein are methods of killing a cell, the method comprising: a) introducing into the cell a polynucleotide sequence according to any one of claims 1-26; b) allowing or initiating the cell to express the expressed thymidine kinase or variant thereof; an c) contacting the cell with an agent that is converted by thymidine kinase to a cytotoxic agent.

In one embodiment, a polynucleotide sequence encodes a mutated form of thymidine kinase from a human herpes simplex virus (HSV-TK) comprising 2, 3, 4, 5, 6, 7, 8, 9, 10 or more modifications. In another embodiment, a polynucleotide sequence encodes a mutated form of thymidine kinase from a human herpes simplex virus (HSV-TK) comprises 2, 3, 4, 5, 6, 7, 8, 9, 10 or more modifications. In another embodiment, a polynucleotide sequence encodes a mutated form of thymidine kinase from a human herpes simplex virus (HSV-TK) comprises 3, 4, 5, 6, 7, 8, 9, 10 or more modifications. In another embodiment, a polynucleotide sequence encodes a mutated form of thymidine kinase from a human herpes simplex virus (HSV-TK) comprises 4, 5, 6, 7, 8, 9, 10 or more modifications. In another embodiment, a polynucleotide sequence encodes a mutated form of thymidine kinase from a human herpes simplex virus (HSV-TK) comprises 5, 6, 7, 8, 9, 10 or more modifications.

In one embodiment, the encoded HSV-TK may be mutated at amino acid residues 167, 168, or a combination thereof to a polar, non-polar, basic or acidic amino acid. For example, the encoded HSV-TK may be mutated at amino acid residue 167 to a polar, non-polar, basic or acidic amino acid. In another example, the encoded HSV-TK may be mutated at amino acid residue 168 to a polar, non-polar, basic or acidic amino acid. In another example, the encoded HSV-TK may be mutated at both amino acid residues 167 and 168 to a polar, non-polar, basic or acidic amino acid.

In another embodiment, amino acid residue 167 of the encoded HSV-TK may be mutated to serine or phenylalanine.

In another embodiment, amino acid residue 168 of the encoded HSV-TK may be mutated to an amino acid selected from the group consisting of: histidine, lysine, cysteine, serine, and phenylalanine.

In another embodiment, the encoded HSV-TK may be mutated at amino acids 25 and 26. For example, amino acid residues 25 and 26 may be mutated to an amino acid chosen from the group consisting of: glycine, serine, and glutamic acid.

In another embodiment, the encoded HSV-TK may be mutated at amino acid residues 32 and 33. For example, amino acid residues 32 and 33 may be mutated to an amino acid chosen from the group consisting of: glycine, serine, and glutamic acid.

In another embodiment, the encoded HSV-TK may be mutated at amino acid residues 25, 26, 32 and 33. For example, amino acid residues 25, 26, 32 and 33 may be mutated to an amino acid chosen from the group consisting of: glycine, serine, and glutamic acid.

In another embodiment, the encoded mutant HSV-TK does not localize exclusively to the nuclear region.

In another embodiment, the encoded modified HSV-TK exhibits a reduced amount of thymidine kinase activity as compared to wild-type HSV-TK.

In another embodiment, the thymidine kinase activity of the encoded modified HSV-TK may be reduced by about 1.5 fold, about 2-fold, about 5-fold, about 10-fold, about 20-fold, about 30-fold, or about 50-fold.

In another embodiment, the thymidine kinase activity of the encoded modified HSV-TK may be reduced by about 1.5%, about 2%, about 5%, about 10%, about 20%, about 30%, about 40%, about 50%, about 60%, about 70%, about 80%, about 90%, about 95%, or about 100%.

In another embodiment, the thymidine kinase activity of the encoded modified HSV-TK may be increased by about 1.5 fold, about 2-fold, about 5-fold, about 10-fold, about 20-fold, about 30-fold, or about 50-fold.

In another embodiment, the thymidine kinase activity of the encoded modified HSV-TK may be increased by about 1.5%, about 2%, about 5%, about 10%, about 20%, about 30%, about 40%, about 50%, about 60%, about 70%, about 80%, about 90%, about 95%, or about 100%.

Provided herein is polynucleotide sequence as described above, where the encoded HSV-TK comprises the mutation A167F, A168H or both.

A polynucleotide sequence described herein may further comprise a polynucleotide sequence coding for a second polypeptide, where said second polypeptide is a therapeutic polypeptide. The therapeutic polypeptide may, in some instances, be a suicide gene. Suicide genes include, but are not limited to, a cytosine deaminase, a VSV-tk, IL-2, nitroreductase (NR), carboxylesterase, beta-glucuronidase, cytochrome p450, beta-galactosidase, diphtheria toxin A-chain (DT-A), carboxypeptidase G2 (CPG2), purine nucleoside phosphorylase (PNP), guanylate kinase, and deoxycytidine kinase (dCK).

In one embodiment, a modified polynucleotide sequence described herein may comprise a nucleic acid sequence set forth as any one of SEQ ID NOS: 12-24.

In another embodiment, a modified polynucleotide sequence described herein may comprise a nucleic acid sequence set forth as any one of SEQ ID NOS: 22-24.

In one embodiment, a polynucleotide sequence described herein comprises a nuclear export signal. For example, a polynucleotide sequence may comprise HSV-TKA168HdmNES (SEQ ID NO: 18).

In another embodiment, a retroviral vector for use in the methods described herein comprises one or more splice site modifications.

In another embodiment, a retroviral vector for use in the methods described herein comprises HSV-TK A167Fsm, wherein 'sm' refers to the single mutation pair R25G-R26S (SEQ ID NO: 13).

In another embodiment, a retroviral vector for use in the methods described herein comprises HSV-TK A168Hsm (SEQ ID NO: 12).

In another embodiment, a retroviral vector for use in the methods described herein comprises HSV-TK A167Fdm, wherein 'dm' refers to the double mutation pair R25G-R26S, R32G-R33S (SEQ ID NO: 17).

In another embodiment, a retroviral vector for use in the methods described herein comprises HSV-TK A168Hdm (SEQ ID NO: 16).

In another embodiment, a retroviral vector for use in the methods described herein comprises HSV-TK A167Fdm and a nuclear export sequence derived from mitogen-activated protein kinase kinase, an example of which is SEQ ID NO: 19.

In another embodiment, a retroviral vector for use in the methods described herein comprises HSV-TK A168Hdm and an NES (SEQ ID NO: 18). In such an embodiment, the sequence comprises HSV-TK A168H.

In another embodiment, a retroviral vector for use in the methods described herein comprises a HSV-TK, wherein such vector comprises an upgraded substrate binding domain and a mNLS/NES set. Examples of this exemplary embodiment include SEQ ID NOS: 18 and 19.

In another embodiment, a retroviral vector for use in the methods described herein comprises a HSV-TK, wherein the vector comprises a selectable marker, a glowing gene and/or one or more kill genes.

In another embodiment, a retroviral vector for use in the methods described herein comprises two modifications.

In another embodiment, a retroviral particle comprises a PiT-2 polynucleotide sequence and the retroviral particle specifically binds to a PiT-2 receptor on the surface of the target cells, thereby allowing for uptake of the retroviral particle into the cell.

In another embodiment, a retroviral vector for use in the methods described herein comprises a HSV-TK, wherein the amino acid sequence encoded by the polynucleotide sequence comprises TK168dmNES.

Provided herein is a method of increasing FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpryrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-, ganciclovir- and penciclovir-like side chains-mediated killing of neoplastic cells in a subject, the method comprising delivering a therapeutically effective amount of vector particles encoding HSV-TK to the subject in conjunction with a gap junction intracellular communication (GJIC)-increasing treatment.

In one embodiment, the HSV-TK used in such methods may be encoded by any of the polynucleotide sequences described herein.

The GJIC-increasing treatment may comprise, for example, delivering a polynucleotide sequence encoding at least one gap junction subunit. A gap junction subunit may be, for example, connexin 43, connexin 30, or connexin 26. The gap junction subunit may be a gap junction subunit modified to prevent posttranslational modifications.

In one embodiment, the GJIC-increasing treatment comprises delivering a polynucleotide sequence encoding E-cadherin.

In another embodiment, the GJIC-increasing treatment comprises delivering to the subject a compound from the group consisting of: gemcitabine; cAMP; a retinoic acid; a carotenoid; a glucocorticoid, a flavanoid, apigenin, or lovastatin.

In another embodiment, the GJIC-increasing treatment comprises proteasome inhibition. Proteasome inhibition may comprise administration of N-Acetyl-Leu-Leu-Nle-CHO (ALLN) and/or chloroquine.

In another embodiment, the GJIC-increasing treatment comprises radiation or photodynamic treatment, including coadministration with oxidative agents and agents that activate MAP kinases.

In another embodiment, the GJIC-increasing treatment comprises electrical treatment.

Provided herein is a method of killing a cell, the method comprising: (a) introducing into the cell a polynucleotide sequence described herein; (b) allowing or initiating the cell to express the expressed thymidine kinase or variant thereof; and (c) contacting the cell with an agent that is converted by thymidine kinase to a cytotoxic agent.

Provided herein is a method of increasing thymidine kinase bystander effect, the method comprising delivering a sequence encoding a gap junction subunit in conjunction with a retroviral vector particle encoding HSV-TK. In some embodiments, the retroviral particles may be targeted to a cell or system of interest. In some embodiments, the retroviral targeting method may comprise the incorporation of a factor that recognizes or binds to the cell or system of interest. In some embodiments, the retroviral targeting method may comprise the incorporation of targeting proteins, including binding to proteins or receptors on the surface of the cell of system of interest, including antibodies, receptor binding proteins or proteins that bind to cellular components, including but not limited to collagen. In some embodiments the targeting protein may comprise proteins that bind to collagen, including but not limited to peptides, proteins and/or protein domains that include a collagen binding domain.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 provides an provides an exemplary schedule of events for Phase IA clinical trial for cohorts 1 to 3.

FIG. 5 provides an provides an exemplary schedule of events for Phase IA clinical trial for cohorts 4 and above.

FIG. 6 provides an provides an exemplary schematic for a Phase IB clinical trial with a composition described herein.

FIG. 7 provides an provides an exemplary schematic for a Schedule A of clinical trial for treatment with a composition described herein.

FIG. 8 provides an provides an exemplary schematic for a Schedule B of clinical trial for treatment with a composition described herein.

FIG. 11A: GM-CSF Minus, HSV-TK 167sm. FIG. 11B: GM-CSF Minus, HSV-TK 168sm. FIG. 11C: GM-CSF Minus, HSV-TK 167dm. FIG. 11D: GM-CSF Minus, HSV-TK 168dm. FIG. 11E: GM-CSF Minus, HSV-TK 167dm+NES. FIG. 11F: GM-CSF Minus, HSV-TK 168dm+NES.

FIG. 13A: RexRed-TK A168H. FIG. 13B: RexRed-TK 167-dm. FIG. 13C: RexRed-TK 168 dm.

FIG. 14A: RexRed-TK 167-dm+NES. FIG. 14B: RexRed-TK 168-dm+NES. FIG. 14C: RexRed-TK 167-dm+NES JCO. FIG. 14D: RexRed-TK 168-dm+NES JCO. JCO=justified codon optimization.

FIG. 15A: RexRed-TK A168F. FIG. 15B: RexRed-TK A168F (GCV specific). FIG. 15C: Rex-Hygro-R-TK A168F containing the hygromycine resistance gene.

FIG. 16A-FIG. 16B provide additional exemplary retroviral vectors. FIG. 16A: Rex-Hygro-R-TK A167F. FIG. 16B: Q-PiT-2 is a vector containing a viral receptor gene that binds to a PiT-2 receptor on the surface of target cells.

FIG. 17A: Original Reximmune-C. FIG. 17B. Reximmune-C containing an upgrade with a mTK39 (HSV-TKSR39) kill gene with neomycin resistance gene ($Neo_R$) and selectable marker inserted.

FIG. 21 discloses SEQ ID NOS:33 and 33-36, respectively, in order of appearance.

FIG. 23A: LNC-EGFP which contains an enhanced green fluorescent protein as a glowing gene. FIG. 23B: RexRed which contains a red fluorescent protein as a glowing gene.

FIG. 24A illustrates a RexRed-TK(−) gene comprising an exemplary glowing gene. FIG. 24B illustrates a Rex-Hygro-R-TK(−) gene comprising a hygromycin resistance gene selectable marker.

FIG. 25A-FIG. 25B show Tk-GCV kill results in parent and PiT-2-CHO-K1 lines. The graphs illustrate the data for a single RxC2-transduction protocol. The same batch of RxC2 was used for all experiments (titer approximately 5E+10 total virus particles per milliliter (TVP) as determined by reverse transcriptase in tandem with quantitative polymerase chain reaction (RT-qPCR)). FIG. 25A: GCV kill of RxC2-transduced CHO-K1 parent line after 4 days in GCV (4 doses). FIG. 25B: GCV kill of RxC2-transduced PiT-2-CHO-K1 after 4 days in GCV (4 doses).

FIG. 26A: GCV kill of RxC2-triple transduced CHO-K1 parent on day 9 (10% plate, 5 doses GCV). FIG. 26B: GCV kill of RxC2-triple transduced PiT-2-CHO-K1 on day 9 (10% plate, 5 doses GCV).

FIG. 34 illustrates immuno histochemistry (IHC) of HSV-TK sub cell Localization in 293T cells Transient Transfection, 24 hour Primary AB (Santa Cruz) with RexC1 HSV-TK (left panel) and RexC2 HSV-TK (right panel)

DETAILED DESCRIPTION OF THE INVENTION

Figure 1:
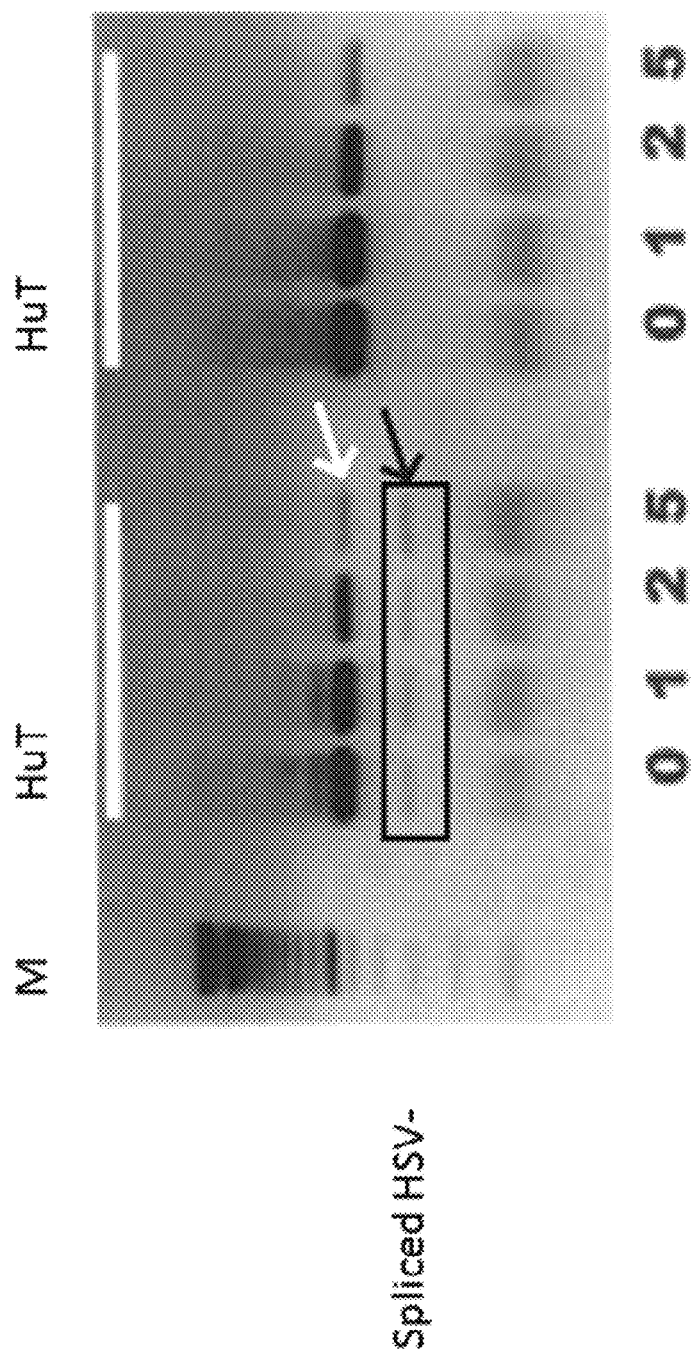
FIG. 1 exemplifies how HSV-TK splice site removal avoids an inactivated form of HSV-TK. PCR analysis of T-cell lines and primary T cells transduced with HSV-TK vectors with (HuT SF/Tk/mut) or without (HuT G1Tk1SvNa) splice site removal.
Figure 2:
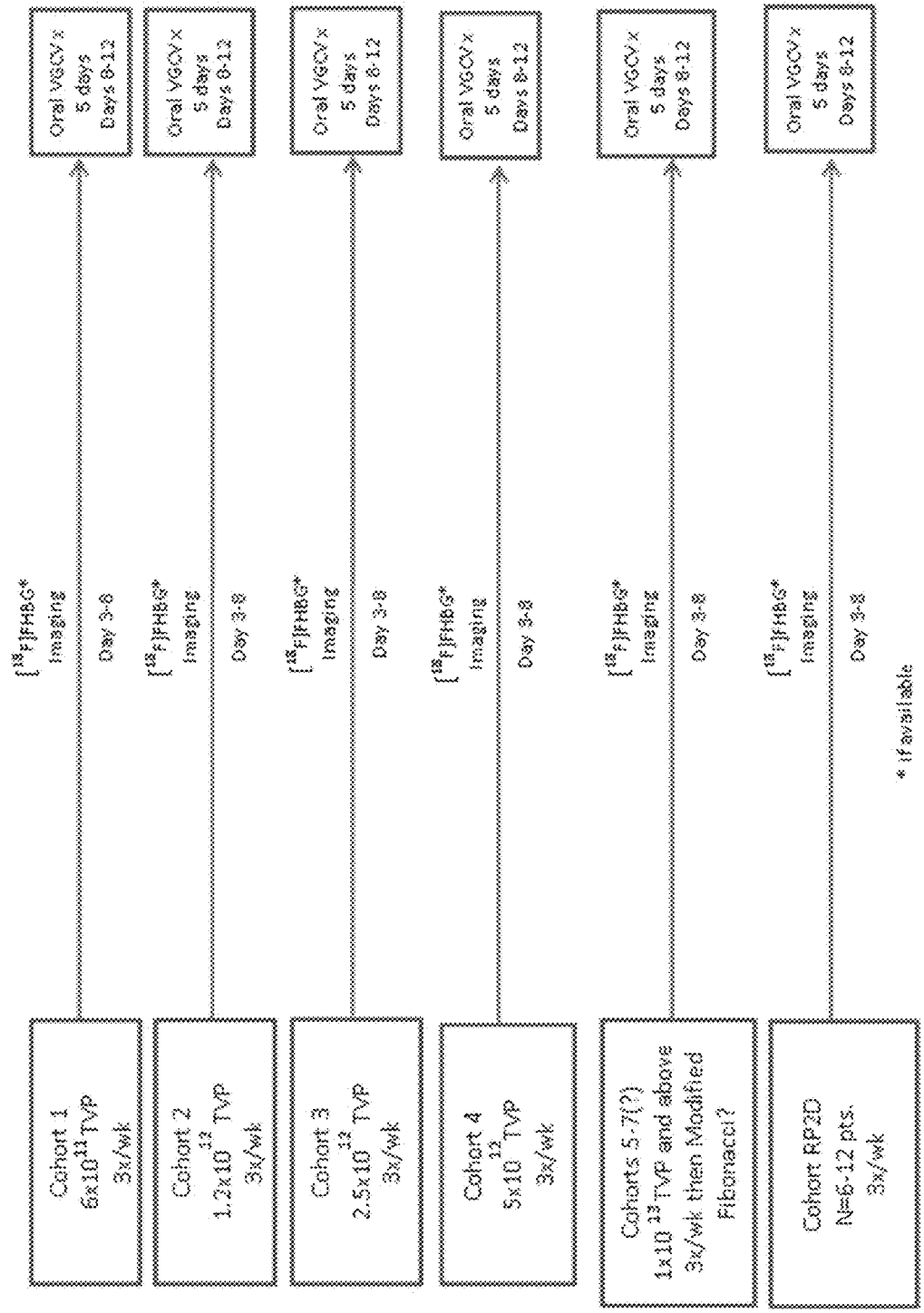
FIG. 2 provides an exemplary schematic for a Phase IA clinical trial with a composition described herein.
Figure 3:
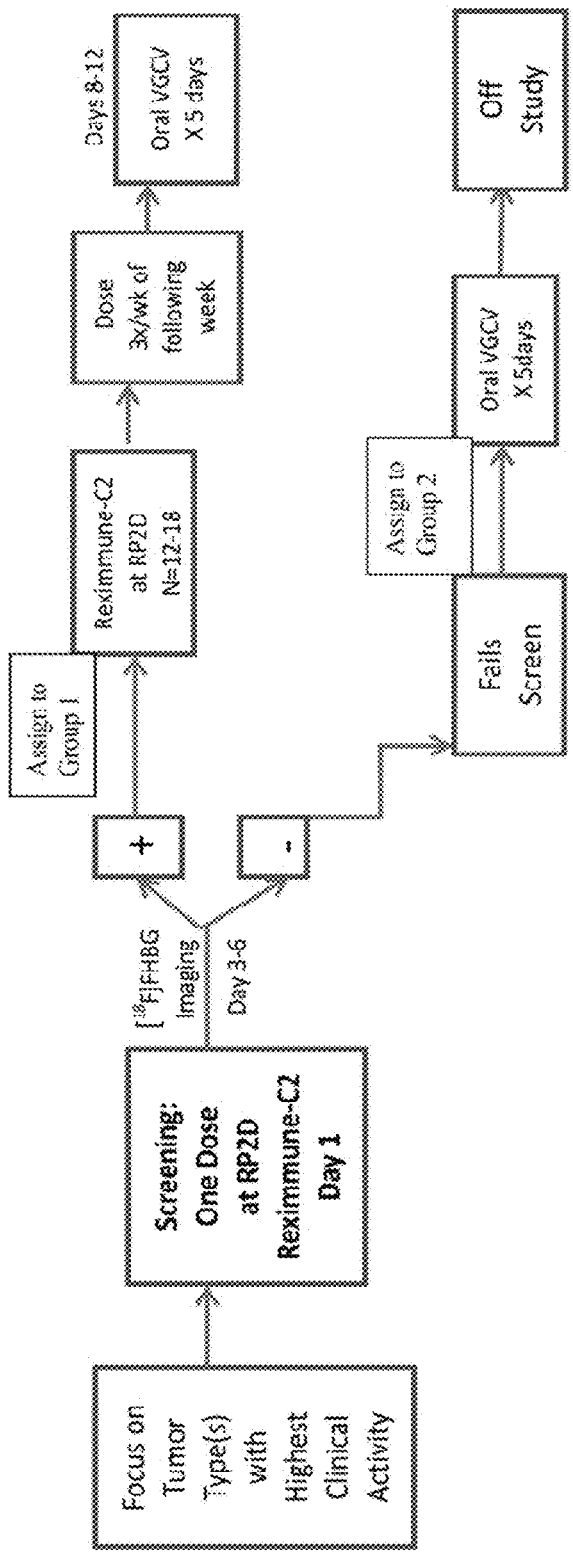
FIG. 3 provides an provides an exemplary schematic for a Phase IB clinical trial with a composition described herein.
Figure 9:
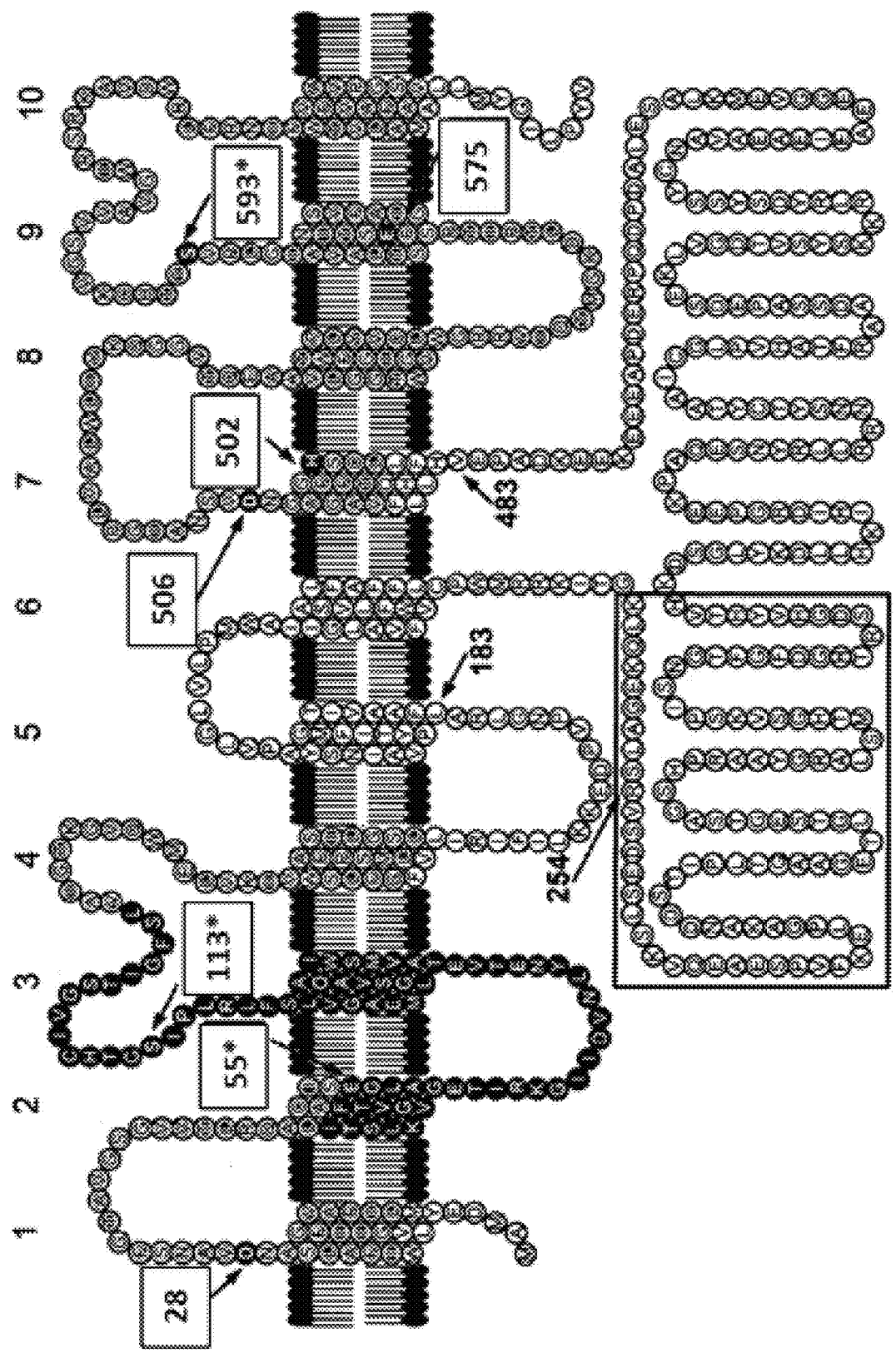
FIG. 9 provides an illustration of a PiT-2 transmembrane molecule (SEQ ID NO: 32). The box represents the approximate location of an Anti-PiT-2 Western antibody binding site.
Figure 10:
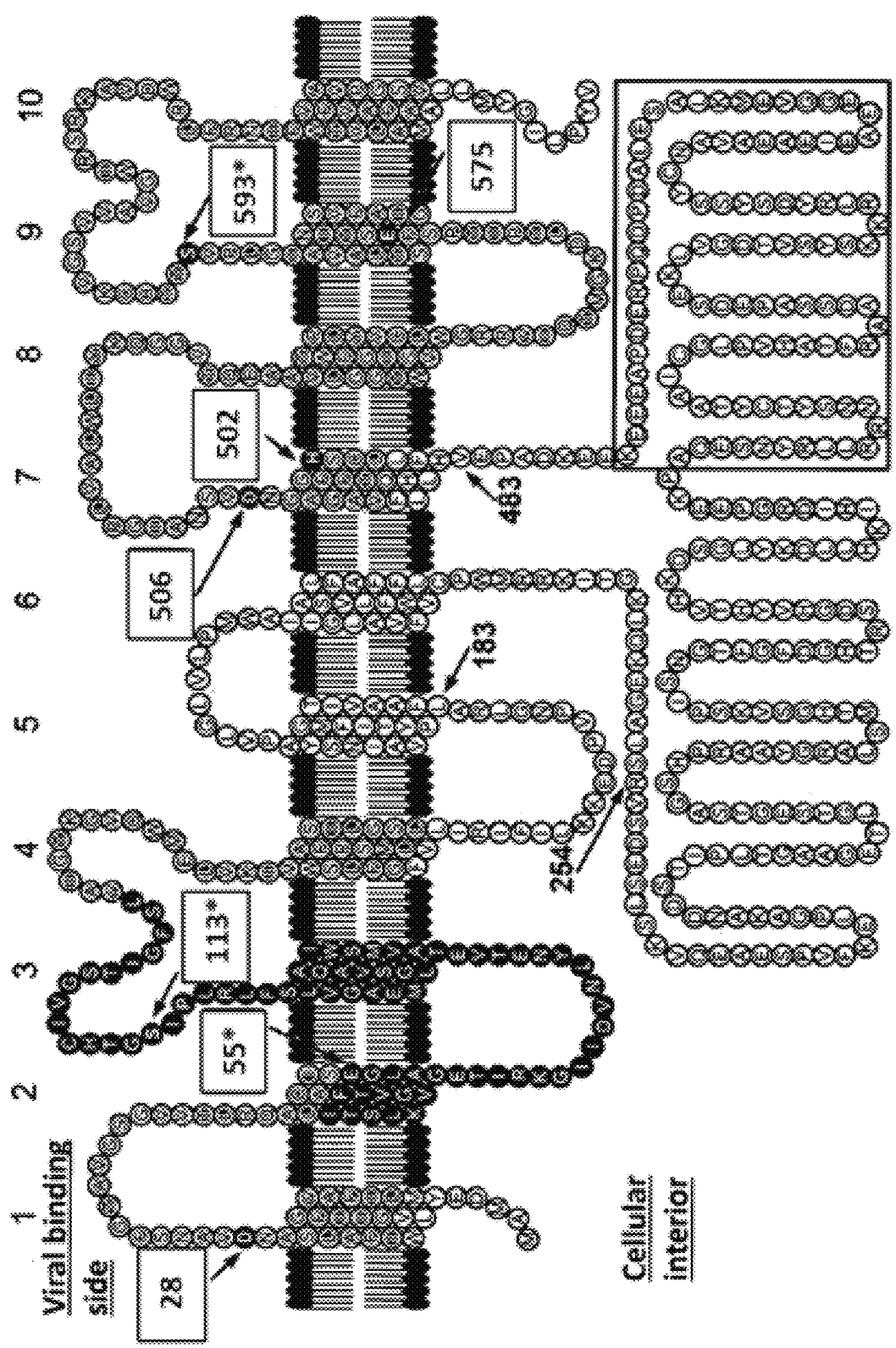
FIG. 10 provides an illustration of a PiT-2 transmembrane molecule (SEQ ID NO: 32). The box represents the approximate location of an Anti-PiT-2 IHC antibody binding site.
Figure 11A:
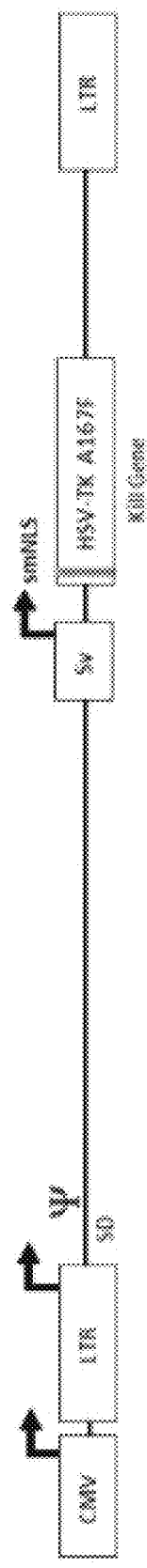
FIG. 11A-FIG. 11F provide exemplary Reximmune constructs with various HSV-TK modifications.
Figure 11B:
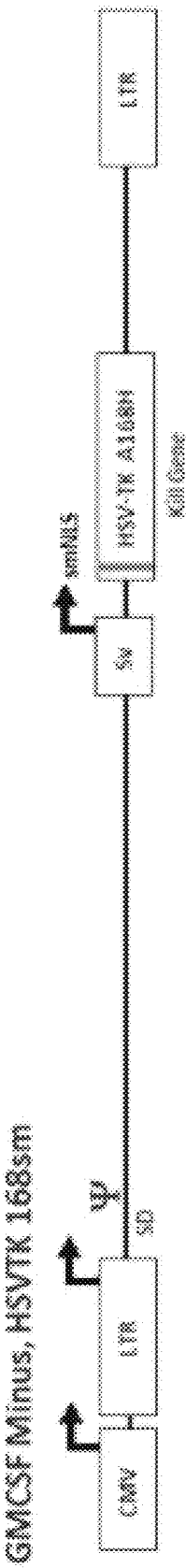
Figure 11C:
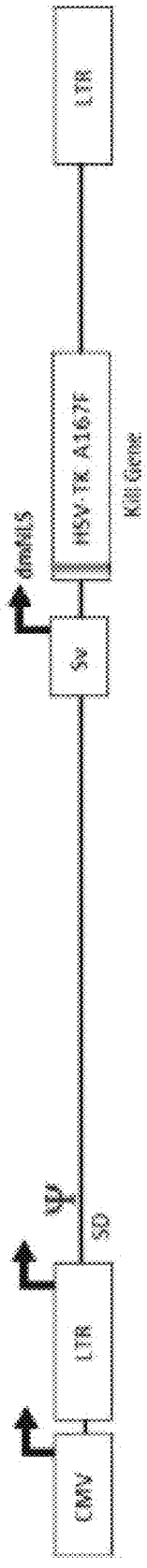
Figure 11D:
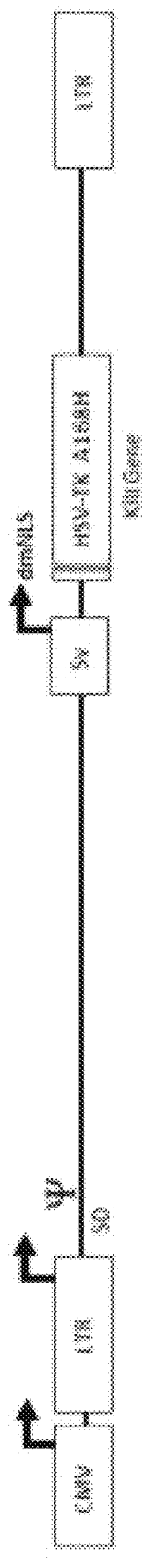
Figure 11E:
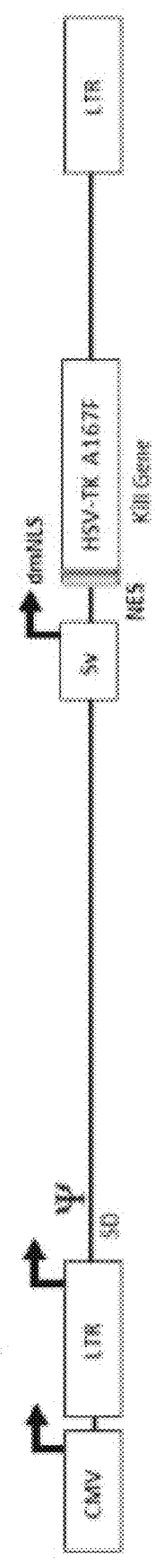
Figure 11F:
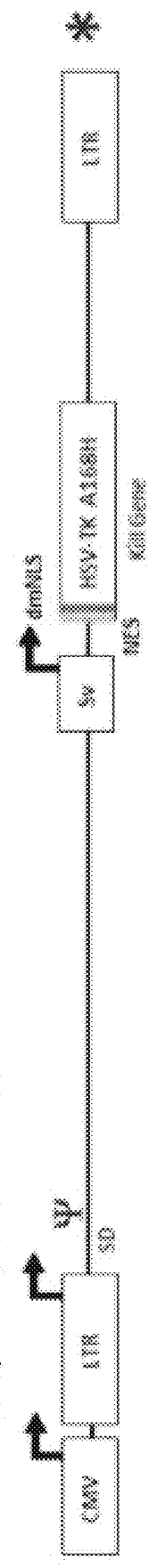
Figure 12:
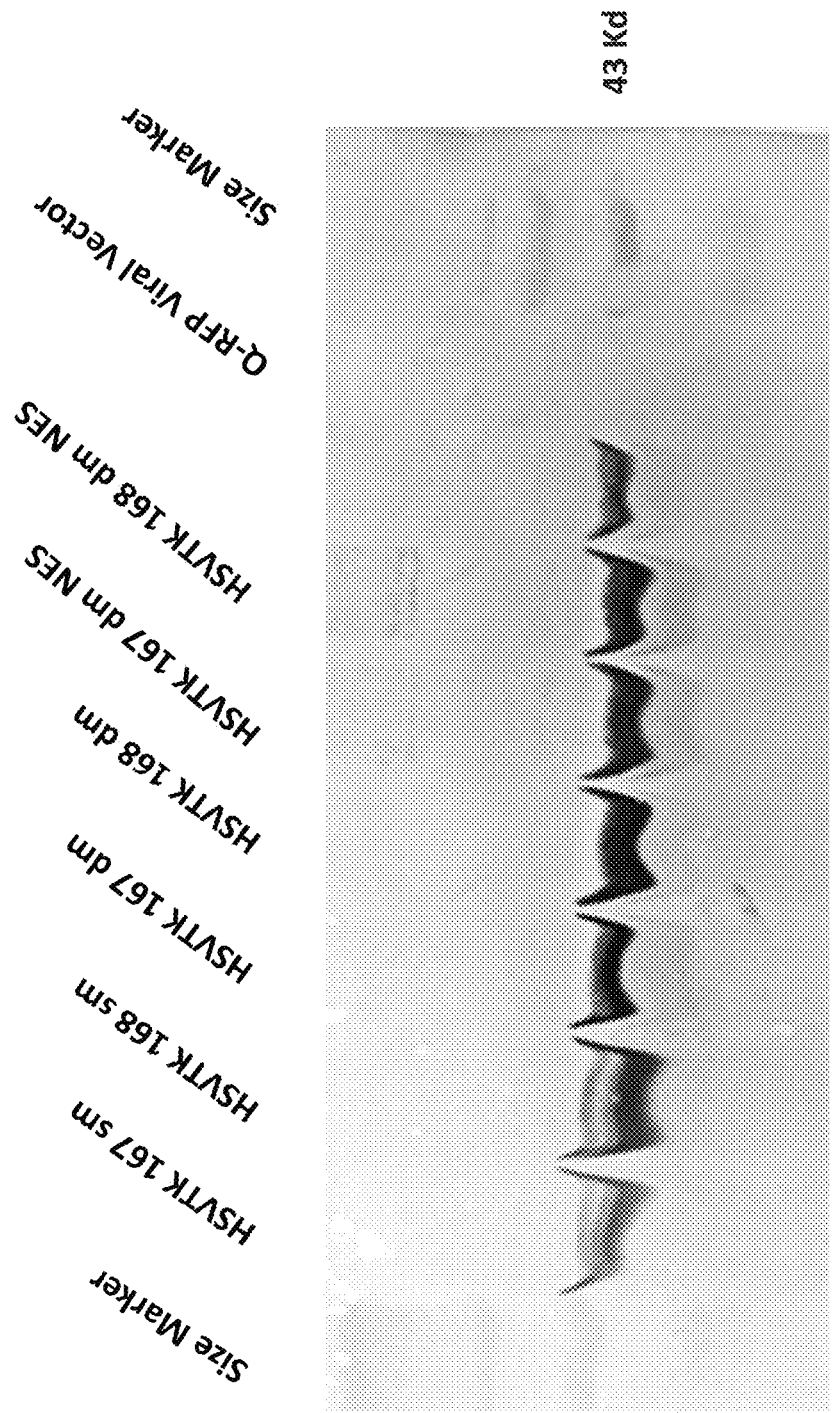
FIG. 12: mHSV-TK, Protein Detection By Western Analysis for the retroviral vectors shown in FIG. 11. Viral DNA was transfected into 293T Vector Producer Cells, the cells were lysed, HSV-TK proteins were detected with an anti-HSV-TK antibody. All of the HSV-TK viral vectors were found to express high levels of HSV-TK protein.
Figure 13A:
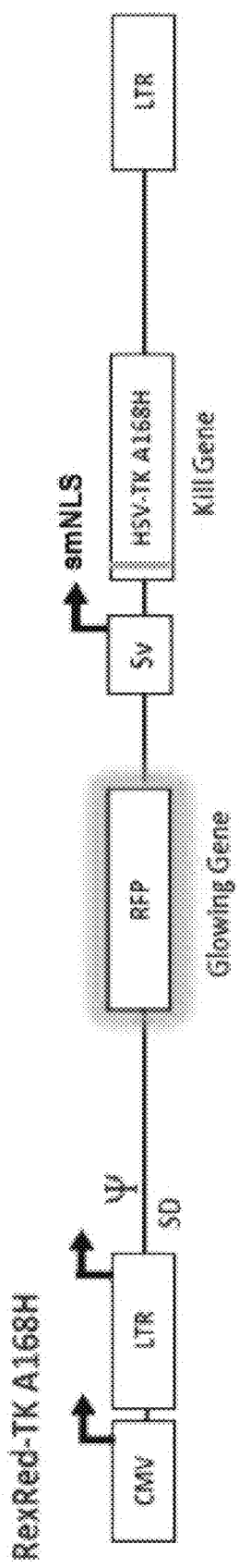
FIG. 13A-FIG. 13C provide exemplary retroviral vectors.
Figure 13B:
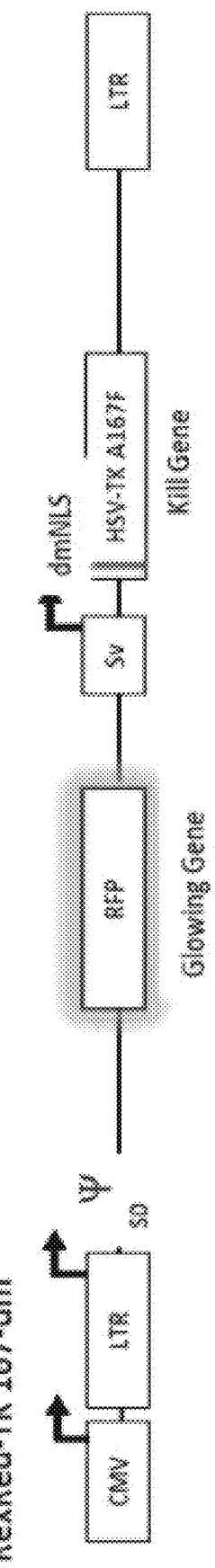
Figure 13C:
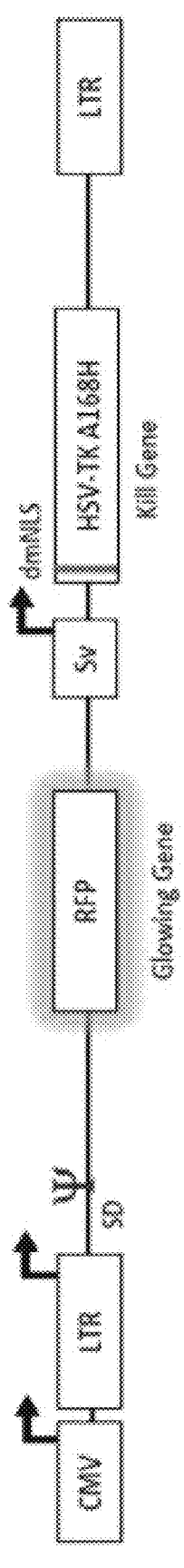
Figure 14A:
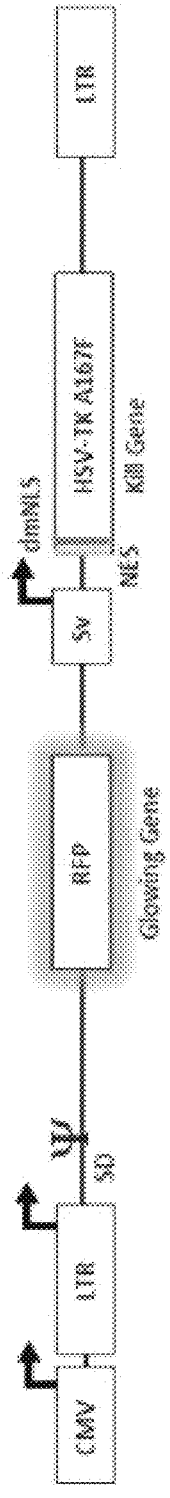
FIG. 14A-FIG. 14D provide additional exemplary retroviral vectors where a particular form of codon optimization was employed.
Figure 14B:
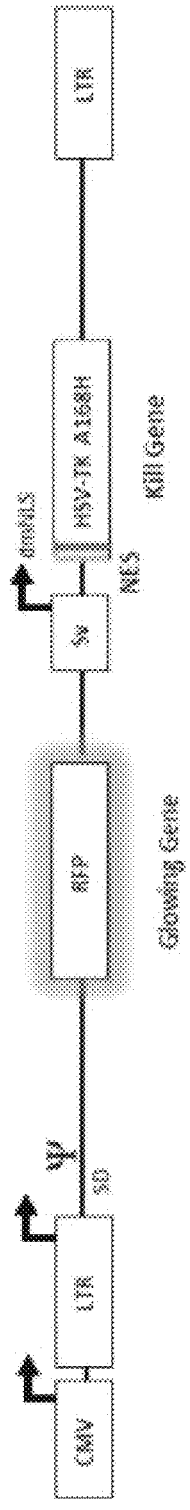
Figure 14C:
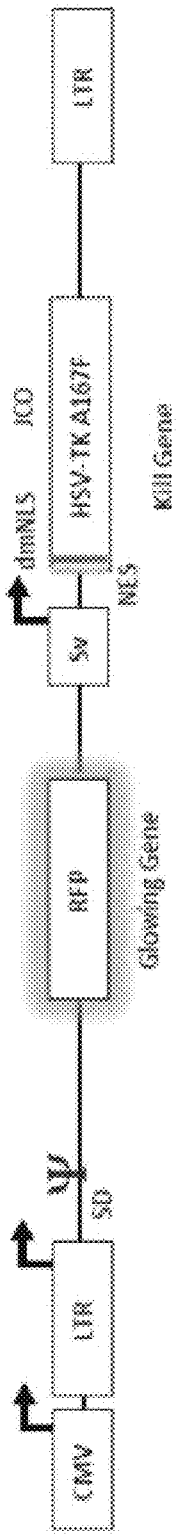
Figure 14D:
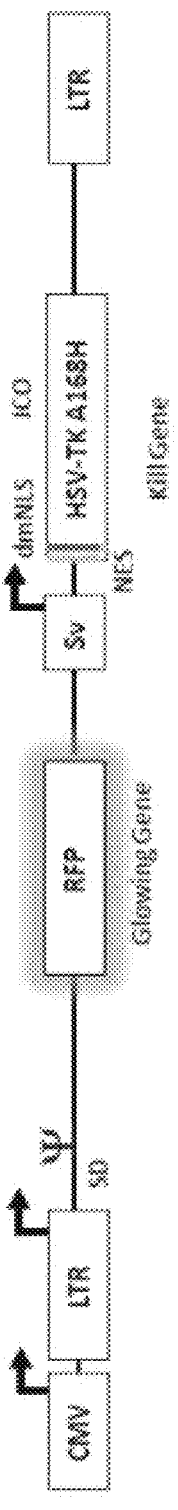
Figure 15A:
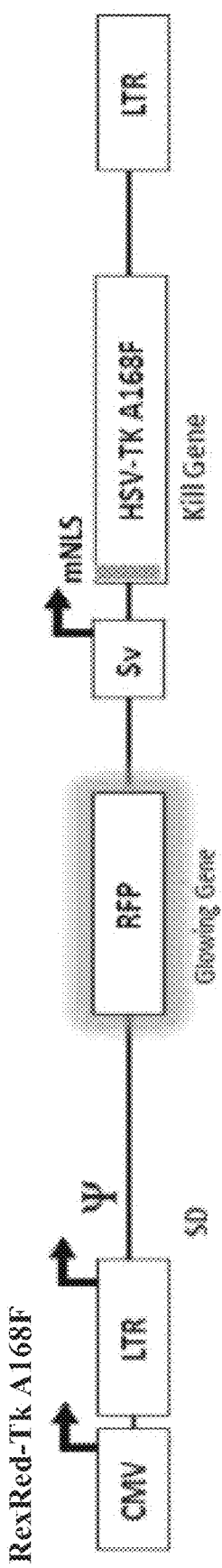
FIG. 15A-FIG. 15C provide additional exemplary retroviral vectors.
Figure 15B:
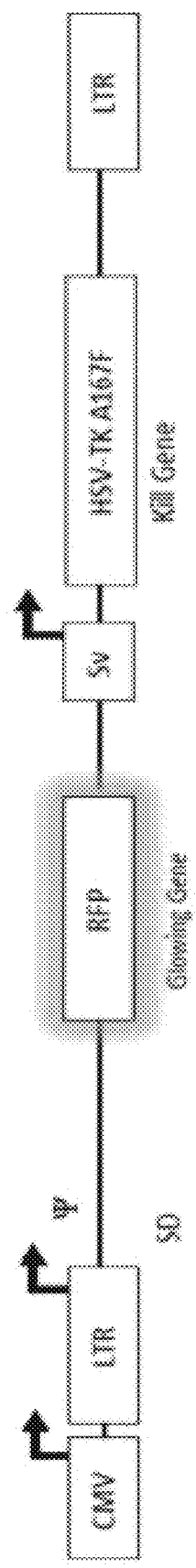
Figure 15C:
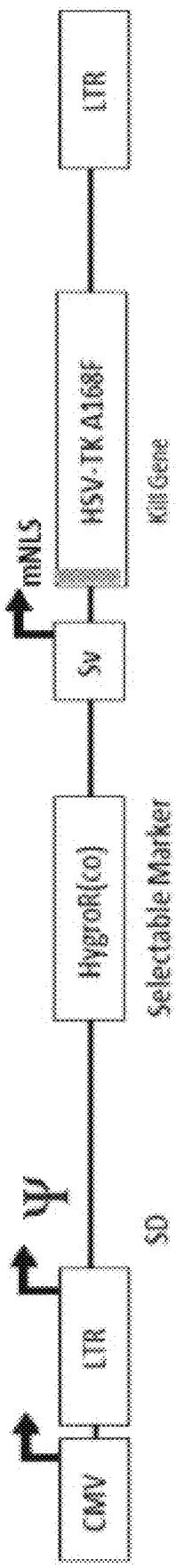
Figure 17A:
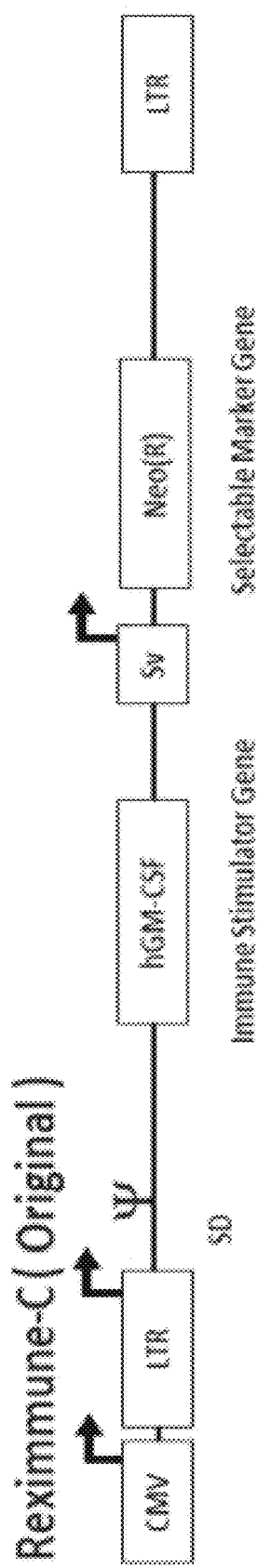
FIG. 17A-FIG. 17B provide additional exemplary retroviral vectors.
Figure 17B:
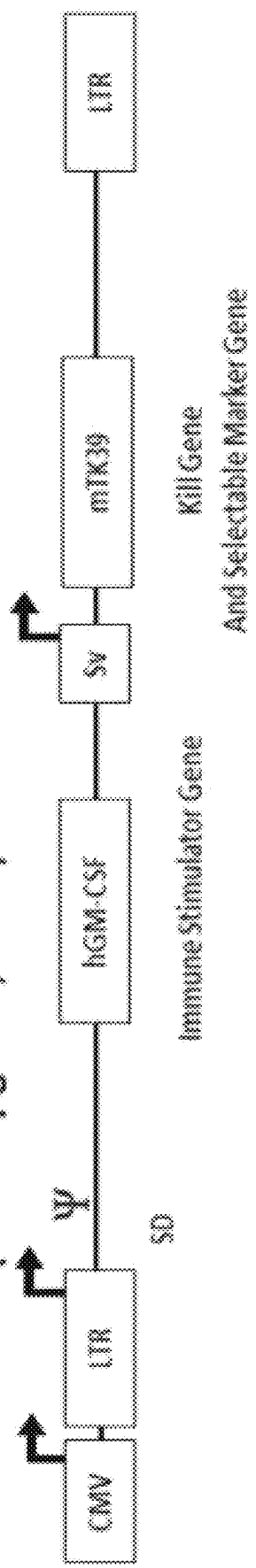
Figure 18:
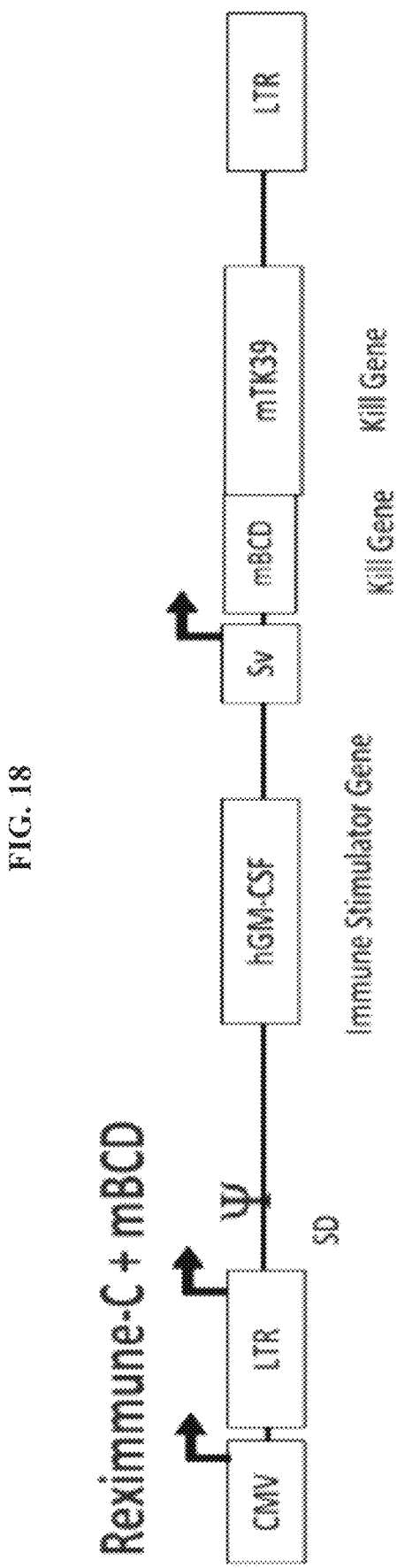
FIG. 18 provides an exemplary of Reximmune-C+a mutated bacterial cytidine deaminase (mBCD) kill gene.

HSV-TK gene therapeutic products are available, but are non-optimal with respect to maximal gene expression and tumor kill activity both in vitro and in vivo including cancer gene therapy.

Disclosed herein for the first time is an optimization of codons within HSV-TK genes to produce improved suicide genes with enhanced pro-drug activation performance in the context of a viral or psuedoviral gene delivery system. The optimized gene delivery system insures both optimal HSV-TK pro-drug enzyme activity and production of high titers of viral particles.

Thus, disclosed herein is the optimization of candidate optimized HSV-TK genes prepared using both bioinformatics software and custom analysis by the present inventors utilizing knowledge of the functions and limitations of the genes and viral vector system.

The following optimization steps represent exemplary methods that were utilized by the present inventors to arrive at the embodiments described herein. Software assisted codon optimization may be utilized to remove rare and low use codons to improve HSV-TK protein expression. The GC content within the newly codon optimized gene may be adjusted to avoid gene synthesis and other problems.

Known splice acceptor and splice donor sequences within HSV-TK may be removed.

Tracts of poly-pyrimidines, particularly those introduced by codon optimization which may be involved in splicing may be removed.

One single strong Kozak translation initiation sequence may be included in front of the start codon (ATG) while possible Kozak sequences within HSV-TK open reading frame may be removed. Some of these sequences may have been introduced by codon optimization and it would be understood that modifications may need to be made in multiple iterations to optimize a gene for improved tumoricidal activity.

Nuclear Localization Sequences (NLSs) within HSV-TK may be removed to export expressed HSV-TK wherein the expressed HSV-TK protein is not localized exclusively to the nucleus, but instead accumulates in the cytoplasm.

Restriction sites flanking HSV-TK gene making it possible to clone the gene into many locations in the disclosed retroviral vectors may be added, while excluding these same restriction sites within the HSV-TK gene itself.

A double stop codon at end of HSV-TK gene may be included to insure complete termination of HSV-TK translation.

Mutations near the substrate binding domain at amino acid locations 159-161 within the HSV-TK gene may be evaluated.

Mutants in the substrate binding domain at amino acid location 167 within the HSV-TK gene may be evaluated for increased enzyme activity towards the pro-drug nucleoside analogue, such as gangciclovir and similar pro-drugs, as well as selectivity for their ability to kill cancer cells.

Mutants in the substrate binding domain at amino acid location 168 within the HSV-TK gene may be evaluated for increased pro-drug GCV enzyme activity and selectivity for their ability to kill cancer cells.

Mutants in the substrate binding domain at amino acid location 167+168 within the HSV-TK gene may be evaluated for increased pro-drug GCV enzyme activity and selectivity for their ability to kill cancer cells.

The use of tags, fusion proteins and linkers of HSV-TK to other genes and proteins may be evaluated.

Further methods of optimization may also be considered for use in the methods described herein. Once a gene is optimized in this way, its gene sequence can be sent to a gene synthesis company for custom gene synthesis.

Definitions

Unless defined otherwise, all technical and scientific terms used herein have the same meaning as is commonly understood by one of skill in the art to which the invention(s) belong. All patents, patent applications, published applications and publications, GenBank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, "nucleic acid" refers to a polynucleotide containing at least two covalently linked nucleotide or nucleotide analog subunits. A nucleic acid is generally a deoxyribonucleic acid (DNA), a ribonucleic acid (RNA), or an analog of DNA or RNA. Nucleotide analogs are commercially available and methods of preparing polynucleotides containing such nucleotide analogs are known (Lin et al. (1994) *Nucl. Acids Res.* 22:5220-5234; Jellinek et al.

(1995) *Biochemistry* 34:11363-11372; Pagratis et al. (1997) *Nature Biotechnol.* 15:68-73). The nucleic acid is generally single-stranded, double-stranded, or a mixture thereof. For purposes herein, unless specified otherwise, the nucleic acid is double-stranded, or it is apparent from the context.

As used herein, "DNA" is meant to include all types and sizes of DNA molecules including cDNA, plasmids and DNA including modified nucleotides and nucleotide analogs.

As used herein, "nucleotides" include nucleoside mono-, di-, and triphosphates. Nucleotides also include modified nucleotides, such as, but are not limited to, phosphorothioate nucleotides and deazapurine nucleotides and other nucleotide analogs.

The term "polynucleotide" as used herein means a polymeric form of nucleotide of any length, and includes ribonucleotides and deoxyribonucleotides. Such term also includes single- and double-stranded DNA, as well as single- and double-stranded RNA. The term also includes modified polynucleotides such as methylated or capped polynucleotides.

As used herein, the term "subject" refers to animals, plants, insects, and birds into which the large DNA molecules are introduced. Included are higher organisms, such as mammals and birds, including humans, primates, rodents, cattle, pigs, rabbits, goats, sheep, mice, rats, guinea pigs, cats, dogs, horses, chicken and others.

As used herein, "administering to a subject" is a procedure by which one or more delivery agents and/or large nucleic acid molecules, together or separately, are introduced into or applied onto a subject such that target cells which are present in the subject are eventually contacted with the agent and/or the large nucleic acid molecules.

As used herein, "delivery vector" or "delivery vehicle" or "therapeutic vector" or "therapeutic system" refers to both viral and non-viral particles that harbor and transport exogenous nucleic acid molecules to a target cell or tissue. Viral vehicles include, but are not limited to, retroviruses, adenoviruses, lentiviral viruses, herpes viruses and adeno-associated viruses. Non-viral vehicles include, but are not limited to, microparticles, nanoparticles, virosomes and liposomes. "Targeted," as used herein, refers to the use of ligands that are associated with the delivery vehicle and target the vehicle to a cell or tissue. Ligands include, but are not limited to, antibodies, receptors and collagen-binding domains.

As used herein, "delivery," which is used interchangeably with "transduction," refers to the process by which exogenous nucleic acid molecules are transferred into a cell such that they are located inside the cell. Delivery of nucleic acids is a distinct process from expression of nucleic acids.

As used herein, a "multiple cloning site (MCS)" is a nucleic acid region in a plasmid that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector.

As used herein, "origin of replication" (often termed "ori"), is a specific nucleic acid sequence at which replication is initiated. Alternatively an autonomously replicating sequence (ARS) can be employed if the host cell is yeast.

As used herein, "selectable or screenable markers" confer an identifiable change to a cell permitting easy identification of cells containing an expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. In some embodiments, screenable enzymes such as herpes simplex virus thymidine kinase (tk) or chloramphenicol acetyltransferase (CAT) are utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

As used herein, "expression" refers to the process by which nucleic acid is translated into peptides or is transcribed into RNA, which, for example, can be translated into peptides, polypeptides or proteins. If the nucleic acid is derived from genomic DNA, expression includes, if an appropriate eukaryotic host cell or organism is selected, splicing of the mRNA. For heterologous nucleic acid to be expressed in a host cell, it must initially be delivered into the cell and then, once in the cell, ultimately reside in the nucleus.

As used herein, a "therapeutic course" refers to the periodic or timed administration of the vectors disclosed herein within a defined period of time. Such a period of time is at least one day, at least two days, at least three days, at least five days, at least one week, at least two weeks, at least three weeks, at least one month, at least two months, or at least six months. Administration could also take place in a chronic manner, i.e., for an undefined period of time. The periodic or timed administration includes once a day, twice a day, three times a day or other set timed administration.

As used herein, the terms "co-administration," "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments, a therapeutic agent as disclosed in the present application will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, a therapeutic agent and the other agent(s) are administered in a single composition. In some embodiments, a therapeutic agent and the other agent(s) are admixed in the composition. In further embodiments, a therapeutic agent and the other agent(s) are administered at separate times in separate doses.

The term "host cell" denotes, for example, microorganisms, yeast cells, insect cells, and mammalian cells, that can be, or have been, used as recipients for multiple constructs for producing a delivery vector. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, "genetic therapy" involves the transfer of heterologous DNA to the certain cells, target cells, of a mammal, particularly a human, with a disorder or conditions for which therapy or diagnosis is sought. The DNA is introduced into the selected target cells in a manner such that the heterologous DNA is expressed and a therapeutic product encoded thereby is produced. In some embodiments, the heterologous DNA, directly or indirectly, mediates expression of DNA that encodes the therapeutic product. In some embodiments, the heterologous DNA encodes a product, such as a peptide or RNA that mediates, directly or indirectly, expression of a therapeutic product. In some embodiments, genetic therapy is used to deliver a nucleic acid encoding a gene product to replace a defective gene or supplement a gene product produced by the mammal or the cell in which it is introduced. In some embodiments, the introduced nucleic acid encodes a therapeutic compound, such as a growth factor or inhibitor thereof, or a tumor necrosis factor or inhibitor thereof, such as a receptor therefore, that is not generally produced in the mammalian host or that is not produced in therapeutically effective amounts or at a therapeutically useful time. In some embodiments, the heterologous DNA encoding the therapeutic product is modified prior to introduction into the cells of the afflicted host in order to enhance or otherwise alter the product or expression thereof.

As used herein, "heterologous nucleic acid sequence" is generally DNA that encodes RNA and proteins that are not normally produced in vivo by the cell in which it is expressed or that mediates or encodes mediators that alter expression of endogenous DNA by affecting transcription, translation, or other regulatable biochemical processes. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. In some embodiments, antibodies that are encoded by heterologous DNA is secreted or expressed on the surface of the cell in which the heterologous DNA has been introduced.

As used herein, the term "thymidine kinase mutant" refers to not only the specific protein described herein (as well as the nucleic acid sequences which encode these proteins), but derivatives thereof which may include various structural forms of the primary protein which retain biological activity.

As used herein, "unmutated thymidine kinase" refers to a native or wild-type thymidine kinase polypeptide sequence.

As used herein, "suicide gene" refers to a nucleic acid encoding a product, wherein the product causes cell death by itself or in the present of other compounds.

As used herein, the term "mutated" or "replaced by another nucleotide" means a nucleotide at a certain position is replaced at that position by a nucleotide other than that which occurs in the unmutated or previously mutated sequence. That is, in some instances, specific modifications may be made in different nucleotides. In some embodiments, the replacements are made such that the relevant splice donor and/or acceptor sites are no longer present in a gene. See, e.g., FIG. 1.

As used herein, a "polar amino acid" refers to amino acid residues Asp(N), Cys (C), Gln (Q), Gly (G), Ser (S), Thr (T) or Tyr (Y).

As used herein, a "non-polar amino acid" refers to amino acid residues Ala (A), Ile (I), Leu (L), Met (M), Phe (F), Pro (P), Trp (W), or Val (V).

As used herein, a "basic amino acid" refers to amino acid residues Arg (R), His (H), or Lys (K).

As used herein, an "acidic amino acid" refers to amino acid residues Asp (D) or Glu (E).

Improved HSV-TK

Thymidine kinase is a salvage pathway enzyme which phosphorylates natural nucleoside substrates as well as nucleoside analogues. Generally, viral thymidine kinase is exploited therapeutically by administration of a nucleoside analogue such as ganciclovir or acyclovir to a cell expressing viral thymidine kinase, wherein the viral thymidine kinase phosphorylates the nucleoside analogue, creating a toxic product capable of killing the cell.

Polynucleotide sequences encoding viral thymidine kinase of the present invention may be prepared from a wide variety of viral thymidine kinases. In some embodiments, the viral thymidine kinase mutant is derived from Herpesviridae thymidine kinase including, for example, both primate herpes viruses, and non-primate herpes viruses such as avian herpes viruses. Representative examples of suitable herpes viruses include, for example, Herpes Simplex Virus (HSV) Type 1, Herpes Simplex Virus Type 2, Varicella zoster Virus, marmoset herpes virus, feline herpes virus type 1, pseudorabies virus, equine herpes virus type 1, bovine herpes virus type 1, turkey herpes virus, Marek's disease virus, herpes virus saimir and Epstein-Barr virus.

Herpes viruses may be readily obtained from commercial sources such as the American Type Culture Collection ("ATCC", Rockville, Md.). Herpesviruses may also be isolated from naturally occurring courses (e.g., an infected animal).

Improvements to TK Gene

Disclosed herein, in some embodiments, is a polynucleotide sequence encoding HSV-TK. In some embodiments, the polynucleotide sequence encodes a wild-type HSV-TK amino acid sequence. In some embodiments, the polynucleotide sequence encodes a mutated HSV-TK amino acid sequence.

Exemplary procedures that may be used in preparation of an optimized polynucleotide sequence provided herein include, but are not limited to: codon optimization; correction of splice sites, removal of poly-pyrimidine tracts and excess GC content; addition of single Kozak sequence, removal of unwanted Kozak sequences; inclusion of restriction sites for subcloning into retroviral or other vectors; removal of nuclear localization sequences or addition of nuclear export sequences; addition of mutation sequences; addition of double stop codon sequences; addition of tags, linkers and fusion sequences; preparation of sequence file for submission to gene synthesis company; subcloning of synthesized gene into retroviral vectors; inclusion of fluorescent protein genes into retroviral vectors; inclusion of selectable marker genes into retroviral vectors; preparation of Maxiprep plasmid DNA; transfection of retroviral producer or other cells; lab, pilot or GMP scale production of retrovirus; transduction of target cells with retrovirus; GCV or analogus pro-drug mediated cell kill assay; Hypoxanthine/Aminopterin/Thymidine (HAT) selection assay; selectable marker drug selection procedure to produce retroviral transduced cell lines; fluorescent microscopy and photography to detect and document retroviral transduced target cells; quantitative fluorescent detection of retroviral transduced target cells; Western protein expression assay; other procedures and assays as needed for HSV-TK analysis; or a combination thereof. Protocols for such methods are described herein, are commercially available or are described in the public literature and databases.

In some embodiments, described herein is a method of obtaining an improved HSV-TK sequence. In some embodiments, the method comprises: a) correction and/or removal of splice sites; and/or b) adjustment to a single Kozak sequence. Optionally, in some embodiments, the method further comprises inclusion of restriction sites for subcloning of the HSV-TK sequence. Optionally, or in addition, in some embodiments, the method further comprises removal of nuclear localization sequences.

Provided herein is a polynucleotide sequence encoding a mutated form of thymidine kinase from human simplex virus (HSV-TK), wherein the encoded HSV-TK is mutated at amino acid residue 25, 26, 32, 33, 167, 168, or a combination thereof, wherein the polynucleotide sequence is mutated compared to a polynucleotide sequence of SEQ ID NO: 1 or 3. In such sequences, 1, 2, 3, 4, 5, 6, 7, 8, 9, 10, 11, 12, 13, or 14 mutations may be made.

Provided herein is a polynucleotide sequence encoding a mutated form of thymidine kinase from human simplex virus (HSV-TK), wherein the encoded HSV-TK is mutated at amino acid residue 25, 26, 32, 33, 167, 168, or a combination thereof, wherein the polynucleotide sequence is mutated compared to a polynucleotide sequence of SEQ ID NO: 1. In such sequences, 1, 2, 3, 4, 5, 6, 7, 8, 9, 10, 11, 12, 13, or 14 mutations may be made.

Provided herein is a polynucleotide sequence encoding a mutated form of thymidine kinase from human simplex virus (HSV-TK), wherein the encoded HSV-TK is mutated at amino acid residue 25, 26, 32, 33, 167, 168, or a combination thereof, wherein the polynucleotide sequence is mutated compared to a polynucleotide sequence of SEQ ID NO: 3. In such sequences, 1, 2, 3, 4, 5, 6, 7, 8, 9, 10, 11, 12, 13, or 14 mutations may be made.

Modifications may be conservative or non-conservative mutations. A mutation may be made such that the encoded amino acid is modified to a polar, non-polar, basic or acidic amino acid.

Provided herein is a polynucleotide sequence encoding a mutated form of viral thymidine kinase from human simplex virus (HSV-TK), wherein the encoded HSV-TK includes a nuclear export sequence. Provided herein is a polynucleotide sequence encoding a mutated form of thymidine kinase from human simplex virus (HSV-TK), where the encoded HSV-TK is improved in function compared to wild-type HSV-TK and comprises A168H dmNES (CL system-CMV enhancer properly fused to LTR promoter regions), where NES refers to a nuclear export sequence. In one embodiment, a mutant HSV-TKA168HdmNES is a mutant HSV-TK gene for inclusion in Reximmune-C2. In one embodiment, the NES is derived from MAP Kinase Kinase (MAPKK). In yet another embodiment, the polynucleotide sequence for NES is CTGCAGAAAAAGCTGGAAGAGCTGGAACTG-GATGGC (SEQ ID NO: 23). In other embodiments, the NES polypeptide sequence is LQKKLEELELDG (SEQ ID NO: 24).

In some embodiments, disclosed herein are mutations to a polynucleotide sequence encoding Human Simplex Virus Thymidine Kinase (HSV-TK) wherein mutations are not made to the polypeptide sequence of wildtype HSV-TK.

Nucleotide positions are referred to by reference to a position in SEQ ID NO: 1 (wildtype (wt) HSV1-TK nucleotide sequence) or SEQ ID NO: 3 (HSV-TK in Reximmune-C HSV-TK; SR39 mutant and R25G-R26S Mutation of the HSV-TK nuclear localization signal (NLS)).

In one embodiment, a Sac I-Kpn I restriction sites bounding the clonable double stranded oligonucleotides of the mutant HSV-TK SR39 mutant region is provided. See, for example, SEQ ID NOS: 6 and 7, where the Sac I and Kpn I sites are shown on the left and right, respectively. Bold, underlining illustrates the sites where mutations may be made. SEQ ID NOS: 8 and 9 illustrate an exemplary sequence after cutting with Sac I and Kpn I. Exemplary forward and reverse primers that may be used to make the mutations are shown as SEQ ID NOS: 10 and 11.

Exemplary optimized HSV-TK polynucleotide sequences are provided, for example, as SEQ ID NOS: 12-24.

However, when such references are made, the invention is not intended to be limited to the exact sequence as set out in SEQ ID NO: 1 or 3, but includes variants and derivatives thereof. Thus, identification of nucleotide locations in other thymidine kinase sequences are contemplated (i.e., identification of nucleotides at positions which the skilled person would consider to correspond to positions recited in SEQ ID NO: 1 or 3).

In some embodiments, nucleotides are replaced by taking note of the genetic code such that a codon is changed to a different codon which codes for the same amino acid residue. In some embodiments, nucleotides are replaced within coding regions of a HSV-TK encoding nucleic acid sequence, yet the nucleic acid sequence maintains wild type HSV-TK protein expression.

In some embodiments, codons are mutated to such that the encoded HSV-TK exhibits increased activity. In some embodiments, the codon GCT is used to represent alanine. In some embodiments, the codon AGA is used to represent arginine. In some embodiments, the codon AAT is used to represent asparagine. In some embodiments, the codon GAT is used to represent aspartic acid. In some embodiments, the codon TGT is used to represent cysteine. In some embodiments, the codon CAG is used to represent glutamine. In some embodiments, the codon GAA is used to represent glutamic acid. In some embodiments, the codon GGA is used to represent glycine. In some embodiments, the codon CAT is used to represent histidine. In some embodiments, the codon ATT is used to represent isoleucine. In some embodiments, the codon CTG is used to represent leucine. In some embodiments, the codon AAA is used to represent lysine. In some embodiments, the codon ATG is used to represent methionine. In some embodiments, the codon TTT is used to represent phenylalanine. In some embodiments, the codon CCT is used to represent proline. In some embodiments, the codon TCT is used to represent serine. In some embodiments, the codon ACA is used to represent threonine. In some embodiments, the codon TGG Is used to represent tryptophan. In some embodiments, the codon TAT is used to represent tyrosine. In some embodiments, the codon GTG is used to represent valine. In some embodiments, the codon TGA is used as a stop codon. Exemplary codon positions for mutation are provided in the following table.

Improved Codon Usage for Designing Human Genes, First Choice Codon Optimization which Reduces G/C content

|   | Amino Acid | Codon |
|---|---|---|
| 1 | Alanine (Ala) (A) | GCT |
| 2 | Arginine (Arg) (R) | AGA |
| 3 | Asparagine (Asp) (N) | AAT |
| 4 | Aspartic Acid (Asp) (D) | GAT |
| 5 | Cysteine (Cys) (C) | TGT |
| 6 | Glutamine (Gln) (Q) | CAG |
| 7 | Glutamic Acid (Glu) (E) | GAA |
| 8 | Glycine (Gly) (G) | GGA |
| 9 | Histidine (His) (H) | CAT |
| 10 | Isoleucine (Ile) (I) | ATT |
| 11 | Leucine (Leu) (L) | CTG |
| 12 | Lysine (Lys) (K) | AAA |
| 13 | Methionine (Met) (M) | ATG |
| 14 | Phenylalanine (Phe) (F) | TTT |
| 15 | Proline (Pro) (P) | CCT |
| 16 | Serine (Ser) (S) | TCT |
| 17 | Threonine (Thr) (T) | ACA |
| 18 | Tryptophan (Trp) (W) | TGG |
| 19 | Tyrosine (Tyr) (Y) | TAT |
| 20 | Valine (Val) (V) | GTG |
| 21 | Stop (Term) (*) | TGA |

In such embodiments, 5/21 codons contain "C or G" in third position (24%); 0/21 codons contain "C" in third position (0%); 5/21 codons contain "G" in third position (24%); and 16/21 codons contain "A or T" in third position (76%).

In yet other embodiments, about 3-7 codons of 21 codons contain "C or G" in the third position; above 0-3 codons of 21 codons contain "C" in the third position; about 3-7 codons of 21 codons contain "G" in the third position; and about 14-18 codons of 21 codons contain "A or T" in the third position.

In some embodiments, the codon GCA is used to represent alanine. In some embodiments, the codon AGG is used to represent arginine. In some embodiments, the codon AAC is used to represent asparagine. In some embodiments, the codon GAC is used to represent aspartic acid. In some embodiments, the codon TGC is used to represent cysteine. In some embodiments, the codon CAA is used to represent glutamine. In some embodiments, the codon GAG is used to represent glutamic acid. In some embodiments, the codon GGC is used to represent glycine. In some embodiments, the codon CAC is used to represent histidine. In some embodiments, the codon ATC is used to represent isoleucine. In some embodiments, the codon CTC is used to represent leucine. In some embodiments, the codon AAG is used to represent lysine. In some embodiments, the codon ATG is used to represent methionine. In some embodiments, the codon TTC is used to represent phenylalanine. In some embodiments, the codon CCA is used to represent proline. In some embodiments, the codon AGC is used to represent serine. In some embodiments, the codon ACT is used to represent threonine. In some embodiments, the codon TGG is used to represent tryptophan. In some embodiments, the codon TAC is used to represent tyrosine. In some embodiments, the codon GTC is used to represent valine. In some embodiments, TAA is used as a stop codon.

Improved Codon Usage for Designing Human Genes, 2nd Choice Codon Optimization which Reduces G/C content

|   | Amino Acid | Codon |
|---|---|---|
| 1 | Alanine (Ala) (A) | GCA |
| 2 | Arginine (Arg) (R) | AGG |
| 3 | Asparagine (Asp) (N) | AAC |
| 4 | Aspartic Acid (Asp) (D) | GAC |
| 5 | Cysteine (Cys) (C) | TGC |
| 6 | Glutamine (Gln) (Q) | CAA |
| 7 | Glutamic Acid (Glu) (E) | GAG |
| 8 | Glycine (Gly) (G) | GGC |
| 9 | Histidine (His) (H) | CAC |
| 10 | Isoleucine (Ile) (I) | ATC |
| 11 | Leucine (Leu) (L) | CTC |
| 12 | Lysine (Lys) (K) | AAG |
| 13 | Methionine (Met) (M) | ATG |
| 14 | Phenylalanine (Phe) (F) | TTC |
| 15 | Proline (Pro) (P) | CCA |
| 16 | Serine (Ser) (S) | AGC |
| 17 | Threonine (Thr) (T) | ACT |
| 18 | Tryptophan (Trp) (W) | TGG |
| 19 | Tyrosine (Tyr) (Y) | TAC |
| 20 | Valine (Val) (V) | GTC |
| 21 | Stop (Term) (*) | TAA |

In such embodiments, 16/21 codons contain "C or G" in third position (76%); 11/21 codons contain "C" in third position (52%); 5/21 codons contain "G" in third position (24%); and 5/21 codons contain "A or T" in third position (24%).

In yet other embodiments, about 14-18 codons of 21 codons contain "C or G" in the third position; about 9-13 codons of 21 codons contain "C" in the third position; about 3-7 codons of 21 codons contain "G" in the third position; and about 3-7 codons of 21 codons contain "A or T" in the third position.

In some embodiments, the following rare codons are are avoided if possible, unless changing the rare codon sequence creates new splice acceptor and/or alternate Kozak sites or adds an unwanted restriction site or other problematic sequence, within the coding region of a polynucleotide encoding mutant HSV-TK, or a variant thereof: GCG for alanine; CGA or CGT for arginine; TTA or CTA for leucine; CCG for proline; TCG for serine; ACG for threonine; and GTA for valine. Rare codons to be avoided if possible are those that have a codon/a.a./fraction per codon per a.a. less than or equal to 0.12.

| Rare Codon | | | |
|---|---|---|---|
| UUU F 0.46 | UCU S 0.19 | UAU Y 0.44 | UGU C 0.46 |
| UUC F 0.54 | UCC S 0.22 | UAC Y 0.56 | UGC C 0.54 |
| UUA L 0.08 | UCA S 0.15 | UAA * 0.30 | UGA * 0.47 |
| UUG L 0.13 | UCG S 0.05 | UAG * 0.24 | UGG W 1.00 |

| Rare Codon | | | |
|---|---|---|---|
| CUU L 0.13 | CCU P 0.29 | CAU H 0.42 | CGU R 0.08 |
| CUC L 0.20 | CCC P 0.32 | CAC H 0.58 | CGC R 0.18 |
| CUA L 0.07 | CCA P 0.28 | CAA Q 0.27 | CGA R 0.11 |
| CUG L 0.40 | CCG P 0.11 | CAG Q 0.73 | CGG R 0.20 |
| AUU I 0.36 | ACU T 0.25 | AAU N 0.47 | AGU S 0.15 |
| AUC I 0.47 | ACC T 0.36 | AAC N 0.53 | AGC S 0.24 |
| AUA I 0.17 | ACA T 0.28 | AAA K 0.43 | AGA R 0.21 |
| AUG M 1.00 | ACG T 0.11 | AAG K 0.57 | AGG R 0.21 |
| GUU V 0.18 | GCU A 0.27 | GAU D 0.46 | GGU G 0.16 |
| GUC V 0.24 | GCC A 0.40 | GAC D 0.54 | GGC G 0.34 |
| GUA V 0.12 | GCA A 0.23 | GAA E 0.42 | GGA G 0.25 |
| GUG V 0.46 | GCG A 0.11 | GAG E 0.58 | GGG G 0.25 |

[Codon/a.a./fraction per codon per a.a.]
Homo sapiens data from the Codon Usage Database In some embodiments, altering codons as described herein results in about 2%, about 5%, about 10%, about 15%, about 20%, about 25%, about 30%, about 35%, about 40%, about 45%, about 50%, about 55%, about 60%, about 70%, about 75%, about 80%, about 85%, about 90%, about 95%, or greater percentage increase in activity.

High percentage Codon Optimization was found to improve protein expression but increases GC gene content. Codon optimization was assessed and determined to have the following characteristics.

| Amino Acid | Codon | H. Sapien Frequency | Order by Freq. | Order by not GC 3rd base | Order by both previous |
|---|---|---|---|---|---|
| Methonine (Met) (M) | ATG | 1 | 1 | 1 | 1 |
| Tryptophan (Trp) (W) | TGG | 1 | 1 | 1 | 1 |
| Asparagine (Asn) (N) | AAT | 0.47 | 2 | 1 | 1 |
| Asparagine (Asn) (N) | AAC | 0.53 | 1 | 2 | 2 |
| Aspartic Acid (Asp) (D) | GAT | 0.46 | 2 | 1 | 1 |
| Aspartic Acid (Asp) (D) | GAC | 0.54 | 1 | 2 | 2 |
| Cysteine (Cys) (C) | TGT | 0.46 | 2 | 1 | 1 |
| Cysteine (Cys) (C) | TGC | 0.54 | 1 | 2 | 2 |
| Glutamic Acid (Glu) (E) | GAA | 0.42 | 2 | 1 | 1 |
| Glutamic Acid (Glu) (E) | GAG | 0.58 | 1 | 2 | 2 |
| Glutamine (Gln) (Q) | CAG | 0.73 | 1 | 2 | 1 |
| Glutamine (Gln) (Q) | CAA | 0.27 | 2 | 1 | 2 |
| Histidine (His) (H) | CAT | 0.42 | 2 | 1 | 1 |
| Histidine (His) (H) | CAC | 0.58 | 1 | 2 | 2 |
| Lysine (Lys) (K) | AAA | 0.43 | 2 | 1 | 1 |
| Lysine (Lys) (K) | AAG | 0.57 | 1 | 2 | 2 |
| Phenylalanine (Phe) (F) | TTT | 0.46 | 2 | 1 | 1 |
| Phenylalanine (Phe) (F) | TTC | 0.54 | 1 | 2 | 2 |
| Tyrosine (Tyr) (Y) | TAT | 0.44 | 2 | 1 | 1 |
| Tyrosine (Tyr) (Y) | TAC | 0.56 | 1 | 2 | 2 |
| Alanine (Ala) (A) | GCT | 0.27 | 2 | 1 | 1 |
| Alanine (Ala) (A) | GCA | 0.23 | 3 | 2 | 2 |
| Alanine (Ala) (A) | GCC | 0.4 | 1 | 3 | 3 |
| Isoluecine (Ile) (I) | ATT | 0.36 | 2 | 1 | 1 |
| Isoluecine (Ile) (I) | ATC | 0.47 | 1 | 3 | 2 |
| Isoluecine (Ile) (I) | ATA | 0.17 | 3 | 2 | 3 |
| Proline (Pro) (P) | CCT | 0.29 | 2 | 1 | 1 |
| Proline (Pro) (P) | CCA | 0.28 | 3 | 2 | 2 |
| Proline (Pro) (P) | CCC | 0.32 | 1 | 3 | 3 |
| Stop (Term) (*) | TGA | 0.47 | 1 | 1 | 1 |
| Stop (Term) (*) | TAA | 0.3 | 2 | 2 | 2 |
| Stop (Term) (*) | TAG | 0.24 | 3 | 3 | 3 |
| Threonine (Thr) (T) | ACA | 0.28 | 2 | 1 | 1 |
| Threonine (Thr) (T) | ACT | 0.25 | 3 | 2 | 2 |
| Threonine (Thr) (T) | ACC | 0.36 | 1 | 3 | 3 |
| Valine (Val) (V) | GTG | 0.46 | 1 | 2 | 1 |
| Valine (Val) (V) | GTC | 0.24 | 2 | 3 | 2 |
| Valine (Val) (V) | GTT | 0.18 | 3 | 1 | 3 |
| Arginine (Arg) (R) | AGA | 0.21 | 1 | 1 | 1 |
| Arginine (Arg) (R) | AGG | 0.21 | 1 | 2 | 2 |
| Arginine (Arg) (R) | CGG | 0.2 | 2 | 3 | 3 |
| Arginine (Arg) (R) | CGC | 0.18 | 3 | 4 | 4 |
| Glycine (Gly) (G) | GGA | 0.25 | 2 | 1 | 1 |
| Glycine (Gly) (G) | GGC | 0.34 | 1 | 3 | 2 |
| Glycine (Gly) (G) | GGG | 0.25 | 3 | 4 | 3 |
| Glycine (Gly) (G) | GGT | 0.16 | 4 | 2 | 4 |
| Luecine (Lue) (L) | CTG | 0.4 | 1 | 2 | 1 |
| Luecine (Lue) (L) | CTC | 0.2 | 2 | 3 | 2 |
| Luecine (Lue) (L) | CTT | 0.13 | 4 | 1 | 3 |
| Luecine (Lue) (L) | TTG | 0.13 | 3 | 4 | 4 |
| Serine (Ser) (S) | TCT | 0.19 | 3 | 1 | 1 |
| Serine (Ser) (S) | AGC | 0.24 | 1 | 3 | 2 |
| Serine (Ser) (S) | TCC | 0.22 | 2 | 4 | 3 |
| Serine (Ser) (S) | TCA | 0.15 | 4 | 2 | 4 |
| Serine (Ser) (S) | AGT | 0.15 | 4 | 2 | 4 |

Because of the unsatisfactory results obtained with fully automated codon optimization software programs, customized codon optimization was performed to increase both protein expression and titers obtained. The initial step includes the use of a codon optimizer program as a first screen in order to set each codon for the correct reading frame to that most preferred in the subject species, including humans, giving a 'raw' codon optimization. Generally, any desired cloning restriction sites are excluded from use during this stage of the process.

The results are further refined by editing DNA sequences in a DNA editor program, and searching for degenerate codons, such as pyrimidines (e.g., by searching for "Y" codons). The following operations are then performed, in this order:

Manual search of the sequence for runs of "Y," generally at least five or more "Y" sequential runs. These sequences are highlighted in a given sequence, and the DNA editor program is used to determine a translation that includes the DNA sequence listed in register to the peptide sequence to insure that changes to codons do not affect the translated protein.

Each codon in a run of 5 or more Y's is evaluated. When available, the wobble base of each codon is converted to the most favorable A-G base for the amino acid (usually an adenine), and the result examined. If the result of the change creates a purine-rich run ending at or near a 3' AG, the changes are manually reversed. If there is no most favorable A-T base available for the wobble base or it causes another sequence conflict, the the most favorable C-G base is used for the wobble base.

If the result is a rare codon (<10% usage), that codon is moved to the next available codon in the frame.

If another codon change can ablate the putative acceptor site, changes are made to revert to the original sequence. If no such alternative change is available, then the original alteration is implemented.

Once this process is complete, the sequence is examined 5' to 3' for alternate reading frames. At each reading frame, the 5 bases 3' of the ATG codon are examined for their suitability as Kozak sequences. If the ATG gives a methionine in the reading frame of the desired gene, options are limited to ablating the Kozak sequence, first by converting the wobble base of the "−1" wobble base to the ATG to a "T" (if possible), then the "−4" wobble base.

In rare cases, it may be desirable to convert the second codon in the reading frame, if originally an "AGN" base (Ser/Arg) to a codon beginning in T (for serine) or C (for arginine). The situation is generally not encountered when strictly applying the above algorithm however, as the "AGN" codons are avoided due to the "AG" sequence pair.

In cases where the alternate reading frame differs from that of the message, AND the Kozak sequence surrounding it fits the consensus "CCACCatgG", the wobble base of the in-frame codon is altered to remove the start codon. This generally happens (but not always) as a result of the codon optimization and/or splice acceptor ablation process.

In-process checks are generally performed to ensure that the peptide sequence is unchanged. At the final check stage, if there are too many 'rare' codons in use (generally 2 or more) it may be desirable to prioritize which are used, with preference to changes given to the longer pyrimidine runs from the 'raw' codon optimized sequence. Finally, any needed restriction sites are added, and a last check is performed to insure that the polypeptide is unchanged from the original sequence before the optimization process is begun and that any desired restriction sites remain unique to those that are added for cloning purposes.

Splice Site Modification

Introns are generally spliced out of RNA in order to join exons. A splice donor site is a site in RNA on the 5' side of the RNA which is removed during the splicing process and which contains the site which is cut and rejoined to a nucleotide residue within a splice acceptor site. Thus, a splice donor site is the junction between the end of an exon and the start of the intron. Generally, a splice donor site in RNA is the dinucleotide GU (or a GT dinucleotide in the corresponding DNA sequence).

A splice acceptor site is a site in RNA on the 3' side of the RNA which is removed during the splicing process and which contains the site which is cut and rejoined to a nucleotide residue within a splice donor site. Thus, a splice acceptor site is the junction between the end of an intron (typically terminating with the dinucleotide AG) and the start of the downstream exon.

In some embodiments, disclosed herein is a nucleic acid sequence encoding a thymidine kinase wherein at least one nucleotide corresponding to a splice donor site is replaced by another nucleotide. See, e.g., FIG. 1 (Chalmers et al., Mol. Ther. 4:146-8 (2001)). In further embodiments, the nucleotides of the splice acceptor sites are not altered. In some embodiments, at least one nucleotide corresponding to a splice acceptor site is replaced by another nucleotide.

In some embodiments, disclosed herein is a nucleic acid sequence encoding a thymidine kinase wherein at least one of the nucleotides corresponding to splice donor site nucleotides at positions 329 and 330 of a polynucleotide sequence (e.g., SEQ ID NO: 1 or 3) is replaced by another nucleotide. In some embodiments, both of the nucleotides at positions 327 and 555 are replaced by other nucleotides. For example, position 327 may be mutated to an amino acid residue selected from: G to A. Alternately, or in addition, position 555 may be mutated to an amino acid residue selected from: G to A. In one embodiment, the modified HSV-TK has a polynucleotide sequence of SEQ ID NO: 18 in which HSV-TK was improved in the following ways:

HSV-TK NESdmNLS A168H, CO & SC
NES=nuclear export sequence from MAP Kinase Kinase (MAPKK)
dmNLS=double mutated HSV-TK Nuclear Localization Sequence
CO=codon optimized
SC=splice donor/acceptor site corrected at 327 and 555, Underlined Sequence

SEQ ID NO: 18 gtcaGCGGCCGCACCGGTACGCGTCCACCATGGCCCTGCAGAAAAAGC

TGGAAGAGCTGGAACTGGATGGCAGCTACCCCGGCCACCAGCACGCCA

GCGCCTTCGACCAGGCCGCCCGCAGCCGCGGCCACAGCAACGGCAGCA

CCGCaCTGCGgCCaGGATCTCAGCAGGAGGCCACCGAGGTGCGCCCCG

AGCAGAAGATGCCCACCCTGCTGCGCGTGTACATCGACGGaCCaCACG

GCATGGGCAAGACCACCACCACCCAGCTGCTGGTGGCCCTGGGCAGCC

GCGACGACATCGTGTACGTGCCCGAGCCCATGACCTACTGGCGCGTGC

TGGGCGCCAGCGAGACCATCGCCAACATCTACACCACCCAGCACCGCC

TGGACCAaGGCGAGATCAGCGCCGGCGACGCCGCCGTGGTGATGACCA

GCGCCCAGATtACaATGGGCATGCCCTACGCCGTGACCGACGCCGTGC

TGGCaCCaCACATCGGCGGCGAGGCCGGCAGCAGCCACGCaCCaCCaC

CaGCaCTGACCCTGATCTTCGACCGgCACCCaATCGCaCACCTGCTGT

GCTACCCgGCaGCaCGCTACCTGATGGGCtccATGACaCCaCAaGCCG

TGCTGGCCTTCGTGGCCCTGATCCCaCCaACaCTGCCCGGCACCAACA

TCGTGCTGGGCGCCCTGCCCGAGGACCGCCACATCGACCGCCTGGCCA

AGCGCCAGCGCCCCGGCGAGCGCCTGGACCTGGCCATGCTGGCCGCCA

TCCGCCGCGTGTACGGCCTGCTGGCCAACACCGTGCGCTACCTGCAGT

GCGGCGGCAGCTGGCGCGAGGACTGGGGCCAGCTGAGCGGCACCGCCG

TGCCaCCaCAGGGCGCCGAGCCaCAGAGCAACGCCGGaCCaCGaCCaC

ACATCGGCGACACCCTGTTCACCCTGTTCCGgGCaCCaGAGCTGCTGG

CaCCaAACGGCGACCTGTACAACGTGTTCGCCTGGGCCCTGGACGTGC

TGGCCAAGCGCCTGCGCtccATGCACGTGTTCATCCTGGACTACGACC

AGtcaCCgGCCGGCTGCCGCGACGCCCTGCTGCAGCTGACCAGCGGCA

TGGTGCAGACCCACGTGACaACaCCCGGCAGCATCCCaACaATCTGCG

ACCTGGCCCGCACCTTCGCCCGCGAGATGGGCGAGGCCAACTAATAGG

GATCCCTCGAGAAGCTTgtca

In some embodiments, disclosed herein is a nucleic acid sequence encoding a thymidine kinase wherein at least one of the nucleotides corresponding to splice acceptor site nucleotides at positions 554 and 555, or at least one of the nucleotides corresponding to splice acceptor site nucleotides at positions 662 and 663, or at least one of the nucleotides corresponding to splice acceptor sites at positions 541 and 542 of the wild type sequence is replaced by another nucleotide. For example, position 541 may be mutated to an amino acid residue selected from: G to A. Position 542 may be mutated to an amino acid residue selected from: G to A. Position 554 may be mutated to an amino acid residue selected from: G to A. Position 555 may be mutated to an amino acid residue selected from: G to A. Position 662 may be mutated to an amino acid residue selected from: G to A. Position 663 may be mutated to an amino acid residue selected from: G to A.

In some embodiments, at least one of the nucleotides of the wild-type HSV-TK encoding sequence is replaced as described in Table 1 below.

TABLE 1

| Position | Mutation |
|---|---|
| 84 | C → A |
| 90 | C → G |
| 93 | C → A |
| 96 | C → G |
| 168 | C → A |
| 171 | C → A |
| 378 | C → T |
| 381 | C → A |
| 420 | C → A |
| 423 | C → A |
| 456 | C → A |
| 459 | C → A |
| 462 | C → A |
| 465 | C → A |
| 468 | C → A |
| 475 | A → C |
| 477 | C → G |
| 478 | T → A |
| 481 | C → T |
| 483 | G → C |
| 489 | C → G |
| 495 | C → A |
| 501 | C → A |
| 502 | T → C |
| 503 | T → A |
| 505 | A → C |
| 518 | C → G |
| 522 | C → A |
| 525 | C → A |
| 541 | A → T |
| 542 | G → C |
| 585 | C → A |
| 588 | C → A |
| 591 | C → A |
| 804 | C → A |
| 807 | C → A |
| 822 | C → A |
| 837 | C → A |
| 843 | C → A |
| 846 | C → A |
| 879 | C → G |
| 882 | C → A |
| 885 | C → A |
| 897 | C → A |
| 900 | C → A |
| 961 | A → T |
| 962 | G → C |
| 994 | A → T |
| 995 | G → C |
| 996 | C → A |
| 999 | C → G |
| 1059 | C → A |
| 1062 | A → C |
| 1077 | C → A |
| 1080 | C → A |

A Kozak sequence flanks the AUG start codon within mRNA and influences the recognition of the start codon by eukaryotic ribosomes. In some embodiments, a polynucleotide sequence encoding HSV-TK comprises no more than one Kozak sequence. In some embodiments, the Kozak sequence is upstream of the coding portion of the DNA sequence. In some embodiments, the Kozak sequence of a polynucleotide encoding HSV-TK is modified to produce a Kozak sequence with a higher efficiency of translation initiation in a mammalian cell. In some embodiments, modification of the Kozak sequence does not produce an amino acid substitution in the encoded HSV-TK polypeptide product. In some embodiments, modification of the Kozak sequence results in at least one amino acid substitution in the encoded HSV-TK polypeptide product. In one embodiment, the modified HSV-TK has a polynucleotide sequence of SEQ ID NO: 18.

In some embodiments, a polynucleotide sequence encoding HSV-TK comprises a modification that inserts one or more restriction sites. The optimal site for insertion of one or more restriction sites may be determined empirically and/or using a computer program to analyze the sequence. In one non-limiting embodiment, a first restriction site is inserted upstream of the Kozak and ATG start site and a second restriction site is inserted at the 3' end of the sequence. See, for example, SEQ ID NO: 18, underlined section below.

HSVTK NESdmNLS A168H, CO & SC
NES=nuclear export sequence from MAPKK
dmNLS=double mutated Nuclear Localization Sequence
CO=codon optimized
SC=splice corrected at 327 and 555, previously described
Kozak Sequence, previously described
Restriction Sites, Underlined and specified as:

(GCGGCCGC ACCGGT ACGCGT = Not-I, Age-I, and MLU-I)

(GGATCC CTCGAG AAGCTT = BamH-I, Xho-I and Hind-III)

SEQ ID NO: 18
gtcaGCGGCCGCACCGGTACGCGTCCACCATGGCCCTGCAGAAAAAGC

TGGAAGAGCTGGAACTGGATGGCAGCTACCCCGGCCACCAGCACGCCA

GCGCCTTCGACCAGGCCGCCCGCAGCCGCGGCCACAGCAACGGCAGCA

CCGCaCTGCGgCCaGGATCTCAGCAGGAGGCCACCGAGGTGCGCCCCG

AGCAGAAGATGCCCACCCTGCTGCGCGTGTACATCGACGGaCCaCACG

GCATGGGCAAGACCACCACCACCCAGCTGCTGGTGGCCCTGGGCAGCC

GCGACGACATCGTGTACGTGCCCGAGCCCATGACCTACTGGCGCGTGC

TGGGCGCCAGCGAGACCATCGCCAACATCTACACCACCCAGCACCGCC

TGGACCAaGGCGAGATCAGCGCCGGCGACGCCGCCGTGGTGATGACCA

GCGCCCAGATtACaATGGGCATGCCCTACGCCGTGACCGACGCCGTGC

TGGCaCCaCACATCGGCGGCGAGGCCGGCAGCAGCCACGCaCCaCCaC

CaGCaCTGACCCTGATCTTCGACCGgCACCCaATCGCaCACCTGCTGT

GCTACCCgGCaGCaCGCTACCTGATGGGCtccATGACaCCaCAaGCCG

TGCTGGCCTTCGTGGCCCTGATCCCaCCaACaCTGCCCGGCACCAACA

TCGTGCTGGGCGCCCTGCCCGAGGACCGCCACATCGACCGCCTGGCCA

AGCGCCAGCGCCCCGGCGAGCGCCTGGACCTGGCCATGCTGGCCGCCA

TCCGCCGCGTGTACGGCCTGCTGGCCAACACCGTGCGCTACCTGCAGT

GCGGCGGCAGCTGGCGCGAGGACTGGGGCCAGCTGAGCGGCACCGCCG

TGCCaCCaCAGGGCGCCGAGCCaCAGAGCAACGCCGGaCCaCGaCCaC

ACATCGGCGACACCCTGTTCACCCTGTTCCGgCaCCaGAGCTGCTGG

CaCCaAACGGCGACCTGTACAACGTGTTCGCCTGGGCCCTGGACGTGC

TGGCCAAGCGCCTGCGCtccATGCACGTGTTCATCCTGGACTACGACC

AGtcaCCgGCCGGCTGCCGCGACGCCCTGCTGCAGCTGACCAGCGGCA

TGGTGCAGACCCACGTGACaAcaCCCGGCAGCATCCCaACaATCTGCG

-continued
ACCTGGCCCGCACCTTCGCCCGCGAGATGGGCGAGGCCAACTAATA<u>GG</u>

<u>GATCCCTCGAG</u>AAGCTTgtca

Other splice site modifications are disclosed in the examples below and are considered for inclusion as a modified TK sequence that can be used in the claimed methods.

In some embodiments, the polynucleotide sequence encoding HSV-TK comprises at least 5, 10, 15, 20, 25, 30, 35, 40, 45, 50, 55, 60, 65, 60, 75, 80, 85, 90, 95, 100 or more codon substitutions. In some embodiments, the polynucleotide sequence encoding HSV-TK comprises at least 5, 10, 15, 20, 25, 30, 35, 40, 45, 50, 55, 60, 65, 60, 75, 80, 85, 90, 95, 100 or more codon substitutions, wherein the codon substitutions comprise the substitution of a codon having a higher frequency of usage in a mammalian cell than the wild type codon at that position. However, in some embodiments, less favored codons may be chosen for individual amino acids depending upon the particular situation.

In some embodiments, the polynucleotide sequence encoding HSV-TK comprising at least 5, 10, 15, 20, 25, 30, 35, 40, 45, 50, 55, 60, 65, 60, 75, 80, 85, 90, 95, 100 or more codon substitutions has less than about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID NO: 1 or 3 wherein the sequence identity is determined over the full length of the coding sequence using a global alignment method. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises at least 5, 10, 15, 20, 25, 30, 35, 40, 45, 50, 55, 60, 65, 60, 75, 80, 85, 90, 95, 100 or more codon substitutions, wherein the codon substitutions comprise the substitution of a codon having the highest frequency of usage in a mammalian cell for the wild type codon at that position. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises at least 5, 10, 15, 20, 25, 30, 35, 40, 45, 50, 55, 60, 65, 60, 75, 80, 85, 90, 95, 100 or more codon substitutions, wherein the substituted codons have a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises less than about 45, 40, 35, 30, 25, 20 or fewer codons, wherein the codons have a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises at least 78%, 79%, 80%, 81%, 82%, 83%, 84%, 85%, 86%, 87%, 88%, 89%, 90%, 91%, 92%, 93%, 94%, 95% or more of codons having a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, or higher. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises at least 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85% or more of codons having the highest frequency of usage in a mammalian cell. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises less than about 21%, 20%, 19%, 18%, 17%, 16%, 15%, 14%, 13%, 12%, 11%, 10% or less of codons having a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25. In some embodiments, the polynucleotide sequence comprises less than about 21%, 20%, 19%, 18%, 17%, 16%, 15%, 14%, 13%, 12%, 11%, 10% or less of codons having a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a mammalian cell. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises codon substitutions, wherein at least 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed as compared to the wild type sequence. In some embodiments, the polynucleotide sequence encoding HSV-TK comprises codon substitutions, wherein at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having a higher frequency of usage in a mammalian cell as compared to the wild type sequence. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises codon substitutions, wherein at least 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having the highest frequency of usage in a mammalian cell as compared to the wild type sequence. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

Non-Conserved Mutations

The viral thymidine kinase gene from the selected herpesvirus may be readily isolated and mutated as described below, in order to construct nucleic acid molecules encoding a thymidine kinase enzyme comprising one or more mutations which increases biological activity of the thymidine kinase, as compared to unmutated wild-type thymidine kinase. The biological activity of a thymidine kinase may be readily determined utilizing any of the assays known in the art, including for example, determination of the rate of nucleoside analogue uptake or determination of the rate of nucleoside or nucleoside analogue phosphorylation. In addition, thymidine kinase mutants may be readily selected which are characterized by other biological properties, such as thermostability and protein stability.

In some embodiments, the polynucleotide sequence encoding HSV-TK is modified to remove or modify a predicted signal sequence. In some embodiments, the polynucleotide is modified to remove or modify a nuclear localization sequence (NLS). In some embodiments, the polynucleotide is modified to remove the nuclear localization sequence. In some embodiments, the polynucleotide is modified to modify the NLS so that if no longer functions to localize HSV-TK exclusively to the nucleus.

In some embodiments, a HSV-TK polypeptide sequence is mutated at amino acid residues 167, 168, or both. In one example, the sequence is mutated at amino acid residue 167. In another example, the sequence is mutated at amino acid residue 168. In another example, the sequence is mutated at amino acid residues 167 and 168. Amino acid residue 167 may be mutated to serine or phenylalanine. Amino acid residue 168 may be mutated to histidine, lysine, cysteine, serine or phenylalanine. In some embodiments, a HSV-TK polypeptide sequence is mutated at amino acid residues 25 and/or 26. In amino acid residues 25 and/or 26 may be mutated to an amino acid chosen from the group consisting of: glycine, serine, and glutamic acid. In some embodiments, the HSV-TK polypeptide sequence is mutated at amino acid residues 32 and/or 33. Amino acid residues 32 and/or 33 may be mutated to an amino acid chosen from the group consisting of: glycine, serine, and glutamic acid. In some embodiments, the HSV-TK polypeptide is mutated at amino acid residues 25, 26, 32, and/or 33. Amino acid residues 25, 26, 32, and/or 33, may be mutated to an amino acid chosen from the group consisting of: glycine, serine, and glutamic acid. Amino acid residue modifications may be made in comparison to a polypeptide sequence of SEQ ID NOS: 2 or 4.

In accordance with the present invention, mutant thymidine kinase enzymes which are encoded by the above-described nucleic acid molecules are provided, as well as vectors which are capable of expressing such molecules. In some embodiments, expression vectors are provided comprising a promoter operably linked to a nucleic acid molecule of the present invention. In some embodiments, the vector is a viral vector capable of directing the expression of a nucleic acid molecule. Representative examples of such viral vectors include herpes simplex viral vectors, adenoviral vectors, adenovirus-associated viral vectors, pox vectors, parvoviral vectors, baculovirus vectors and retroviral vectors. In some embodiments, viral vectors are provided which are capable of directing the expression of a nucleic acid molecule which encodes a thymidine kinase enzyme comprising one or more mutations, at least one of the mutations encoding an amino acid substitution which increases a biological activity of thymidine kinase, as compared to unmutated (i.e., wild-type) thymidine kinase.

In some embodiments, a nucleic acid molecule provided herein encodes a thymidine kinase enzyme capable of phosphorylating a nucleoside analogue at a level at least 10% greater than the level of phosphorylation of the nucleoside analogue by a wild-type thymidine kinase enzyme. In some embodiments, the thymidine kinase enzyme is capable of phosphorylating a nucleoside analogue at a level at least 15%, at least 20%, at least 25%, at least 50%, at least 75%, at least 100%, at least 150%, at least 200%, at least 300%, or at least 500% greater than the level of phosphorylation of the nucleoside analogue by a wild-type thymidine kinase enzyme. Representative examples of suitable nucleoside analogues include gancyclovir, acyclovir, famciclovir, buciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2, 5'-dideoxyuridine, idoxuridine, AZT, AIU, dideoxycytidine and AraC. In some embodiments, the improved TK mutant lacks thymidine kinase activity.

In some embodiments, the $K_m$ value for thymidine kinase activity of a disclosed HSV-TK mutant is at least 2.5 µm. In some embodiments, the $K_m$ value for thymidine kinase activity of a disclosed HSV-TK mutant is at least 5 µm, at least 10 µm, at least 15 µm, at least 20 µm, at least 25 µm, at least 30 µm, at least 40 µm, at least 50 µm, at least 60 µm, at least 70 µm, at least 80 µm, at least 90 µm, at least 100 µm, at least 150 µm, at least 200 µm, at least 250 µm, at least 300 µm, at least 400 µm, at least 500 µm, at least 600 µm, at least 700 µm, at least 800 µm, at least 900 µm, or at least 1000 µm. In some embodiments, the percent $K_m$ of a disclosed HSV-TK mutant compared to wild-type HSV-TK is at least 15%, at least 20%, at least 25%, at least 50%, at least 75%, at least 100%, at least 150%, at least 200%, at least 300%, or at least 500%.

Within one embodiment of the present invention, truncated derivatives of HSV-TK mutants are provided. For example, site-directed mutagenesis may be readily performed in order to delete the N-terminal 45 amino acids of a thymidine kinase mutant, thereby constructing a truncated form of the mutant which retains its biological activity.

Mutations in nucleotide sequences constructed for expression of derivatives of thymidine kinase mutants should preserve the reading frame phase of the coding sequences. Furthermore, the mutations will preferably not create complementary regions that could hybridize to produce secondary mRNA structures, such as loops or hairpins, which would adversely affect translation of the receptor mRNA. Such derivatives may be readily constructed using a wide variety of techniques, including those discussed above.

Modified Thymidine Kinase Mutants

Using the methods described herein, the inventors determined that the majority of the candidates for optimized HSV-TK genes appeared to be compatible with a retroviral expression system and produce biologically useful retroviral titers.

Furthermore, the optimized HSV-TK genes which incorporated most of these optimizations (SEQ ID NO: 18 exhibited pro-drug GCV enzyme activity and selectivity for their ability to kill cancer cells following retroviral transduction delivery. The mutant HSV-TK gene A168H, which was codon optimized and splice corrected appeared to have the highest GCV mediated cancer kill activity (SEQ ID NOs: 12, 16, 18, or 22). The same version of this HSV-TK gene A168H and mutated at amino acids 159-161 from LIF to IFL exhibited GCV mediated cancer cell kill activity.

The mutant HSV-TK gene A167F (SEQ ID NOs: 13, 17, or 19), which was codon optimized and splice corrected had very high GCV mediated cancer kill activity following retroviral transduction delivery, but more surprisingly had NO thymidine kinase activity as determined by expressing this gene following retroviral transduction delivery in 3T3 TK(-) cells selected with HAT medium. To our knowledge, this is the most GCV selective HSV-TK synthetic gene product for GCV activation which has no Thymidine activity (HAT assay) ever evaluated biologically.

The double mutant HSV-TK gene A167F+A168H (SEQ ID NO: 14) unexpectedly ablates both GCV and Thymidine enzyme activity by exhibiting very little GCV mediated cancer kill activity and very little thymidine activity (HAT assay).

The present inventors identified that it is possible to produce functional HSV-TK fusions of genes such as bacterial cytosine deaminase, yeast cytosine deaminase, neomycin phosphotransferase and include linker sequences and retain HSV-TK GCV mediated cancer cell killing activity.

In one embodiment, a codon optimized HSV-TK gene with GCV-mediated cancer killing activity may be made which retains one or more nuclear localization sequences which is not fused to one or more other therapeutic genes.

Additional modifications to and/or evaluations of an optimized HSV-TK gene described herein may include one or more of the following: removal of known nuclear localization sequences within HSV-TK; increased pro-drug GCV enzyme activity and selectivity for their ability to kill cancer cells, evaluate the use of more tags, fusion proteins and linkers of HSV-TK to other genes and proteins, co-expression of HSV-TK optimized genes with other optimized suicide and cancer killer genes in cancer cells, include optimized HSV-TK genes in a Reximmune-C type retroviral vector system; production and testing of a Reximmune-C type GMP product, or any combination thereof.

Exemplary Polynucleotide Sequences

In one embodiment, a polynucleotide sequence described herein comprises a nuclear export signal. For example, a polynucleotide sequence may comprise TK168dmNES.

In another embodiment, a retroviral vector for use in the methods described herein comprises one or more splice site modifications.

In another embodiment, a retroviral vector for use in the methods described herein comprises HSV-TK A167Fsm (SEQ ID NO: 13).

In another embodiment, a retroviral vector for use in the methods described herein comprises HSV-TK A168Hsm (SEQ ID NO: 12).

In another embodiment, a retroviral vector for use in the methods described herein comprises HSV-TK A167Fdm (SEQ ID NO: 17).

In another embodiment, a retroviral vector for use in the methods described herein comprises HSV-TK A168dm (SEQ ID NO: 16).

In another embodiment, a retroviral vector for use in the methods described herein comprises HSV-TK A167Fdm and an NES (SEQ ID NO: 19).

In another embodiment, a retroviral vector for use in the methods described herein comprises HSV-TK A168Hdm and an NES (SEQ ID NO: 18). In such an embodiment, the sequence comprises HSV-TK A168H.

In another embodiment, a retroviral vector for use in the methods described herein comprises a HSV-TK, wherein such vector comprises an upgraded substrate binding domain and a mNLS/NES set.

In another embodiment, a retroviral vector for use in the methods described herein comprises a HSV-TK, wherein the vector comprises a selectable marker, a glowing, fluorescent or bioluminescent gene and/or one or more kill genes.

In another embodiment, a retroviral vector for use in the methods described herein comprises at least two modifications.

Construction of Thymidine Kinase Mutants

Thymidine kinase mutants of the present invention may be constructed using a wide variety of techniques. For example, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Deletion or truncation derivatives of thymidine kinase mutants may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (Molecular cloning: A Laboratory Manual, $2^{nd}$ Ed., Cold Spring Harbor Laboratory Press, 1989).

Other derivatives of the thymidine kinase mutants disclosed herein include conjugates of thymidine kinase mutants along with other proteins or polypeptides. This may be accomplished, for example, by the synthesis of N-terminal or C-terminal fusion proteins which may be added to facilitate purification or identification of thymidine kinase mutants (see U.S. Pat. No. 4,851,341, see also, Hopp et al., *Bio/Technology* 6:1204, 1988.).

Improvement of HSV-Mediated Killing

In some embodiments, the polynucleotide sequence encoding HSV-TK further comprises a sequence encoding a secondary therapeutic agent or polypeptide. In some embodiments, secondary therapeutic agent or polypeptide is a diagnostic or therapeutic agent or polypeptide.

In some embodiments, the secondary therapeutic agent or polypeptide is an additional "suicide protein" that causes cell death by itself or in the presence of other compounds. In some embodiments, the second suicide gene is chosen from the group including: penicillin-V-amidase, penicillin- G-amidase, beta-lactamase, carboxypeptidase A, linamarase (also referred to as β-glucosidase), the *E. coli* gpt gene, and the *E. coli* Deo gene, a cytosine deaminase, a VSV-tk, IL-2, nitroreductase (NR), carboxylesterase, beta-glucuronidase, cytochrome p450, beta-galactosidase, diphtheria toxin A-chain (DT-A), carboxypeptide G2 (CPG2), purine nucleoside phosphorylase (PNP), and deoxycytidine kinase (dCK).

In some embodiments, the second suicide protein converts a prodrug into a toxic compound. As used herein, "prodrug" means any compound useful in the methods disclosed herein that can be converted to a toxic product, i.e., toxic to tumor cells. The prodrug is converted to a toxic product by the suicide protein. Representative examples of such prodrugs include: FHBG (9-[4-fluoro-3-(hydroxymethyl)butyl]guanine), FHPG (9-([3-fluoro-1-hydroxypropoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpryrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-, ganciclovir- and penciclovir-like side chains for thymidine kinase; ifosfamide for oxidoreductase; 6-methoxypurine arabinoside for VZV-TK; 5-fluorocytosine for cytosine deaminase; doxorubicin for beta-glucuronidase; CB1954 and nitrofurazone for nitroreductase; and N-(Cyanoacetyl)-L-phenylalanine or N-(3-chloropropionyl)-L-phenylalanine for carboxypeptidase A.

In some embodiments, the secondary therapeutic agent or polypeptide is chosen from the group including, but are not limited to, cell cycle control agents, agents which inhibit cyclin proteins, such as antisense polynucleotides to the cyclin A and/or D genes, growth factors such as, for example, epidermal growth factor (EGF), vascular endothelial growth factor (VEGF), erythropoietin, G-CSF, GM-CSF, TGF-α, TGF-β, and fibroblast growth factor, cytokines, including, but not limited to, Interleukins 1 through 13 and tumor necrosis factors, anticoagulants, anti-platelet agents, anti-inflammatory agents, anti-angiogenic factors, tumor suppressor proteins, clotting factors, including Factor VII, Factor VIII and Factor IX, protein S, protein C, antithrombin III, von Willebrand Factor, cystic fibrosis transmembrane conductance regulator (CFTR), and negative selective markers.

In some embodiments, a secondary therapeutic agent or polypeptide is a cancer suppressor, for example p53 or Rb, or a nucleic acid encoding such a protein or polypeptide.

Other examples of secondary therapeutic agents or polypeptides include pro-apoptotic therapeutic proteins and polypeptides, for example, p15, p16, or p21/WAF-1.

In some embodiments, a secondary therapeutic agent or polypeptide is a cytokine. Examples of cytokines include: GM-CSF (granulocyte macrophage colony stimulating factor); TNF-alpha (Tumor necrosis factor alpha); Interferons including, but not limited to, IFN-alpha and IFN-gamma; and Interleukins including, but not limited to, Interleukin-1 (IL1), Interleukin-Beta (IL-beta), Interleukin-2 (IL2), Interleukin-4 (IL4), Interleukin-5 (IL5), Interleukin-6 (IL6), Interleukin-8 (IL8), Interleukin-10 (IL10), Interleukin-12 (IL12), Interleukin-13 (IL13), Interleukin-14 (IL14), Interleukin-15 (IL15), Interleukin-16 (IL16), Interleukin-18 (IL18), Interleukin-23 (IL23), Interleukin-24 (IL24), although other embodiments are known in the art.

In some embodiments, the secondary therapeutic agent or polypeptide is pro-apoptotic. Examples of pro-apoptotic proteins or polypeptides include, but are not limited to: Bax, Bad, Bik, Bak, Bim, cytochrome C, apoptosis-inducing factor (AIF), Puma, CT 10-regulated kinase (CRK), Bok, glyceraldehyde-3-phosphate dehydrogenase, Prostate Apoptosis Response Protein-4 (Par-4), Smac, Kinase C6, Fas, inhibitory PAS domain protein (IPAS), and Hrk.

In some embodiments, the secondary therapeutic agent or polypeptide is involved in cell to cell communication. In some embodiments, the secondary therapeutic agent or polypeptide is involved in gap cell junctions. In some embodiments, the secondary therapeutic agent or polypeptide is a connexin. In some embodiments, the therapeutic protein or polypeptide is a connexin chosen from the group connexin 43, connexin 32 and connexin 26.

In some embodiments, the secondary therapeutic agent or polypeptide is encoded by the human receptor gene PiT-2 (SLC20A2). The Amphotropic Envelope gene product included in the Reximmune-C1 and 2 retroviral vector binds to the PiT-2 receptor prior to target cell infection. In some embodiments, the secondary therapeutic agent or polypeptide is encoded by the human receptor gene PiT-1 (SLC20A1). The Gibbon Ape Luekemia Virus (GALV) Envelope gene product binds to the PiT-1 receptor prior to target cell infection.

In some embodiments, the secondary therapeutic agent or polypeptide is an N-terminal truncation of a retroviral protein, wherein the N-terminal truncation comprises a functional receptor binding domain of the envelope protein.

Increasing Intracellular Communication to Improve Treatment

Increase in Bystander Effect

Disclosed herein, in some embodiments, is a method of increasing the HSV-TK prodrug substrate bystander effect. As used herein, the "bystander effect" refers to the phenomenon by which a HSV-TK positive exerts a kill effect on neighboring HSV-TK negative cells following induction of expression of HSV-TK expression in the HSV-TK positive cells.

In some embodiments, is a method of increasing the HSV-TK prodrug-mediated bystander effect, for example after treatment with GCV, in conjunction with increasing gap junction intracellular communication. In some embodiments, HSV-TK prodrug-mediate bystander effect increases the kill rate by 10%, by 20%, by 30%, by 40%, by 50%, by 60%, by 70%, by 80%, by 90% or by 100% or more.

Gap junctions are regions of the cell membrane with clusters of gap junction channels that directly connect the cytoplasm of one cell with the cytoplasm of another cell. A gap junction channel is composed of two hemichannels (connexons) provided by each of two neighboring cells. A connexon is comprised most often of six connexin proteins, which are a large family of proteins having a basic structure comprising four transmembrane domains, two extracellular loops, and a cytoplasmic loops.

Gap junctions serve in various physiological roles, such as growth control and homeostasis (i.e., rapid equilibration of ions, nutrients, and fluids between cells). In addition, gap junctions serve as electrical synapses in cells that are able to propagate electrical signals, such as cardiac myocytes, smooth muscle cells, and neurons.

Once phosphorylated, GCV can travel through GJ into adjoining cells that share the junctions. GCV-P will be phosphorylated further in those cells and trigger cell death as in the HSK-TK expressing cell. The extend of the Bystander effect depends on the existence of GAP junctions and therefore it will differ between cell types. But see, Dahle et al. "Gap junctional intercellular communication is not a major mediator in the bystander effect in photodynamic treatment of MDCKII cells." Radiation Res. 154: 331-341 (September 2000).

The viral TK enzyme is sensitive to the prodrug ganciclovir (GCV) which resembles the DNA base guanine.

When GCV is added to cell medium, the viral TK (but not the host non-viral TK) phosphorylates the GCV, converting it into a drug as, now phosphorylated, it will compete with dGTP for incorporation into DNA because of its similarity with guanine.

Incorporation will cause termination of the DNA chain synthesis. Transfer of GCV-monoP into non-cancer cells will not be toxic to them unless they are actively dividing. The normal cells at risk are only those in close contact to the viral TK-expressing cells when treated with high levels of GCV drug.

Disclosed herein, in some embodiments, is a method of increasing the viral thymidine-kinase mediated killing of target cells in a subject, the method comprising delivering vector particles encoding HSV-TK in conjunction with gap junction intracellular communication (GJIC)-increasing treatment. In some embodiments, the target cells are neoplastic cells. In some embodiments, the GJIC-increasing treatment comprises delivering to the cells a polynucleotide sequence encoding at least one gap junction subunit. In some embodiments, the at least one gap junction subunit is a wild type or mutant connexin. In some embodiments, the gap junction subunit is chosen from the group consisting of wild type or mutant connexin 43, connexin 30, and connexin 26. In other embodiments, the gap junction subunit is connexin 30.3, connexin 31, connexin 31.1, connexin 32, connexin 33, connexin 37, connexin 40, connexin 45, connexin 46 and connexin 50. In some embodiments, the gap junction subunit is modified to prevent posttranslational modifications. In some embodiments, the GJIC-increasing treatment comprises delivering to the cells a polynucleotide sequence encoding E-cadherin.

In some embodiments, a GJIC-increasing treatment comprises delivery of a compound to a subject. In some embodiments, the GJIC-increasing treatment comprises delivering to the subject a compound from the group comprising: gemcitabine; cAMP; a retinoic acid; a carotenoid; a glucocorticoid, a flavanoid, apigenin, and/or lovastatin.

In some embodiments, the GJIC-increasing treatment comprises proteasome inhibition. In some embodiments, the GJIC-increasing treatment comprises proteasome inhibition by administration of N-Acetyl-Leu-Leu-Nle-CHO (ALLN) and/or chloroquine.

In some embodiments, the GJIC-increasing treatment comprises radiation treatment.

In some embodiments, the GJIC-increasing treatment comprises electrical treatment.

Methods of Detection

Disclosed herein, in some embodiments, is a method of measuring the HSV-TK-mediated bystander effect, the method comprising: a) transfecting cells with a polynucleotide sequence encoding HSV-TK and a first fluorescent protein; b) transfecting cells with a second polynucleotide sequence encoding a second fluorescent protein that is optically discernible from the first fluorescent protein; c) treating the cells with titrated doses of gancyclovir; and d) measuring the relative amount of expression of the first fluorescent protein and the second fluorescent protein.

In one embodiment, red fluorescent proteins (RFPs) are used to quantitate the number of target tumor cells transduced with both the first fluorescent protein fluorescent protein and the second and Hygro® can be used to select a population of tumor cells in which all express both Hygro® and HSV-TK. RFPs are commercially available and are contemplated for use herein (see, for example, RFPs described in literature references 1-14 below.

In another embodiment, green fluorescent proteins (GFP) are used to quantitate the number of transduced target tumor cells. GFPs are are commercially available and are contemplated for use herein including, but not limited to, enhanced green fluorescent protein (EGFP).

Plasmids and Production of HSV-TK

In some embodiments, disclosed herein are, nucleic acid molecules encoding HSV-TK, or mutants and/or derivatives thereof, which are operably linked to suitable transcriptional or translational regulatory elements. In some embodiments, suitable regulatory elements are derived from bacterial, fungal, viral, mammalian, insect, or plant genes. Selection of appropriate regulatory elements is dependent on the chosen host cell and, in some embodiments, includes: a transcriptional promoter and enhancer or RNA polymerase binding sequence, and a ribosomal binding sequence, including a translation initiation signal.

Described herein are plasmids, comprising a nucleic acid sequence encoding HSV-TK, or a mutant and/or variant thereof, as described above. In some embodiments, disclosed herein are plasmids encoding HSV-TK fused to a second peptidic component. In some embodiments, the second peptidic component is a therapeutic agent or polypeptide. In some embodiments, the second peptidic component is a diagnostic polypeptide.

In some embodiments, disclosed herein is a variety of both viral and non-viral vectors suitable for directing the expression of the nucleic acid molecules encoding HSV-TK disclosed herein.

In some embodiments, disclosed herein are plasmids for transfecting and producing delivery vectors or therapeutic vectors for use in therapeutic and diagnostic procedures. In general, such plasmids provide nucleic acid sequences that encode components, viral or non-viral, of targeted vectors disclosed herein. Such plasmids include nucleic acid sequences that encode, for example, the MoMLV envelope protein. In some embodiments, the MoMLV envelope protein is modified to contain a collagen binding domain. Additional plasmids can include a nucleic acid sequence operably linked to a promoter. The sequence generally encodes a viral gag-pol polypeptide. The plasmid further includes a nucleic acid sequence operably linked to a promoter, and the sequence encodes a polypeptide that confers drug resistance on the producer cell. An origin of replication is also included. In some embodiments, additional plasmids comprise an improved HSV-TK encoding sequence, as disclosed herein, 5' and 3' long terminal repeat sequences; a Ψ retroviral packaging sequence, a CMV enhancer upstream of the 5' LTR promoter, a nucleic acid sequence operably linked to a promoter, and an SV40 origin of replication.

In some embodiments, the polynucleotide encoding HSV-TK is under the control of a suitable promoter. Suitable promoters include, but are not limited to, the retroviral LTR; the SV40 promoter; the cytomegalovirus (CMV) promoter; the Rous Sarcoma Virus (RSV) promoter; the histone promoter; the polIII promoter, the β-actin promoter; inducible promoters, such as the MMTV promoter, the metallothionein promoter; heat shock promoters; adenovirus promoters;

the albumin promoter; the ApoAI promoter; B19 parvovirus promoters; human globin promoters; viral thymidine kinase promoters, such as the Herpes Simplex Virus thymidine kinase promoter; retroviral LTRs; human growth hormone promoters, and the MxIFN inducible promoter. In some embodiments, the promoter is a tissue-specific promoter. In some embodiments, a tissue specific promoters is chosen from the group including the tyrosinase related promoters (TRP-1 and TRP-2), DF3 enhancer (for breast cells), SLPI promoter (secretory leucoprotease inhibitor—expressed in many types of carcinomas), TRS (tissue specific regulatory sequences), α-fetoprotein promoters (specific for normal hepatocytes and transformed hepatocytes, respectively), the carcino-embryonic antigen promoter (for use in transformed cells of the gastrointestinal tract, lung, breast and other tissues), the tyrosine hydroxylase promoter (for melanocytes), choline acetyl transferase or neuron specific enolase promoters for use in neuroblastomas, the regulatory sequence for glial fibroblastomas, the tyrosine hydroxylase promoter, c-erb B-2 promoter, PGK promoter, PEPCK promoter, whey acidic promoter (breast tissue), and casein promoter (breast tissue) and the adipocyte P2 promoter. In some embodiments, the promoter is a viral-specific promoter (e.g., retroviral promoters, as well as others such as HIV promoters), hepatitis, herpes (e.g., EBV). In some embodiments, the promoter is the native HSV-TK promoter. In some embodiments, the promoter is a bacterial, fungal or parasitic (e.g., malarial)-specific promoter is utilized in order to target a specific cell or tissue which is infected with a virus, bacteria, fungus or parasite.

In some embodiments, the delivery vectors or therapeutic vectors may include a targeting moiety that targets the delivery vectors or therapeutic vectors to a desired cell or system. In some embodiments, the targeting moiety refers to a ligand expressed by the delivery vector or therapeutic vector that is associated with the delivery vehicle and target the vehicle to a cell or tissue. In some embodiments, the ligand may include, but is not limited to, antibodies, receptors and proteins that bind to cellular components exposed in or on the targeted cell or system. In some embodiments, the exposed cellular components may include collagen. In some embodiments, the ligand binding to exposed cellular components comprises proteins that include a collagen binding domain.

The plasmids disclosed herein may be produced by genetic engineering techniques known to those skilled in the art. In addition, the plasmids may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., PNAS USA 75:1929-1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning. A Laboratory Manual, 2nd edition, Cold Spring Harbor Laboratory Press, 1989; for plant cells see Czako and Marton, *Plant Physiol.* 104:1067-1071, 1994; and Paszkowski et al., *Biotech.* 24:387-392, 1992).

Protocols for the transfection of mammalian cells are well known to those of ordinary skill in the art. Representative methods include calcium and/or magnesium phosphate mediated transfection, electroporation, lipofection, retroviral, lentiviral, adenoviral and protoplast fusion-mediated.

In some embodiments, HSV-TK, or a mutant thereof, is prepared by culturing the host/vector systems described above, in order to express the recombinant thymidine kinase mutants. Recombinantly produced thymidine kinase mutants may be further purified according to methods well known in the art.

In some embodiments, the nucleic acid molecules described herein are introduced into a wide variety of host cells. Representative examples of such host cells include plant cells, eukaryotic cells, and prokaryotic cells. In some embodiments, the nucleic acid molecules are introduced into cells from a vertebrate or warm-blooded animal, such as a human, macaque, dog, cow, horse, pig, sheep, rat, hamster, mouse or fish cell, or any hybrid thereof.

In some embodiments, the nucleic acid molecules described herein are introduced into a mammalian cell. In some embodiments, the mammalian cell is chosen from the group including COS, BHK, CHO, HeLa, 293 and NS-1 cells. In some embodiments, suitable expression vectors for directing expression in mammalian cells include a promoter, as well as other transcriptional and translational control sequences. Common promoters include SV40, MMTV, metallothionein-1, adenovirus E1a, Cytomegalovirus Immediate Early Promoter, and the Cytomegalovirus Immediate Late Promoter.

In some embodiments, the nucleic acid molecules described herein are introduced into a yeast or fungi cell. Yeast and fungi host cells suitable for carrying out the present invention include, among others *Saccharomyces pombe, Saccharomyces cerevisiae*, the genera *Pichia* or *Kluyveromyces* and various species of the genus *Aspergillus*. Suitable expression vectors for yeast and fungi include, among others, YCp 50 for yeast, and the amdS cloning vector pV3. In some embodiments, transformation of yeast is accomplished either by preparation of spheroplasts of yeast with DNA or by treatment with alkaline salts such as LiCl. In some embodiments, transformation of fungi is carried out using polyethylene glycol.

In some embodiments, the nucleic acid molecules described herein are introduced into a bacterial cell. Bacterial host cells suitable for carrying out the present invention include *E. coli, B. subtilis, Salmonella typhimurium*, and various species within the genus' *Pseudomonas, Streptomyces*, and *Staphylococcus*, as well as many other bacterial species well known to one of ordinary skill in the art. Representative examples of bacterial host cells include DH5a (Stratagene, La Jolla, Calif.).

In some embodiments, bacterial expression vectors comprise a promoter which functions in the host cell, one or more selectable phenotypic markers, and a bacterial origin of replication. Representative promoters include the β-lactamase (penicillinase) and lactose promoter system, the T7 RNA polymerase promoter, the lambda promoter, the trp promoter and the tac promoter. Representative selectable markers include various antibiotic resistance markers such as the kanamycin or ampicillin resistance genes. In some embodiments, plasmids suitable for transforming host bacterial cells include, among others, pBR322, the pUC plasmids pUC18, pUC19, pUC118, pUC119, pNH8A, pNH16a, pNH18a, and Bluescript M13 (Stratagene, La Jolla, Calif.).

In some embodiments, the nucleic acid molecules described herein are expressed in non-human transgenic animals such as mice, rats, rabbits, sheep, dogs and pigs. In some embodiments, an expression unit, including a nucleic acid molecule to be expressed together with appropriately positioned expression control sequences, is introduced into pronuclei of fertilized eggs, for example, by microinjection.

In some embodiments, integration of the injected DNA is detected by blot analysis of DNA from tissue samples. In some embodiments, the introduced DNA is incorporated into the germ line of the animal so that it is passed on to the animal's progeny. In some embodiments, tissue-specific expression is achieved through the use of a tissue-specific promoter, or through the use of an inducible promoter, such as the metallothionein gene promoter, which allows regulated expression of the transgene.

In some embodiments, the nucleic acid molecules described herein are introduced into host cells by a wide variety of mechanisms, including for example calcium phosphate-mediated transfection; lipofection; gene gun; electroporation; retroviral, adenoviral, protoplast fusion-mediated transfection or DEAE-dextran mediated transfection.

Vectors and Methods of Production Thereof

Disclosed herein is a vector particle, comprising an improved HSV-TK encoding sequence, as described above, which is to be expressed in a desired cell. In some embodiments, the vector particle is a viral vector particle. In some embodiments, the viral vector particle is a retroviral vector particle.

In some embodiments, a vector particle comprising an improved HSV-TK encoding sequence contains or expresses a wide variety of additional nucleic acid molecules in addition to the improved HSV-TK encoding sequence. In some embodiments, the vector additionally expresses a lymphokine, antisense sequence, toxin or "replacement" protein (e.g., adenosine deaminase). Representative examples of lymphokines include, for example, IL-1, IL-2, IL-3, IL-4, IL-5, IL-6, IL-7, IL-8, IL-9, IL-10, IL-11, IL-12, IL-13, IL-14, IL-15, GM-CSF, G-CSF, M-CSF, alpha-interferon, beta-interferon, gamma interferon, and tumor necrosis factors (TNFs). Representative examples of antisense sequences include, but are not limited to: antisense myc, antisense p53, antisense ras, as well as antisense sequences which block the expression or production of viruses such as HIV, HBV and HCV. Representative examples of toxins include, but are not limited to: ricin, abrin, diphtheria toxin, cholera toxin, gelonin, botulinum, pokeweed antiviral protein, tritin, Shigella toxin, and Pseudomonas exotoxin A. Representative examples of suicide genes include, but are not limited to: a cytosine deaminase, a VSV-tk, IL-2, nitroreductase (NR), carboxylesterase, beta-glucuronidase, cytochrome p450, beta-galactosidase, diphtheria toxin A-chain (DT-A), carboxypeptidase G2 (CPG2), purine nucleoside phosphorylase (PNP), and deoxycytidine kinase (dCK). In some instances, the vector additionally expresses a yeast and/or a bacterial cytosine deaminase.

Additional therapeutic sequences include, but are not limited to, Yeast or Bacterial Cytosine Deaminase, other suicide genes, p53 and other apoptotic genes, guanylate kinase, IL-12 and other immune stimulatory or cytokine genes, GFP, RFP, iRFP, LUC2, GLUC and other fluorescent and bioluminescent genes, Cyclin A, D and other cell cycle regulatory genes, Viral genes, bacterial genes, human genes, synthetic genes, SIRNA, RNAi, Micro RNA, antisense of genes, inhibitory or stimulatory sequences, genes captured from library strategies, repeat sequence, replication sequence, promoter or enhancer sequence, DNA binding sequences, any therapeutic sequence, etc.

In some embodiments, a polynucleotide sequence encoding a receptor to a gamma retrovirus is included. Disclosed herein in the present application are experiments demonstrating that that the receptor binding domain (RBD) of amphotropic viral vector envelope gene product binds to a PiT-2 receptor on the cell membrane of target cells and allows for enhancement of viral vector transduction. Using a topological model for PiT-2 and a murine leukemia virus (A-MuLV) receptor-binding assay on CHO-K1 and BHK cells, Feldman et al. (Eiden M V. J Virol. (2004) 78: 595-602) identified the extracellular domain one (ECD1) of the human PiT-2 receptor as being important for amphotrophic virus binding and infection. Studies by Bottger and Petersen (2004) showed that the part needed for binding the virus could be narrowed down to the 182 aa N-Term region and 170 aa C-Term region.

Accordingly, also provided herein in select embodiments are polynucleotide sequences encoding a mutated form of thymidine kinase from human simplex virus (HSV-TK), wherein the encoded HSV-TK includes a polynucleotide sequence to encode PiT-2, PiT-1, MCAT and other receptors used by gamma retrovirus.

Gap Junction Intracellular Communication

In some embodiments, a vector particle additionally comprises a gap junction intracellular communication (GJIC)-increasing treatment, as described herein. In some embodiments, a vector particle additionally expresses one or more genes which encode proteins that facilitate or increase the biological activity of thymidine kinase. In some embodiments, a vector further comprises a sequence encoding a DNA polymerase (e.g., a Herpes DNA polymerase) and/or guanylate kinase.

One of the most frequently used delivery systems for achieving gene therapy involves viral vectors, most commonly adenoviral and retroviral vectors. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805; each of which is incorporated by reference with respect to the disclosures regarding recombinant retroviruses), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described by Curiel (Hum. Gene Ther. (1992) 3:147) can also be employed.

Retroviruses generally have three common open reading frames, gag, pol, and env, which encode the matrix, gag and nucleocapsid structural proteins, encode enzymes including reverse transcriptase, integrase and protease, and encode envelope proteins and transmembrane fusogenic proteins, respectively. Generally, retroviral vector particles are produced by packaging cell lines that provide the necessary gag, pol, and env gene products in trans. This approach results in the production of retroviral vector particles which transduce mammalian cells, but are incapable of further replication after they have integrated into the genome of the cell.

For gene delivery purposes, a viral particle can be developed from a virus that is native to a target cell or from a virus that is non-native to a target cell. Generally, it is desirable to use a non-native virus vector rather than a native virus vector. While native virus vectors may possess a natural affinity for target cells, such viruses pose a greater hazard since they possess a greater potential for propagation in target cells. In this regard, animal virus vectors, wherein they are not naturally designed for propagation in human cells, can be useful for gene delivery to human cells. In order to obtain sufficient yields of such animal virus vectors for use in gene delivery, however, it is necessary to carry out production in a native animal packaging cell. Virus vectors produced in this way, however, normally lack any components either as part of the envelope or as part of the capsid that can provide tropism for human cells. For example, current practices for the production of non-human virus vectors, such as ecotropic mouse (murine) retroviruses like MMLV, are produced in a mouse packaging cell line. Another component required for human cell tropism must be provided.

In general, the propagation of a viral vector (without a helper virus) proceeds in a packaging cell in which nucleic acid sequences for packaging components are stably integrated into the cellular genome and nucleic acid coding for viral nucleic acid is introduced in such a cell line.

In some embodiments, the retroviral plasmid vector includes a polynucleotide comprising the improved HSV-TK encoding sequence, and the expression vehicle including the polynucleotide comprising the improved HSV-TK encoding sequence are transduced into a packaging cell line including nucleic acid sequences encoding the gag, pol, and wild-type (i.e., unmodified) env retroviral proteins. Examples of such packaging cell lines include, but are not limited to, the PE501, PA317 (ATCC No. CRL 9078),'-2, -AM, PA12, T19-14X, VT-19-17-H2, TCRE, TCRIP, GP+E-86, GP+envAm12, and DAN cell lines as described in Miller, Human Gene Therap, Vol. 1, pgs. 5-14 (1990), which is incorporated herein by reference in its entirety, or the 293T cell line (U.S. Pat. No. 5,952,225). The vector(s) may be transfected into the packaging cells through any means known in the art. Such means include, but are not limited to, electroporation, and use of liposomes, such as hereinabove described, and $CaPO_4$ precipitation. Such producer cells generally generate infectious retroviral vector particles which include the first, or unmodified wild-type retroviral envelope protein, a chimeric retroviral envelope protein, and a polynucleotide encoding the therapeutic or diagnostic agent.

In some embodiments, there is provided a packaging cell which includes polynucleotides encoding the gag and pol proteins, a polynucleotide encoding a first retroviral envelope protein free of non-retroviral peptides (which, in some embodiments, is a wild-type retroviral envelope protein), and a polynucleotide encoding a chimeric retroviral envelope protein. In some embodiments, a producer cell for generating retroviral vector particles which include the first and chimeric envelope proteins is produced by introducing into such packaging cell either a retroviral vector particle or a retroviral plasmid vector, in each case including a polynucleotide encoding the therapeutic or diagnostic agent. In some embodiments, the producer cell line thus generates infectious retroviral vector particles including the polynucleotide comprising the improved HSV-TK encoding sequence.

In some embodiments, disclosed herein is a kit for the production of viral vectors, the kit comprising: a) a container containing a first plasmid comprising a nucleic acid sequence encoding a retroviral envelope protein, wherein the nucleic acid sequence is operably linked to a promoter; b) a container containing a second plasmid comprising: a nucleic acid sequence operably linked to a promoter, wherein the sequence encodes a viral gag-pol polypeptide, a nucleic acid sequence operably linked to a promoter, wherein the sequence encodes a polypeptide that confers drug resistance on the producer cell, and an SV40 origin of replication; c) a container containing a third plasmid comprising: an improved HSV-TK encoding sequence operably linked to a promoter, 5' and 3' long terminal repeat sequences (LTRs), a Ψ retroviral packaging sequence, a CMV promoter upstream of the 5' LTR; a nucleic acid sequence operably linked to a promoter, wherein the sequence encodes a polypeptide that confers drug resistance on the producer cell, an SV40 origin of replication, d) a container containing a producer cell that expresses SV40 large T antigen; and e) instructions for transiently transfecting the producer cell of d) with the plasmids of a), b), and c) and culturing the transfected producer cell under conditions that allow viral particles to be produced.

It is recognized that the delivery vectors or therapeutic vectors disclosed herein include viral and non-viral particles. Non-viral delivery systems, such as microparticles or nanoparticles including, for example, cationic liposomes and polycations, provide alternative methods for delivery systems and are encompassed by the present disclosure. Non-viral particles include encapsulated nucleoproteins, including wholly or partially assembled viral particles, in lipid bilayers. Methods for encapsulating viruses into lipid bilayers are known in the art. They include passive entrapment into lipid bilayer-enclosed vesicles (liposomes), and incubation of virions with liposomes (U.S. Pat. No. 5,962,429; Fasbender, et al., J. Biol. Chem. 272:6479-6489; Hodgson and Solaiman, Nature Biotechnology 14:339-342 (1996)). Without being limited by a theory, we assume that acidic proteins exposed on the surface of a virion provide an interface for complexation with the cationic lipid/cationic polymer component of the delivery vector or therapeutic vector and serve as a "scaffold" for the bilayer formation by the neutral lipid component.

Examples of non-viral delivery systems include, for example, Wheeler et al., U.S. Pat. Nos. 5,976,567 and 5,981,501. These patents disclose preparation of serum-stable plasmid-lipid particles by contacting an aqueous solution of a plasmid with an organic solution containing cationic and non-cationic lipids. Thierry et al., U.S. Pat. No. 6,096,335 disclose preparation of a complex comprising a globally anionic biologically active substance, a cationic constituent, and an anionic constituent. Allen and Stuart, PCT/US98/12937 (WO 98/58630) disclose forming polynucleotide-cationic lipid particles in a lipid solvent suitable for solubilization of the cationic lipid, adding neutral vesicle-forming lipid to the solvent containing the particles, and evaporating the lipid solvent to form liposomes having the polynucleotide entrapped within. Allen and Stuart, U.S. Pat. No. 6,120,798, disclose forming polynucleotide-lipid microparticles by dissolving a polynucleotide in a first, e.g., aqueous, solvent, dissolving a lipid in a second, e.g., organic, solvent immiscible with said first solvent, adding a third solvent to effect formation of a single phase, and further adding an amount of the first and second solvents to effect formation of two liquid phases. Bally et al. U.S. Pat. No. 5,705,385, and Zhang et al. U.S. Pat. No. 6,110,745 disclose a method for preparing a lipid-nucleic acid particle by contacting a nucleic acid with a solution containing a non-cationic lipid and a cationic lipid to form a lipid-nucleic acid mixture. Maurer et al., PCT/CA00/00843 (WO 01/06574) disclose a method for preparing fully lipid-encapsulated therapeutic agent particles of a charged therapeutic agent including combining preformed lipid vesicles, a charged therapeutic agent, and a destabilizing agent to form a mixture thereof in a destabilizing solvent that destabilizes, but does not disrupt, the vesicles, and subsequently removing the destabilizing agent.

A Particle-Forming Component ("PFC") typically comprises a lipid, such as a cationic lipid, optionally in combination with a PFC other than a cationic lipid. A cationic lipid is a lipid whose molecule is capable of electrolytic dissociation producing net positive ionic charge in the range of pH from about 3 to about 10, preferably in the physiological pH range from about 4 to about 9. Such cationic lipids encompass, for example, cationic detergents such as cationic amphiphiles having a single hydrocarbon chain. Patent and scientific literature describes numerous cationic lipids having nucleic acid transfection-enhancing properties. These transfection-enhancing cationic lipids include, for example: 1,2-dioleyloxy-3-(N,N,N-trimethylammonio)propane chloride-, DOTMA (U.S. Pat. No. 4,897,355); DOSPA (see Hawley-Nelson, et al., Focus 15(3):73 (1993)); N,N-distearyl-N,N-dimethyl-ammonium bromide, or DDAB (U.S. Pat. No. 5,279,833); 1,2-dioleoyloxy-3-(N,N,N-trimethylammonio) propane chloride-DOTAP (Stamatatos, et al., Biochemistry 27: 3917-3925 (1988)); glycerol based lipids (see Leventis, et al., Biochem. Biophys. Acta 1023:124 (1990); arginyl-PE (U.S. Pat. No. 5,980,935); lysinyl-PE (Puyal, et al. J. Biochem. 228:697 (1995)), lipopolyamines (U.S. Pat. No. 5,171,678) and cholesterol based lipids (WO 93/05162, U.S. Pat. No. 5,283,185); CHIM (1-(3-cholesteryl)-oxycarbonyl-aminomethylimidazole); and the like. Cationic lipids for transfection are reviewed, for example, in: Behr, Bioconjugate Chemistry, 5:382-389 (1994). Preferable cationic lipids are DDAB, CHIM, or combinations thereof. Examples of cationic lipids that are cationic detergents include (C12-C18)-alkyl- and (C 12-C18)-alkenyl-trimethylammonium salts, N—(C12-C18)-alkyl- and N—(C12-C18)-alkenyl-pyridinium salts, and the like.

In some embodiments, the size of a delivery vector or therapeutic vector formed is within the range of about 40 to about 1500 nm. In some embodiments, the delivery vector or therapeutic vector is in the range of about 50-500 nm in size. In some embodiments, the delivery vector or therapeutic vector is in the range of about 20-150 nm in size. This size selection advantageously aids the delivery vector, when it is administered to the body, to penetrate from the blood vessels into the diseased tissues such as malignant tumors, and transfer a therapeutic nucleic acid therein. It is also a characteristic and advantageous property of the delivery vector that its size, as measured for example, by dynamic light scattering method, does not substantially increase in the presence of extracellular biological fluids such as in vitro cell culture media or blood plasma.

Alternatively, in some embodiments, cells which produce retroviruses are injected into a tumor. In some embodiments, the retrovirus-producing cells so introduced are engineered to actively produce a delivery vector, such as a viral vector particle, so that continuous productions of the vector occurred within the tumor mass in situ. In some embodiments, proliferating tumor cells are transduced in vivo by proximity to retroviral vector-producing cells.

Methods of Use

In some embodiments, disclosed herein is a method of providing to target cells a polynucleotide encoding HSV-TK, as disclosed herein, the method comprising and then exposing the cells to an appropriate substrate which is converted to a toxic substance to kill those cells expressing the mutant HSV-1 thymidine kinase gene as well as those in the vicinity of the mutant HSV-1 thymidine kinase gene-expressing cells, i.e., bystander cells. The mutant HSV-1 thymidine kinase gene can be administered directly to the targeted or desired cells or systemically in combination with a targeting means, such as through the selection of a particular viral vector or delivery formulation. Cells can be treated in vivo, within the patient to be treated, or treated in vitro, then injected into the patient. Following introduction of the mutant HSV-1 thymidine kinase gene into cells in the patient, the prodrug is administered, systemically or locally, in an effective amount to be converted by the mutant HSV-1 thymidine kinase into a sufficient amount of toxic substance to kill the targeted cells. A nucleoside analog which is a substrate for HSV-1 TK to produce a toxic substance which kills target cells is referred to herein as a "prodrug".

In some embodiments, disclosed herein is a method of killing a cell, the method comprising: i) introducing into the cell a polynucleotide or vector as disclosed herein; ii) allowing or directing the cell to express thymidine kinase; and iii) contacting the cell with an agent that is converted by thymidine kinase to a cytotoxic agent.

In some embodiments of the present invention there is provided herein a method of preventing graft-versus-host disease (GvHD) in a patient comprising: (i) administering to a host T-cells genetically engineered to include a polynucleotide or vector of the present invention; and (ii) administering to said host, prior to the occurrence of graft-versus-host disease, an agent capable of being converted by thymidine kinase to a cytotoxic agent in an amount effective to kill genetically engineered T-cells capable of effecting GvHD. During an allogeneic bone marrow transplant, alloreactive T lymphocytes can be removed from the graft in order to prevent graft versus host disease. GvHD occurs when T-cells in the transplant stem cell graft attack the transplant recipient's body. However, removal of the T-cells can increase the incidence of disease relapse, graft rejection and reactivation of viral infection. To counter the possibility of GvHD, allogeneic bone marrow transplant patients can be treated by introducing donor T lymphocytes after a delay following the allogeneic bone marrow transplant. However, delayed introduction of donor T lymphocytes following allogeneic bone marrow transplant is limited by GvHD, a frequent and potentially lethal complication of the treatment. By administering to a transplant recipient T-cells genetically engineered to include a polynucleotide encoding a "suicide gene," the T-cells can be killed if they begin to attack the transplant recipient's body.

In some embodiments, the retroviral vector particles, which include a chimeric retroviral envelope protein and a polynucleotide encoding a therapeutic agent, are administered to a host in order to express the therapeutic agent in the host. In some embodiments, the polynucleotide encoding a therapeutic agent is a polynucleotide encoding HSV-TK, or a mutant and/or variant thereof, as disclosed herein.

In some embodiments, cells are obtained from a patient, and retroviral vector particles are used to introduce a therapeutic agent or polypeptide into the cells, and such modified cells are administered to the patient. In some embodiments, retroviral vector particles are administered to the patient in vivo, whereby the retroviral vector particles transduce cells of the patient in vivo.

In some embodiments, disclosed herein is a method of delivering a therapeutic agent or polypeptide to a site of tissue injury in a subject, comprising directly or intravenously delivering to the site of tissue injury a retroviral particle comprising: i) a chimeric retroviral envelope protein and ii) at least one polynucleotide encoding a therapeutic polypeptide, wherein the viral particle binds to collagen exposed at the site of tissue injury and expresses the therapeutic polypeptide at the site of tissue injury. In some embodiments, the tissue injury is selected from the group consisting of tissue injury due to tumor invasion, vascular lesion, ulcerative lesions, inflammatory tissue injury, laser injury to eyes, surgery, arthritic joints, scars, and keloids. In some embodiments, the tissue injury is a lesion of tissue due to growth of a tumor in the host.

In some embodiments, therapeutic vectors, as disclosed herein, are employed in the treatment of cancer, including malignant and nonmalignant tumors. In some embodiments, the therapeutic vectors further comprise an extracellular matrix binding peptide or peptide domain. In some embodiments, the extracellular matrix binding peptide or peptide domain is a collagen binding domain or peptide. In some embodiments, the tumors include, but are not limited to, all solid tumors.

In some embodiments, therapeutic vectors, as disclosed herein, are employed in the treatment of cancer being selected from the group consisting of breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, melanoma, osteosarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neurons, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas. In other embodiments, the cancer being treated is pancreatic cancer, liver cancer, breast cancer, osteosarcoma, lung cancer, soft tissue sarcoma, cancer of the larynx, melanoma, ovarian cancer, brain cancer, Ewing's sarcoma or colon cancer.

In other embodiments, the cancer to be treated is chosen from the group consisting of primary hepatocellular carcinoma, metastatic breast carcinoma to liver, metastatic pancreatic cancer to liver, metastatic gastric cancer to liver, metastatic esophageal cancer to liver, metastatic lung cancer to liver, metastatic melanoma to liver, metastatic ovarian carcinoma to liver and metastatic kidney cancer to liver.

The therapeutic vectors may be administered alone or in conjunction with other therapeutic treatments or active agents. Examples of other active agents that may be used include, but are not limited to, chemotherapeutic agents, anti-inflammatory agents, protease inhibitors, such as HIV protease inhibitors, nucleoside analogs, such as AZT. In some embodiments, the methods of treatment further comprise administering to the subject a chemotherapeutic agent, a biologic agent, or radiotherapy prior to, contemporaneously with, or subsequent to the administration of the therapeutic viral particles. One of skill in the art will appreciate that the retroviral particles described herein may be administered either by the same route as the one or more agents (e.g., the retroviral vector and the agent are both administered intravenously) or by different routes (e.g., the retroviral vector is administered intravenously and the one or more agents are administered orally).

The dosage of the therapeutic viral particles lies preferably within a range of circulating concentrations that include the $ED_{50}$ with little or no toxicity. The dosage may vary within this range depending upon the dosage form employed and the route of administration utilized. A therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection or a half-maximal inhibition) as determined in cell culture. Such information can be used to more accurately determine useful doses in humans. Levels in plasma may be measured, for example, by RT-qPCR or ddPCR methods.

An effective amount or therapeutically effective of the retroviral particles disclosed herein to be administered to a subject in need of treatment may be determined in a variety of ways. By way of example, the amount may be based on viral titer or efficacy in an animal model. Alternatively the dosing regimes used in clinical trials may be used as general guidelines.

In some embodiments, the daily dose may be administered in a single dose or in portions at various hours of the day. In some embodiments, a higher dosage may be required and may be reduced over time when the optimal initial response is obtained. In some embodiments, treatment may be continuous for days, weeks, or years, or may be at intervals with intervening rest periods. In some embodiments, the dosage is modified in accordance with other treatments the individual may be receiving. However, the method of treatment is in no way limited to a particular concentration or range of the retroviral particle and may be varied for each individual being treated and for each derivative used.

Individualization of dosage may be required to achieve the maximum effect for a given individual. In some embodiments, the dosage administered to an individual being treated varies depending on the individual's age, severity or stage of the disease and response to the course of treatment. In some embodiments, clinical parameters for determining dosage include, but are not limited to, tumor size, alteration in the level of tumor markers used in clinical testing for particular malignancies. In some embodiments, the treating physician determines the therapeutically effective amount to be used for a given individual. In some embodiments, the therapies disclosed herein are administered as often as necessary and for the period of time judged necessary by the treating physician.

The therapeutic vectors, including but not limited to the therapeutic retroviral particles that are specifically to the cell or system of interest, may be systemically or regionally (locally) delivered to a subject in need of treatment. For example, the therapeutic vectors may be systemically administered intravenously. Alternatively, the therapeutic vectors may also be administered intra-arterially. The therapeutic vectors may also be administered topically, intravenously, intra-arterially, intra-tumorally, intracolonically, intratracheally, intraperitoneally, intranasally, intravascularly, intrathecally, intracranially, intramarrowly, intrapleurally, intradermally, subcutaneously, intramuscularly, intraocularly, intraosseously and/or intrasynovially or sterotactically. A combination of delivery modes may also be used, for example, a patient may receive the therapeutic vectors both systemically and regionally (locally) to improve tumor responses with treatment of the therapeutic vectors.

In some embodiments, multiple therapeutic courses (e.g., first and second therapeutic course) are administered to a subject in need of treatment. In some embodiments, the first and/or second therapeutic course is administered intravenously. In other embodiments, the first and/or second therapeutic course is administered via intra-arterial infusion, including but not limited to infusion through the hepatic artery, cerebral artery, coronary artery, pulmonary artery, iliac artery, celiac trunk, gastric artery, splenic artery, renal artery, gonadal artery, subclavian artery, vertebral artery, axilary artery, brachial artery, radial artery, ulnar artery, carotid artery, femoral artery, inferior mesenteric artery and/or superior mesenteric artery. Intra-arterial infusion may be accomplished using endovascular procedures, percutaneous procedures or open surgical approaches. In some embodiments, the first and second therapeutic course may be administered sequentially. In yet other embodiments, the first and second therapeutic course may be administered simultaneously. In still other embodiments, the optional third therapeutic course may be administered sequentially or simultaneously with the first and second therapeutic courses.

In some embodiments, the therapeutic vectors disclosed herein may be administered in conjunction with a sequential or concurrently administered therapeutic course(s) in high doses on a cumulative basis. For example, in some embodiments, a patient in need thereof may be systemically administered, e.g., intravenously administered, with a first therapeutic course of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis. The first therapeutic course may be systemically administered. Alternatively, the first therapeutic course may be administered in a localized manner, e.g., intra-arterially, for example a patient in need thereof may be administered via intra-arterial infusion with at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis.

In yet other embodiments, a subject in need thereof may receive a combination, either sequentially or concurrently, of systemic and intra-arterial infusions administration of high doses of delivery vector. For example, a patient in need thereof may be first systemically administered with at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis, followed by an additional therapeutic course of intra-arterial infusion, e.g., hepatic arterial infusion, administered delivery vector of at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP on a cumulative basis. In still another embodiment, a patient in need thereof may receive a combination of intra-arterial infusion and systemic administration of delivery vector in high doses. For example, a patient in need thereof may be first be administered via intra-arterial infusion with at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis, followed by an additional therapeutic course of systemically administered delivery vector of at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP on a cumulative basis. The therapeutic courses may also be administered simultaneously, i.e., a therapeutic course of high doses of delivery vector, for example, at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis, together with a therapeutic course of intra-arterial infusion, e.g., hepatic arterial infusion, administered delivery vector of at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP on a cumulative basis.

In still other embodiments, a subject in need thereof may additionally receive, either sequentially or concurrently with the first and second therapeutic courses, additional therapeutic courses (e.g., third therapeutic course, fourth therapeutic course, fifth therapeutic course) of cumulative dose of delivery vector, for example, at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis.

In some embodiments, the subject in need of treatment is administered systemically (e.g., intravenously) a dose of at least $1\times10^{11}$ TVP, followed by the administration via intra-arterial infusion (e.g., hepatic-arterial infusion) of a dose of at least $1\times10^{11}$ TVP. In other embodiments, the patient in need of treatment may be administered systemically (e.g., intravenously) a cumulative dose of at least $1\times10^{12}$ TVP, followed by the administration via intra-arterial infusion (e.g., hepatic-arterial infusion) of a dose of at least $1\times10^{12}$ TVP. In one embodiment, the patient in need of treatment may be administered systemically (e.g., intravenously) a dose of at least $1\times10^{13}$ TVP, followed by the administration via intra-arterial infusion (e.g., hepatic-arterial infusion) of a dose of at least $1\times10^{13}$ TVP. In yet other embodiments, the patient in need of treatment may be administered systemically (e.g., intravenously) a dose of at least $1\times10^{14}$ TVP, concurrently with the administration via intra-arterial infusion (e.g., hepatic-arterial infusion) of a dose of at least $1\times10^{14}$ TVP. In still other embodiments, the patient in need of treatment may be administered systemically (e.g., intravenously) a dose of at least $1\times10^{15}$ TVP, together with the administration via intra-arterial infusion (e.g., hepatic-arterial infusion) of a dose of at least $1\times10^{15}$ TVP. In yet other embodiments, the patient in need of treatment may be administered systemically (e.g., intravenously) a dose of at least $1\times10^{16}$ TVP, concurrently with the administration via intra-arterial infusion (e.g., hepatic-arterial infusion) of a dose of at least $1\times10^{16}$ TVP. In still other embodiments, the patient in need of treatment may be administered systemically (e.g., intravenously) a dose of at least $1\times10^{13}7$ TVP, together with the administration via intra-arterial infusion (e.g., hepatic-arterial infusion) of a dose of at least $1\times10^{17}$ TVP.

A subject in need of treatment may also be administered, either systemically or localized (for example intra-arterial infusion, such as hepatic arterial infusion) a therapeutic course of delivery vector for a defined period of time. In some embodiments, the period of time may be at least one day, at least two days, at least three days, at least four days, at least five days, at least six days, at least seven days, at least one week, at least two weeks, at least three weeks, at least four weeks, at least five weeks, at least six weeks, at least seven weeks, at least eight weeks, at least 2 months, at least three months, at least four months, at least five months, at least six months, at least seven months, at least eight months, at least nine months, at least ten months, at least eleven months, at least one year, at least two years, at least three years, at least four years, or at least five years. Administration could also take place in a chronic manner, i.e., for an undefined or indefinite period of time.

Administration of the therapeutic vector may also occur in a periodic manner, e.g., at least once a day, at least twice a day, at least three times a day, at least four times a day, at least five times a day. Periodic administration of the delivery vector may be dependent upon the time of delivery vector as well as the mode of administration. For example, parenteral administration may take place only once a day over an extended period of time, whereas oral administration of the delivery vector may take place more than once a day wherein administration of the delivery vector takes place over a shorter period of time.

In one embodiment, the subject is allowed to rest 1 to 2 days between the first therapeutic course and second therapeutic course. In some embodiments, the subject is allowed to rest 2 to 4 days between the first therapeutic course and second therapeutic course. In other embodiments, the subject is allowed to rest at least 2 days between the first and second therapeutic course. In yet other embodiments, the subject is allowed to rest at least 4 days between the first and second therapeutic course. In still other embodiments, the subject is allowed to rest at least 6 days between the first and second therapeutic course. In some embodiments, the subject is allowed to rest at least 1 week between the first and second therapeutic course. In yet other embodiments, the subject is allowed to rest at least 2 weeks between the first and second therapeutic course. In one embodiment, the subject is allowed to rest at least one month between the first and second therapeutic course. In some embodiments, the subject is allowed to rest at least 1-7 days between the second therapeutic course and the optional third therapeutic course. In yet other embodiments, the subject is allowed to rest at least 1-2 weeks between the second therapeutic course and the optional third therapeutic course.

In some embodiments, the therapeutic vector is administered to increase local concentration of the peptide or vector. In some embodiments, the therapeutic vector is administered via intra-arterial infusion, which increases local concentration of the therapeutic vector to a specific organ system. In yet other embodiments, the therapeutic vector is administered intra-tumorally. Dependent upon the location of the target lesions, in some embodiments, catheterization of the hepatic artery is followed by infusion into the pancreaticoduodenal, right hepatic, and middle hepatic artery, respectively, in order to locally target hepatic lesions. In some embodiments, localized distribution to other organ systems, including the lung, gastrointestinal, brain, reproductive, splenic or other defined organ system, of the peptide or delivery vector is accomplished via catheterization or other localized delivery system. In some embodiments, intra-arterial infusions are accomplished via any other available arterial source, including but not limited to infusion through the hepatic artery, cerebral artery, coronary artery, pulmonary artery, iliac artery, celiac trunk, gastric artery, splenic artery, renal artery, gonadal artery, subclavian artery, vertebral artery, axilary artery, brachial artery, radial artery, ulnar artery, carotid artery, femoral artery, inferior mesenteric artery and/or superior mesenteric artery. In some embodiments, intra-arterial infusion is accomplished using endovascular procedures, percutaneous procedures or open surgical approaches.

Formulations

Pharmaceutical compositions comprising a therapeutic vector can be formulated in any conventional manner by mixing a selected amount of the therapeutic vector with one or more physiologically acceptable carriers or excipients. For example, the therapeutic vector may be suspended in a carrier such as PBS (phosphate buffered saline). The active compounds can be administered by any appropriate route, for example, orally, parenterally, intravenously, intradermally, subcutaneously, or topically, in liquid, semi-liquid or solid form and are formulated in a manner suitable for each route of administration.

In some embodiments, the therapeutic vector and physiologically acceptable salts and solvates are formulated for administration by inhalation or insufflation (either through the mouth or the nose) or for oral, buccal, parenteral or rectal administration. In some embodiments, for administration by inhalation, the therapeutic vector is delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In some embodiments, a pressurized aerosol dosage unit or a valve to deliver a metered amount. In some embodiments, capsules and cartridges (e.g., of gelatin) for use in an inhaler or insufflator are formulated containing a powder mix of a therapeutic compound and a suitable powder base such as lactose or starch.

In some embodiments, the pharmaceutical compositions are formulated for oral administration as tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). In some embodiments, the tablets are coated by methods well known in the art. In some embodiments, liquid preparations for oral administration are in the form of, for example, solutions, syrups or suspensions, or they are formulated as a dry product for constitution with water or other suitable vehicle before use. In some embodiments, such liquid preparations are prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils);

and preservatives (e.g., methyl or propyl-p-hydroxybenzoates or sorbic acid). In some embodiments, the preparations also contain buffer salts, flavoring, coloring and sweetening agents as appropriate. In some embodiments, pharmaceutical compositions are formulated oral administration to give controlled release of the active compound. In some embodiments, the pharmaceutical compositions are formulated for buccal in the form of tablets or lozenges formulated in conventional manner.

In some embodiments, the therapeutic vector is formulated for parenteral administration by injection, e.g., by bolus injection, or continuous infusion. In some embodiments, formulations for injection are in unit dosage form, e.g., in ampoules or in multi-dose containers, with an added preservative. In some embodiments, the compositions are formulated as suspensions, solutions or emulsions in oily or aqueous vehicles. In some embodiments, the formulations comprise formulatory agents such as suspending, stabilizing and/or dispersing agents. Alternatively, in some embodiments, the active ingredient is in powder lyophilized form for constitution with a suitable vehicle, e.g., sterile pyrogen-free water, before use.

In some embodiments, the therapeutic vector is formulated as a depot preparation. In some embodiments, such long acting formulations are administered by implantation (for example, subcutaneously or intramuscularly) or by intramuscular injection. Thus, for example, in some embodiments, the therapeutic compounds are formulated with suitable polymeric or hydrophobic materials (for example, as an emulsion in an acceptable oil) or ion exchange resins, or as sparingly soluble derivatives, for example, as a sparingly soluble salt.

In some embodiments, the active agents are formulated for local or topical application, such as for topical application to the skin and mucous membranes, such as in the eye, in the form of gels, creams, and lotions and for application to the eye or for intracisternal or intraspinal application. In some embodiments, such solutions, particularly those intended for ophthalmic use, are formulated as 0.01%-10% isotonic solutions, pH about 5-9, with appropriate salts. In some embodiments, the compounds are formulated as aerosols for topical application, such as by inhalation.

The concentration of active compound in the drug composition will depend on absorption, inactivation and excretion rates of the active compound, the dosage schedule, and amount administered as well as other factors known to those of skill in the art.

In some embodiments, the compositions are presented in a pack or dispenser device which comprise one or more unit dosage forms containing the active ingredient. In some embodiments, the pack may comprises metal or plastic foil, such as a blister pack. In some embodiments, the pack or dispenser device is accompanied by instructions for administration.

In some embodiments, the active agents are packaged as articles of manufacture containing packaging material, an agent provided herein, and a label that indicates the disorder for which the agent is provided.

Animal Models

In some embodiments, the retroviral vector particles, hereinabove described are administered to an animal in vivo as part of an animal model for the study of the effectiveness of a gene therapy treatment. In some embodiments, the retroviral vector particles are administered in varying doses to different animals of the same species. The animals then are evaluated for in vivo expression of the desired therapeutic or diagnostic agent. In some embodiments, from the data obtained from such evaluations, a person of ordinary skill in the art determines the amount of retroviral vector particles to be administered to a human patient.

Kits

Also provided are kits or drug delivery systems comprising the compositions for use in the methods described herein. All the essential materials and reagents required for administration of the retroviral particles disclosed herein may be assembled in a kit (e.g., packaging cell construct or cell line, cytokine expression vector). The components of the kit may be provided in a variety of formulations as described above. The one or more therapeutic retroviral particles may be formulated with one or more agents (e.g., a chemotherapeutic agent) into a single pharmaceutically acceptable composition or separate pharmaceutically acceptable compositions.

The components of these kits or drug delivery systems may also be provided in dried or lyophilized forms. When reagents or components are provided as a dried form, reconstitution generally is by the addition of a suitable solvent, which may also be provided in another container means.

Container means of the kits may generally include at least one vial, test tube, flask, bottle, syringe and/or other container means, into which the at least one substance can be placed.

The kits disclosed herein may also comprise instructions regarding the dosage and/or administration information for the retroviral particle. Instructions can include instructions for practicing any of the methods described herein including treatment methods. Instructions can additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

In some embodiments, the kits or drug delivery systems include a means for containing the vials in close confinement for commercial sale such as, e.g., injection or blow-molded plastic containers into which the desired vials are retained. Irrespective of the number or type of containers, the kits may also comprise, or be packaged with, an instrument for assisting with the injection/administration or placement of the ultimate complex composition within the body of a subject. Such an instrument may be an applicator, inhalant, syringe, pipette, forceps, measured spoon, eye dropper or any such medically approved delivery vehicle.

Packages and kits can further include a label specifying, for example, a product description, mode of administration and/or indication of treatment. Packages provided herein can include any of the compositions as described herein. The package can further include a label for treating one or more diseases and/or conditions.

The term "packaging material" refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method described herein. A kit can include a compound in a pack, or dispenser together with instructions for administering the compound in a method described herein.

EXAMPLES

In order that those in the art may be better able to practice the compositions and methods described herein, the following examples are provided for illustration purposes.

Example 1: Cell Line Generation

First, retroviral supernatant is generated by transfection of a 3 or 4 plasmid system with calcium phosphate reagent into 293 T cells. Supernatant is filtered through a 0.45 μm filter. Filtered supernatant can be used fresh, stored up to 48 hours at 4° C., or stored at −80° C.

Cell lines are generated by seeding $1 \times 10^4$ cells/well in a 6 well tissue culture dish. The next day retroviral supernatant is added with 8 μg/mL polybrene for 16-24 hours and selected with the appropriate dose of selection drug (G418, hygromycin or puromycin). The dose of the selection drug is the minimum amount to cause 100% kill on non-HSV-TK cells at least 4 days post addition of drug, in order to avoid excessive toxicity to cells.

Example 2: GCV Sensitivity Assay

Cells expressing HSV-TK, or a mutant and/or variant thereof, are seeded at $1 \times 10^5$ in 6 well dishes. The next day, 5 serial 10 fold dilution of GCV are added with a final concentration ranging from 1 mM to 0.1 μm. Three (3) days after GCV treatment, methylene blue is added to stain live cells.

Example 3: Bystander Assay

Cells are seeded at $1\text{-}4 \times 10^4$ cells/well in a 96 well plate, in triplicate, with mixtures of TK cells ranging from 0-100%. The next day GCV is added at doses ranging from 10 μm to 1 mM. Cells plates at confluency are split 1:30 into 3 plates, 20-24 hours after GCV addition. 5 days later, cells are analyzed by Presto Blue for live cell metabolism and read on a microplate reader. Cell plates at sub-confluency are analyzed 3 days after GCV treatment by Presto Blue.

In one assay, the inventors used HSV-TK clonal cell lines were generated; using Neomycin-HSV-TK, Hygromycin-HSV-TK, Red Fluorescent protein (RFP)-HSV-TK cell lines and several mutants of HSV-TK gene were compared.

RexC2 carries an improved version of the Herpes simplex virus (HSV) Thymidine Kinase gene (TK). A cellular host that has been efficiently infected (transduced) with RxC2 will integrate the viral TK in its genome and express this enzyme. HSV-TK phosphorylates the DNA base thymidine for its incorporation into newly synthesized DNA in dividing cells.

A typical 96-well plate plan for cell seeding and GCV treatment is shown in the table below (HK=HSV-TK):

| | media 1 | 20 uM 2 | 20 uM 3 | 20 uM 4 | 10 uM 5 | 10 uM 6 | 10 uM 7 | NO GCV 8 | NO GCV 9 | NO GCV 10 | NO GCV 11 |
|---|---|---|---|---|---|---|---|---|---|---|---|
| A | media | media | media | media | media | media | media | media | media | media | media |
| B | media | 0% TK | 0% TK | 0% TK | 0% TK | 0% TK | 0% TK | 0% TK | 0% TK | 0% TK | 0% TK |
| C | media | 2% TK | 2% TK | 2% TK | 2% TK | 2% TK | 2% TK | 2% TK | 2% TK | 2% TK | 2% TK |
| D | media | 5% TK | 5% TK | 5% TK | 5% TK | 5% TK | 5% TK | 5% TK | 5% TK | 5% TK | 5% TK |
| E | media | 10% TK | 10% TK | 10% TK | 10% TK | 10% TK | 10% TK | 10% TK | 10% TK | 10% TK | 10% TK |
| F | media | 25% TK | 25% TK | 25% TK | 25% TK | 25% TK | 25% TK | 25% TK | 25% TK | 25% TK | 25% TK |
| G | media | 100% TK | 100% TK | 100% TK | 100% TK | 100% TK | 100% TK | 100% TK | 100% TK | 100% TK | 100% TK |
| H | media | media | media | media | media | media | media | media | media | media | media |

Figure 19:
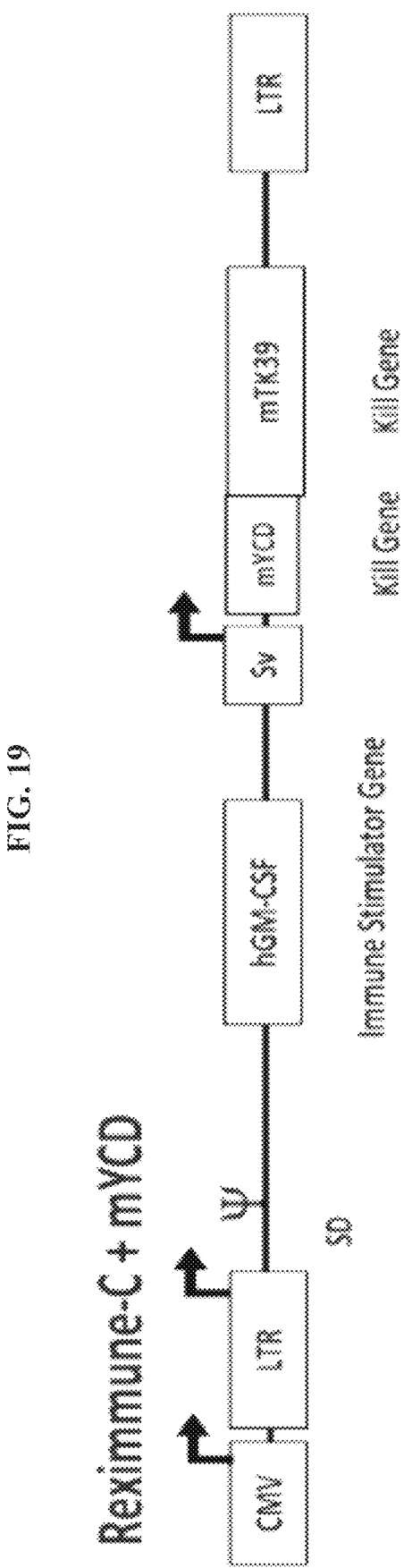
FIG. 19 provides an exemplary of Reximmune-C+a mutated yeast cytidine deaminase (mYCD) kill gene.
Figure 20:
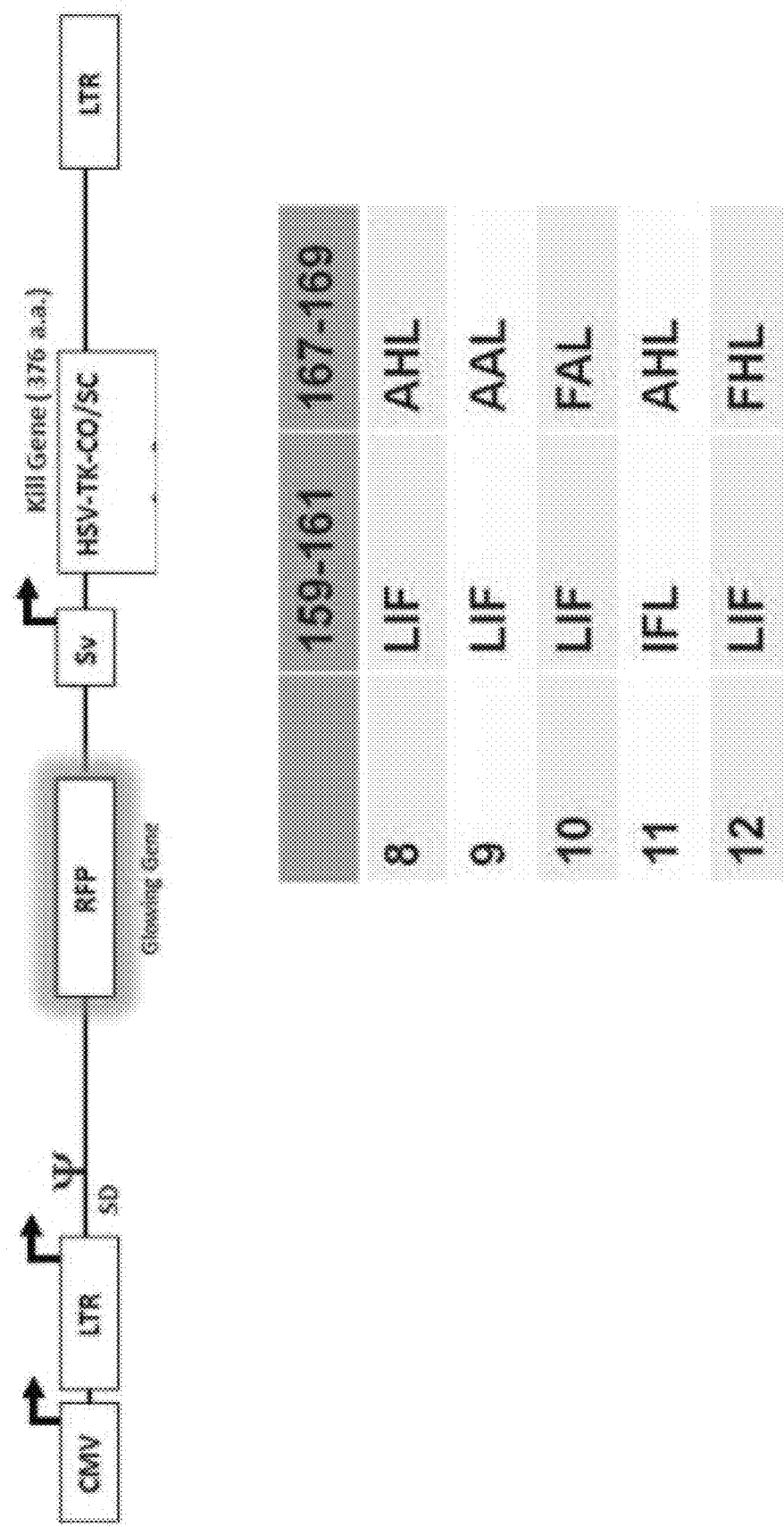
FIG. 20 illustrates one example of a RexRed Super TK which includes a glowing gene (RFP) and a kill gene that contains the identified sequences at the noted positions.
Figure 21:
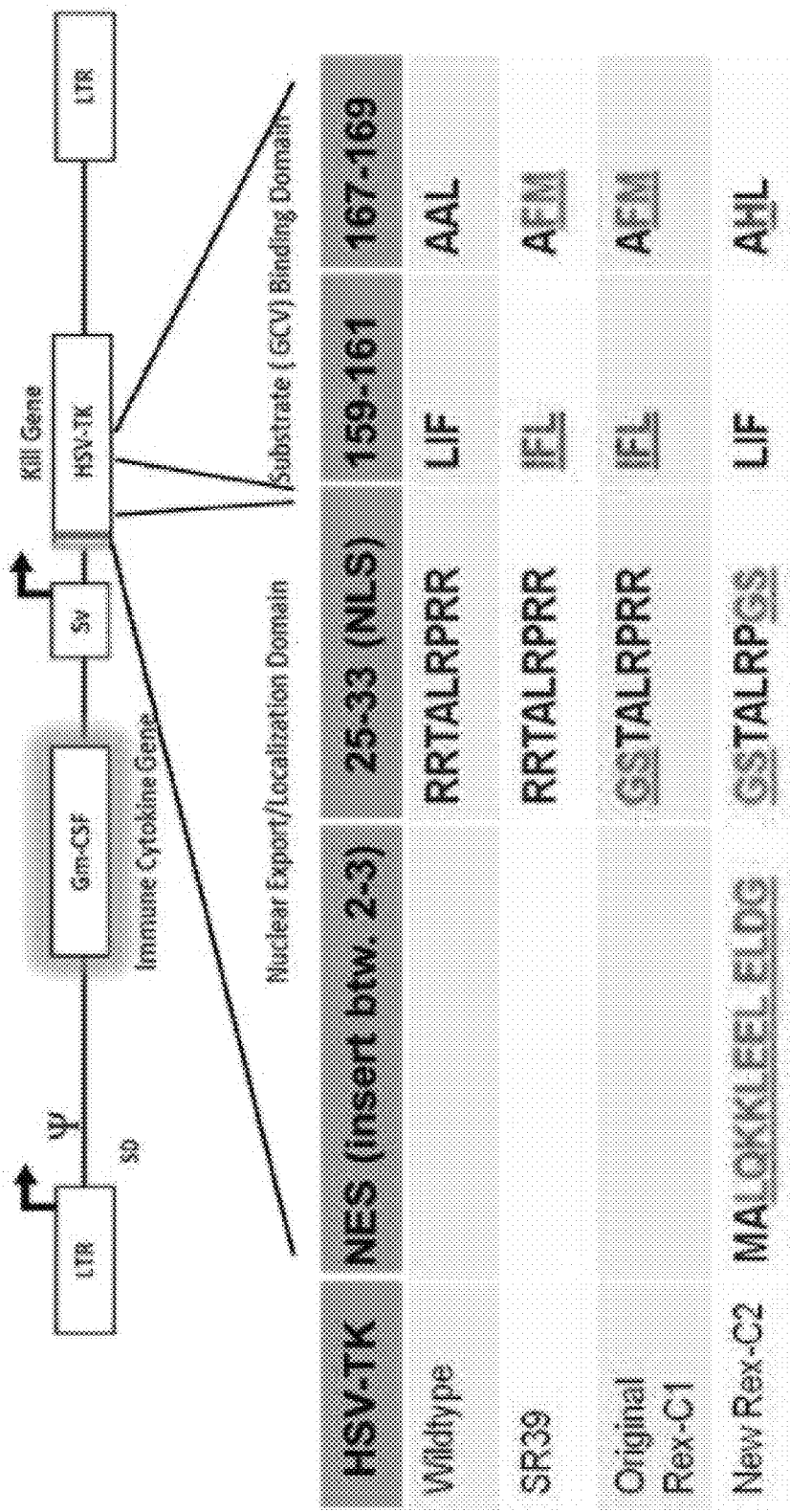
FIG. 21 provides an illustration of retroviral vectors having an updated substrate binding domain and +/−mNLS and/or +/−NES set, highlighting the sequence differences between Reximmune-C1 or 2, SR-39 and the Wildtype HSV-TK gene, and having installed a second therapeutic gene in place of the RFP gene between the LTR and SV40 promoters.
Figure 22:
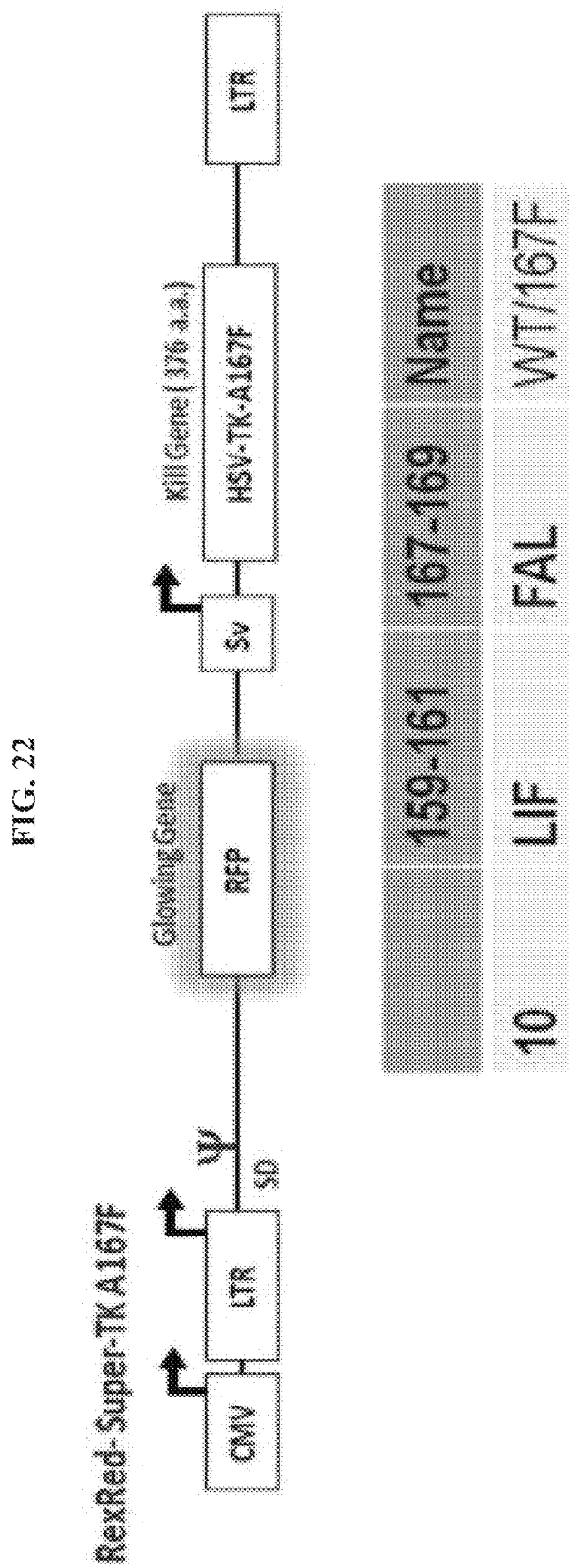
FIG. 22 illustrates RexRed Super TK A167F which includes a glowing gene (RFP) and a kill gene that contains the noted sequences at positions 159-161 and 167-169.
Figure 23A:
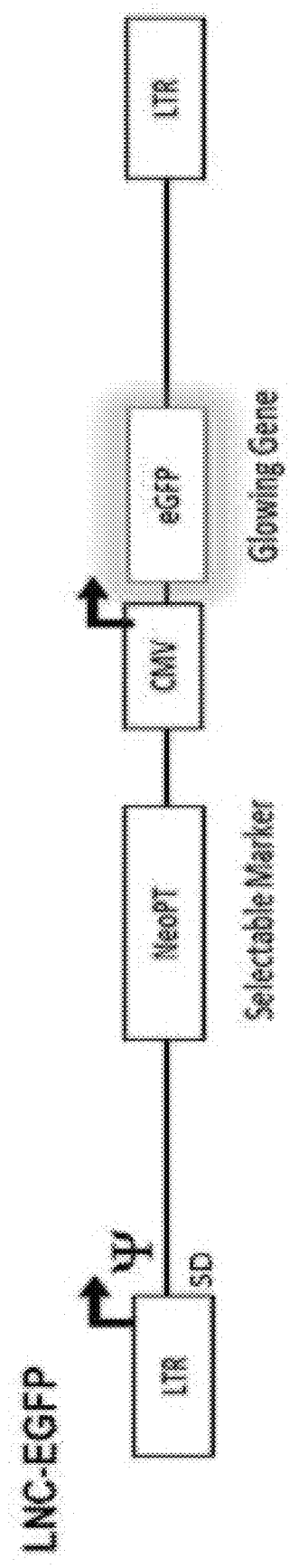
FIG. 23A-FIG. 23B provide exemplary retroviral vectors that are Reximmune-C multicolor clones of LNCE A375 transduced cells.
Figure 23B:
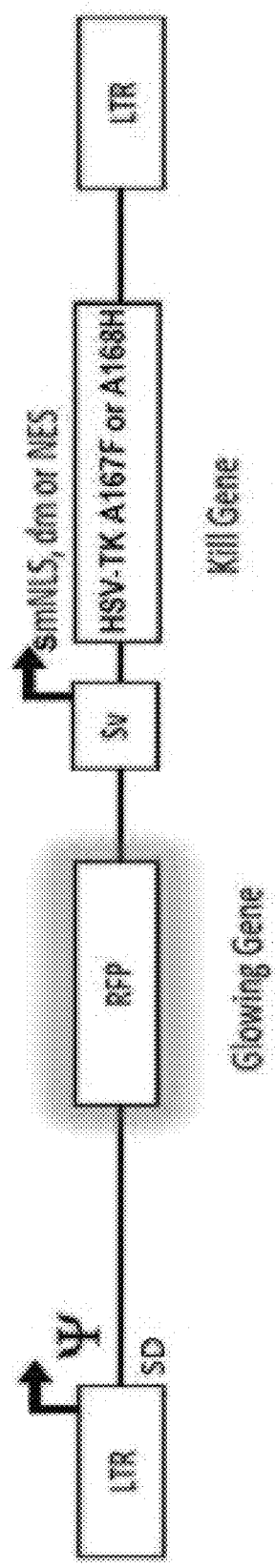
Figure 24A:
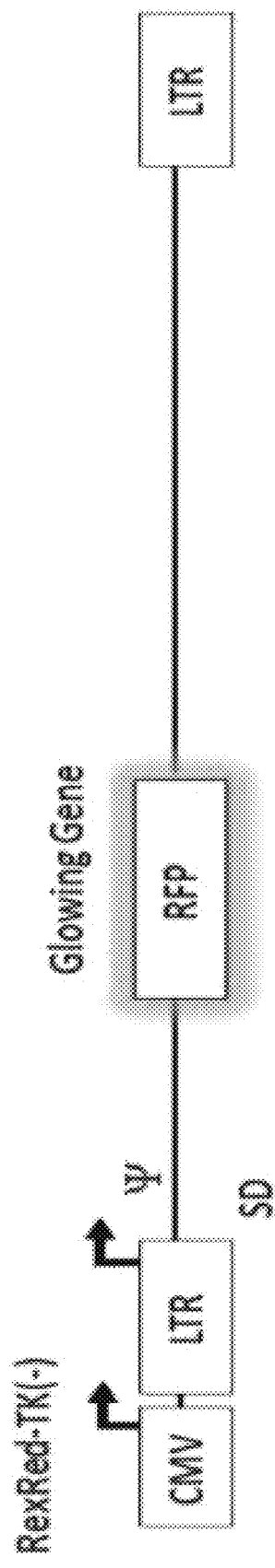
FIG. 24A-FIG. 24B provide exemplary vectors that a glowing gene only or a hygromycin resistance gene selectable marker only.
Figure 24B:
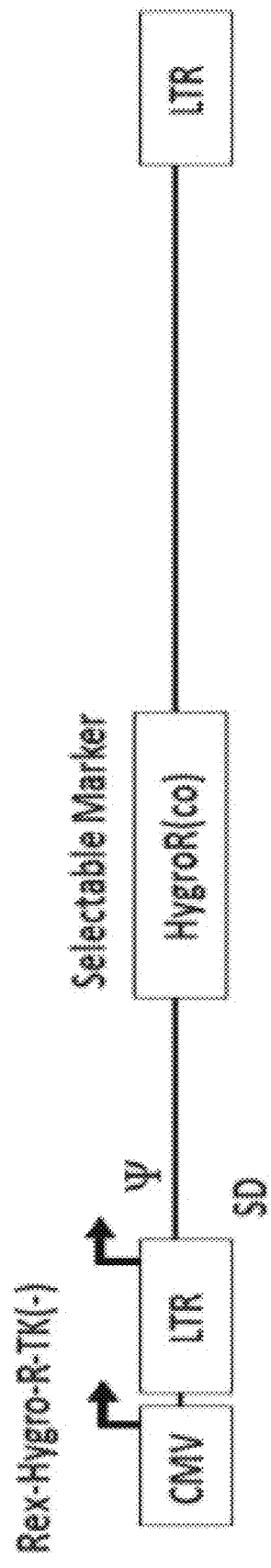

Graphic results of a bystander assay experiment are shown in FIGS. 19 and 20.

More than 40 bystander assays were performed using different mutants HSV-TK and clonal populations.

The data was compiled with GCV sensitivity and enzyme kinetics measurements and viral titer of production for the mutants with potential.

The careful examination of all these parameters allowed the selection of the mutant HSV-TK168dmNES to be the TK gene in Reximmune C-2.

Example 4: Quantitation of Spliced Form of TK RNA by Real Time PCR

The unspliced and truncated form of HSV-TK are subcloned into a pCR2.1 TOPO vector (Invitrogen). Two quantitative real time PCRs are set-up with two different sets of primers and probes able to selectively amplify and detect the unspliced and spliced form of HSV-TK, using the TaqMan®/ABI PRISM 7700 sequence detection system. For the HSV-TK unspliced form, primers and probe are designed in the spliced region of the HSV-tk gene Real Time PCR for the unspliced form is performed in a 25 μl reaction mixture containing 100-500 ng of genomic DNA or 10 μl of cDNA, 1× TaqMan® Universal PCR Master Mix, 300 nM of each of the two primers TKwtfor (5'-CGG CGG TGG TAA TGA CAA G-3') (SEQ ID NO: 25) and Tkwtrev (5'-GCG TCG GTC ACG GCA TA-3') (SEQ ID NO: 26) and 200 nM of TKwt MGB probe (5'-FAM CCA GAT AAC AAT GGG C-3') (SEQ ID NO: 27).

A TaqMan® probe encompassing the splice junction is designed to selectively detect the HSV-TK spliced form. Quantitative Real time PCR specific for the TK spliced (truncated) form was performed in a 25 μl reaction mixture containing 100-500 ng of genomic DNA or 10 μl of cDNA, 1× Master Mix (PE Applied Biosystems) 300 nM of each of the two primers. Thermal cycling conditions are as follows: initial activation of UNG at 50° C. for 2 min, followed by activation of Taq Gold and inactivation of UNG at 95° C. for 15 min. Subsequently, 40 cycles of amplification are performed at 95° C. for 15 s and 60° C. for 1 min. Both PCRs are performed in parallel in MicroAmp® optical 96-well reaction plates (Applied Biosystems) using the ABI Prism 7700 Sequence Detection Systems (Applied Biosystems). Mean baseline fluorescence was calculated from PCR cycles 3 to 15, and Ct was defined as the PCR cycle in which the normalized fluorescence intensity of the reporter dye equaled 0.05. Two standard curves with known copy numbers (from 10<6> to 4 copies/reaction) are generated in each TaqMan® assay by plotting the Ct values against the logarithm of the initial input of DNA amount. Standard dilutions and cDNA samples are analyzed in duplicate and triplicate, respectively.

Example 5: Clinical Trial

A dose escalation trial was conducted to evaluate the safety, pharmacokinetics, and pharmacodynamics of Reximmune-C2 (Thymidine Kinase and GM-CSF Genes) in refractory subjects with primary hepatocellular carcinoma or tumors metastatic to the liver.

Background and Rationale

Reximmune-C2 is comprised of a genetic delivery platform containing an internal payload that encodes for therapeutic proteins of interest. The genetic delivery platform has been dosed in over 280 subjects worldwide; approximately 270 subjects were treated with the vector containing dnG1 as a payload (Rexin-G) and 16 subjects with thymidine kinase (vTK) and the immune stimulator Granulocyte Macrophage Colony Stimulating Factor (GM-CSF) as a payload (Reximmune-C). The genetic delivery platform is a highly engineered non-recombinant Mouse Moloney Viral vector (MoMLV). Previously, a Phase 1 dose escalation trial was performed investigating the combination of Rexin-G and Reximmune-C in subjects with refractory primary or metastatic solid tumors (Genevieve Trial). This proposed Phase I clinical trial (entitled Genevieve 2 Trial) is an extension of a trial undertaken investigating Reximmune-C2 alone—without the Rexin-G—utilizing an improved form of thymidine kinase in a thymidine kinase plus GM-CSF combination.

In the original Genevieve trial, sixteen subject were recruited over 3 dose levels with the mean exposure in the highest dose group being $8.0 \times 10^{10}$ cfus (# of pts=7) and the longest duration 6 cycles (range of cycles 3-6). For Part A of the study, treatment consisted of a previously determined safe and effective (optimal) dose of Rexin-G, and escalating doses of Reximmune-C. Specifically, Rexin-G, $2 \times 10^{11}$ cfu, on Days 1, 3, 5, 8, 10 and 12, Reximmune-C, 1.0, 2.0 or $3.0 \times 10^{10}$ cfu on Day 3 (Dose Levels I, II, III respectively), and valacyclovir at 1 gm p.o. three times a day on Days 6-19, as one cycle. For the Part B part of the study, subjects who had no toxicity or in whom toxicity had resolved to Grade 1 or less could receive additional cycles of therapy up to a total of 6 treatment cycles.

There were no dose-limiting toxicities at any dose level. Unrelated adverse events were reported for the 16 subjects in the study, but the number of events was low (in most cases 1 or 2 occurrences per preferred term), and most were Grade 1 or 2. Related non-serious adverse events occurred in 2 subjects and both were Grade 2. Four subjects experienced serious adverse events, all of which were deemed not related to the study drug.

The rationale for continuation of this Phase 1 trial is that: (1) thymidine kinase itself could prove to be an effective anticancer agent particularly in subjects whose tumors demonstrate a bystander effect; (2) administration of the genetic delivery platform to date to an international group of subjects has demonstrated a very high degree of safety; and (3) biodistribution in animals suggests a high biodistribution to the liver. Moreover, the addition of GM-CSF could contribute to an immunological effect and enhanced tumor cell kill through tumor associated antigens through recruitment of the appropriate immune cells.

The biodistribution of the viral particles is highest to the liver, followed by spleen, then lung—this is the rationale for focusing initially on hepatocellular tumors where the dose intensity should be the highest. There is also a high clinical unmet need for effective anticancer agents for these cancers.

It is understood that the embodiments disclosed herein are not limited to the particular methods and components and other processes described as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Example 6: Clinical Trial for Gene Therapy Applications

This clinical trial is divided into two phases: Phase IA in which Reximmune-C2 was administered as a single intravenous dose on three out of five days. Valganciclovir (the oral form of ganciclovir) dosing is initiated on day 8 for 5 days irrespective of the PET scan results. An approximately one week drug holiday follows. Each cycle will be of three weeks duration.

There will be three patients in the first and subsequent cohorts until a patient experiences Dose Limiting Toxicity (DLT) or two instances of NCI-CTC Grade 2 toxicities attributed to the study drug (except nausea/vomiting, fatigue, anorexia, alopecia, or anemia). If there are no DLTs, patients will move to the next dose level. If there is a DLT, the cohort will be expanded to 6 patients and the dose level will not be exceeded if 2 or more patients exhibit DLTs.

Once the Maximum Administered Dose (MAD) is reached, a modified Fibonacci schedule will be followed starting with the cohort dose which had no DLTs and continuing until dose-limiting toxicities are observed in two patients at a dose level. Once the Recommended Phase 2 Dose (RP2D) is defined, 6-12 patients will be recruited.

Phase IB is designed to explore the activity of Reximmune-C2 in patients of a defined tumor type and stage based on the Phase IA data and who are [$^{18}$F]FHBG scan positive day three to six after one dose (RP2D) of Reximmune-C2. If the scan is positive, the patient is accepted into the Phase IB treatment phase of the protocol and the RP2D is given as three doses within 5 days, followed by 5 days of valganciclovir beginning on day 8 of that phase, followed by a one week drug holiday. Each cycle is of three week duration. Patients who have a negative [$^{18}$F]FHBG PET scan after one single dose of Reximmune-C2 will be dosed with 5 days of valganciclovir and will not continue in the study.

The patient DLT will be defined as the occurrence of any of the following events which is attributed to Reximmune-C2 and occurring during the first cycle (3 weeks) of drug administration:

Grade 4 neutropenia (i.e., absolute neutrophil count (ANC)<500 cells/mm$^3$) for 7 or more consecutive days or febrile neutropenia (i.e., fever ≥38.5° C. with an ANC<1000 cells/mm$^3$); Grade 4 thrombocytopenia (<25,000 cells/mm$^3$ or bleeding episode requiring platelet transfusion); Grade 3 or greater nausea and/or vomiting despite the use of adequate/maximal medical intervention and/or prophylaxis; Any Grade 3 or greater non-hematological toxicity (except Grade 3 injection site reaction, alopecia, fatigue); Retreatment delay of more than 3 weeks due to delayed recovery from a toxicity related to treatment with Reximmune-C2; and Grade 3 or greater hypersensitivity reaction despite the appropriate use of premedications (by Common Toxicity Criteria defined as "symptomatic bronchospasm, requiring parenteral medications(s), with or without urticaria; allergy-related edema-angioedema").

Reximmune-C2 is infused intravenously over 15-60 minutes (depending on the dose) via an infusion pump. Reximmune-C2 is provided in 30 ml vials stored at −80° C.±10° C.

In this Phase I trial, the safety, pharmacokinetics, and pharmacodynamics of escalating doses of Reximmune-C2 will be investigated. The maximum tolerated dose will be identified and a recommended Phase 2 dose will be defined for Reximmune C2. Any antitumor activity and clinical responses to Reximmune-C2 treatment will be described.

The starting dose in this trial is based on: human clinical safety experience with the related vector platform drug products Rexin-G and Reximmune-C and the results of the 21 day rat GLP toxicology study for Reximmune-C2.

Objectives

The primary objective of the study is to determine the maximum tolerated dose (MTD), dose limiting toxicity (DLT), safety, and a recommended Phase 2 dose (RP2D) of Reximmune-C2 administered over a three week cycle consisting of a series of three doses given intraveneously within five days in week 1, followed by 5 daily doses of valganciclovir in week 2 in patients enrolled in this study who have been diagnosed with advanced primary or metastatic tumors to the liver.

Secondary objectives include: (i) evaluation of the plasma pharmacokinetics of Reximmune-C2; (ii) assessment of the surrogate of HSV-TK-m2 protein expression from Reximmune-C2 via serial [$^{18}$F]FHBG PET and/or SPECT imaging; (iii) description and assessment of any preliminary evidence of anti-tumor activity of Reximmune-C2; and (iv) to provide clinical research testing for antibodies to retrovector gp70 env, replication-competent retrovirus in peripheral blood lymphocytes (PBLs); vector integration into genomic DNA of PBLs, and circulating hGM-CSF protein.

Methods

Study Design: Parallel group, open label dose escalation, three-center clinical trial.

Stratification: None.

Therapy: Reximmune-C2 will be administered as an intravenous infusion to separate patients. In Phase IA—investigating Reximmune-C2—the dose will be escalated among cohorts of patients until DLT is observed. At the RP2D, additional patients will be recruited. In Phase IB patients will be pre-screened by [$^{18}$F]FHBG PET for expression of the HSV-TK-m2. Those that express HSV-TK-m2 will receive additional doses of Reximmune-C2. Patients will not be pre-medicated unless hypersensitivity reactions occur.

Statistical Methods: Descriptive statistics will be used for statistical analysis.

Sample Size Determination: Precise sample size cannot be defined, as it is dependent on the observed toxicity. For each schedule, cohorts of three to six subjects will be treated at each dose level until the MTD is defined. Once the MTD is identified, this dose level will be expanded to a maximum of 12 patients who will be treated to better define the tolerability and pharmacokinetics of the dose and schedule. It is expected that 45-70 subjects will be enrolled, with 33 to 46 in the IA portion.

Enrollment Criteria

Subjects must meet all of the following inclusion criteria to be eligible for randomization into the study:

1. Diagnosis of histologically documented, advanced stage, primary or metastatic adult solid tumors in the liver that are refractory to standard therapy or for which no curative standard therapy exists.

2. Evidence of radiographically measurable or evaluable disease.

3. All acute toxic effects of any prior radiotherapy, chemotherapy, or surgical procedures must have resolved to National Cancer Institute (NCI) Common Toxicity Criteria (CTC)(Version 4.0) Grade <1.

4. Age must be >18 years.

5. Last dose of antineoplastic therapy except for hormonal therapy must be >21 days. External beam radiotherapy must have been <25% bone marrow-containing skeleton.

6. Patients may be Hepatitis B and C positive. (Patients may continue their antiviral medications).

7. Patients may have intracranial metastases of any number if they have been brain irradiated and stable for 6 weeks. Patients may be taking anti-seizure medicines but must not be on steroids.

8. Karnofsky performance status must be ≥70.

9. Life expectancy of at least 3 months.

10. Patients must be able to travel to St. Luke's Medical Center for the PET scans.

11. Required baseline laboratory data include:

| | |
|---|---|
| Absolute neutrophil count (ANC) | ≥1,500/mm$^3$ [SI units 10$^9$/L] |
| Platelets | ≥75,000/mm$^3$ [SI units 10$^9$/L] |
| Hemoglobin | ≥8.0 gm/dL [SI units mmol/L] |
| Serum Creatinine | ≤1.5 × laboratory upper limit of normal (L-ULN) |
| Bilirubin | ≤2.0 mg/dL |
| Alkaline phosphatase | ≤5 × L-ULN |
| AST, ALT | ≤5 × L-ULN |
| LDH | ≤5 × L-ULN |

| | |
|---|---|
| Pregnancy test (females of childbearing potential) | Negative within 7 days of starting Protocol |

12. Signed informed consent indicating that they are aware of the neoplastic nature of their disease and have been informed of the procedures to be followed, the experimental nature of the therapy, alternatives, potential benefits, side effects, risks, and discomforts.

13. Willing and able to comply with scheduled visits, treatment plan, and laboratory tests.

The presence of any of the following will exclude a subject from study enrollment 1. Concurrent therapy with any anticancer therapy including any other investigational agent.
2. Known intracranial edema or a CVA within 6 weeks of screening.
3. Pregnant or breast-feeding women. Female subjects must agree to use effective contraception, must be surgically sterile, or must be postmenopausal. Male subjects must agree to use effective contraception or be surgically sterile. The definition of effective contraception will be based on the judgment of the Investigator or a designated associate. All at-risk female subjects must have a negative pregnancy test within 7 days prior to the start of study treatment.
4. Clinically significant cardiac disease (New York Heart Association, Class III or IV).
5. Dementia or altered mental status that would prohibit informed consent.
6. Other severe, acute, or chronic medical or psychiatric condition or laboratory abnormality that may increase the risk associated with study participation or study drug administration or may interfere with the interpretation of study results and, in the judgment of the Principal Investigator, would make the subject inappropriate for this study.
7. Known side effects to antivirals in the ganciclovir class.
8. Patients who are known to be HIV positive.
9. Patient must not be taking steroids at the time of screening.

Rationale for the Starting Dose and Schedule

Reximmune-C has been dosed in 16 patients over a range of 1.0, 2.0 or $3.0 \times 10^{10}$ cfu (Dose Levels I, II, III respectively on day 3 of the cycle). There were no dose-limiting toxicities at any dose level. Unrelated adverse events were reported for the 16 patients in the study, but the number of events was low (in most cases 1 or 2 occurrences per preferred term), and most were Grade 1 or 2. Related nonserious adverse events occurred in 2 patients and both were Grade 2. Four patients experienced serious adverse events, all of which were deemed not related to the study drug. The trial was closed prior to determining the optimal dose and schedule of Reximmune-C. In this trial, the new Genevieve-2 Trial, initial dosing will be based on the 21 day toxicology and the HSV-TK-m1 study. Future dosing will proceed using total viral particles (TVP)/ml which is a more accurate measure of titer than cfu per mL.

The schedule is based on the rationale that Reximmune-C2 exposure will not transduce all of the tumor cells. Therefore, patients will be dosed three times in a cycle over a period of 5 days.

The time between exposure to GDS and the expression of HSV-TK-m2 (and hGM-CSF) is estimated to be 48 to 72 hours. Therefore, 72 hours after the third dose of Reximmune-C2, valganciclovir will be initiated. The dose (which will be adjusted for renal function) will be given at conventional antiviral dose levels. Due to the potential toxicity of valganciclovir and the published observations that 5 days of ganciclovir should be sufficient to kill the majority of cells containing HSV-TK-m2, 5 days of therapy was chosen. Due to the potential toxicity of both Reximmune-C2 and valganciclovir, this will be followed by an approximately 9 day drug holiday. The hGM-CSF may be at sufficient concentrations at the time of valganciclovir addition to influence the presentation of any tumor associated antigens (TAAs) that may appear during tumor cell apoptosis.

Plasma samples will be taken after the first and third doses in Cycle One and after the first dose in Cycle Two for pharmacokinetics.

As distribution is primarily to the liver, toxicities will be carefully monitored there and because of the implications, the bone marrow.

This clinical protocol calls for the administration of Reximmune-C2 via intravenous infusion to patients with advanced malignancies, either primary hepatocellular or tumors metastatic to the liver. There will be two parts: Phase IA (dose escalation 3 doses/week every three weeks) and Phase IB (pre-screening after one dose of Reximmune-C2 and an [$^{18}$F]FHBG scan). If the PET scan is positive, the patient will continue on study. If the PET scan is negative, the patient will receive 5 days of valganciclovir and will not continue in the trial. For Phase IA, dose escalation will follow an accelerated titration design, incorporating three patients per dose level until either one instance of DLT or two instances of NCI-CTC Grade 2 toxicities attributed to the study drug (except nausea/vomiting, fatigue, anorexia, alopecia or anemia) are observed. Thereafter, dosing in the clinical protocol will follow a modified Fibonacci schedule until dose-limiting toxicities are achieved.

Trial Design

This is a Phase 1, open-label, four center, dose-escalating trial. The dose will be increased until DLT is observed, and the MTD is defined.

Reximmune-C2 will be administered as an IV infusion over 15-60 minutes. It is anticipated that 33-70 patients will be treated during the course of the study.

For Phase IA, the dose of Reximmune-C2 will be escalated from $6.0 \times 10^{11}$ TVP. In the accelerated dose escalation phase, cohorts of three patients will be enrolled at each dose level. The dose escalation increment will be 100% until a DLT or two CTC Grade 2 or greater toxicities are observed. When the accelerated dose escalation ends, the dose escalation for a new patient in the standard dose escalation will follow a modified Fibonacci scheme (i.e., dose increments of 67%, 50%, 40%, 33% and 25%). A minimum of three patients per dose level will be enrolled. For Phase IB, the dose of Reximmune-C2 will be the RP2D. DLT will be assessed. If a DLT is observed in ≥2 out of six patients at a dose level, there will be no further dose escalation; this dose level will define the maximum administered dose (MAD).

The dose just below the MAD will be considered the MTD. Once the MTD is defined, this dose level can be expanded to a maximum of twelve patients to further characterize the pharmacokinetic and pharmacodynamic parameters and suitability as a recommended dose for Phase 2 clinical studies.

Treatment of Patients

Only qualified personnel who are familiar with procedures that minimize undue exposure to themselves and to the environment should undertake the preparation, handling, and safe disposal of biotherapeutic agents in an appropriate environment.

Reximmune C2 is a Moloney Murine replication incompetent retrovector particle containing the genes encoding for a HSV-TK-m2 and hGM-CSF. The drug product contains DMEM (low glucose), RD-Retrovector Particles, L-glutamine, Sodium pyruvate, human serum albumin, n-butyric acid, Pulmozyme®, magnesium and other excipients.

Drug product is available in one vial size: 30 mL type 1 clear glass vials with a 20 mm finish (containing 25 mL of $\geq 1.0 \times 10^{10}$ TVP). The vials are closed with 20 mm Teflon coated serum stoppers and 20 mm flip-off lacquered flip tops.

Reximmune-C2 will be administered intravenously by infusion pump over 15 minutes up to a volume of 100 mL, from >100 mL to 200 mL over 30 minutes, from >200 mL to 300 mL over 45 minutes, and from >300 mL to 400 mL over 60 minutes. Volumes over 400 mL will be administered at a rate determined by the Investigator and the Gleneagles Medical Monitor. Once the MTD has been identified for the schedule, the time of administration may be changed, if indicated (and as agreed between the Investigator and the Gleneagles Medical Monitor).

Valganciclovir is administered orally, and should be taken with food. Serum creatinine or creatinine clearance levels should be monitored carefully. Dosage adjustment is required based on creatinine clearance as shown in the Table below. Valganciclovir dosing may begin on day 7 to 9 of the cycle but must be given for 5 consecutive days.

Creatinine clearance can be calculated from serum creatinine by the following formula:

For males=$\{(140-\text{age[years]}) \times (\text{body weight [kg]})\} / \{(72) \times (0.011 \times \text{serum creatinine [micromol/L]})\}$ For females=0.85× male value.

TABLE I

Valganciclovir Dosing for Renally Impaired Patients

| Cr CL (ml/min) | Dose Day 1 | Dose Days 2-5 |
|---|---|---|
| ≥60 ml/min | 900 mg (two 450 mg tablets) bid | 900 mg (two 450 mg tablets) qday |
| 40-59 ml/min | 450 mg bid | 450 mg qday |
| 25-39 ml/min | 450 mg | 450 mg Day 3 and Day 5 |
| 10-24 ml/min | 450 mg | 450 mg Day 4 |
| <10 ml/min | Not recommended | Not recommended |

The purpose of the Phase 1 study is to establish the MTD, DLT, safety and a RP2D of the investigational agent. Toxic effects are thus the primary study endpoint and will be assessed continuously. Response information will be obtained if patients have disease that can readily be measured and re-assessed. These assessments will be made with every cycle. Furthermore, a response must be noted between two examinations at least 6 weeks apart in order to be documented as a confirmed response to therapy.

Evaluable for toxicity—All patients will be evaluable for toxicity if they receive any study drug.

Evaluable for response—All patients who have received at least a single cycle of treatment and had tumor re-assessment will be considered evaluable for response. In addition, those patients who develop early progressive disease will also be considered evaluable for response. Patients on therapy for at least two cycles of treatment will have their response evaluated.

The determination of antitumor efficacy will be based on objective tumor assessments made according to the Immune-Related Response Criteria (irRC) system of evaluation and treatment decisions by the Investigator will be based on these assessments.

Given the presence of the GM-CSF transgene in Reximmune-C2 and the possibility of an immune response contributing to the tumor effect, the Immune response Criteria will be utilized for clinical response. The reasons for using The immune Response Criteria vs RECIST 1.1 are as follows: (1) the appearance of measurable anti-tumor activity may take longer for immune therapies than for cytotoxic therapies; (2) responses to immune therapy occur after conventional PD; (3) discontinuation of immune therapy may not be appropriate in some cases, unless PD is confirmed (as is usually done for response); (4) allowance for "clinically insufficient" PD (e.g. small new lesions in the presence of other responsive lesions) is recommended; and (5) durable SD may represent antitumor activity.

The comparisons between RECIST 1.1 and the Immune-Related Response Criteria are listed below:

TABLE II

Comparison of WHO RECIST and Immune-Related Response Criteria

| | WHO | irRC |
|---|---|---|
| New measurable lesions (i.e., ≥5 × 5 mm) | Always represent PD | Incorporated into tumor burden |
| New, nonmeasurable lesions (i.e., <5 × 5 mm) | Always represent PD | Do not define progression (but preclude irCR) |
| Non-index lesions | Changes contribute to defining BOR of CR, PR, SD, and PD | Contribute to defining irCR (complete disappearance required) |
| CR | Disappearance of all lesions in two consecutive observations not less than 4 wk apart | Disappearance of all lesions in two consecutive observations not less than 4 wk apart |
| PR | ≥50% decrease in SPD of all index lesions compared with baseline in two observations at least 4 wk apart, in absence of new lesions or unequivocal progression of non-index lesions | ≥50% decrease in tumor burden compared with baseline in two observations at least 4 wk apart |

TABLE II-continued

Comparison of WHO RECIST and Immune-Related Response Criteria

| | WHO | irRC |
|---|---|---|
| SD | 50% decrease in SPD compared with baseline cannot be established nor 25% increase compared with nadir, in absence of new lesions or unequivocal progression of non-index lesions | 50% decrease in tumor burden compared with baseline cannot be established nor 25% increase compared with nadir |
| PD | At least 25% increase in SPD compared with nadir and/or unequivocal progression of non-index lesions and/or appearance of new lesions (any any single time point) | At least 25% increase in tumor burden compared with nadir (at any single time point) in two consecutive observations at least 4 wk apart |

Timing and Type of Assessments

All baseline imaging-based tumor assessments are to be performed within 14 days prior to the start of treatment. For the purposes of this study, all patients' tumor assessments should be re-evaluated starting 9 weeks after initiation of treatment and every 6 weeks thereafter (e.g., Week 9, Week 15, Week 21, etc.) for both Phase IA and Phase IB. All patients with responding tumors (irCR or irPR) must have the response confirmed no less than 6 weeks after the first documentation of response. All patients with tumor progression must have progression confirmed no less than 6 weeks after the first documentation of progression.

The same method of assessment and the same technique should be used to characterize each identified and reported lesion at baseline and during follow-up. Imaging-based evaluation is preferred to evaluation by clinical examination when both methods have been used to assess the antitumor effect of treatment. All measurements should be recorded in metric notation.

CT and CT/PET are the methods for tumor assessments. Conventional CT should be performed with cuts of 10 mm or less in slice thickness contiguously. Spiral CT should be performed using a 5 mm contiguous reconstruction algorithm. This applies to the chest, abdomen, and pelvis.

Chest CT will used for assessment of pulmonary lesions.

Clinical lesions will only be considered measurable when they are superficial (e.g., skin nodules, palpable lymph nodes). In the case of skin lesions, documentation by color photography including a ruler to estimate the size of the lesion is recommended.

[$^{18}$F]FHBG PET-CT scans will be obtained after the patient receives the first three doses of Reximmune-C2 (cycle 1) in Phase IA and after the screening dose of Reximmune-C2 in Phase IB. In Phase IA additional [$^{18}$F] FHBG PET-CT scans can be obtained in subsequent cycles at the discretion of the Investigator and with approval of the Medical Monitor.

Ultrasound should not be used to measure tumor lesions that are clinically not easily accessible for objective response evaluation, e.g., visceral lesions. It is a possible alternative to clinical measurements of superficial palpable nodes, SC lesions, and thyroid nodules. Ultrasound might also be useful to confirm the complete disappearance of superficial lesions usually assessed by clinical examination.

Endoscopy, laparoscopy, and radionuclide scan should not be used for response assessment.

All patients' files and radiological images must be available for source verification and may be submitted for extramural review for final assessment of antitumor activity.

Measurability of Tumor Lesions

At baseline, tumor lesions will be categorized by the Investigator as measurable or non-measurable by the criteria as described below:

Measurable: Lesions that can be accurately measured in at least one dimension (longest diameter to be recorded) as ≥20 mm with conventional techniques or as ≥10 mm with spiral CT scan. Clinical lesions will only be considered measurable when they are superficial (e.g., skin nodules, palpable lymph nodes).

Non-Measurable: All other lesions, including small lesions (longest diameter <20 mm with conventional techniques or <10 mm with spiral CT scan) and bone lesions, leptomeningeal disease, ascites, pleural or pericardial effusions, lymphangitis of the skin or lung, abdominal masses that are not confirmed and followed by imaging techniques, cystic lesions, previously irradiated lesions, and disease documented by indirect evidence only (e.g., by laboratory tests such as alkaline phosphatase).

Note:

Cytology and histology: If measurable disease is restricted to a solitary lesion, its neoplastic nature should be confirmed by cytology/histology.

Response to therapy may also be assessed by independent, central, radiologic blinded review.

Recording Tumor Measurements

All measurable lesions up to a maximum of 10 lesions, representative of all involved organs, should be identified as target lesions and measured and recorded at baseline and at the stipulated intervals during treatment. Target lesions should be selected on the basis of their size (lesion with the longest diameters) and their suitability for accurate repetitive measurements (either by imaging techniques or clinically).

The longest diameter will be recorded for each target lesion. The sum of the longest diameter for all target lesions will be calculated and recorded as the baseline. The sum of the longest diameters is to be used as reference to further characterize the objective tumor response of the measurable dimension of the disease during treatment. All measurements should be recorded in metric notation in centimeters.

All other lesions (or sites of disease) should be identified as non-target lesions and should also be recorded at baseline.

Measurements are not required and these lesions should be followed as "present" or "absent."

Definitions of Tumor Response

Immune-Related Response Criteria criteria will be followed for assessment of tumor response.

Determination of Overall Response by Immune-Related Response Criteria

Target Lesions for Solid Tumors

Complete response (irCR) is defined as the disappearance of all lesions (whether measurable or not, and no new lesions); confirmation by a repeat, consecutive assessment no less than 6 weeks from the date first documented.

Partial response (irPR) is defined as a >50% decrease in tumor burden relative to baseline confirmed by a consecutive assessment at least 6 weeks after the first documentation.

Progressive disease (irPD) is defined as a >25% increase in tumor burden relative to nadir (minimum recorded tumor burden) confirmed by a repeat, consecutive assessment no less than 6 weeks from the date first documented lesions recorded since the treatment started, or the appearance of one or more new lesions.

Stable Disease (irSD) is defined as not meeting the criteria for irCR or irPR, in absence of irPD.

Non-Target Lesions for Solid Tumors

The cytological confirmation of the neoplastic origin of any effusion that appears or worsens during treatment when the measurable tumor has met criteria for response or irSD is mandatory to differentiate between response or irSD and irPD.

Confirmation of Tumor Response

To be assigned a status of irPR or irCR, changes in tumor measurements in patients with responding tumors must be confirmed by repeat studies that should be performed ≥6 weeks after the criteria for response are first met. In the case of irSD, follow-up measurements must have met the irSD criteria at least once after study entry at a minimum interval of 6 weeks. When both target and non-target lesions are present, individual assessments will be recorded separately. The overall assessment of response will involve all parameters as depicted in Table III.

The best overall response is the best response recorded from the start of the treatment until disease progression/recurrence (taking as a reference for tumor progression the smallest measurements recorded since the treatment started). The patient's best response assignment will depend on the achievement of both measurement and confirmation criteria.

Patients will be defined as being not evaluable (NE) for response if there is no post-randomization oncologic assessment. These patients will be counted as failures in the analysis of tumor response data.

Clinical Efficacy Assessment: Performance Status.

Patients will be graded according to the Karnofsky performance status scale.

Tumor Marker Response

Method of Assessment

While not a fully validated measure of efficacy in many malignancies, serial determinations of tumor markers may allow evaluation of an easily performed, inexpensive, quantitative, clinical tool as a potential additional means for following the course of the illness during therapy.

A tumor marker decrease or increase will not be assessed as an objective measure of outcome. In particular, a rising tumor marker value will not be considered in the definition of tumor progression, but should prompt a repeat radiographic evaluation to document whether or not radiographic tumor progression has occurred.

Calculated Endpoint Definitions

Survival is defined as the time from date of first study drug treatment to date of death. In the absence of confirmation of death, survival time will be censored at the last date of follow-up.

Tumor response rate is defined as the proportion of patients who have any evidence of objective irCR or irPR.

TTP is defined as the time from treatment to first confirmed documentation of tumor progression or to death due to any cause. For patients who do not have objective evidence of tumor progression and who are either removed from study treatment or are given antitumor treatment other than the study treatment, TTP will be censored. A tumor marker increase meeting criteria for tumor marker progression does not constitute adequate objective evidence of tumor progression. However, such a tumor marker increase should prompt a repeat radiographic evaluation to document whether or not objective tumor progression has occurred.

TTF is defined as the time from treatment to first confirmed documentation of tumor progression, or to off-treatment date, or to death due to any cause, whichever comes first. Patients who are still on treatment at the time of the analysis and patients who are removed from therapy by their physicians during an objective response and who, at the off-treatment date, have no evidence for objective tumor progression will not be considered to have experienced treatment failure, unless the withdrawal is due to the occurrence of a medical event. For these patients, TTF will be censored at the off-study date. Censoring for TTF will also be performed in those patients who are given antitumor treatment, other than the study treatment, before the first of objective tumor progression, off-study date, or death. A tumor marker increase meeting criteria for tumor marker progression does not constitute adequate objective evidence of treatment failure. However, such a tumor marker increase should prompt a repeat radiographic evaluation to document whether or not objective tumor progression (and thus treatment failure) has occurred.

Time to first definitive performance status worsening is the time from treatment until the last time the performance status was no worse than at baseline or to death, due to any cause, in the absence of previous documentation of definitive confimed performance status worsening. For patients who do not have definitive performance status worsening and who are either removed from study or are given antitumor treatment other than the study treatment, definitive performance status worsening will be censored.

Time to first definitive weight loss is defined as the time from treatment until the last time the percent weight decrease from baseline was <5% or to death due to any cause in the absence of previous documentation of definitive weight loss. For patients who do not have definitive weight loss and who are either removed from study or are given antitumor treatment other than study treatment, definitive weight loss will be censored.

Additional evaluations of the data may include best objective response, confirmed and unconfirmed objective response rate, duration of study treatment, time to first occurrence of new lesions, time to tumor response, stable disease at 24 weeks, and rate of progression free survival at 24 weeks. Data may be evaluated by RECIST 1.1 criteria, if needed.

Treatment Administration Assessment

For both Phase IA and IB: dose intensity is defined as the total dose/cycle times the number of weeks between start of treatment and last treatment plus 13 days.

Percent relative dose intensity is defined as the proportion of the actual dose intensity divided by the planned dose intensity for that same period of time.

Example 7: RxC2-GCV Kill Assay

Kill assays were conducted as follows. The percentage of cell kill by GCV after treatment with RxC2 depends on the infectability (transducibility) of the cancer cells tested. Cells for each cell line were plated in a 6 well dish. The following day, the cells were transduced with retrovector containg the EGFP (Enhanced Green Fluorescent Protein Gene) diluted 1:5. After 48 hours cells were collected. The fluorescent and non-fluorescent cells were counted using an automated fluorescent cells counter to determine the percent transduced. The efficiency of transduction was examined using a virus carrying the gene for Green fluorescent protein where ransduction efficiency is shown in decreasing order.

| Tissue origin | cell line | EGFP + cells (%) |
|---|---|---|
| BREAST | Hs578T | 66 +/− 5 |
| BREAST | HCC-38 | 59 +/− 2.3 |
| SKIN | A375 | 57.7 +/− 7.1 |
| LUNG | NCI-H460 | 25.9 +/− 1.7 |
| LIVER | SkHep1 | 21.4 +/− 4 |
| PANCREAS | MIA Paca-2 | 19.7 +/− 2 |
| PANCREAS | Su8686 | 19.6 +/− 3.3 |
| LIVER | HepG2 | 18.4 +/− 4.3 |
| LUNG | A549 | 16.3 +/− 1.5 |
| PANCREAS | BxPC3 | 13.8 +/− 3.2 |
| LUNG | NCI-H23 | 7.9 +/− 1.2 |
| COLON | DLD-1 | 3.9 +/− 2.3 |
| COLON | HT-29 | 0.7 +/− 0.3 |
| COLON | HCT-15 | 0.3 +/− 1.5 |
| COLON | RKO | 0.13/− 0.2 |

The same viral preparation was used for all cell lines shown here (titer 2.72E+10 TVP)

Example 8: Analysis of Reximmune-C2 Mediated GCV Kill of Cell Lines Expressing PiT-2

Cell lines expressing PiT-2 were established by transduction of target cells with a E-Rex expression retroviral vector containing the PiT-2 and Neomycin Resistance genes. Stable cell lines were then drug selected (G418) to establish a pure population of PiT-2 expressing cells. The cell lines were verified by amphotropic retrovial vector transduction of the LUC-2 gene into PiT2 expressing cells followed by bioluminescent analysis. For Reximmune-C2 cell kill analysis, PiT2 expressing cell lines were then plated in 48 well plates. The following day cells were transduced with the Reximmune-C2 retrovector. After transduction, cells were exposed to a daily dose of 20-40 μM GCV. After four days of GCV treatment the cells were analyzed for cell viability using the PrestoBlue reagent. This reagent is a resazurin-based solution that in the presence of the reducing environment of viable cells converts the reagent into fluorescence that is quantitated using absorbance measurements.

Human colon cancer lines HCT-15 demonstrated poor HSV-TK-GCV kill and RKO cell line demonstrated no cell kill following Reximmune-C2 transduction and GCV exposure. PiT-2 expressing HCT-15 and RKO lines were generated and their transduction efficiency examined; resutls are provided in the following table.

| Cell Line | EGFP + cells (%) |
|---|---|
| PiT-2-CHO-K1 | 34 +/− 2.9 |
| PiT-2-MIA-PaCa-2 | 78.6 +/− 2.2 |
| PiT-2-HA-HCT-15 | 14.9 +/− 1.2 |
| PiT-2-RKO | 43.1 +/− 1.6 |

A considerable increase of LNCE-RVE transduction efficiency was observed in all PiT-2 expressing cell lines demonstrating that the kill activity is increased when target cells express PiT2.

Using cells lines expressing PiT-2, the data shows that the requirement of PiT-2 receptor presence for LNCE-RVE transduction is reflected by the level of EGFP expression in cells analyzed by fluorescent microscopy (data not shown). The requirement of PiT-2 presence for Reximmune-C2 infectivity has also been shown by a GCV cell kill assay. Therefore, PiT-2 represents a good biomarker for Reximmune-C2.

It was determined that Pit2 expression correlated to Reximmune-C2 mediated GCV cell kill. HSV-TK-GCV kill of CHO-K1 parent line versus PIT2 expressing CHO-K1 lines.

Figure 26A:
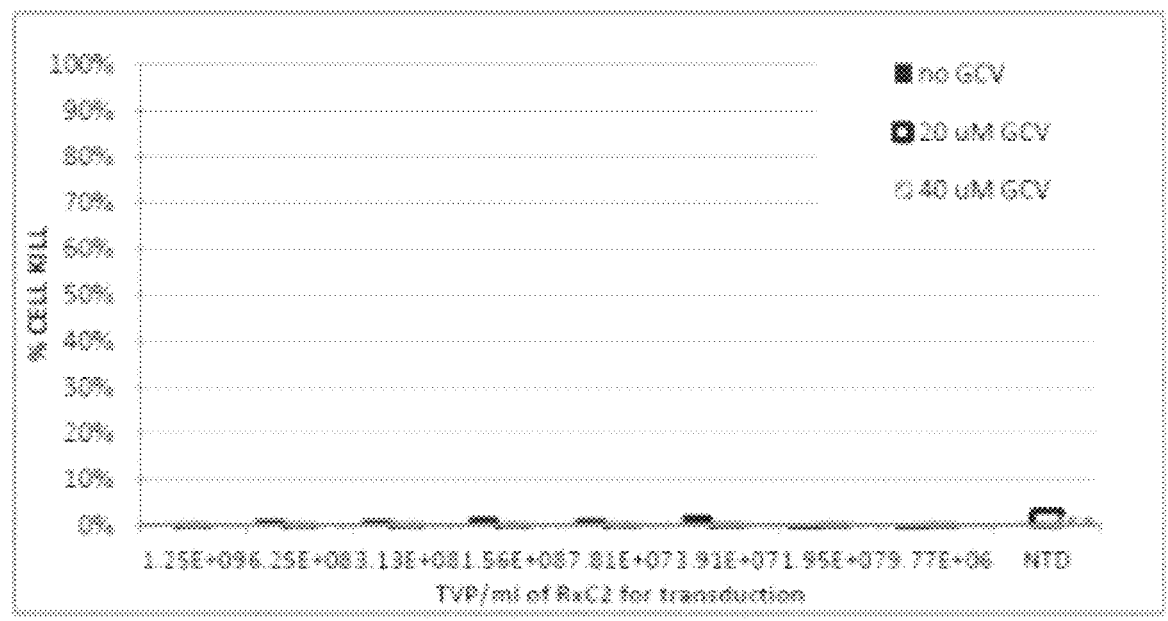
FIG. 26A-FIG. 26B show Tk-GCV kill in parent and PiT-2-CHO-K1 following a Triple RxC2-transduction protocol.
Figure 26B:
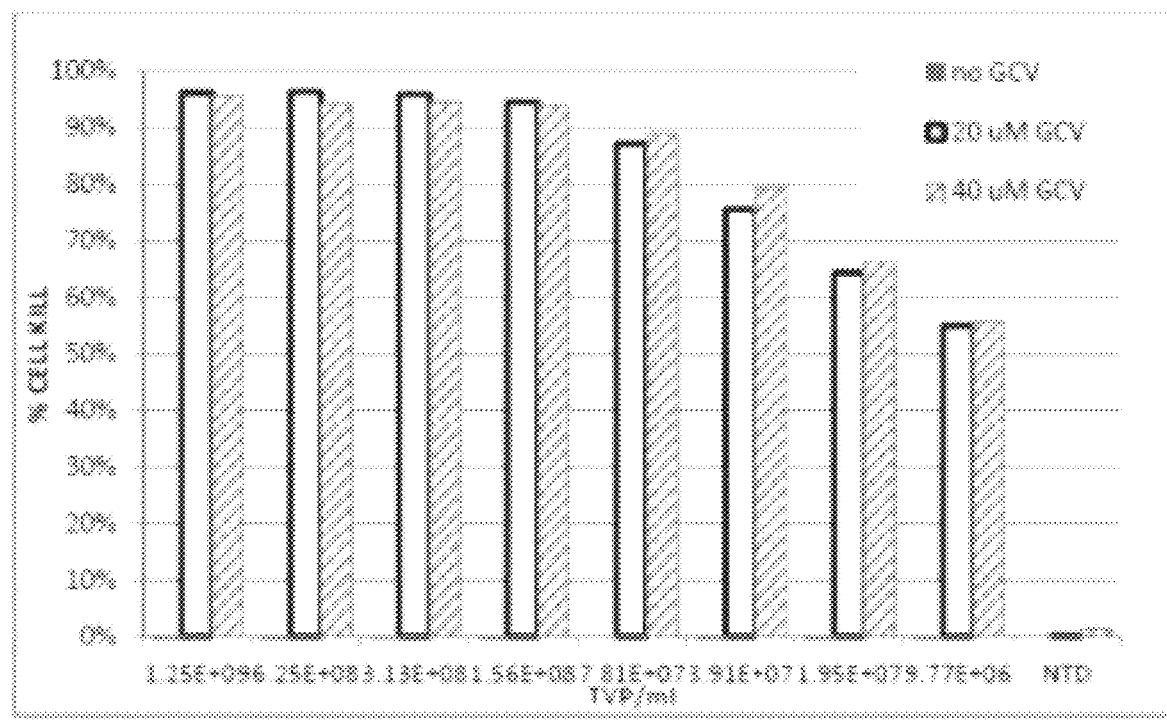

FIGS. 25 and 26 provide graph results HSV-TK-GCV kill after single or triple transduction in various cell lines following single or triple transduction in the absence of PiT-2 (panel A of each figure) or presence of PiT-2 (panel B of each figure).

Figure 27:
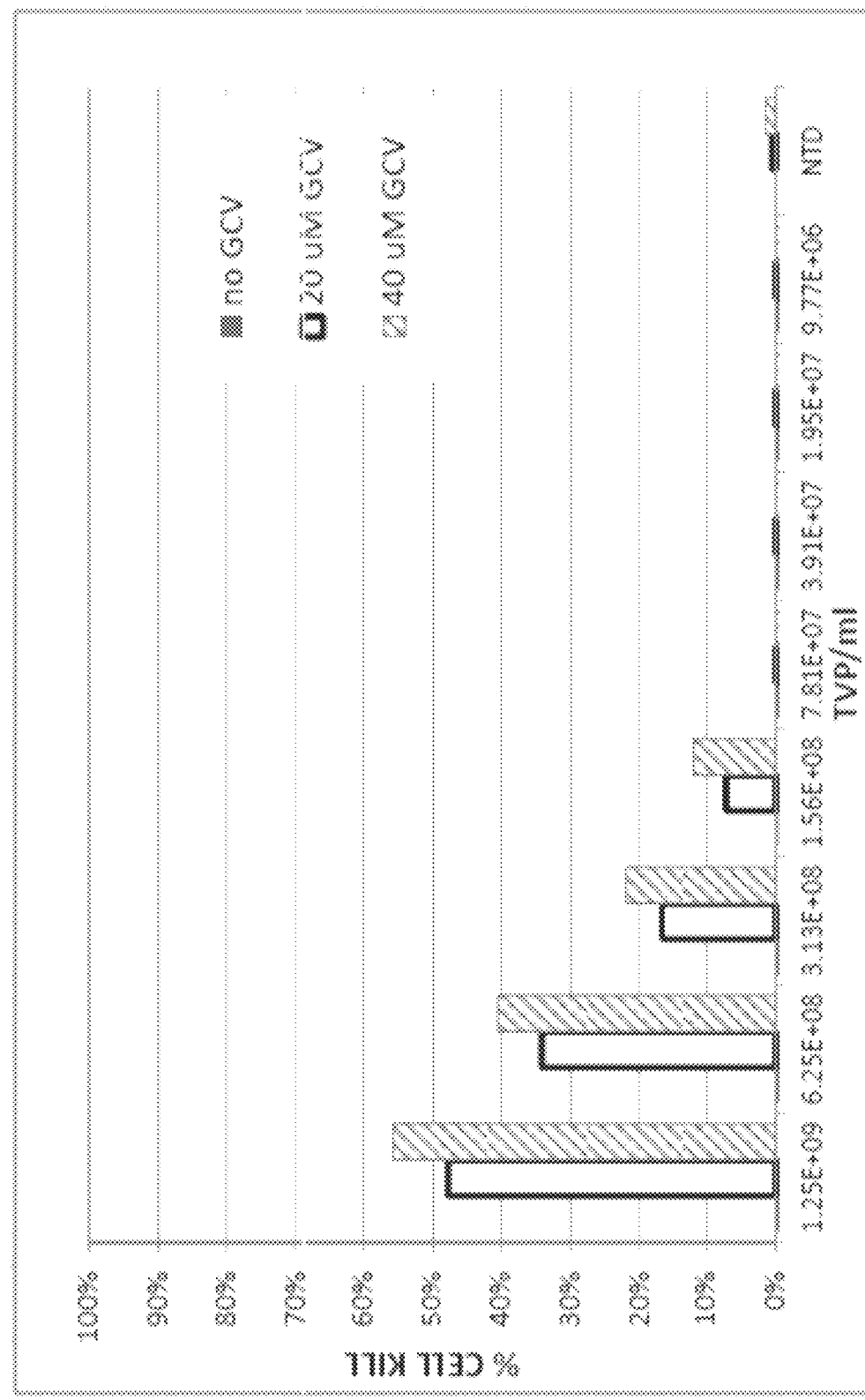
FIG. 27: illustrates TK-GCV kill after triple transduction with Reximmune-C2 (HSV-TKA168HdmNES) (SEQ ID NO: 18) in a MIA-PaCa-2 human pancreatic carconima cell line. GCV kill of RxC2-triple transduced MIA-PaCa2, 25% of initial cells reseeded, day 8, with various concentrations of GCV.

FIG. 27 provides the results of TK-GCV kill after triple transduction with Reximmune-C2 in a MIA-PaCa-2 human pancreatic carconima cell line. GCV kill was effective at the higher concentrations of TVP.

Figure 28:
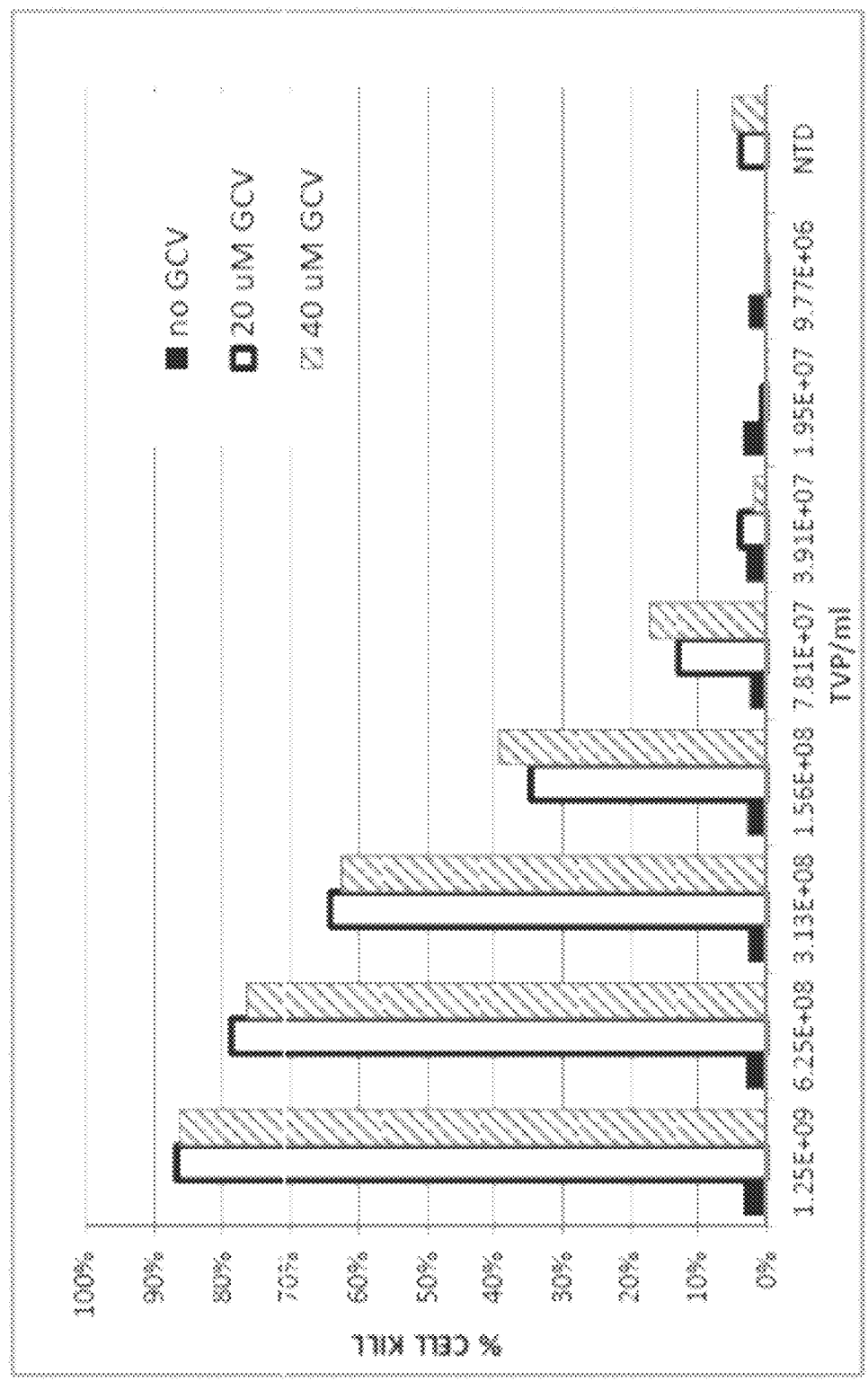
FIG. 28 illustrates TK-GCV kill after triple transduction of PiT-2-MIA-PaCa-2 cells with Reximmune-C2. GCV kill of RxC2-triple transduced PiT-2-MIA-PaCa2, 25% of initial cells, day 8 with various concentrations of GCV.

FIG. 28 provides the results of HSV-TK-GCV kill after triple transduction of PiT-2-MIA-PaCa-2 cells with Reximmune-C2. GCV kill of RxC2-triple transduced PiT-2-MIA-PaCa2 human pancreatic carconima cell line. The presence of PiT-2 dramatically increased the amount of cell killing at lower concentrations of TVP.

Figure 32:
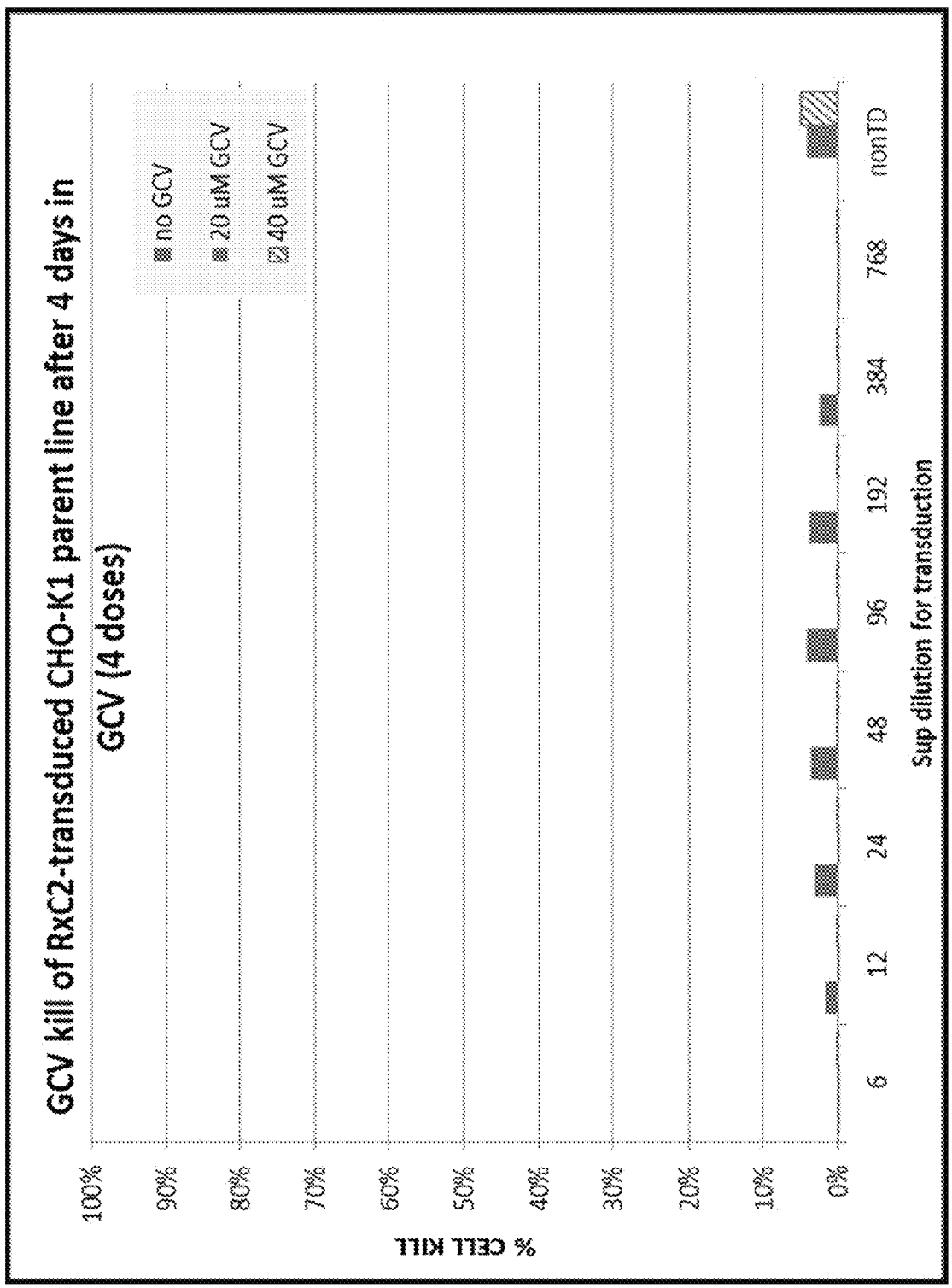
FIG. 32 illustrates a graph of RxC2-tranduced CHO-K1 cell lines after four days in GCV.

FIG. 32 illustrates a graph of RxC2-tranduced CHO-K1 cell lines after four days in GCV.

Figure 33:
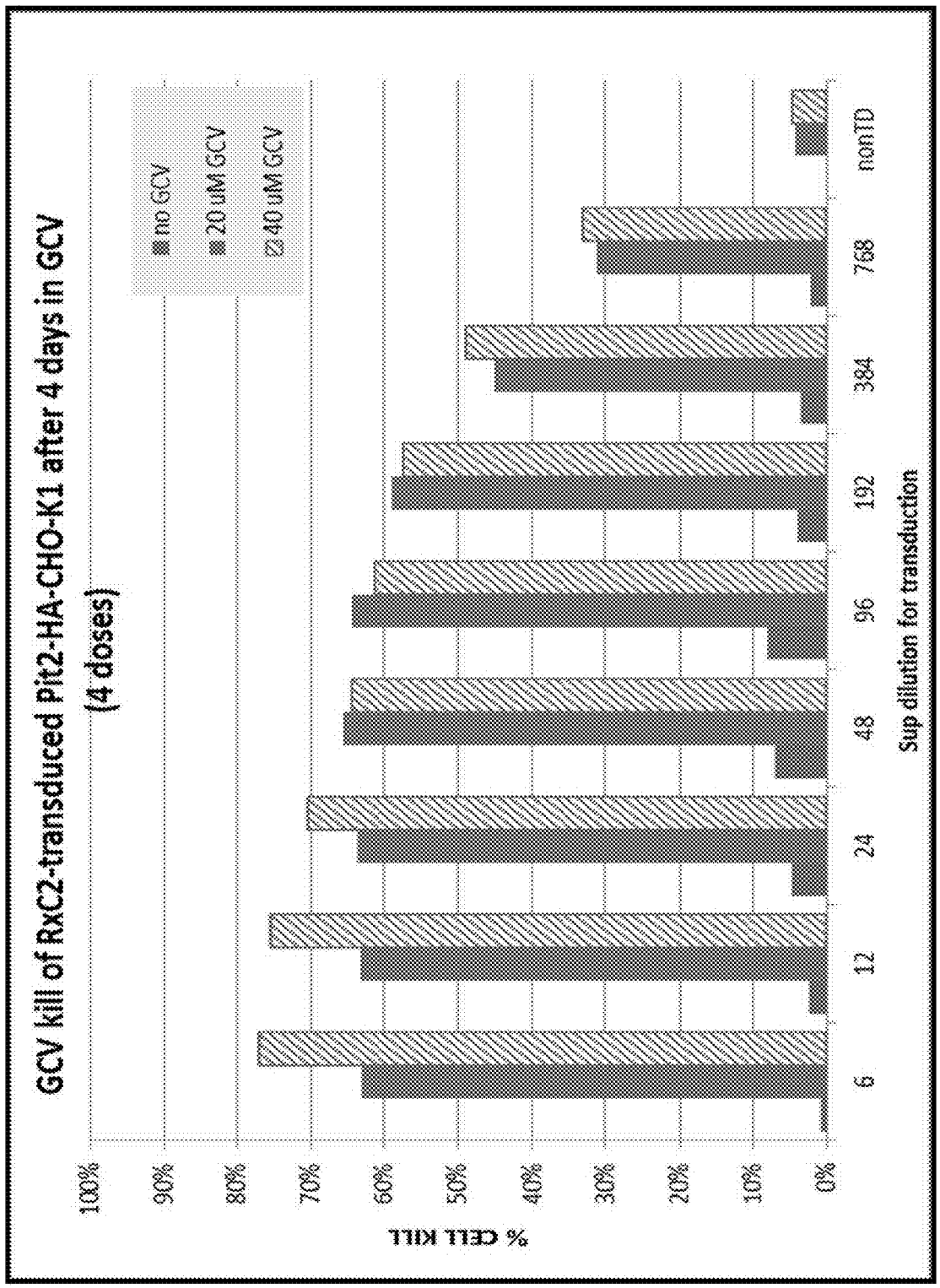
FIG. 33 illustrates a graph of RxC2-tranduced PiT-2-HA-CHO-K1 cell lines after four days in GCV.

FIG. 33 illustrates a graph of RxC2-tranduced PiT-2-HA-CHO-K1 cell lines after four days in GCV.

It is very apparent that, even at the lowest concentration of GCV, the presence of PiT-2 allows for significantly greater transduction and cell killing.

Example 9: Transduction Efficiency Versus GCV Kill after Reximmune C2 Triple Transduction To demonstrate transduction efficiency and GCV kill, cells were plated into 48 well plates. The next day cells are transduced with Reximmune-C2 diluted in the range of 1:40 to 1:5120. Following the last of three transductions, the cells were exposed a daily doses of GCV (20-40 μM) for four days. One day following the last dose of GCV the cells were analyzed using the Prestoblue reagent for cell viability. This reagent is a resazurin-based solution that in the presence of the reducing environment of viable cells converts the reagent into fluorescence that is quantitated using absorbance measurements. The results are reported as percent kill based on the non-transduced cell viability.

| Cell Line | EGFP + cells (%) |
|---|---|
| HCC-38 | 59 +/− 2.3 |
| A375 | 57.7 +/− 7.1 |
| NCI-H460 | 25.9 +/− 1.7 |
| A549 | 16.3 +/− 1.5 |
| BxPC3 | 13.8 +/− 3.2 |
| HCT-15 | 0.3 +/− 1.5 |

Figure 31:
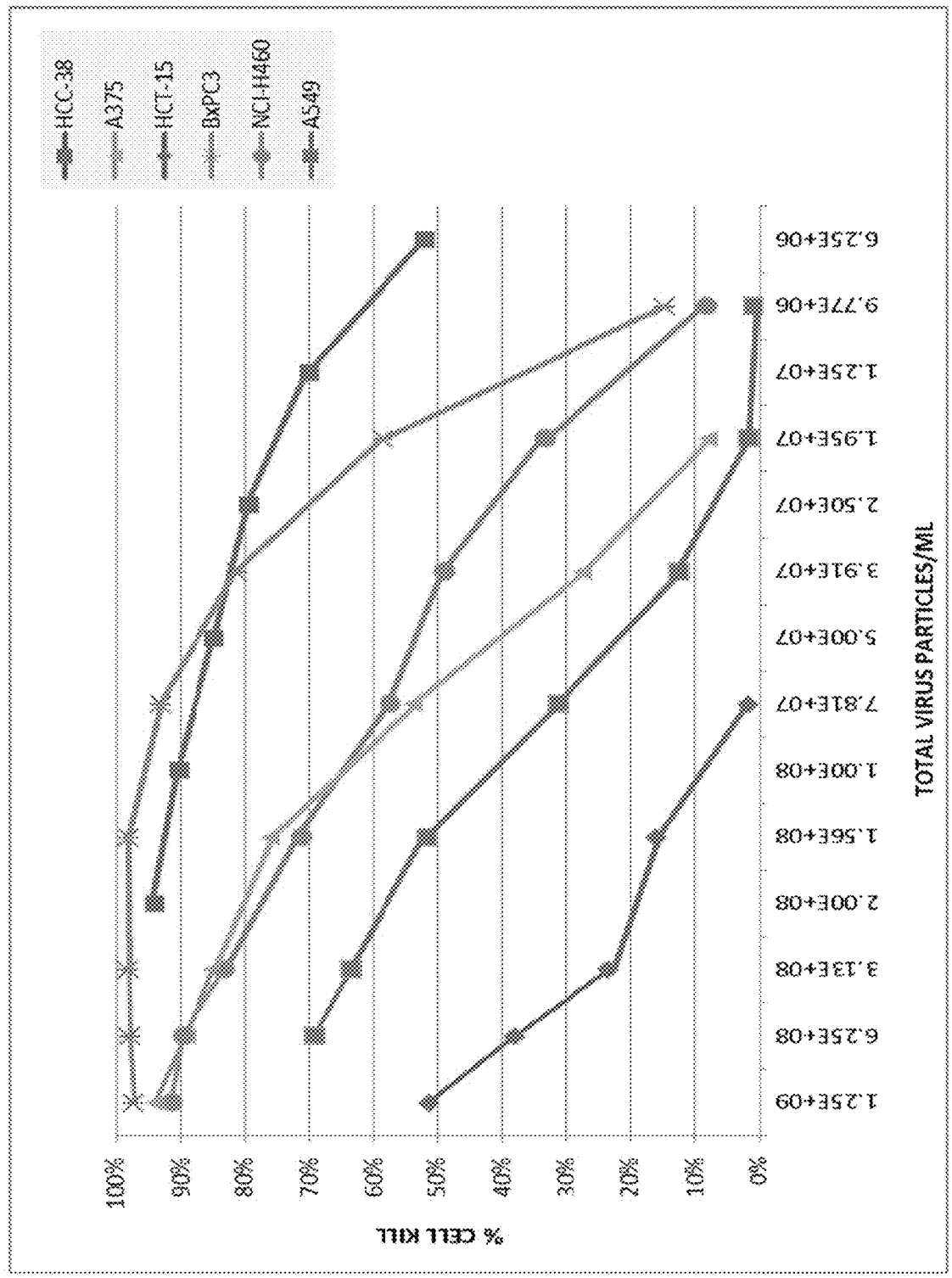
FIG. 31 is a graph depicting the percentage of GCV kill after Reximmune-C2 triple transduction of various cancer cell lines.

FIG. 31 is a graph depicting the percentage of GCV kill after Reximmune-C2 triple transduction of various cancer cell lines. The graph demonstrates the variation in GCV kill amongst the different cell lines. The cell lines are comparable across each dilution converted to the total virus particles/mL against the percent cell kill. The table gives the transduction efficiencies for the cell lines represented in the graph. The percent efficiency does not seem to have a direct correlation with the cell kill, but a trend is evident in which higher efficiency leads to higher cell kill.

Example 10: Immunohistochemistry (IHC) of Mutant HSV-TK Cellular Protein Expression Either Reximmune C1 or C2 plasmids were transiently trasfected into 293T cells and incubated under standard condition on tissue culture slides aparatus, a couple days later cells were fixed with about 2% formalin, washed with PBS and permeabilized with 0.1% triton x 100 or equivalent detergent. Primary anti HSV-TK antibody (Santa Cruz Biotechnology) at effective dilution is incubated with these cells 4 degrees C. overnight. Cells are washed and incubated for 1-2 hours with secondary anti primary antibody conjugated with horse radish peroxidase (HRPO) at ambient room temperature. Cells are again washed and HRPO detection stain reagent is applied for 5-30 minutes at room temperature. IHC images are acquired with a light microscope fitted with a CCD digital camera, pictures are captured with image analysis software. Note: IHC in this example can also be described as ImmunoCyto Chemistry (ICC).

Wild type vector was found to localize to the nucleus (As determined with fluorescent genes fused to wild type HSV-TK), Data not shown.

RexC1 distributes between nucleus and cytoplasm in fluorescent fusion (data not shown), but mostly nuclear in Immunohistochemistry (IHC; see, FIG. 37, left panel).

RexC2 is almost entirely cytoplasmic in fluorescent fusion (data not shown), with some shift to the cytoplasm seen in IHC (see, FIG. 37, right panel).

Example 11: Improved Mutants

The effect of various mutations were compared to previously disclosed constructs such as those described by Margaret Black. Rescue of BL21 DE3 tk(−) Cells by HSV-TK Variant pET Constructs is shown in the following table:

| Construct Name | Thymidine Concentration (mg/mL) | | | | |
|---|---|---|---|---|---|
| | 2 | 5 | 10 | 100 | 200 |
| Wild type | ++++ | ++++ | ++++ | N.D. | N.D. |
| SR39 | ++++ | ++++ | ++++ | N.D. | N.D. |
| A167Y(SR39) | − | − | − | − | − |
| A167F-dmNES | − | − | + | + | + |
| A168H-dmNES | − | − | ++ | ++++ | ++++ |

The following table depicts GCV Kill after Rescue of BL21 DE3 tk(−) Cells by HSV-TK Variant pET Constructs.

| | Growth after 24 hr incubation at 37 C. | | | | | | | | |
|---|---|---|---|---|---|---|---|---|---|
| | IPTG | | | | | | | | 2xYT |
| | − | + | − | + | − | + | − | + | |
| | | | | | GCV | | | | |
| | − | − | 2 µg/ml | 2 µg/ml | 20 µg/ml | 20 µg/ml | 50 µg/ml | 50 µg/ml | − |
| pTK1 | − | ++ | − | ++ | − | ++ | − | ++ | +++ |
| pTK2 | − | − | − | − | − | − | − | − | +++ |
| pTK3 | − | ++ | − | ++ | − | +/− | − | − | +++ |
| pTK4 | − | − | − | − | − | − | − | − | +++ |
| pTK5 | − | ++ | − | + | − | + | − | + | +++ |
| pET24a | − | − | − | − | − | − | − | − | +++ |

Key:
pTK# = pET30a-based bacterial protein expression vector encoding an HSV-TK gene or variant;
pTK1 = wild-type HSV-TK;
pTK2 = HSV-TK NESdmNLS A167Y(SR39);
pTK3 = HSV-TK(SR39) (As in Reximmune-C1);
pTK4 = HSV-TK-NESdmNLS A167F;
pTK5 = HSV-TK- NESdmNLS A168H (As in Reximmune-C2);
pET24a = empty expression vector as negative control;
GCV = ganciclovir (at the indicated concentrations),
IPTG = isopropyl b-D-1-thiogalactopyranoside (as lac operon inducer for HSV-TK protein expression);

2xYT = 2x yeast/tryptone bacterial media in agar plates, where the trials in the column so labeled lack both IPTG and GCV. All of these HSV-TK's are codon optimized for expression in prokaryotes and expressed in the IPTG inducible pET30a plasmid. Note; HSV-TK Mutants which do not have Thymidine enzymatic activity will not support the growth of these TK minus bacterial cells.

Example 12: In Vitro Bystander Assays

Experiments were conducted at our laboratory to demonstrate the bystander effect in vitro on mixtures of cancer cells expressing various TK mutants with non-expressing cells. A375 human melanoma and C6 rat glioma stable pure population cell lines were established containing the A168H mutated HSV-TK-m2 gene. The bystander assays were conducted by plating the cancer cells with mixtures of the parental non-HSV-TK-m2 cells with the corresponding HSV-TK-m2 cell line ranging from 0-100% HSV-TK-m2. The mixtures of cancer cells were subsequently exposed to 5-20 μM GCV and cell kill is plotted in the figures below. The results clearly show significant increases in the mixed populations over what would be considered theoretical, without a bystander effect.

More than 40 bystander assays were performed using different mutant TK and clonal populations. The data was compiled with GCV sensitivity and enzyme kinetic measurements as well as viral titer of production for the mutants with potential.

Figure 29:
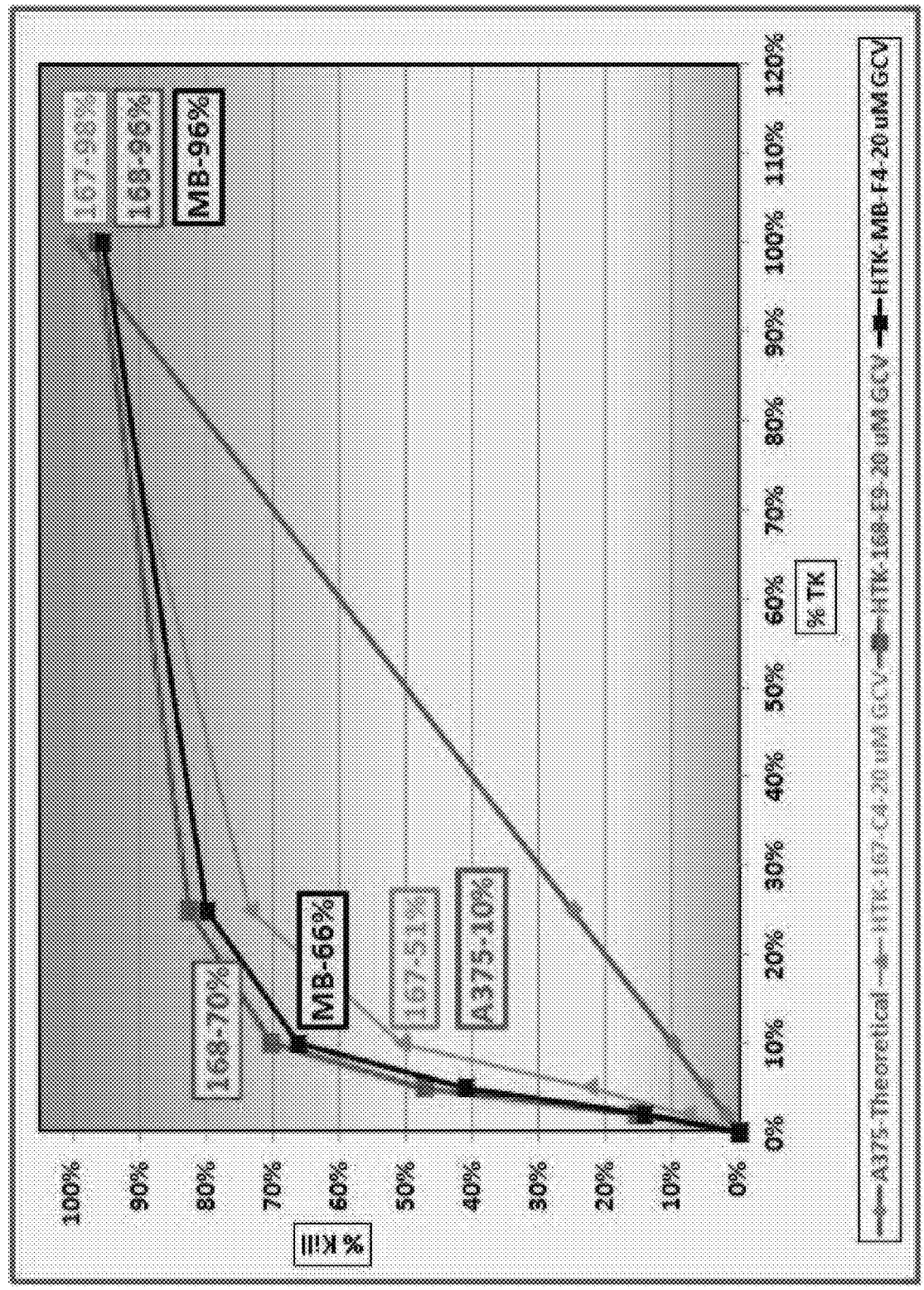
FIG. 29 illustrates graphic results from a bystander in vitro assay where human melanoma A375 Hygro TK clones were treated with 20 mM GCV.

FIG. 29 provides graphic results from one bystander in vitro assay for various mutants. The data support that mutated HSV-TK A168H gene has a higher cell kill and bystander effect than the HSV-TK 167 or Margaret Black mutants.

Figure 30:
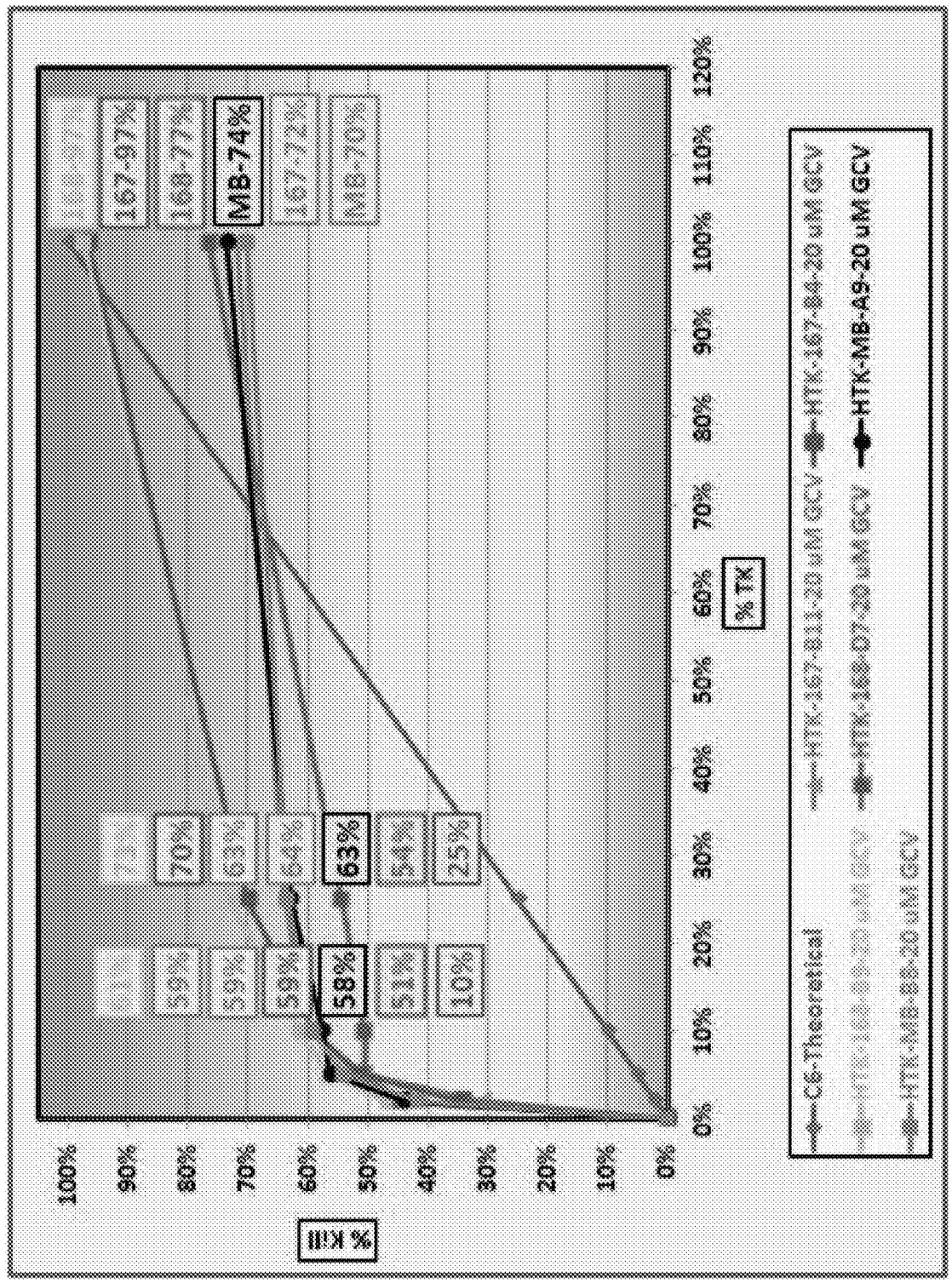
FIG. 30 illustrates graphic results from a bystander in vitro assay where C6-Hygro-TK clones were treated with 20 mM GCV.

FIG. 30 provides a graphic from a bystander in vitro assay where C6-Hygro-TK clones were treated with 20 mM GCV. The data further support that HSV-TK Margaret Black mutants had the lowest cell kill of the other mutants tested.

Analysis of all of the mutants identified mutant TK168dmNES to be a lead candidate for the TK gene in Reximmune C-2.

Example 13: Sequences of Modified TK Molecules

```
HSV-TK Splice Sites Removal; Codon-optimized TK1
(splice sites corrected)
                                        (SEQ ID NO: 28)
ATGGCCAGCTACCCCGGCCACCAGCACGCCAGCGCCTTCGACCAGGCC

GCCCGCAGCCGCGGCCACAGCAACGGCAGCACCGCCCTGCGCCCCCGC

CGCCAGCAGGAGGCCACCGAGGTGCGCCCCGAGCAGAAGATGCCCACC

CTGCTGCGCGTGTACATCGACGGCCCCCACGGCATGGGCAAGACCACC

ACCACCCAGCTGCTGGTGGCCCTGGGCAGCCGCGACGACATCGTGTAC

GTGCCCGAGCCCATGACCTACTGGCGCGTGCTGGGCGCCAGCGAGACC

ATCGCCAACATCTACACCACCCAGCACCGCCTGGACCAaGGCGAGATC

AGCGCCGGCGACGCCGCCGTGGTGATGACCAGCGCCCAGATCACCATG

GGCATGCCCTACGCCGTGACCGACGCCGTGCTGGCCCCCCACATCGGC

GGCGAGGCCGGCAGCAGCCACGCCCCCCCCCCGCCCTGACCATCTTC

CTGGACCGCCACCCCATCGCCTTCATGCTGTGCTACCCCGCCGCCCGC

TACCTGATGGGCAGCATGACaCCaCAaGCCGTGCTGGCCTTCGTGGCC

CTGATCCCCCCACCCTGCCCGGCACCAACATCGTGCTGGGCGCCCTG

CCCGAGGACCGCCACATCGACCGCCTGGCCAAGCGCCAGCGCCCCGGC

GAGCGCCTGGACCTGGCCATGCTGGCCGCCATCCGCCGCGTGTACGGC

CTGCTGGCCAACACCGTGCGCTACCTGCAGTGCGGCGGCAGCTGGCGC
```

-continued
```
GAGGACTGGGGCCAGCTGAGCGGCACCGCCGTGCCCCCCCAGGGCGCC

GAGCCCCAGAGCAACGCCGGCCCCCGCCCCCACATCGGCGACACCCTG

TTCACCCTGTTCCGCGCCCCCGAGCTGCTGGCCCCCAACGGCGACCTG

TACAACGTGTTCGCCTGGGCCCTGGACGTGCTGGCCAAGCGCCTGCGC

AGCATGCACGTGTTCATCCTGGACTACGACCAGAGCCCCGCCGGCTGC

CGCGACGCCCTGCTGCAGCTGACCAGCGGCATGGTGCAGACCCACGTG

ACCACCCCCGGCAGCATCCCCACCATCTGCGACCTGGCCCGCACCTTC

GCCCGCGAGATGGGCGAGGCCAACTAA.
```

```
Codon-optimized, all putative splice acceptor
sites ablated, TK1 with RE's, + Kozak,
2xTK A168H (LIF . . . AHL)
                                        (SEQ ID NO: 29)
gtcaGCGGCCGCACCGGTACGCGTCCACCATGGCCAGCTACCCCGGCC

ACCAGCACGCCAGCGCCTTCGACCAGGCCGCCCGCAGCCGCGGCCACA

GCAACGGCAGCACCGCaCTGCGgCCaCGgCGCCAGCAGGAGGCCACCG

AGGTGCGCCCCGAGCAGAAGATGCCCACCCTGCTGCGCGTGTACATCG

ACGGaCCaCACGGCATGGGCAAGACCACCACCACCCAGCTGCTGGTGG

CCCTGGGCAGCCGCGACGACATCGTGTACGTGCCCGAGCCCATGACCT

ACTGGCGCGTGCTGGGCGCCAGCGAGACCATCGCCAACATCTACACCA

CCCAGCACCGCCTGGACCAaGGCGAGATCAGCGCCGGCGACGCCGCCG

TGGTGATGACCAGCGCCCAGATtACaATGGGCATGCCCTACGCCGTGA

CCGACGCCGTGCTGGCaCCaCACATCGGCGGCGAGGCCGGCAGCAGCC

ACGCaCCaCCaCCaGCaCTGACCCTGATCTTCGACCGgCACCCaATCG

CaCACCTGCTGTGCTACCCgGCaGCaCGCTACCTGATGGGCtccATGA

CaCCaCAaGCCGTGCTGGCCTTCGTGGCCCTGATCCCaCCaACaCTGC

CCGGCACCAACATCGTGCTGGGCGCCCTGCCCGAGGACCGCCACATCG

ACCGCCTGGCCAAGCGCCAGCGCCCCGGCGAGCGCCTGGACCTGGCCA

TGCTGGCCGCCATCCGCCGCGTGTACGGCCTGCTGGCCAACACCGTGC

GCTACCTGCAGTGCGGCGGCAGCTGGCGCGAGGACTGGGGCCAGCTGA

GCGGCACCGCCGTGCCaCCaCAGGGCGCCGAGCCaCAGAGCAACGCCG

GaCCaCGaCCaCACATCGGCGACACCCTGTTCACCCTGTTCCGgGCaC

CaGAGCTGCTGGCaCCaAACGGCGACCTGTACAACGTGTTCGCCTGGG

CCCTGGACGTGCTGGCCAAGCGCCTGCGCtccATGCACGTGTTCATCC

TGGACTACGACCAGtcaCCgGCCGGCTGCCGCGACGCCCTGCTGCAGC

TGACCAGCGGCATGGTGCAGACCCACGTGACaACaCCCGGCAGCATCC

CaACaATCTGCGACCTGGCCCGCACCTTCGCCCGCGAGATGGGCGAGG

CCAACTAATAGGGATCCCTCGAGAAGCTTgtca.
```

```
HSV-TK Splice Sites Removal Improves Codon
Optimization
                                        (SEQ ID NO: 12)
gtcaGCGGCCGCACCGGTACGCGTCCACCATGGCCAGCTACCCCGGCC

ACCAGCACGCCAGCGCCTTCGACCAGGCCGCCCGCAGCCGCGGCCACA

GCAACGGCAGCACCGCaCTGCGgCCaCGgCGCCAGCAGGAGGCCACCG

AGGTGCGCCCCGAGCAGAAGATGCCCACCCTGCTGCGCGTGTACATCG
```

-continued

ACGGaCCaCACGGCATGGGCAAGACCACCACCACCCAGCTGCTGGTGG

CCCTGGGCAGCCGCGACGACATCGTGTACGTGCCCGAGCCCATGACCT

ACTGGCGCGTGCTGGGCGCCAGCGAGACCATCGCCAACATCTACACCA

CCCAGCACCGCCTGGACCAaGGCGAGATCAGCGCCGGCGACGCCGCCG

TGGTGATGACCAGCGCCCAGATtACaATGGGCATGCCCTACGCCGTGA

CCGACGCCGTGCTGGCaCCaCACATCGGCGGCGAGGCCGGCAGCAGCC

ACGCaCCaCCaCCaGCaCTGACCCTGATCTTCGACCGgCACCCaATCG

CaCACCTGCTGTGCTACCCgGCaGCaCGCTACCTGATGGGCtccATGA

CaCCaCAaGCCGTGCTGGCCTTCGTGGCCCTGATCCCaCCaACaCTGC

CCGGCACCAACATCGTGCTGGGCGCCCTGCCCGAGGACCGCCACATCG

ACCGCCTGGCCAAGCGCCAGCGCCCCGGCGAGCGCCTGGACCTGGCCA

TGCTGGCCGCCATCCGCCGCGTGTACGGCCTGCTGGCCAACACCGTGC

GCTACCTGCAGTGCGGCGGCAGCTGGCGCGAGGACTGGGGCCAGCTGA

GCGGCACCGCCGTGCCaCCaCAGGGCGCCGAGCCaCAGAGCAACGCCG

GaCCaCGaCCaCACATCGGCGACACCCTGTTCACCCTGTTCCGgGCaC

CaGAGCTGCTGGCaCCaAACGGCGACCTGTACAACGTGTTCGCCTGGG

CCCTGGACGTGCTGGCCAAGCGCCTGCGCtccATGCACGTGTTCATCC

TGGACTACGACCAGtcaCCgGCCGGCTGCCGCGACGCCCTGCTGCAGC

TGACCAGCGGCATGGTGCAGACCCACGTGACaACaCCCGGCAGCATCC

CaACaATCTGCGACCTGGCCCGCACCTTCGCCCGCGAGATGGGCGAGG

CCAACTAATAGGGATCCCTCGAGAAGCTTgtca.

HSV-TK NLS Removal and substitute in NES
(SEQ ID NO: 30)
gtcaGCGGCCGCACCGGTACGCGTCCACCATGGCCAGCTACCCCGGCC

ACCAGCACGCCAGCGCCTTCGACCAGGCCGCCCGCAGCCGCGGCCACA

GCAACGGCAGCACCGCaCTGCGgCCaGGATCTCAGCAGGAGGCCACCG

AGGTGCGCCCCGAGCAGAAGATGCCCACCCTGCTGCGCGTGTACATCG

ACGGaCCaCACGGCATGGGCAAGACCACCACCACCCAGCTGCTGGTGG

CCCTGGGCAGCCGCGACGACATCGTGTACGTGCCCGAGCCCATGACCT

ACTGGCGCGTGCTGGGCGCCAGCGAGACCATCGCCAACATCTACACCA

CCCAGCACCGCCTGGACCAaGGCGAGATCAGCGCCGGCGACGCCGCCG

TGGTGATGACCAGCGCCCAGATtACaATGGGCATGCCCTACGCCGTGA

CCGACGCCGTGCTGGCaCCaCACATCGGCGGCGAGGCCGGCAGCAGCC

ACGCaCCaCCaCCaGCaCTGACCCTGATCTTCGACCGgCACCCaATCG

CaCACCTGCTGTGCTACCCgGCaGCaCGCTACCTGATGGGCtccATGA

CaCCaCAaGCCGTGCTGGCCTTCGTGGCCCTGATCCCaCCaACaCTGC

CCGGCACCAACATCGTGCTGGGCGCCCTGCCCGAGGACCGCCACATCG

ACCGCCTGGCCAAGCGCCAGCGCCCCGGCGAGCGCCTGGACCTGGCCA

TGCTGGCCGCCATCCGCCGCGTGTACGGCCTGCTGGCCAACACCGTGC

GCTACCTGCAGTGCGGCGGCAGCTGGCGCGAGGACTGGGGCCAGCTGA

GCGGCACCGCCGTGCCaCCaCAGGGCGCCGAGCCaCAGAGCAACGCCG

GaCCaCGaCCaCACATCGGCGACACCCTGTTCACCCTGTTCCGgGCaC

CaGAGCTGCTGGCaCCaAACGGCGACCTGTACAACGTGTTCGCCTGGG

CCCTGGACGTGCTGGCCAAGCGCCTGCGCtccATGCACGTGTTCATCC

TGGACTACGACCAGtcaCCgGCCGGCTGCCGCGACGCCCTGCTGCAGC

TGACCAGCGGCATGGTGCAGACCCACGTGACaACaCCCGGCAGCATCC

CaACaATCTGCGACCTGGCCCGCACCTTCGCCCGCGAGATGGGCGAGG

CCAACTAATAGGGATCCCTCGAGAAGCTTgtca.

HSV-TK NLS Removal
(SEQ ID NO: 16)
gtcaGCGGCCGCACCGGTACGCGTCCACCATGGCCAGCTACCCCGGCC

ACCAGCACGCCAGCGCCTTCGACCAGGCCGCCCGCAGCCGCGGCCACA

GCAACGGCAGCACCGCaCTGCGgCCaGGATCTCAGCAGGAGGCCACCG

AGGTGCGCCCCGAGCAGAAGATGCCCACCCTGCTGCGCGTGTACATCG

ACGGaCCaCACGGCATGGGCAAGACCACCACCACCCAGCTGCTGGTGG

CCCTGGGCAGCCGCGACGACATCGTGTACGTGCCCGAGCCCATGACCT

ACTGGCGCGTGCTGGGCGCCAGCGAGACCATCGCCAACATCTACACCA

CCCAGCACCGCCTGGACCAaGGCGAGATCAGCGCCGGCGACGCCGCCG

TGGTGATGACCAGCGCCCAGATtACaATGGGCATGCCCTACGCCGTGA

CCGACGCCGTGCTGGCaCCaCACATCGGCGGCGAGGCCGGCAGCAGCC

ACGCaCCaCCaCCaGCaCTGACCCTGATCTTCGACCGgCACCCaATCG

CaCACCTGCTGTGCTACCCgGCaGCaCGCTACCTGATGGGCtccATGA

CaCCaCAaGCCGTGCTGGCCTTCGTGGCCCTGATCCCaCCaACaCTGC

CCGGCACCAACATCGTGCTGGGCGCCCTGCCCGAGGACCGCCACATCG

ACCGCCTGGCCAAGCGCCAGCGCCCCGGCGAGCGCCTGGACCTGGCCA

TGCTGGCCGCCATCCGCCGCGTGTACGGCCTGCTGGCCAACACCGTGC

GCTACCTGCAGTGCGGCGGCAGCTGGCGCGAGGACTGGGGCCAGCTGA

GCGGCACCGCCGTGCCaCCaCAGGGCGCCGAGCCaCAGAGCAACGCCG

GaCCaCGaCCaCACATCGGCGACACCCTGTTCACCCTGTTCCGgGCaC

CaGAGCTGCTGGCaCCaAACGGCGACCTGTACAACGTGTTCGCCTGGG

CCCTGGACGTGCTGGCCAAGCGCCTGCGCtccATGCACGTGTTCATCC

TGGACTACGACCAGtcaCCgGCCGGCTGCCGCGACGCCCTGCTGCAGC

TGACCAGCGGCATGGTGCAGACCCACGTGACaACaCCCGGCAGCATCC

CaACaATCTGCGACCTGGCCCGCACCTTCGCCCGCGAGATGGGCGAGG

CCAACTAATAGGGATCCCTCGAGAAGCTTgtca.

HSV-TK Custom Codon Optimization
(SEQ ID NO: 31)
gtcaGCGGCCGCACCGGTACGCGTCCACCATGGCCCTGCAGAAAAAGC

TGGAAGAGCTGGAACTGGATGGCTCTTATCCTGGACATCAGCATGCTT

CTGCTTTTGATCAGGCTGCCAGATCTAGAGGACATTCTAATGGCAGCA

CAGCACTGCGCCAGGATCTCAGCAGGAAGCTACAGAAGTGAGACCTG

AACAGAAAATGCCTACACTGCTGAGAGTGTATATTGATGGACCACATG

GAATGGGAAAAACAACCACAACCCAGCTGCTGGTGGCTCTCGGATCTA

GAGATGATATTGTGTATGTGCCTGAACCTATGACATATTGGAGAGTGC

TGGGAGCTTCTGAAACAATTGCTAATATCTATACAACACAGCATAGAC

```
TGGATCAAGGAGAAATTTCTGCCGGAGATGCTGCCGTGGTGATGACAT
CTGCTCAGATTACAATGGGAATGCCTTATGCTGTGACAGATGCTGTGC
TGGCACCACATATTGGAGGCGAAGCTGGAAGCTCTCATGCACCACCAC
CAGCACTGACACTGATTTTTGATCGGCATCCAATTGCACATCTGCTGT
GTTATCCGGCAGCAAGATATCTGATGGGAAGCATGACACCACAAGCCG
TGCTGGCTTTTGTGGCTCTGATTCCACCAACACTGCCTGGAACAAACA
TCGTGCTGGGAGCTCTGCCTGAAGATAGACATATCGATCGGCTGGCCA
AACGGCAGAGACCTGGAGAACGGCTGGATCTGGCCATGCTGGCTGCCA
TTCGGAGAGTGTATGGCCTGCTGGCTAACACAGTGAGATATCTGCAGT
GTGGAGGCTCTTGGAGAGAGGATTGGGGACAGCTGTCTGGCACAGCTG
TGCCACCACAGGGAGCCGAACCACAGAGCAATGCTGGACCACGACCAC
ATATCGGAGACACACTGTTTACACTGTTTCGGGCACCAGAACTGCTGG
CACCAAATGGAGACCTGTACAACGTGTTTGCCTGGGCTCTGGATGTGC
TGGCTAAACGGCTGAGATCTATGCATGTGTTTATCCTGGACTATGATC
AGTCACCGGCCGGATGTCGCGATGCCCTGCTGCAGCTGACATCTGGGA
TGGTGCAGACACATGTGACAACACCTGGATCTATCCCAACAATCTGTG
ATCTGGCTAGAACATTCGCTAGGGAGATGGGAGAGGCCAACTAATAGG
GATCCCTCGAGAAGCTTgtca.
```

HSV-TK NLS Removal NES and Addition (SEQ ID NO: 18)

```
gtcaGCGGCCGCACCGGTACGCGTCCACCATGGCCCTGCAGAAAAAGC
TGGAAGAGCTGGAACTGGATGGCAGCTACCCCGGCCACCAGCACGCCA
GCGCCTTCGACCAGGCCGCCCGCAGCCGCGGCCACAGCAACGGCAGCA
CCGCaCTGCGgCCaGGATCTCAGCAGGAGGCCACCGAGGTGCGCCCCG
AGCAGAAGATGCCCACCCTGCTGCGCGTGTACATCGACGGaCCaCACG
GCATGGGCAAGACCACCACCACCCAGCTGCTGGTGGCCCTGGGCAGCC
GCGACGACATCGTGTACGTGCCCGAGCCCATGACCTACTGGCGCGTGC
TGGGCGCCAGCGAGACCATCGCCAACATCTACACCACCCAGCACCGCC
TGGACCAaGGCGAGATCAGCGCCGGCGACGCCGCCGTGGTGATGACCA
GCGCCCAGATtAcAATGGGCATGCCCTACGCCGTGACCGACGCCGTGC
TGGCaCCaCACATCGGCGGCGAGGCCGGCAGCAGCCACGCaCCaCCaC
CaGcCaCTGACCCTGATCTTCGACCGgCACCCaATCGCaCACCTGCTGT
GCTACCCggCaGCaCGCTACCTGATGGGCtccATGACaCCaCAaGCCG
TGCTGGCCTTCGTGGCCCTGATCCCaCCaACaCTGCCCGGCACCAACA
TCGTGCTGGGCGCCCTGCCCGAGGACCGCCACATCGACCGCCTGGCCA
AGCGCCAGCGCCCCGGCGAGCGCCTGGACCTGGCCATGCTGGCCGCCA
TCCGCCGCGTGTACGGCCTGCTGGCCAACACCGTGCGCTACCTGCAGT
GCGGCGGCAGCTGGCGCGAGGACTGGGGCCAGCTGAGCGGCACCGCCG
TGCCaCCaCAGGGCGCCGAGCCaCAGAGCAACGCCGGaCCaCGaCCaC
ACATCGGCGACACCCTGTTCACCCTGTTCCGgGCaCCaGAGCTGCTGG
CaCCaAACGGCGACCTGTACAACGTGTTCGCCTGGGCCCTGGACGTGC
TGGCCAAGCGCCTGCGCtccATGCACGTGTTCATCCTGGACTACGACC
AGtcaCCggCCGCCGGCTGCCGCGACGCCCTGCTGCAGCTGACCAGCGGCA
TGGTGCAGACCCACGTGACaACaCCCGGCAGCATCCCaACaATCTGCG
ACCTGGCCCGCACCTTCGCCCGCGAGATGGGCGAGGCCAACTAATAGG
GATCCCTCGAGAAGCTTgtca.
```

HSV-TK Custom Codon Optimization (SEQ ID NO: 31)

```
gtcaGCGGCCGCACCGGTACGCGTCCACCATGGCCCTGCAGAAAAAGC
TGGAAGAGCTGGAACTGGATGGCTCTTATCCTGGACATCAGCATGCTT
CTGCTTTTGATCAGGCTGCCAGATCTAGAGGACATTCTAATGGCAGCA
CAGCACTGCGGCCAGGATCTCAGCAGGAAGCTACAGAAGTGAGACCTG
AACAGAAAATGCCTACACTGCTGAGAGTGTATATTGATGGACCACATG
GAATGGGAAAAACAACCACAACCCAGCTGCTGGTGGCTCTCGGATCTA
GAGATGATATTGTGTATGTGCCTGAACCTATGACATATTGGAGAGTGC
TGGGAGCTTCTGAAACAATTGCTAATATCTATACAACACAGCATAGAC
TGGATCAAGGAGAAATTTCTGCCGGAGATGCTGCCGTGGTGATGACAT
CTGCTCAGATTACAATGGGAATGCCTTATGCTGTGACAGATGCTGTGC
TGGCACCACATATTGGAGGCGAAGCTGGAAGCTCTCATGCACCACCAC
CAGCACTGACACTGATTTTTGATCGGCATCCAATTGCACATCTGCTGT
GTTATCCGGCAGCAAGATATCTGATGGGAAGCATGACACCACAAGCCG
TGCTGGCTTTTGTGGCTCTGATTCCACCAACACTGCCTGGAACAAACA
TCGTGCTGGGAGCTCTGCCTGAAGATAGACATATCGATCGGCTGGCCA
AACGGCAGAGACCTGGAGAACGGCTGGATCTGGCCATGCTGGCTGCCA
TTCGGAGAGTGTATGGCCTGCTGGCTAACACAGTGAGATATCTGCAGT
GTGGAGGCTCTTGGAGAGAGGATTGGGGACAGCTGTCTGGCACAGCTG
TGCCACCACAGGGAGCCGAACCACAGAGCAATGCTGGACCACGACCAC
ATATCGGAGACACACTGTTTACACTGTTTCGGGCACCAGAACTGCTGG
CACCAAATGGAGACCTGTACAACGTGTTTGCCTGGGCTCTGGATGTGC
TGGCTAAACGGCTGAGATCTATGCATGTGTTTATCCTGGACTATGATC
AGtcACCGGCCGGATGTCGCGATGCCCTGCTGCAGCTGACATCTGGGA
TGGTGCAGACACATGTGACAACACCTGGATCTATCCCAACAATCTGTG
ATCTGGCTAGAACATTCGCTAGGGAGATGGGAGAGGCCAACTAATAGG
GATCCCTCGAGAAGCTTgtca.
```

Example 14: HAT Assay

Retroviral Vectors of RexRed Super TK A168H and RexRed TK 167F were produced in 293T cells and used to transduce 3T3(TK-) cells. These transduced cells were HAT selected for 7-14 days. Untransduced 3T3(TK-) cells will die post HAT selection. These same cells transduced with RexRed Super TK A168H did survive HAT selection, however 3T3(TK-) cells transduced with RexRed TK 167F did not survive HAT selction. This is a plus/minus cell survival assay, surviving cells are fixed and stained with 1% methylene blue in methanol.

Previous transduction based HAT cell kill assays reveal a GCV specificity over thymidine for the A167F HSV-TK mutants in retroviral vectors containing the RFP marker. That specificity is found in NIH 3T3 cells in a 72 hour and 7 day assay at 1×HAT dose.

Current transduction based HAT cell kill assays reveal a GCV specificity over thymidine for the A167F HSV-TK mutants in retroviral vectors containing the RFP marker. That specificity is found in NIH 3T3 cells in a 7 day assay at 2×HAT dose.

Transduction based HAT cell kill assays reveal a GCV specificity over thymidine for the A167F HSV-TK mutants in retroviral vectors containing the RFP marker. That specificity is found in NIH 3T3 cells in a 72 hour assay and 7 day assay at 1×HAT dose.

Transduction based HAT cell kill assays reveal a GCV specificity over thymidine for the A167F HSV-TK mutants in retroviral vectors containing the HygroR marker. That specificity is found in NIH 3T3 cells in a 72 hour and 7 day assay at 1×HAT dose.

Example 15: GCV Kill Assay

Cells were seeded in a 24 well dish. Cells were transduced the next day with 6 dilutions of the retroviral vectors (1:4-4096). The next day 0-200 µM GCV was added to the cells. After seven days of GCV treatment the cells were fixed and the live cells stain with 1% methylene blue in methanol. The higher the potency of the viral mutants leads to more cell kill.

Previous transduction based HSV-TK/GCV cell kill assays reveal a potency order for A168F, A167F and A168H HSV-TK mutants in retroviral vectors containing the RFP marker. That order is A168H>A168F=A167F when tested in RgA375 cells in a 72 hour and 7 day assay at high GCV dose (1 mM-125 mM).

Current transduction based HSV-TK/GCV cell kill assays reveal a potency order for A167F and A168H HSV-TK mutants in retroviral vectors containing the RFP marker. That order is A168H>A167F when tested in RgA375 cells in a 7 day assay at high GCV dose (0.2 mM-0.05 mM). The addition of dm NLS or NES does not appear to change this order. The use of JCO does appear to lower titer and aggregate HSV-TK cell kill activity.

Transduction based HSV-TK/GCV cell kill assays reveal a potency order for A168F, A167F and A168H HSV-TK mutants in retroviral vectors containing the RFP marker. That order is A168H>A168F=A167F when tested in A375 and RgA375 cells in a 72 hour assay at high GCV dose (1 mM-125 mM).

Transduction based HSV-TK/GCV cell kill assays reveal a potency order for A168F, A167F and A168H HSV-TK mutants in retroviral vectors containing the RFP marker. That order is A168H>A168F=A167F when tested in NIH 3T3 cells in a 72 hour assay at high GCV dose (1 mM-500 mM).

Transduction based HSV-TK/GCV cell kill assays reveal a potency order for A168F, A167F and A168H HSV-TK mutants in retroviral vectors containing the RFP marker. That order is A168H>A168F=A167F when tested in RgA375 cells in a 72 hour and 7 day assay at high GCV dose (1 mM-125 mM).

Transduction based HSV-TK/GCV cell kill assays reveal a potency order for A168F, A167F and A168H HSV-TK mutants in retroviral vectors containing the RFP or HygroR marker. That order is A168H>A168F=A167F when tested in A375, RgA375 or NIH 3T3 cells in a 72 hour assay at high GCV dose (1 mM-125 mM).

Transduction based HSV-TK/GCV cell kill assays reveal a potency order for A168F, A167F and A168H HSV-TK mutants in retroviral vectors containing the HygroR marker. That order is A168H>A168F=A167F when tested in A375 and RgA375 cells in a 72 hour assay at high GCV dose (1 mM-125 mM).

Transduction based HSV-TK/GCV cell kill assays reveal a potency order for A168F, A167F and A168H HSV-TK mutants in retroviral vectors containing the HygroR marker. That order is A168H>A168F=A167F when tested in NIH 3T3 cells in a 72 hour assay at high GCV dose (1 mM-500 mM).

Example 16: Hygro Resistance

Cell lines transduced with retrovector Hygro-HSV-TK mutants were selected in the presence of hygromycin to produce a pure population of cells containg the Hygro-HSV-TK mutants and expressing the hygromycin resistence gene.

A375 Reximmune-C2 like Cell lines: A375 Hygro selected HSV-TK dmNESA168H cell lines have been converted to Luc(+). The above cell line has same GCV kill as parental line. A A375 Luc(+) only cell line has same Luc activity as above cell line.

C6 Reximmune-C2 like Cell lines: C6 Hygro selected HSV-TK dmNESA168H cell lines have been converted to Luc(+). The above cell line has same GCV kill as parental line. A C6 Luc(+) only cell line has same Luc activity as above cell line.

While preferred embodiments have been shown and described herein, it will be obvious to those skilled in the art that such embodiments are provided by way of example only. Numerous variations, changes, and substitutions will now occur to those skilled in the art without departing from the disclosed embodiments. It should be understood that various alternatives to the embodiments described herein may be employed in practicing the embodiments. It is intended that the following claims define the scope of the embodiments and that methods and structures within the scope

ABBREVIATIONS

ALT Alanine aminotransferase
ANC Absolute neutrophil count
AST Aspartate aminotransferase
AUC Area under the plasma concentration-time curve
BSA Body surface area (mg/m$^2$)
CL Systemic plasma clearance
$C_{max}$ Peak plasma concentration
CR Complete response
CRF Case report form
CT Computerized tomography
CTC Common Toxicity Criteria
DLT Dose Limiting Toxicities
EOI End of infusion
FDA Food and Drug Administration
G-CSF Granulocyte-colony stimulating factor (filgrastim, Neupogen®)
GCP Good clinical practice
GM-CSF Granulocyte-macrophage colony-stimulating factor (sargramostim, Leukine®)
HIV Human Immunodeficiency Virus
HR Hazard ratio
IEC Independent Ethics Committee
i.p. Intraperitoneal
IRB Institutional Review Board IV Intravenous, intravenously
LD$_{10}$ or Dose that is lethal to 10% or 50% of animals LD$_{50}$
LDH Lactate dehydrogenase
MAD Maximum Administered Dose
MRI Magnetic resonance imaging
MTD Maximum tolerated dose
NCI National Cancer Institute
NE Not evaluable for tumor response
NOAEL No Observed Adverse Effect Level
Non-CR Non-complete response
Non-PD Non-progressive disease
PBMC Peripheral Blood Mononuclear Cells
PCE Propylene Glycol: Cremophor® EL: Ethanol
PD Progressive disease
PR Partial response
SAER-S Serious Adverse Event Report-Study
SC Subcutaneous, subcutaneously
SD Stable disease
STD$_{10}$ Dose that is severely toxic to 10% of animals
TTP Time to Progression
TTF Time to Failure
T$_{1/2}$ Half-life
T$_{max}$ Time of maximum plasma concentration
V$_{ss}$ Steady state volume of distribution

REFERENCES

1. Lentivirus-based DsRed-2-transfected pancreatic cancer cells for deep in vivo imaging of metastatic disease. Yu Z, Zhou J, Hoffman R M., Methods Mol Biol. 2012; 872: 69-83. doi: 10.1007/978-1-61779-797-2_5.
2. Color-coded real-time subcellular fluorescence imaging of the interaction between cancer and host cells in live mice. Yamauchi K, Tome Y, Yamamoto N, Hayashi K, Kimura H, Tsuchiya H, Tomita K, Bouvet M, Hoffman R M. Anticancer Res. 2012 January; 32(1):39-43.
3. Lentivirus-based DsRed-2-transfected pancreatic cancer cells for deep in vivo imaging of metastatic disease. Zhou J, Yu Z, Zhao S, Hu L, Zheng J, Yang D, Bouvet M, Hoffman R M. J Surg Res. 2009 November; 157(1):63-70. doi: 10.1016/j.jss.2008.08.027. Epub 2008 Oct. 9.
4. Fluorescent LYVE-1 antibody to image dynamically lymphatic trafficking of cancer cells in vivo. McElroy M, Hayashi K, Garmy-Susini B, Kaushal S, Varner J A, Moossa A R, Hoffman R M, Bouvet M. J Surg Res. 2009 January; 151(1):68-73. doi: 10.1016/j.jss.2007.12.769. Epub 2008 Jan. 18.
5. Lentiviral reporter constructs for fluorescence tracking of the temporo spatial pattern of Smad3 signaling. Stuelten C H, Kamaraju A K, Wakefield L M, Roberts A B. Biotechniques. 2007 September; 43(3):289-90, 292, 294.
6. Subcellular imaging in the live mouse. Hoffman R M, Yang M. Nat Protoc. 2006; 1(2):775-82.
7. In vivo color-coded imaging of the interaction of colon cancer cells and splenocytes in the formation of liver metastases. Bouvet M, Tsuji K, Yang M, Jiang P, Moossa A R, Hoffman R M. Cancer Res. 2006 Dec. 1; 66(23): 11293-7.
8. Dual-color imaging of nuclear-cytoplasmic dynamics, viability, and proliferation of cancer cells in the portal vein area. Tsuji K, Yamauchi K, Yang M, Jiang P, Bouvet M, Endo H, Kanai Y, Yamashita K, Moossa A R, Hoffman R M. Cancer Res. 2006 Jan. 1; 66(1):303-6.
9. FL-CTL assay: fluorolysometric determination of cell-mediated cytotoxicity using green fluorescent protein and red fluorescent protein expressing target cells. Chen K, Chen L, Zhao P, Marrero L, Keoshkerian E, Ramsay A, Cui Y. J Immunol Methods. 2005 May; 300(1-2):100-14.
10. Murine leukemia virus (MLV) replication monitored with fluorescent proteins. Sliva K, Erlwein O, Bittner A, Schnierle B S. Virol J. 2004 Dec. 20; 1:14.
11. Real-time whole-body imaging of an orthotopic metastatic prostate cancer model expressing red fluorescent protein. Yang M, Jiang P, Yamamoto N, Li L, Geller J, Moossa A R, Hoffman R M. Prostate. 2005 Mar. 1; 62(4):374-9.
12. Cellular dynamics visualized in live cells in vitro and in vivo by differential dual-color nuclear-cytoplasmic fluorescent-protein expression. Yamamoto N, Jiang P, Yang M, Xu M, Yamauchi K, Tsuchiya H, Tomita K, Wahl G M, Moossa A R, Hoffman R M. Cancer Res. 2004 Jun. 15; 64(12):4251-6.
13. In vivo imaging with fluorescent proteins: the new cell biology. Hoffman R M. Acta Histochem. 2004; 106(2): 77-87.
14. Real-time imaging of individual fluorescent-protein color-coded metastatic colonies in vivo. Yamamoto N, Yang M, Jiang P, Xu M, Tsuchiya H, Tomita K, Moossa A R, Hoffman R M. Clin Exp Metastasis. 2003; 20(7): 633-8.
15. Yaghoubi S, Barrio J R, Dahlbom M, Iyer M, Namavari M, Satyamurthy N, Goldman R, Herschman H R, Phelps M E, Gambhir S S. Human pharmacokinetic and dosimetry studies of [(18)F]FHBG: a reporter probe for imaging herpes simplex virus type-1 thymidine kinase reporter gene expression. J Nucl Med. 2001 August; 42(8):1225-34.
16. Pañeda A, Collantes M, Beattie S G, Otano I, Snapper J, Timmermans E, Guembe L, Petry H, Lanciego J L, Benito A, Prieto J, Rodriguez-Pena M S, Peñuelas I, Gonzalez-Aseguinolaza G. Adeno-associated virus liver transduction efficiency measured by in vivo [$^{18}$F]FHBG positron emission tomography imaging in rodents and nonhuman primates. Hum Gene Ther. 2011 August; 22(8):999-1009. doi: 10.1089/hum.2010.190. Epub 2011 Apr. 6.
17. Johnson M, Karanikolas B D, Priceman S J, Powell R, Black M E, Wu H M, Czernin J, Huang S C, Wu L. Titration of variant HSV1-tk gene expression to determine the sensitivity of $^{18}$F-FHBG PET imaging in a prostate tumor. J Nucl Med. 2009 May; 50(5):757-64. doi: 10.2967/jnumed.108.058438. Epub 2009 Apr. 16.
18. Peñuelas I, Mazzolini G, Boán J F, Sangro B, Martí-Climent J, Ruiz M, Ruiz J, Satyamurthy N, Qian C, Barrio J R, Phelps M E, Richter J A, Gambhir S S, Prieto J. Positron Emission Tomography Imaging of Adenoviral-Mediated Transgene Expression in Liver Cancer Patients Gastro (2005)128:1787.
19. Sangro B, Mazzolini G, Ruiz M, Ruiz J, Quiroga J, Herrero I, Qian C, Benito A, Larrache J, Olagüe C, Boan J, Peñuelas I, Sádaba B, Prieto J. A phase I clinical trial of thymidine kinase-based gene therapy in advanced hepatocellular carcinoma Can. Gene Ther. (2010) 17: 837-843.
20. Willmann J K, Paulmurugan R, Rodriguez-Porcel M, Stein W, Brinton T J, Connolly A J, Nielsen C H, Lutz A M, Lyons J, Ikeno F, Suzuki Y, Rosenberg J, Chen I Y, Wu J C, Yeung A C, Yock P, Robbins R C, Gambhir S S. Imaging gene expression in human mesenchymal stem cells: from small to large animals. Radiology. 2009 July; 252(1):117-27. doi: 10.1148/radiol.2513081616. Epub 2009 Apr. 14. PubMed PMID: 19366903; PubMed Central PMCID: PMC2702468.

21. Yaghoubi S S, Jensen M C, Satyamurthy N, Budhiraja S, Paik D, Czernin J, Gambhir S S. Noninvasive detection of therapeutic cytolytic T cells with $^{18}$F-FHBG PET in a patient with glioma. Nat Clin Pract Oncol. 2009 January; 6(1):53-8. doi: 10.1038/ncponc1278. Epub 2008 Nov. 18. PubMed PMID: 19015650; PubMed Central PMCID: PMC3526373.

22. Roelants V, Labar D, de Meester C, Havaux X, Tabilio A, Gambhir S S, Di lanni M, Bol A, Bertrand L, Vanoverschelde J L. Comparison between adenoviral and retroviral vectors for the transduction of the thymidine kinase PET reporter gene in rat mesenchymal stem cells. J Nucl Med. 2008 November; 49(11):1836-44. doi: 10.2967/jnumed.108.052175. Erratum in: J Nucl Med. 2009 January; 50(1):17. PubMed PMID: 18984872.

23. Lee S W, Padmanabhan P, Ray P, Gambhir S S, Doyle T, Contag C, Goodman S B, Biswal S. Stem cell-mediated accelerated bone healing observed with in vivo molecular and small animal imaging technologies in a model of skeletal injury. J Orthop Res. 2009 March; 27(3):295-302. doi: 10.1002/jor.20736. PubMed PMID: 18752273.

24. Chin F T, Namavari M, Levi J, Subbarayan M, Ray P, Chen X, Gambhir S S. Semiautomated radiosynthesis and biological evaluation of [$^{18}$F]FEAU: a novel PET imaging agent for HSV1-tk/sr39tk reporter gene expression. Mol Imaging Biol. 2008 March-April; 10(2):82-91. Epub 2007 Dec. 22. PubMed PMID: 18157580.

25. Yaghoubi S S, Gambhir S S. PET imaging of herpes simplex virus type 1 thymidine kinase (HSV1-tk) or mutant HSV1-sr39tk reporter gene expression in mice and humans using [$^{18}$F]FHBG. Nat Protoc. 2006; 1(6):3069-75. PubMed PMID: 17406570.

26. Deroose C M, De A, Loening A M, Chow P L, Ray P, Chatziioannou A F, Gambhir S S. Multimodality imaging of tumor xenografts and metastases in mice with combined small-animal PET, small-animal C T, and bioluminescence imaging. J Nucl Med. 2007 February; 48(2): 295-303. PubMed PMID: 17268028; PubMed Central PMCID: PMC3263830.

27. Kim S J, Doudet D J, Studenov A R, Nian C, Ruth T J, Gambhir S S, McIntosh C H. Quantitative micro positron emission tomography (PET) imaging for the in vivo determination of pancreatic islet graft survival. Nat Med. 2006 December; 12(12):1423-8. Epub 2006 Dec. 3. PubMed PMID: 17143277.

28. Yaghoubi S S, Couto M A, Chen C C, Polavaram L, Cui G, Sen L, Gambhir S S. Preclinical safety evaluation of $^{18}$F-FHBG: a PET reporter probe for imaging herpes simplex virus type 1 thymidine kinase (HSV1-tk) or mutant HSV1-sr39tk's expression. J Nucl Med. 2006 April; 47(4):706-15. PubMed PMID: 16595506.

29. Xiong Z, Cheng Z, Zhang X, Patel M, Wu J C, Gambhir S S, Chen X. Imaging chemically modified adenovirus for targeting tumors expressing integrin alphavbeta3 in living mice with mutant herpes simplex virus type 1 thymidine kinase PET reporter gene. J Nucl Med. 2006 January; 47(1):130-9. PubMed PMID: 16391197.

30. Shu C J, Guo S, Kim Y J, Shelly S M, Nijagal A, Ray P, Gambhir S S, Radu C G, Witte O N. Visualization of a primary anti-tumor immune response by positron emission tomography. Proc Natl Acad Sci USA. 2005 Nov. 29; 102(48):17412-7. Epub 2005 Nov. 17. PubMed PMID: 16293690; PubMed Central PMCID: PMC1283986.

31. Sen L, Gambhir S S, Furukawa H, Stout D B, Linh Lam A, Laks H, Cui G. Noninvasive imaging of ex vivo intracoronarily delivered nonviral therapeutic transgene expression in heart. Mol Ther. 2005 July; 12(1):49-57. PubMed PMID: 15963920.

32. Yaghoubi S S, Barrio J R, Namavari M, Satyamurthy N, Phelps M E, Herschman H R, Gambhir S S. Imaging progress of herpes simplex virus type 1 thymidine kinase suicide gene therapy in living subjects with positron emission tomography. Cancer Gene Ther. 2005 March; 12(3):329-39. PubMed PMID: 15592447.

33. Miyagawa M, Anton M, Haubner R, Simoes M V, Stadele C, Erhardt W, Reder S, Lehner T, Wagner B, Noll S, Noll B, Grote M, Gambhir S S, Gansbacher B, Schwaiger M, Bengel F M. PET of cardiac transgene expression: comparison of 2 approaches based on herpesviral thymidine kinase reporter gene. J Nucl Med. 2004 November; 45(11):1917-23. PubMed PMID: 15534063.

34. Green L A, Nguyen K, Berenji B, Iyer M, Bauer E, Barrio J R, Namavari M, Satyamurthy N, Gambhir S S. A tracer kinetic model for $^{18}$F-FHBG for quantitating herpes simplex virus type 1 thymidine kinase reporter gene expression in living animals using PET. J Nucl Med. 2004 September; 45(9):1560-70. PubMed PMID: 15347725.

35. Wu J C, Chen I Y, Wang Y, Tseng J R, Chhabra A, Salek M, Min J J, Fishbein M C, Crystal R, Gambhir S S. Molecular imaging of the kinetics of vascular endothelial growth factor gene expression in ischemic myocardium. Circulation. 2004 Aug. 10; 110(6):685-91. PubMed PMID: 15302807.

36. Su H, Forbes A, Gambhir S S, Braun J. Quantitation of cell number by a positron emission tomography reporter gene strategy. Mol Imaging Biol. 2004 May-June; 6(3): 139-48. PubMed PMID: 15193248.

37. Chen I Y, Wu J C, Min J J, Sundaresan G, Lewis X, Liang Q, Herschman H R, Gambhir S S. Micro-positron emission tomography imaging of cardiac gene expression in rats using bicistronic adenoviral vector-mediated gene delivery. Circulation. 2004 Mar. 23; 109(11):1415-20. Epub 2004 Mar. 8. PubMed PMID: 15007006.

38. Sundaresan G, Paulmurugan R, Berger F, Stiles B, Nagayama Y, Wu H, Gambhir S S. MicroPET imaging of Cre-loxP-mediated conditional activation of a herpes simplex virus type 1 thymidine kinase reporter gene. Gene Ther. 2004 April; 11(7):609-18. PubMed PMID: 14724687.

39. Green L A, Yap C S, Nguyen K, Barrio J R, Namavari M, Satyamurthy N, Phelps M E, Sandgren E P, Herschman H R, Gambhir S S. Indirect monitoring of endogenous gene expression by positron emission tomography (PET) imaging of reporter gene expression in transgenic mice. Mol Imaging Biol. 2002 January; 4(1):71-81. PubMed PMID: 14538050.

40. Miller, A. and Wolgamot, G. Murine retroviruses use at least six different receptors for entry into Mus dunni cells. J. Virol. 1997 June; 9:4531-35.

41. Chaudry G. J., et al. Gibbon ape leukemia virus receptor functions of Type III phosphate transporters from CHOK1 cells are disrupted by two mechanisms. J. Virol. 1999 April; 73:2916-20.

42. Xu and Eiden. Primate gammaretroviruses require an ancillary factor not required for murine gammaretroviruses to infect BHK cells. J. Virol. 2011 April; 85:3498-506.

43. Zeijl et al. A human amphotrophic retrovirus receptor is a second member of the gibbon ape leukemia virus receptor family. Proc. Nat'l Acad. Sci. 1994 February; 91:1168-72.

44. Feldman et al. Identification of an extracellular domain within the Human PiT-2 receptor that is required for amphotrophic murine leukemia virus binding. J. Virol. 2004 January; 78:595-602.
45. MacDonald et al. Effect of changes in the expression of the amphotrophic retroviral receptor PiT-2 on transduction efficiency and viral titer: Implications for gene therapy. Hum. Gene Ther. 2000 March; 11:587-95.
46. Farrell et al. New structural arrangement of the extracellular regions of the phosphate transporter SLC20A1, the receptor for gibbon ape leukemia virus. J. Biol. Chem. 2009 October; 284:29979-987.
47. Farrell et al. Fusion defective gibbon ape leukemia virus vectors can be rescued by homologous but not heterologous soluble envelope proteins. J. Virol. 2002 May; 76:4267-74.
48. Orlic et al. The level of mRNA encoding the amphotrophic retrovirus receptor in mouse and human hematopoietic stem cells is low and correlates with with the efficiency of retrovirus transduction. Proc. Nat'l Acad. Sci 1996 October; 93:11097-102.
49. Naviaus et al. pCL vector system: rapid production of helper-free, high-titer, recombinant retroviruses. J. Virol. 1996 August; 70:5701-5.
50. Fuchita et al. Bacterial cytosine deaminase mutants created by molecular engineering show improved 5-fluorocytosine-mediated cell killing in vitro and in vivo. Cancer Res. 2009 June; 69:4791-9.
51. Stolworthy et al. Yeast cytosine deaminase mutants with increased thermostability impart sensitivity to 5-fluorocytosine. J. Mol. Biol. 2008 March; 377:854-69.
52. Grabarczyk et al. Expression of PiT-1 and PiT-2 retroviral receptors and transduction efficiency of tumor cells. Acta Biochim. Pol. 2002; 49:333-9.
53. Miller and Rosman. Improved retroviral vectors for gene transfer and expression. Biotechniques 1989 October; 7:980-2; 984-6; 989-90.
54. Chalmers et al. Elimination of the truncated message from the herpes simplex virus thymidine kinase suicide gene. Mol. Ther. 4:146-8 (2001).

```
                                SEQUENCES

SEQ ID NO: 1: wild type HSV1-TK nucleotide sequence
atggcttcgtaccccggccatcaacacgcgtctgcgttcgaccaggctgcgcgttctcgcggccata gcaaccgacgtacggcgttgcgccctcgccggcagcaagaagccacggaagtccgcccggagcagaa aatgcccacgctactgcgggtttatatagacggtccccacgggatggggaaaaccaccaccacgcaa ctgctggtggccctgggtcgcgcgacgatatcgtctacgtacccgagccgatgacttactggcggg tgctggggcttccgagacaatcgcgaacatctacaccacacaacaccgcctcgaccagggtgagat atcggccggggacgcggcggtggtaatgacaagcgcccagataacaatgggcatgccttatgccgtg accgacgccgttctggctcctcatatcgggggggaggctgggagctcacatgccccgcccccggccc tcaccctcatcttcgaccgccatcccatcgccgccctcctgtgctacccggccgcgcggtaccttat gggcagcatgacccccaggccgtgctggcgttcgtggccctcatcccgccgaccttgcccggcacc aacatcgtgcttggggcccttccggaggacagacacatcgaccgcctggccaaacgccagcgcccg gcgagcggctggacctggctatgctggctgcgattcgccgcgtttacgggctacttgccaatacggt gcggtatctgcagtgcggcgggtcgtggcgggaggactggggacagctttcggggacggccgtgccg ccccagggtgccgagcccagagcaacgcgggcccacgaccccatatcggggacacgttatttaccc tgtttcgggcccccgagttgctggccccaacggcgacctgtataacgtgtttgcctgggccttgga cgtcttggccaaacgcctccgttccatgcacgtctttatcctggattacgaccaatcgcccgccggc tgccgggacgccctgctgcaacttacctccgggatggtccagacccacgtcaccaccccggctcca taccgacgatatgcgacctggcgcgcacgtttgcccgggagatgggggaggctaactga SEQ ID NO: 2: wild type HSV1-TK amino acid sequence
MASYPGHQHASAFDQAARSRGHSNRRTALRPRRQQEATEVRPEQKMPTLLRVYIDGPHGMGKTTTTQ

LLVALGSRDDIVYVPEPMTYWRVLGASETIANIYTTQHRLDQGEISAGDAAVVMTSAQITMGMPYAV

TDAVLAPHIGGEAGSSHAPPPALTLIFDRHPIAALLCYPAARYLMGSMTPQAVLAFVALIPPTLPGT

NIVLGALPEDRHIDRLAKRQRPGERLDLAMLAAIRRVYGLLANTVRYLQCGGSWREDWGQLSGTAVP

PQGAEPQSNAGPRPHIGDTLFTLFRAPELLAPNGDLYNVFAWALDVLAKRLRSMHVFILDYDQSPAG

CRDALLQLTSGMVQTHVTTPGSIPTICDLARTFAREMGEAN

SEQ ID NO: 3: HSV-TK in Reximmune-C HSV-TK; SR 39 mutant and
    R25G-R26S Mutation of NLS
    atggcctcgtaccccggccatcaacacgcgtctgcgttcgaccaggctgcgcgttctcgcggccata gcaacggatccacggcgttgcgccctcgccggcagcaagaagccacggaagtccgcccggagcagaa
```

| SEQUENCES |
|---|
| aatgcccacgctactgcgggtttatatagacggtccccacgggatggggaaaaccaccaccacgcaa |
| ctgctggtggccctgggttcgcgcgacgatatcgtctacgtacccgagccgatgacttactggcggg |
| tgctgggggcttccgagacaatcgcgaacatctacaccacacaacaccgcctcgaccagggtgagat |
| atcggccggggacgcggcggtggtaatgacaagcgcccagataacaatgggcatgccttatgccgtg |
| accgacgccgttctggctcctcatatcggggggaggctgggagctcacatgccccgccccggccc |
| tcaccatcttcctcgaccgccatcccatcgccttcatgctgtgctacccggccgcgcggtaccttat |
| gggcagcatgacccccaggccgtgctggcgttcgtggccctcatcccgccgaccttgcccggcacc |
| aacatcgtgcttggggcccttccggaggacagacatcgaccgcctggccaaacgccagcgccccg |
| gcgagcggctggacctggctatgctggctgcgattcgccgcgtttacgggctacttgccaatacggt |
| gcggtatctgcagtgcggcgggtcgtggcgggaggactggggacagctttcggggacggccgtgccg |
| ccccagggtgccgagcccagagcaacgcgggcccacgaccccatatcggggacacgttatttaccc |
| tgtttcggggccccgagttgctggccccaacggcgacctgtataacgtgtttgcctgggccttgga |
| cgtcttggccaaacgcctccgttccatgcacgtctttatcctggattacgaccaatcgcccgccggc |
| tgccgggacgccctgctgcaacttacctccgggatggtccagacccacgtcaccaccccggctcca |
| taccgacgatatgcgacctggcgcgcacgtttgcccgggagatggggaggctaactga |

SEQ ID NO: 4 (amino acid sequence encoded by SEQ ID NO: 3)
MASYPGHQHASAFDQAARSRGHSNGSTALRPRRQQEATEVRPEQKMPTLLRVYIDGPHGMGKTTTTQ

LLVALGSRDDIVYVPEPMTYWRVLGASETIANIYTTQHRLDQGEISAGDAAVVMTSAQITMGMPYAV

TDAVLAPHIGGEAGSSHAPPPALTIFLDRHPIAFMLCYPAARYLMGSMTPQAVLAFVALIPPTLPGT

NIVLGALPEDRHIDRLAKRQRPGERLDLAMLAAIRRVYGLLANTVRYLQCGGSWREDWGQLSGTAVP

PQGAEPQSNAGPRPHIGDTLFTLFRAPELLAPNGDLYNVFAWALDVLAKRLRSMHVFILDYDQSPAG

CRDALLQLTSGMVQTHVTTPGSIPTICDLARTFAREMGEAN

SEQ ID NO: 5: HSV-TK Sites to mutate are in bold, underlining
(HSV-TK nuclear localization sequence, RR, and Substrate Binding
Domain, LIF and AAL

| | |
|---|---|
| atggcctcgtacccggccatcaacacgcgtctgcgttcgaccaggctgcgcgttctcgc<br>M  A  S  Y  P  G  H  Q  H  A  S  A  F  D  Q  A  A  R  S  R | 60 |
| ggccatagcaaccgacgtacggcgttgcgccctcgccggcagcaagaagccacggaagtc<br>G  H  S  N  R  R  T  A  L  R  P  R  R  Q  Q  E  A  T  E  V | 120 |
| cgcccggagcagaaaatgcccacgctactgcgggtttatatagacggtccccacgggatg<br>R  P  E  Q  K  M  P  T  L  L  R  V  Y  I  D  G  P  H  G  M | 180 |
| gggaaaaccaccaccacgcaactgctggtggccctgggttcgcgcgacgatatcgtctac<br>G  K  T  T  T  T  Q  L  L  V  A  L  G  S  R  D  D  I  V  Y | 240 |
| gtacccgagccgatgacttactggcgggtgctgggggcttccgagacaatcgcgaacatc<br>V  P  E  P  M  T  Y  W  R  V  L  G  A  S  E  T  I  A  N  I | 300 |
| tacaccacacaacaccgcctcgaccagggtgagatatcggccggggacgcggcggtggta<br>Y  T  T  Q  H  R  L  D  Q  G  E  I  S  A  G  D  A  A  V  V | 360 |
| atgacaagcgcccagataacaatgggcatgccttatgccgtgaccgacgccgttctggct<br>M  T  S  A  Q  I  T  M  G  M  P  Y  A  V  T  D  A  V  L  A | 420 |
| cctcatatcggggggaggctgggagctcacatgccccgccccggccctcaccctcatc<br>P  H  I  G  G  E  A  G  S  S  H  A  P  P  P  A  L  T  L  I | 480 |
| ttcgaccgccatcccatcgccgccctcctgtgctacccggccgcgcggtaccttatgggc<br>F  D  R  H  P  I  A  A  L  L  C  Y  P  A  A  R  Y  L  M  G | 540 |
| agcatgacccccaggccgtgctggcgttcgtggccctcatcccgccgaccttgcccggc<br>S  M  T  P  Q  A  V  L  A  F  V  A  L  I  P  P  T  L  P  G | 600 |

| SEQUENCES | |
|---|---|
| accaacatcgtgcttggggcccttccggaggacagacacatcgaccgcctggccaaacgc<br>T  N  I  V  L  G  A  L  P  E  D  R  H  I  D  R  L  A  K  R | 660 |
| cagcgccccggcgagcggctggacctggctatgctggctgcgattcgccgcgtttacggg<br>Q  R  P  G  E  R  L  D  L  A  M  L  A  A  I  R  R  V  Y  G | 720 |
| ctacttgccaatacggtgcggtatctgcagtgcggcgggtcgtggcgggaggactggga<br>L  L  A  N  T  V  R  Y  L  Q  C  G  G  S  W  R  E  D  W  G | 780 |
| cagctttcggggacggccgtgccgccccaggtgccgagcccagagcaacgcgggccca<br>Q  L  S  G  T  A  V  P  P  Q  G  A  E  P  Q  S  N  A  G  P | 840 |
| cgacccatatcggggacacgttatttaccctgtttcggccccgagttgctggccccc<br>R  P  H  I  G  D  T  L  F  T  L  F  R  A  P  E  L  L  A  P | 900 |
| aacggcgacctgtataacgtgtttgcctgggccttggacgtcttggccaaacgcctccgt<br>N  G  D  L  Y  N  V  F  A  W  A  L  D  V  L  A  K  R  L  R | 960 |
| tccatgcacgtctttatcctggattacgaccaatcgcccgccggctgccgggacgccctg<br>S  M  H  V  F  I  L  D  Y  D  Q  S  P  A  G  C  R  D  A  L | 1020 |
| ctgcaacttacctccgggatggtccagacccacgtcaccaccccggctccataccgacg<br>L  Q  L  T  S  G  M  V  Q  T  H  V  T  T  P  G  S  I  P  T | 1080 |
| atatgcgacctggcgcgcacgtttgcccgggagatgggggaggctaactga<br>I  C  D  L  A  R  T  F  A  R  E  M  G  E  A  N  * | |
| SEQ ID NOS: 6 and 7: Sac I-Kpn I (SR39) mutant region<br>GAGCTCACATGCCCCGCCCCCGGCCCTCACCATCTTCCTCGACCGCCATCCCATCGCC-<br>CTCGAGTGTACGGGGCGGGGGCCGGGAGTGGTAGAAGGAGCTGGCGGTAGGGTAGCGG-<br>Sac I<br><br>-TTCATGCTGTGCTACCCGGCCGCGCGGTACC (SEQ ID NO: 6)<br>-AAGTACGACACGATGGGCCGGCGCGCCATGG (SEQ ID NO: 7)<br>                                Kpn I | |

| Kpn I | GGTACC | G<br>C | /  | G<br>C | T<br>A | A<br>T | C<br>G | /  | C<br>G | GTAC-3' |
|---|---|---|---|---|---|---|---|---|---|---|
| Sac I | GAGCTC | G<br>C | /  | A<br>T | G<br>C | C<br>G | T<br>A | /  | C<br>G | AGCT-3' |

| SEQ ID NOS: 8 and 9: Sac I-Kpn I (SR39) mutant region (cut)<br>CACATGCCCCGCCCCCGGCCCTCACCATCTTCCTCGACCGCCATCCCATCGCCTTCATG<br>TCGAGTGTACGGGGCGGGGGCCGGGAGTGGTAGAAGGAGCTGGCGGTAGGGTAGCGGAA<br>Sac I (cut)<br><br>CTGTGCTACCCGGCCGCGCGGTAC (SEQ ID NO: 8)<br>GTACGACACGATGGGCCGGC (SEQ ID NO: 9)<br>             Kpn I(cut) | |
|---|---|

| Kpn I | GGTACC | G<br>C | /  | G<br>C | T<br>A | A<br>T | C<br>G | /  | C<br>G | GTAC-3' |
|---|---|---|---|---|---|---|---|---|---|---|

SEQ ID NOS: 10 and 11: Primers
SR39sackpn F1

(SEQ ID NO: 10)

5'CACATGCCCCGCCCCCGGCCCTCACCATCTTCCTCGACCGCCATCCCATCGCCTTCATGCTGTGC
TACCCGGCCGCGCGGTAC 3'

SR39sackpn R1

(SEQ ID NO: 11)

5' CGCGCGGCCGGGTAGCACAGCATGAAGGCGATGGGATGGCGGTCGAGGAAGATGGTGAGGGCCGG
GGGCGGGGCATGTGAGCT 3'

SEQ ID NO: 12 Gene #3 mHSV-TK CO A168H(LIF . . . AHL): Length: 1185
GTCAGCGGCCGCACCGGTACGCGTCCACCATGGCCAGCTACCCCGGCCACCAGCACGCCAGCGCCTT

CGACCAGGCCGCCCGCAGCCGCGGCCACAGCAACGGCAGCACCGCACTGCGGCCACGGCGCCAGCAG

GAGGCCACCGAGGTGCGCCCCGAGCAGAAGATGCCCACCCTGCTGCGCGTGTACATCGACGGACCAC

ACGGCATGGGCAAGACCACCACCACCCAGCTGCTGGTGGCCCTGGGCAGCCGCGACGACATCGTGTA

CGTGCCCGAGCCCATGACCTACTGGCGCGTGCTGGGCGCCAGCGAGACCATCGCCAACATCTACACC

| SEQUENCES |
|---|
| ACCCAGCACCGCCTGGACCAAGGCGAGATCAGCGCCGGCGACGCCGCCGTGGTGATGACCAGCGCCC |
| AGATTACAATGGGCATGCCCTACGCCGTGACCGACGCCGTGCTGGCACCACACATCGGCGGCGAGGC |
| CGGCAGCAGCCACGCACCACCACCAGCACTGACCCTGATCTTCGACCGGCACCCAATCGCACACCTG |
| CTGTGCTACCCGGCAGCACGCTACCTGATGGGCTCCATGACACCACAAGCCGTGCTGGCCTTCGTGG |
| CCCTGATCCCACCAACACTGCCCGGCACCAACATCGTGCTGGGCGCCCTGCCCGAGGACCGCCACAT |
| CGACCGCCTGGCCAAGCGCCAGCGCCCCGGCGAGCGCCTGGACCTGGCCATGCTGGCCGCCATCCGC |
| CGCGTGTACGGCCTGCTGGCCAACACCGTGCGCTACCTGCAGTGCGGCGGCAGCTGGCGCGAGGACT |
| GGGGCCAGCTGAGCGGCACCGCCGTGCCACCACAGGGCGCCGAGCCACAGAGCAACGCCGGACCACG |
| ACCACACATCGGCGACACCCTGTTCACCCTGTTCCGGGCACCAGAGCTGCTGGCACCAAACGGCGAC |
| CTGTACAACGTGTTCGCCTGGGCCCTGGACGTGCTGGCCAAGCGCCTGCGCTCCATGCACGTGTTCA |
| TCCTGGACTACGACCAGTCACCGGCCGGCTGCCGCGACGCCCTGCTGCAGCTGACCAGCGGCATGGT |
| GCAGACCCACGTGACAACACCCGGCAGCATCCCAACAATCTGCGACCTGGCCCGCACCTTCGCCCGC |
| GAGATGGGCGAGGCCAACTAATAGGGATCCCTCGAGAAGCTTGTCA |
| SEQ ID NO: 13 Gene #4 mHSV-TK CO TK A167F(LIF . . . FAL): Length: 1185<br>GTCAGCGGCCGCACCGGTACGCGTCCACCATGGCCAGCTACCCCGGCCACCAGCACGCCAGCGCCTT |
| CGACCAGGCCGCCCGCAGCCGCGGCCACAGCAACGGCAGCACCGCACTGCGGCCACGGCGCCAGCAG |
| GAGGCCACCGAGGTGCGCCCCGAGCAGAAGATGCCCACCCTGCTGCGCGTGTACATCGACGGACCAC |
| ACGGCATGGGCAAGACCACCACCACCCAGCTGCTGGTGGCCCTGGGCAGCCGCGACGACATCGTGTA |
| CGTGCCCGAGCCCATGACCTACTGGCGCGTGCTGGGCGCCAGCGAGACCATCGCCAACATCTACACC |
| ACCCAGCACCGCCTGGACCAAGGCGAGATCAGCGCCGGCGACGCCGCCGTGGTGATGACCAGCGCCC |
| AGATTACAATGGGCATGCCCTACGCCGTGACCGACGCCGTGCTGGCACCACACATCGGCGGCGAGGC |
| CGGCAGCAGCCACGCACCACCACCAGCACTGACCCTGATCTTCGACCGGCACCCAATCTTCGCACTG |
| CTGTGCTACCCGGCAGCACGCTACCTGATGGGCTCCATGACACCACAAGCCGTGCTGGCCTTCGTGG |
| CCCTGATCCCACCAACACTGCCCGGCACCAACATCGTGCTGGGCGCCCTGCCCGAGGACCGCCACAT |
| CGACCGCCTGGCCAAGCGCCAGCGCCCCGGCGAGCGCCTGGACCTGGCCATGCTGGCCGCCATCCGC |
| CGCGTGTACGGCCTGCTGGCCAACACCGTGCGCTACCTGCAGTGCGGCGGCAGCTGGCGCGAGGACT |
| GGGGCCAGCTGAGCGGCACCGCCGTGCCACCACAGGGCGCCGAGCCACAGAGCAACGCCGGACCACG |
| ACCACACATCGGCGACACCCTGTTCACCCTGTTCCGGGCACCAGAGCTGCTGGCACCAAACGGCGAC |
| CTGTACAACGTGTTCGCCTGGGCCCTGGACGTGCTGGCCAAGCGCCTGCGCTCCATGCACGTGTTCA |
| TCCTGGACTACGACCAGTCACCGGCCGGCTGCCGCGACGCCCTGCTGCAGCTGACCAGCGGCATGGT |
| GCAGACCCACGTGACAACACCCGGCAGCATCCCAACAATCTGCGACCTGGCCCGCACCTTCGCCCGC |
| GAGATGGGCGAGGCCAACTAATAGGGATCCCTCGAGAAGCTTGTCA |
| SEQ ID NO: 14 Gene #5 mHSV-TK CO dual mutant A167F-A168H (LIF . . . FHL):<br>Length: 1185<br>GTCAGCGGCCGCACCGGTACGCGTCCACCATGGCCAGCTACCCCGGCCACCAGCACGCCAGCGCCTT |
| CGACCAGGCCGCCCGCAGCCGCGGCCACAGCAACGGCAGCACCGCACTGCGGCCACGGCGCCAGCAG |
| GAGGCCACCGAGGTGCGCCCCGAGCAGAAGATGCCCACCCTGCTGCGCGTGTACATCGACGGACCAC |
| ACGGCATGGGCAAGACCACCACCACCCAGCTGCTGGTGGCCCTGGGCAGCCGCGACGACATCGTGTA |
| CGTGCCCGAGCCCATGACCTACTGGCGCGTGCTGGGCGCCAGCGAGACCATCGCCAACATCTACACC |
| ACCCAGCACCGCCTGGACCAAGGCGAGATCAGCGCCGGCGACGCCGCCGTGGTGATGACCAGCGCCC |

| SEQUENCES |
|---|
| AGATTACAATGGGCATGCCCTACGCCGTGACCGACGCCGTGCTGGCACCACACATCGGCGGCGAGGC |
| CGGCAGCAGCCACGCACCACCACCAGCACTGACCCTGATCTTCGACCGGCACCCAATCTTCCACCTG |
| CTGTGCTACCCGGCAGCACGCTACCTGATGGGCTCCATGACACCACAAGCCGTGCTGGCCTTCGTGG |
| CCCTGATCCCACCAACACTGCCCGGCACCAACATCGTGCTGGGCGCCCTGCCCGAGGACCGCCACAT |
| CGACCGCCTGGCCAAGCGCCAGCGCCCCGGCGAGCGCCTGGACCTGGCCATGCTGGCCGCCATCCGC |
| CGCGTGTACGGCCTGCTGGCCAACACCGTGCGCTACCTGCAGTGCGGCGGCAGCTGGCGCGAGGACT |
| GGGGCCAGCTGAGCGGCACCGCCGTGCCACCACAGGGCGCCGAGCCACAGAGCAACGCCGGACCACG |
| ACCACACATCGGCGACACCCTGTTCACCCTGTTCCGGGCACCAGAGCTGCTGGCACCAAACGGCGAC |
| CTGTACAACGTGTTCGCCTGGGCCCTGGACGTGCTGGCCAAGCGCCTGCGCTCCATGCACGTGTTCA |
| TCCTGGACTACGACCAGTCACCGGCCGGCTGCCGCGACGCCCTGCTGCAGCTGACCAGCGGCATGGT |
| GCAGACCCACGTGACAACACCCGGCAGCATCCCAACAATCTGCGACCTGGCCCGCACCTTCGCCCGC |
| GAGATGGGCGAGGCCAACTAATAGGGATCCCTCGAGAAGCTTGTCA |
| SEQ ID NO: 15 Gene #6 mHSV-TK CO MB-IFL A168H(IFL . . . AHL): Length: 1185 <br> GTCAGCGGCCGCACCGGTACGCGTCCACCATGGCCAGCTACCCCGGCCACCAGCACGCCAGCGCCTT |
| CGACCAGGCCGCCCGCAGCCGCGGCCACAGCAACGGCAGCACCGCACTGCGGCCACGGCGCCAGCAG |
| GAGGCCACCGAGGTGCGCCCCGAGCAGAAGATGCCCACCCTGCTGCGCGTGTACATCGACGGACCAC |
| ACGGCATGGGCAAGACCACCACCACCCAGCTGCTGGTGGCCCTGGGCAGCCGCGACGACATCGTGTA |
| CGTGCCCGAGCCCATGACCTACTGGCGCGTGCTGGGCGCCAGCGAGACCATCGCCAACATCTACACC |
| ACCCAGCACCGCCTGGACCAAGGCGAGATCAGCGCCGGCGACGCCGCCGTGGTGATGACCAGCGCCC |
| AGATTACAATGGGCATGCCCTACGCCGTGACCGACGCCGTGCTGGCACCACACATCGGCGGCGAGGC |
| CGGCAGCAGCCACGCACCACCACCAGCACTGACCATCTTCCTGGACCGGCACCCAATCGCACACCTG |
| CTGTGCTACCCGGCAGCACGCTACCTGATGGGCTCCATGACACCACAAGCCGTGCTGGCCTTCGTGG |
| CCCTGATCCCACCAACACTGCCCGGCACCAACATCGTGCTGGGCGCCCTGCCCGAGGACCGCCACAT |
| CGACCGCCTGGCCAAGCGCCAGCGCCCCGGCGAGCGCCTGGACCTGGCCATGCTGGCCGCCATCCGC |
| CGCGTGTACGGCCTGCTGGCCAACACCGTGCGCTACCTGCAGTGCGGCGGCAGCTGGCGCGAGGACT |
| GGGGCCAGCTGAGCGGCACCGCCGTGCCACCACAGGGCGCCGAGCCACAGAGCAACGCCGGACCACG |
| ACCACACATCGGCGACACCCTGTTCACCCTGTTCCGGGCACCAGAGCTGCTGGCACCAAACGGCGAC |
| CTGTACAACGTGTTCGCCTGGGCCCTGGACGTGCTGGCCAAGCGCCTGCGCTCCATGCACGTGTTCA |
| TCCTGGACTACGACCAGTCACCGGCCGGCTGCCGCGACGCCCTGCTGCAGCTGACCAGCGGCATGGT |
| GCAGACCCACGTGACAACACCCGGCAGCATCCCAACAATCTGCGACCTGGCCCGCACCTTCGCCCGC |
| GAGATGGGCGAGGCCAACTAATAGGGATCCCTCGAGAAGCTTGTCA |
| SEQ ID NO: 16 Gene #1 HSV-TK A168H dmNLS CO SC: Length: 1185 <br> GTCAGCGGCCGCACCGGTACGCGTCCACCATGGCCAGCTACCCCGGCCACCAGCACGCCAGCGCCTT |
| CGACCAGGCCGCCCGCAGCCGCGGCCACAGCAACGGCAGCACCGCACTGCGGCCAGGATCTCAGCAG |
| GAGGCCACCGAGGTGCGCCCCGAGCAGAAGATGCCCACCCTGCTGCGCGTGTACATCGACGGACCAC |
| ACGGCATGGGCAAGACCACCACCACCCAGCTGCTGGTGGCCCTGGGCAGCCGCGACGACATCGTGTA |
| CGTGCCCGAGCCCATGACCTACTGGCGCGTGCTGGGCGCCAGCGAGACCATCGCCAACATCTACACC |
| ACCCAGCACCGCCTGGACCAAGGCGAGATCAGCGCCGGCGACGCCGCCGTGGTGATGACCAGCGCCC |
| AGATTACAATGGGCATGCCCTACGCCGTGACCGACGCCGTGCTGGCACCACACATCGGCGGCGAGGC |

| SEQUENCES |
| --- |
| CGGCAGCAGCCACGCACCACCACCAGCACTGACCCTGATCTTCGACCGGCACCCAATCGCACACCTG |
| CTGTGCTACCCGGCAGCACGCTACCTGATGGGCTCCATGACACCACAAGCCGTGCTGGCCTTCGTGG |
| CCCTGATCCCACCAACACTGCCCGGCACCAACATCGTGCTGGGCGCCCTGCCCGAGGACCGCCACAT |
| CGACCGCCTGGCCAAGCGCCAGCGCCCCGGCGAGCGCCTGGACCTGGCCATGCTGGCCGCCATCCGC |
| CGCGTGTACGGCCTGCTGGCCAACACCGTGCGCTACCTGCAGTGCGGCGGCAGCTGGCGCGAGGACT |
| GGGGCCAGCTGAGCGGCACCGCCGTGCCACCACAGGGCGCCGAGCCACAGAGCAACGCCGGACCACG |
| ACCACACATCGGCGACACCCTGTTCACCCTGTTCCGGGCACCAGAGCTGCTGGCACCAAACGGCGAC |
| CTGTACAACGTGTTCGCCTGGGCCCTGGACGTGCTGGCCAAGCGCCTGCGCTCCATGCACGTGTTCA |
| TCCTGGACTACGACCAGTCACCGGCCGGCTGCCGCGACGCCCTGCTGCAGCTGACCAGCGGCATGGT |
| GCAGACCCACGTGACAACACCCGGCAGCATCCCAACAATCTGCGACCTGGCCCGCACCTTCGCCCGC |
| GAGATGGGCGAGGCCAACTAATAGGGATCCCTCGAGAAGCTTGTCA |
| SEQ ID NO: 17 Gene #2 HSV-TK A167F dmNLS CO SC: Length: 1185<br>GTCAGCGGCCGCACCGGTACGCGTCCACCATGGCCAGCTACCCCGGCCACCAGCACGCCAGCGCCTT |
| CGACCAGGCCGCCCGCAGCCGCGGCCACAGCAACGGCAGCACCGCACTGCGGCCAGGATCTCAGCAG |
| GAGGCCACCGAGGTGCGCCCCGAGCAGAAGATGCCCACCCTGCTGCGCGTGTACATCGACGGACCAC |
| ACGGCATGGGCAAGACCACCACCACCCAGCTGCTGGTGGCCCTGGGCAGCCGCGACGACATCGTGTA |
| CGTGCCCGAGCCCATGACCTACTGGCGCGTGCTGGGCGCCAGCGAGACCATCGCCAACATCTACACC |
| ACCCAGCACCGCCTGGACCAAGGCGAGATCAGCGCCGGCGACGCCGCCGTGGTGATGACCAGCGCCC |
| AGATTACAATGGGCATGCCCTACGCCGTGACCGACGCCGTGCTGGCACCACACATCGGCGGCGAGGC |
| CGGCAGCAGCCACGCACCACCACCAGCACTGACCCTGATCTTCGACCGGCACCCAATCTTCGCACTG |
| CTGTGCTACCCGGCAGCACGCTACCTGATGGGCTCCATGACACCACAAGCCGTGCTGGCCTTCGTGG |
| CCCTGATCCCACCAACACTGCCCGGCACCAACATCGTGCTGGGCGCCCTGCCCGAGGACCGCCACAT |
| CGACCGCCTGGCCAAGCGCCAGCGCCCCGGCGAGCGCCTGGACCTGGCCATGCTGGCCGCCATCCGC |
| CGCGTGTACGGCCTGCTGGCCAACACCGTGCGCTACCTGCAGTGCGGCGGCAGCTGGCGCGAGGACT |
| GGGGCCAGCTGAGCGGCACCGCCGTGCCACCACAGGGCGCCGAGCCACAGAGCAACGCCGGACCACG |
| ACCACACATCGGCGACACCCTGTTCACCCTGTTCCGGGCACCAGAGCTGCTGGCACCAAACGGCGAC |
| CTGTACAACGTGTTCGCCTGGGCCCTGGACGTGCTGGCCAAGCGCCTGCGCTCCATGCACGTGTTCA |
| TCCTGGACTACGACCAGTCACCGGCCGGCTGCCGCGACGCCCTGCTGCAGCTGACCAGCGGCATGGT |
| GCAGACCCACGTGACAACACCCGGCAGCATCCCAACAATCTGCGACCTGGCCCGCACCTTCGCCCGC |
| GAGATGGGCGAGGCCAACTAATAGGGATCCCTCGAGAAGCTTGTCA |
| SEQ ID NO: 18 Gene #3 HSV-TK A168H NESdmNLS CO SC: Length: 1221<br>GTCAGCGGCCGCACCGGTACGCGTCCACCATGGCCCTGCAGAAAAAGCTGGAAGAGCTGGAACTGGA |
| TGGCAGCTACCCCGGCCACCAGCACGCCAGCGCCTTCGACCAGGCCGCCCGCAGCCGCGGCCACAGC |
| AACGGCAGCACCGCACTGCGGCCAGGATCTCAGCAGGAGGCCACCGAGGTGCGCCCCGAGCAGAAGA |
| TGCCCACCCTGCTGCGCGTGTACATCGACGGACCACACGGCATGGGCAAGACCACCACCACCCAGCT |
| GCTGGTGGCCCTGGGCAGCCGCGACGACATCGTGTACGTGCCCGAGCCCATGACCTACTGGCGCGTG |
| CTGGGCGCCAGCGAGACCATCGCCAACATCTACACCACCCAGCACCGCCTGGACCAAGGCGAGATCA |
| GCGCCGGCGACGCCGCCGTGGTGATGACCAGCGCCCAGATTACAATGGGCATGCCCTACGCCGTGAC |
| CGACGCCGTGCTGGCACCACACATCGGCGGCGAGGCCGGCAGCAGCCACGCACCACCACCAGCACTG |
| ACCCTGATCTTCGACCGGCACCCAATCGCACACCTGCTGTGCTACCCGGCAGCACGCTACCTGATGG |

| SEQUENCES |
| --- |
| GCTCCATGACACCACAAGCCGTGCTGGCCTTCGTGGCCCTGATCCCACCAACACTGCCCGGCACCAA |
| CATCGTGCTGGGCGCCCTGCCCGAGGACCGCCACATCGACCGCCTGGCCAAGCGCCAGCGCCCCGGC |
| GAGCGCCTGGACCTGGCCATGCTGGCCGCCATCCGCCGCGTGTACGGCCTGCTGGCCAACACCGTGC |
| GCTACCTGCAGTGCGGCGGCAGCTGGCGCGAGGACTGGGGCCAGCTGAGCGGCACCGCCGTGCCACC |
| ACAGGGCGCCGAGCCACAGAGCAACGCCGGACCACGACCACACATCGGCGACACCCTGTTCACCCTG |
| TTCCGGGCACCAGAGCTGCTGGCACCAAACGGCGACCTGTACAACGTGTTCGCCTGGGCCCTGGACG |
| TGCTGGCCAAGCGCCTGCGCTCCATGCACGTGTTCATCCTGGACTACGACCAGTCACCGGCCGGCTG |
| CCGCGACGCCCTGCTGCAGCTGACCAGCGGCATGGTGCAGACCCACGTGACAACACCCGGCAGCATC |
| CCAACAATCTGCGACCTGGCCCGCACCTTCGCCCGCGAGATGGGCGAGGCCAACTAATAGGGATCCC |
| TCGAGAAGCTTGTCA |
| SEQ ID NO: 19 Gene #4 HSV-TK A167F NESdmNLS CO SC: Length: 1221<br>GTCAGCGGCCGCACCGGTACGCGTCCACCATGGCCCTGCAGAAAAAGCTGGAAGAGCTGGAACTGGA |
| TGGCAGCTACCCCGGCCACCAGCACGCCAGCGCCTTCGACCAGGCCGCCCGCAGCCGCGGCCACAGC |
| AACGGCAGCACCGCACTGCGGCCAGGATCTCAGCAGGAGGCCACCGAGGTGCGCCCCGAGCAGAAGA |
| TGCCCACCCTGCTGCGCGTGTACATCGACGGACCACACGGCATGGGCAAGACCACCACCACCCAGCT |
| GCTGGTGGCCCTGGGCAGCCGCGACGACATCGTGTACGTGCCCGAGCCCATGACCTACTGGCGCGTG |
| CTGGGCGCCAGCGAGACCATCGCCAACATCTACACCACCCAGCACCGCCTGGACCAAGGCGAGATCA |
| GCGCCGGCGACGCCGCCGTGGTGATGACCAGCGCCCAGATTACAATGGGCATGCCCTACGCCGTGAC |
| CGACGCCGTGCTGGCACCACACATCGGCGGCGAGGCCGGCAGCAGCCACGCACCACCACCAGCACTG |
| ACCCTGATCTTCGACCGGCACCCAATCTTCGCACTGCTGTGCTACCCGGCAGCACGCTACCTGATGG |
| GCTCCATGACACCACAAGCCGTGCTGGCCTTCGTGGCCCTGATCCCACCAACACTGCCCGGCACCAA |
| CATCGTGCTGGGCGCCCTGCCCGAGGACCGCCACATCGACCGCCTGGCCAAGCGCCAGCGCCCCGGC |
| GAGCGCCTGGACCTGGCCATGCTGGCCGCCATCCGCCGCGTGTACGGCCTGCTGGCCAACACCGTGC |
| GCTACCTGCAGTGCGGCGGCAGCTGGCGCGAGGACTGGGGCCAGCTGAGCGGCACCGCCGTGCCACC |
| ACAGGGCGCCGAGCCACAGAGCAACGCCGGACCACGACCACACATCGGCGACACCCTGTTCACCCTG |
| TTCCGGGCACCAGAGCTGCTGGCACCAAACGGCGACCTGTACAACGTGTTCGCCTGGGCCCTGGACG |
| TGCTGGCCAAGCGCCTGCGCTCCATGCACGTGTTCATCCTGGACTACGACCAGTCACCGGCCGGCTG |
| CCGCGACGCCCTGCTGCAGCTGACCAGCGGCATGGTGCAGACCCACGTGACAACACCCGGCAGCATC |
| CCAACAATCTGCGACCTGGCCCGCACCTTCGCCCGCGAGATGGGCGAGGCCAACTAATAGGGATCCC |
| TCGAGAAGCTTGTCA |
| SEQ ID NO: 20 Gene #5 HSV-TK A168H NESdmNLS JCO SC: Length: 1221<br>GTCAGCGGCCGCACCGGTACGCGTCCACCATGGCTCTGCAGAAAAAGCTGGAAGAGCTGGAACTGGA |
| TGGCTCTTATCCTGGACATCAGCATGCTTCTGCTTTTGATCAGGCTGCCAGATCTAGAGGACATTCT |
| AATGGCAGCACAGCACTGCGGCCAGGATCTCAGCAGGAAGCTACAGAAGTGAGACCTGAACAGAAAA |
| TGCCTACACTGCTGAGAGTGTATATTGATGGACCACATGGAATGGGAAAAACAACCACAACCCAGCT |
| GCTGGTGGCTCTCGGATCTAGAGATGATATTGTGTATGTGCCTGAACCTATGACATATTGGAGAGTG |
| CTGGGAGCTTCTGAAACAATTGCTAATATCTATACAACACAGCATAGACTGGATCAAGGAGAAATTT |
| CTGCCGGAGATGCTGCCGTGGTGATGACATCTGCTCAGATTACAATGGGAATGCCTTATGCTGTGAC |
| AGATGCTGTGCTGGCACCACATATTGGAGGCGAAGCTGGAAGCTCTCATGCACCACCACCAGCACTG |
| ACACTGATTTTTGATCGGCATCCAATTGCACATCTGCTGTGTTATCCGGCAGCAAGATATCTGATGG |

```
GAAGCATGACACCACAAGCCGTGCTGGCTTTTGTGGCTCTGATTCCACCAACACTGCCTGGAACAAA

CATCGTGCTGGGAGCTCTGCCTGAAGATAGACATATCGATCGGCTGGCCAAACGGCAGAGACCTGGA

GAACGGCTGGATCTGGCCATGCTGGCTGCCATTCGGAGAGTGTATGGCCTGCTGGCTAACACAGTGA

GATATCTGCAGTGTGGAGGCTCTTGGAGAGAGGATTGGGGACAGCTGTCTGGCACAGCTGTGCCACC

ACAGGGAGCCGAACCACAGAGCAATGCTGGACCACGACCACATATCGGAGACACACTGTTTACACTG

TTTCGGGCACCAGAACTGCTGGCACCAAATGGAGACCTGTACAACGTGTTTGCCTGGGCTCTGGATG

TGCTGGCTAAACGGCTGAGATCTATGCATGTGTTTATCCTGGACTATGATCAGTCACCGGCCGGATG

TCGCGATGCCCTGCTGCAGCTGACATCTGGGATGGTGCAGACACATGTGACAACACCTGGATCTATC

CCAACAATCTGTGATCTGGCTAGAACATTCGCTAGGGAGATGGGAGAGGCCAACTAATGAGGATCCC

TCGAGAAGCTTGTCA

SEQ ID NO: 21 Gene #6 HSV-TK A167F NESdmNLS JCO SC: Length: 1221
GTCAGCGGCCGCACCGGTACGCGTCCACCATGGCTCTGCAGAAAAAGCTGGAAGAGCTGGAACTGGA

TGGCTCTTATCCTGGACATCAGCATGCTTCTGCTTTTGATCAGGCTGCCAGATCTAGAGGACATTCT

AATGGCAGCACAGCACTGCGGCCAGGATCTCAGCAGGAAGCTACAGAAGTGAGACCTGAACAGAAAA

TGCCTACACTGCTGAGAGTGTATATTGATGGACCACATGGAATGGGAAAAACAACCACAACCCAGCT

GCTGGTGGCTCTCGGATCTAGAGATGATATTGTGTATGTGCCTGAACCTATGACATATTGGAGAGTG

CTGGGAGCTTCTGAAACAATTGCTAATATCTATACAACACAGCATAGACTGGATCAAGGAGAAATTT

CTGCCGGAGATGCTGCCGTGGTGATGACATCTGCTCAGATTACAATGGGAATGCCTTATGCTGTGAC

AGATGCTGTGCTGGCACCACATATTGGAGGCGAAGCTGGAAGCTCTCATGCACCACCACCAGCACTG

ACACTGATTTTTGATCGGCATCCAATTTTCGCACTGCTGTGTTATCCGGCAGCAAGATATCTGATGG

GAAGCATGACACCACAAGCCGTGCTGGCTTTTGTGGCTCTGATTCCACCAACACTGCCTGGAACAAA

CATCGTGCTGGGAGCTCTGCCTGAAGATAGACATATCGATCGGCTGGCCAAACGGCAGAGACCTGGA

GAACGGCTGGATCTGGCCATGCTGGCTGCCATTCGGAGAGTGTATGGCCTGCTGGCTAACACAGTGA

GATATCTGCAGTGTGGAGGCTCTTGGAGAGAGGATTGGGGACAGCTGTCTGGCACAGCTGTGCCACC

ACAGGGAGCCGAACCACAGAGCAATGCTGGACCACGACCACATATCGGAGACACACTGTTTACACTG

TTTCGGGCACCAGAACTGCTGGCACCAAATGGAGACCTGTACAACGTGTTTGCCTGGGCTCTGGATG

TGCTGGCTAAACGGCTGAGATCTATGCATGTGTTTATCCTGGACTATGATCAGTCACCGGCCGGATG

TCGCGATGCCCTGCTGCAGCTGACATCTGGGATGGTGCAGACACATGTGACAACACCTGGATCTATC

CCAACAATCTGTGATCTGGCTAGAACATTCGCTAGGGAGATGGGAGAGGCCAACTAATGAGGATCCC

TCGAGAAGCTTGTCA

SEQ ID NO: 22
HSV-TK dmNLS A168H, CO & SC
dmNLS = double mutated Nuclear Localization Sequence
CO = codon optimized
SC = splice corrected at 327 and 555
Kozak Sequence, Underlined
gtcaGCGGCCGCACCGGTACGCGTCCACCATGGCCAGCTACCCCGGCCACCAGCACGCCAGCGCCTT CGACCAGGCCGCCCGCAGCCGCGGCCACAGCAACGGCAGCACCGCaCTGCGgCCaGGATCTCAGCAG GAGGCCACCGAGGTGCGCCCCGAGCAGAAGATGCCCACCCTGCTGCGCGTGTACATCGACGGaCcaC

ACGGCATGGGCAAGACCACCACCACCCAGCTGCTGGTGGCCCTGGGCAGCCGCGACGACATCGTGTA

CGTGCCCGAGCCCATGACCTACTGGCGCGTGCTGGGCGCCAGCGAGACCATCGCCAACATCTACACC

ACCCAGCACCGCCTGGACCAaGGCGAGATCAGCGCCGGCGACGCCGCCGTGGTGATGACCAGCGCCC
```

| SEQUENCES |
|---|
| AGATtACaATGGGCATGCCCTACGCCGTGACCGACGCCGTGCTGGCaCCaCACATCGGCGGCGAGGC |
| CGGCAGCAGCCACGCaCCaCCaCCaGCaCTGACCCTGATCTTCGACCGgCACCCaATCGCaCACCTG |
| CTGTGCTACCCgGCaGCaCGCTACCTGATGGGCtccATGACaCCaCAaGCCGTGCTGGCCTTCGTGG |
| CCCTGATCCCaCCaACaCTGCCCGGCACCAACATCGTGCTGGGCGCCCTGCCCGAGGACCGCCACAT |
| CGACCGCCTGGCCAAGCGCCAGCGCCCCGGCGAGCGCCTGGACCTGGCCATGCTGGCCGCCATCCGC |
| CGCGTGTACGGCCTGCTGGCCAACACCGTGCGCTACCTGCAGTGCGGCGGCAGCTGGCGCGAGGACT |
| GGGGCCAGCTGAGCGGCACCGCCGTGCCaCCaCAGGGCGCCGAGCCaCAGAGCAACGCCGGaCCaCG |
| aCCaCACATCGGCGACACCCTGTTCACCCTGTTCCGgGCaCCaGAGCTGCTGGCaCCaAACGGCGAC |
| CTGTACAACGTGTTCGCCTGGGCCCTGGACGTGCTGGCCAAGCGCCTGCGCtccATGCACGTGTTCA |
| TCCTGGACTACGACCAGtcaCCgGCCGGCTGCCGCGACGCCCTGCTGCAGCTGACCAGCGGCATGGT |
| GCAGACCCACGTGACaACaCCCGGCAGCATCCCaACaATCTGCGACCTGGCCCGCACCTTCGCCCGC |
| GAGATGGGCGAGGCCAACTAATAGGGATCCCTCGAGAAGCTTgtca |

SEQ ID NO: 23 - MAP Kinase Kinase Nuclear Export Polynucleotide Sequence
CTGCAGAAAAAGCTGGAAGAGCTGGAACTGGATGGC SEQ ID NO: 24 - MAP Kinase Kinase Nuclear Export Polypeptide Sequence
LQKKLEELELDG

What is claimed is:

1. A polynucleotide sequence encoding a mutated form of thymidine kinase from a human herpes simplex virus type 1 (HSV1-TK) for increasing cell kill activity, wherein the encoded HSV1-TK is mutated at either amino acid residue 32 or 33 or both, wherein the amino acid residues correspond to positions 32 and 33 of SEQ ID NO: 2, wherein amino acid residues 32 and 33 are each independently mutated to an acidic amino acid or to cysteine, and wherein the mutated form of thymidine kinase increases cell kill activity relative to a wild-type thymidine kinase.

2. A polynucleotide according to claim 1, wherein the amino acid residues 32 and 33 are each independently mutated to an acidic amino acid.

3. A polynucleotide according to claim 2, wherein the amino acid residues 32 and 33 are each independently mutated to aspartic acid or glutamic acid.

4. A polynucleotide according to claim 1, wherein the encoded HSV1-TK is further mutated at at least one of amino acid residues 25, 26, or 168, wherein the amino acid residues correspond to positions 25, 26, and 168 of SEQ ID NO: 2.

5. A polynucleotide according to claim 4, wherein the amino acid residues 25 and 26 are each independently mutated to an amino acid chosen from the group consisting of: glycine, serine, glutamic acid, aspartic acid, and cysteine.

6. A polynucleotide according to claim 4, wherein the amino acid residue 168 is mutated to a polar or non-polar amino acid.

7. A polynucleotide according to claim 6, wherein the amino acid residue 168 is mutated to an amino acid chosen from the group consisting of: histidine, lysine, cysteine, serine, and phenylalanine.

8. A polynucleotide according to claim 4, wherein the encoded HSV1-TK is mutated at amino acid residue 32 and at least one of amino acid residues 25, 26, or 168, wherein the amino acid residues correspond to positions 25, 26, 32, and 168 of SEQ ID NO: 2.

9. A polynucleotide according to claim 4, wherein the encoded HSV1-TK is mutated at amino acid residue 33 and at least one of amino acid residues 25, 26, or 168, wherein the amino acid residues correspond to positions 25, 26, 33, and 168 of SEQ ID NO: 2.

10. A polynucleotide according to claim 1, wherein the encoded HSV1-TK is further mutated at amino acid residue 167, wherein the amino acid residue corresponds to position 167 of SEQ ID NO: 2.

11. A polynucleotide according to claim 10, wherein the amino acid residue 167 is mutated to a polar or non-polar amino acid.

12. A polynucleotide according to claim 1, wherein the encoded HSV1-TK sequence further comprises a nuclear export signal.

13. A polynucleotide according to claim 12, wherein the nuclear export signal sequence is LQKKLEELELDG (SEQ ID NO: 24).

14. A polynucleotide according to claim 1, wherein the encoded modified HSV1-TK exhibits a reduced amount of thymidine kinase activity as compared to wild-type HSV1-TK.

15. A retroviral vector comprising the polynucleotide of claim 1 encoding a modified HSV1-TK polypeptide.

16. The retroviral vector of claim 15, further comprising a polynucleotide encoding for a PiT-2 or PiT-1 polypeptide.

17. The retroviral vector of claim 15, further comprising a polynucleotide encoding for a targeting polypeptide.

18. The retroviral vector of claim 17, wherein the targeting polypeptide binds to an extracellular protein.

19. The retroviral vector of claim 18, wherein the extracellular protein is collagen.

20. A method of treating cancer in a patient in need thereof, the method comprising delivering a therapeutically effective amount of a retroviral vector particle of claim 15, followed by administration of a nucleoside analogue or a prodrug thereof to the patient in need thereof.

21. The method of claim 20, wherein the retroviral particle is administered intravenously, intramuscularly, subcutaneously, intra-arterially, intra-hepatic arterially, intrathecally, intra-peritoneally and/or intra-tumorally.

22. The method of claim 20, wherein at least $1 \times 10^{15}$ TVP of retroviral vector is administered cumulatively to the subject in need thereof.

23. The method of claim 20, wherein the prodrug is administered between about 1-2 days after administration of the retroviral vector particle.

24. The method of claim 20, wherein the nucleoside analogue is ganciclovir.

25. A method of inducing cell kill activity in a cancer cell of interest, the method comprising:
   a) contacting the cancer cell with a retroviral vector particle of claim 15;
   b) contacting the cancer cell with a nucleoside analogue or a prodrug thereof; and
   c) transducing the cancer cell with the polynucleotide encoding the modified HSV1-TK, thereby inducing cell kill activity in the cancer cell.

26. The method of claim 25, wherein the nucleoside analogue is ganciclovir.

27. The method of claim 25, further comprising administering a therapeutically effective amount of the retroviral vector particle of claim 15 and nucleoside analogue or prodrug thereof to a patient in need thereof, wherein the method in vivo induces cell kill activity in a cancer cell of interest in the patient in need thereof.

* * * * *